United States Patent
Chen et al.

(10) Patent No.: US 7,847,062 B2
(45) Date of Patent: Dec. 7, 2010

(54) PHARMACOKINETIC MODULATION AND COMPOSITIONS FOR MODIFIED FN3 POLYPEPTIDES

(75) Inventors: Yan Chen, Lexington, MA (US); Elena Getmanova, Lexington, MA (US); Martin C. Wright, Boston, MA (US); Alan S. Harris, Andover, MA (US); Ai Ching Lim, Mercer Island, WA (US); Jochem Gokemeijer, Boston, MA (US); Lin Sun, West Roxbury, MA (US); Michael Wittekind, Bainbridge Island, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 331 days.

(21) Appl. No.: 11/482,641

(22) Filed: Jul. 7, 2006

(65) Prior Publication Data
US 2007/0160533 A1    Jul. 12, 2007

Related U.S. Application Data

(63) Continuation of application No. 11/448,171, filed on Jun. 5, 2006, which is a continuation of application No. PCT/US2004/040885, filed on Dec. 6, 2004.

(60) Provisional application No. 60/527,886, filed on Dec. 5, 2003.

(51) Int. Cl.
*C07K 14/78*    (2006.01)
*A61K 38/39*    (2006.01)

(52) U.S. Cl. .................... 530/320; 530/345; 530/350; 530/402; 514/12

(58) Field of Classification Search .................... None
See application file for complete search history.

(56) References Cited

U.S. PATENT DOCUMENTS

| | | | |
|---|---|---|---|
| 5,235,041 | A | 8/1993 | Cappello et al. |
| 5,514,581 | A | 5/1996 | Ferrari et al. |
| 5,545,620 | A | 8/1996 | Wahl et al. |
| 5,641,648 | A | 6/1997 | Ferrari et al. |
| 5,770,697 | A | 6/1998 | Ferrari et al. |
| 5,792,742 | A | 8/1998 | Gold et al. |
| 6,018,030 | A | 1/2000 | Ferrari et al. |
| 6,207,446 | B1 | 3/2001 | Szostak et al. |
| 6,214,553 | B1 | 4/2001 | Szostak et al. |

(Continued)

FOREIGN PATENT DOCUMENTS

WO    WO-98/12226    3/1998

(Continued)

OTHER PUBLICATIONS

Wells (1990) Biochemistry 29(37): 8509-8517.*

(Continued)

*Primary Examiner*—Bridget E Bunner
*Assistant Examiner*—Zachary C Howard
(74) *Attorney, Agent, or Firm*—Ropes & Gray LLP

(57) ABSTRACT

The present disclosure relates to novel vascular endothelial growth factor receptor (VEGFR)-binding polypeptides and methods for using these polypeptides to inhibit biological activities mediated by vascular endothelial growth factors (VEGFs). The present disclosure also provides various improvements relating to single domain binding polypeptides.

15 Claims, 23 Drawing Sheets

U.S. PATENT DOCUMENTS

| | | | |
|---|---|---|---|
| 6,258,558 | B1 | 7/2001 | Szostak et al. |
| 6,261,804 | B1 | 7/2001 | Szostak et al. |
| 6,281,344 | B1 | 8/2001 | Szostak et al. |
| 6,383,775 | B1 | 5/2002 | Duff et al. |
| 6,462,189 | B1 | 10/2002 | Koide |
| 6,518,018 | B1 | 2/2003 | Szostak et al. |
| 6,524,583 | B1 | 2/2003 | Thorpe et al. |
| 6,559,126 | B2 | 5/2003 | Tournaire et al. |
| 6,660,492 | B1 | 12/2003 | Bode et al. |
| 6,818,418 | B1 | 11/2004 | Lipovsek |
| 7,115,396 | B2 | 10/2006 | Lipovsek et al. |
| 2002/0019517 | A1 | 2/2002 | Koide |
| 2002/0061307 | A1* | 5/2002 | Whitlow et al. ......... 424/178.1 |
| 2003/0104520 | A1 | 6/2003 | Ellington et al. |
| 2003/0170753 | A1 | 9/2003 | Koide |
| 2005/0255548 | A1 | 11/2005 | Lipovsek |

FOREIGN PATENT DOCUMENTS

| | | |
|---|---|---|
| WO | WO-98/31700 | 7/1998 |
| WO | WO-98/56915 | 12/1998 |
| WO | WO-99/51773 | 10/1999 |
| WO | WO-00/34784 | 6/2000 |
| WO | WO-01/64942 | 9/2001 |
| WO | WO-02/04523 | 1/2002 |
| WO | WO-02/32925 | 4/2002 |
| WO | WO-03/022858 | 3/2003 |
| WO | WO-2008/097497 | 8/2008 |
| WO | WO-2009/025806 | 2/2009 |
| WO | WO-2009/073115 | 6/2009 |

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only.*

Bork (2000) Genome Research 10:398.*

Skolnick et al (2000) Trends in Biotech. 18(1): 34.*

Doerks et al (1998) Trends in Genetics 14(6): 248.*

Smith et al (1997) Nature Biotechnology 15:1222.*

Brenner (1999) Trends in Genetics 15(4): 132.*

Bork et al (1996) Trends in Genetics 12(10): 425.*

Choy et al (2002. Rheumatology. 41: 1133-1137).*

Muyldermans (2001. Reviews in Molecular Biology 74: 277-302).*

Maeda et al (2001. Advanced Drug Delivery Reviews. 46: 169-185).*

Yang et al (Oct. 2003. Protein Engineering. 16(10): 761-770).*

Zdanov, A., et al., "Structure of a single-chain antibody variable domain (Fv) fragment complexed with a carbohydrate antigen at 1.7-Åresolution," PNAS, 91:6421-6427 (1994).

Caliceti, P., et al., "Pharmacokinetic and biodistribution properties of poly(ethylene glycol)—protein conjugates," *Advanced Drug Delivery Reviews*, 55:1261-1277 (2003).

Matsushima et al. Modification of *E. coli* Asparaginase with 2,4-Bis(O-Methoxypolyethylene Glycol) -6-Chloro-S-Triazine (Activated PEG2); Disappearance of Binding Ability Towards Anti-Serum and Retention of Enzymic Activity. Chemistry Letters, p. 773-776 (1990).

Posey et al. A Phase I Trial of an Anti-KDR (VEGFR2) Chimeric Antibody in Patients with Liver Metastases in Colorectal Cancer (CRC). 2002 American Society of Clinical Oncology—Slides from the annual meeting (May 18-21).

Shibuya, M. "Vascular endothelial growth factor receptor-2: Its unique signaling and specific ligand, VEGF-E," *Cancer Sci.*, 94(9):751-756 (2003).

Apte et al., Anchor-Ligated cDNA Libraries: A Technique for Generating a cDNA Library for the Immediate Cloning of the 5' Ends of mRNAs. *Biotechniques* 15, 890-893 (1993).

Bea et al., Arginine-Rich Anti-Vascular Endothelial Growth Factor Peptides Inhibit Tumor Growth and Metastasis by Blocking Angiogenesis, *J. Biol. Chem.*, 275:13588 (2000).

Baggio et al., Identification of epitope-like consensus motifs using mRNA display, *J. Mol. Recognit.*, 15: 126-134 (2002).

Baron et al., Protein Modules, *Elsevier Science Publishers Ltd..* (UK), 13-17 (1991).

Baron et al., H NMR Assignment and Secondary Structure of the Cell Adhesion Type III Module of Fibronectin. *Biochemistry* 31, 2068-2073 (1992).

Batori et al., *Protein Eng.*, Exploring the Potential of the Monobody Scaffold: Effects of Loop Elongation on the Stability of a Fibronectin Type III Domain, 15(12):1015-1020 (2002).

Bianchi et al., High Level Expression and Rational Mutagenesis of a Designed Protein, the Minibody. *J. Mol. Biol.* 236, 649-659 (1994).

Boder et al., Yeast Surface Display for Screening Combinatorial Polypeptide Libraries. *Nat. Biotech.* 15, 553-557 (1997).

Boldicke et al., Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34$^+$ Cells from Cord Blood., *Stem Cells*, 19(1):224-36 (2001).

Bork and Doolittle, Proposed Acquisition of an Animal Protein Domain by Bacteria. *PNAS* 89, 8990-94 (1992).

Bork et al., The Immunoglobulin Fold Structural Classification, Sequence Patterns and Common Core, *J. Mol. Biol.*, 242(4):309-320 (1994).

Brock, K. et al., Nucleotide sequencing of 5' and 3' termini of bovine viral diarrhea virus by RNA ligation and PCR, *J. Virol. Methods* 38, 39-46 (1992).

Bruzik, J. et al., "Spliced leader RNAs from lower eukaryotes are trans-spliced in mammalian cells," *Nature* 360, 692-695 (1992).

Campbell & Spitzfaden, Building Proteins with Fibronectin Type III Modules, *Structure*, 2(5):333-337 (1994).

Clackson and Wells, In Vitro Selection from Protein and Peptide Libraries. *TIB Tech* 12, 173-184 (1994).

Clackson et al., Making Antibody Fragments Using Phage Display Libraries. *Nature* 352, 624-628 (1991).

Claffey et al., Vascular Endothelial Growth Factor, *J. Biol. Chem.*, 267:16317-16322 (1992).

Clarke et al., Folding and Stability of a Fibronectin Type III Domain of Human Tenascin. *J. Mol. Biol.* 270, 771-778 (1997).

Copie et al., Solution Structure and Dynamics of Linked Cell Attachment Modules of Mouse Fibronectin Containing the RGD and Synergy Regions: Comparison with the Human Fibronectin Crystal Structure. *J. Mol. Biol.* 277, 663-682 (1998).

Cota et al., Two Proteins with the Same Structure Respond Very Differently to Mutation: The Role of Plasticity in Protein Stability. *J. Mol. Biol.* 302, 713-725 (2000).

Cujec et al., Seclection of v-Abl Tyrosine Kinase Substrate Sequences from Randomized Peptide and Cellular Proteomic Libraries Using mRNA Display, *Chemistry & Biology* 9, 253-264 (2002).

DGENE Search Results (pp. 1-33) STN search results.

Dickinson et al., Crystal Structure of the Tenth Type III Cell Adhesion Module of Human Fibronectin. *J. Mol. Biol.* 236, 1079-1092 (1994).

Dickinson et al., Crystals of the Cell-Binding Module of Fibronectin Obtained from a Series of Recombinant Fragments Differing in Length. *J. Mol. Biol.* 238, 123-127 (1994).

Ely et al., Common Molecular Scaffold for two Unrelated RGD Molecules. *Prot. Eng.* 8, 823-827 (1995).

Ferguson, K. et al., The SL1 trans-spliced leader RNA performs an essential embryonic function in Caenorhabditis elegans that can also be supplied by SL2 RNA., *Genes Dev.* 10, 1543-1556 (1996).

Ghosh et al., Structure of NF-KB p50 Homodimer Bound to a kB Site. *Nature* 373, 303-310 (1995).

Grant et al., Structural Requirements for Biological Activity of the Ninth and Tenth Fill Domains, of Human Fibronectin. *J. Biol. Chem.* 272, 6159-6166 (1997).

Hamers-Casterman et al., Naturally Occurring Antibodies Devoid of Light Chains. *Nature* 363, 446-448 (1993).

Hammond et al., In Vitro Selection and Characterization of Bcl-$X_L$-binding Proteins from a Mix of Tissue-Specific mRNA Display Libraries, *The Journal of Biological Chemestry*, vol. 276, No. 24, 2898-20898-20906 (2001).

Harpaz & Chothia, Many of the Immunoglobulin Superfamily Domains in Cell Adhesion Molecules and Surface Receptors Belong to a New Structural Set Which Is Close to That Containing Variable Domains, *J. Mol. Biol.*, 238(4):528-539 (1994).

Hocking et al., A Novel Role for the Integrin-Binding III-10 Module in Fibronectin Matrix Assembly. *J. Cell Biol.* 133, 431-444 (1996).

Hocking et al., Activation of Distinct Alpha5Beta1-Mediated Signalling Pathways by Fibronectin's Cell Adhesion and Matrix Assembly Domains. *J. Cell. Biol.* 141, 241-253 (1998).

Hynes, Integrins: Versatility, Modulation, and Signaling in Cell Adhesion. *Cell* 69, 11-25 (1992).

Jacob et al., The Chick Embryo Chorioallantoic Membrane as a Bioassy for Angiogenesis Factors: Reactions Induced By Carrier Materials, *Exp. Path.*, 15:1234 (1978).

Jain et al., Dissecting Tumour Pathophysiology Using Intravital Microscopy, *Nat. Rev. Cancer*, 2:266-276 (2002).

Jung et al., A Functionalo Protein Chip for Pathway Optimization and in Vitro Metabolic Engineering, *Science* 34, 428-431 (2004).

Keefe et al., Functional Proteins From a Random-Sequence Library, *Nature*, 410, 715-718 (2001).

Koide et al., Directed Evolution of Fibronectin Type III Domain to Novel Ligand Binding Proteins. Designing Small and Large Molecules I, *Abstract* 1739, 1997. FASEB J. 11(9) :A1155.

Koide et al., Directed Evolution of Fibnronectin Type III Domain to Novel Ligand Binding Proteins. *FASEB J.* 11(9), Supp., Abstract M40, 1997. FASEB J. 11(9) : A837.

Koide et al., Stabilization of a Fibronectin Type III Domain by the Removal of Unfavorable Electrostatic Interactions on the Protein Surface, *Biochemistry*, 40(34):10326-10333 (2001).

Koide et al., The Fibronectin Type III Domain as a Scaffold for Novel Binding Proteins. *J. Mol. Biol.* 284, 1141-1151 (1998).

Ku and Schultz, Alternate Protein Frameworks for Molecular Recognition. *PNAS* 92, 6552-6556 (1995).

Kurz, Psoralen Photo-Crosslinked mRNA-puromycin Conjugates: A Novel Template for the Rapid and Facile Preparation of mRNA-Protein Fusions, *Nucleic Acids Research* 28, No. 18, 1-5 (2000).

Leahy et al., Structure of a Fibronectin Type III Domain from Tenascin Phased by MAD Analysis of the Selenomethionyl Protein. *Science* 258, 987-991 (1992).

Lee et al., Strong Inhibition of Fibrogen Binding to Platelet Receptor Alpha2b beta 3 by RGD Sequences Installed into a Presentation Scaffold, *Prot. Eng.* 6, 745-754 (1993).

Lipovsek et al., In-vitro Protein Evolution by Ribosome Display and mRNA display, *Journal of Immunological Methods* 290, 51-67 (2004).

Litvinovich and Ingham, Interactions Between Type III Domains in the 110 kDa Cell-Binding Fragment of Fibronectin. *J. Mol. Biol.* 248, 611-626 (1995).

Lombardo et al., Conformational Flexibility and Crystallization of Tandemly Linked Type III Modules of Human Firbonectin. *Prot. Sci.* 5, 1934-1938 (1996).

Lyden et al., Impaired Recruitment of Bone-Marrow-Derived Endothelial and Hematopoietic Precursor Cells Blocks Tumor Angiogenesis and Growth, *Nature Medicine*, 7:1194 (2001).

Main et al., The Three-Dimensional Structure of the Tenth Type III Module of Fibronectin: An Insight into RGD-Mediated Interactions. *Cell* 71, 671-678 (1992).

Markland et al., Iterative Optimization of High-Affinity Protease Inhibitors Using Phage Display. 1. Plasmin. *Biochemistry* 35, 8045-8057 (1996).

Maruyama, K. et al., Oligo-cappin: a single method to replace the cap structure of eukaryotic mRNAs with oligoribonucieotides. *Gene* 138, 171-174 (1994).

McConnell and Hoess, Tendamistat as a Scaffold for Conformationally Constrained Phage Peptide Libraries. *J. Mol. Biol.* 250, 460-470 (1995).

McLeod DS et al., Localization of VEGF Receptor-2 (KDR/Flk-1) and Effects of Blocking it in Oxygen-Induced Retinoptahy, *Invest. Ophthalmol Vis. Sci.*, 43(2) :474-482 (2002).

Meinke et al., Cellulose-Binding Polypeptides from Cellulomonas fimi: Endoglucanase D (CenD), a Family A Beta-1, 4-Glucanase. *J. Bacteriol.* 175, 1910-1918 (1993).

Meyer et al., Comparative Structure-Function Analysis of VEGFR-1 and VEGFR-2: What Have We Learned from Chimeric Systems?, *Ann. N.Y. Acad. Sci.*, 995:200-207 (2003).

Muller et al., Structure of the NF-kB p50 Homodimer Bound to DNA. *Nature* 373, 311-317 (1995).

Nemoto et al., In Vitro Virus: Bonding of mRNA bearing puromycin at the 3'-Terminal End to the C-Terminal End of its Encoded Protein on the Ribosome in Vitro, *FEBS* 414, 405-408 (1997).

Ngo et al., Computational Complexity. Protein Structure Prediction, and the Levinthal Paradox in the Protein Folding Problem and Tertiary Structure Prediction, Merz & Le Grand, ed. Birkhauser, *Boston*, p. 491-495 (1994).

Nilsen, T., Trans-Splicing in Protozoa and Helminths, *Infect Agents Dis.* 1, 212-218 (1992).

Nord et al.. A Combinatorial Library of an Alpha-Helical Bacterial Receptor Domain. *Prot. Eng.* 8, 601-608 (1995).

Nord et al., Binding Proteins Selected from Combinatorial Libraries of an Alpha-Helical Bacterial Receptor Domain. *Nat. Biotech.* 15, 772-777 (1997).

Nygren and Uhlen, Scaffolds for Engineering Novel Binding Sites in Proteins. *Curr. Op. Struc. Biol.*, 463-469 (1997).

Plaxco et al. A Comparison of the Folding Kinetics and Thermodynamics of Two Homologous Fibronectin Type III Modules. *J. Mol. Biol.* 270, 763-770 (1997).

Plaxco et al. Rapid Refolding at a Proline-Rich All-Beta-Sheet Fibronectin Type III Module. *PNAS* 93, 10703-10706 (1996).

Potts and Campbell. Structure and Function of Fibronectin Modules. *Matrix Biol.* 15, 313-320 (1996).

Potts and Campbell. Fibronectin Structure and Assembly, *Curr. Opin. Cell Biol.* 6, 648-655 (1994).

Roberts and Szostak. RNA-Peptide Fusions for the In Vitro Selection of Peptides and Proteins. *PNAS* 94, 12297-12302 (1997).

Roberts, R.W. Totally in vitro protein selection using mRNA-protein fusions and ribosome display. Current Opinion in Chemical Biology, Current Biology Ltd, London, GB, 3, 268-273 (1999), XP002180767 ISSN: 1367-5931.

Rottgen and Collins. A Human Pancreatic Secretory Trypsin Inhibitor Presenting a Hypervariable Highly Constrained Epitope Via Monovalent Phagemid Display. *Gene* 164, 243 -250 (1995).

Shibata et al., An Attempt to Substitute the Cell Binding Domain of Human Fibronectin in Lambda Phage J Protein: Computer Design and Expression. *Biochimie*, 75, 459-465 (1993).

Shima et al., The Mouse Gene for Vascular Endothelial Growth Factor, *J. Biol. Chem.*, 271:3877-3883 (1996).

Smith and Petrenko. Phage Display. *Chem. Rev.* 97, 391-410 (1997).

Tischer et al., The Human Gene for Vascular Endothelial Growth Factor, *J. Biol. Chem.*, 266:11947-11954 (1991).

Tramontano et al. The Making of the Minibody: An Engineered Beta-Protein for the Display of Conformationally Constrained Peptides. *J. Mol. Recog.* 7, 9-24 (1994).

Verheul et al., Targeting Vascular Endothelial Growth Factor Blockade: Ascites and Pleural Effusion Formation, The *Oncologist*, 5(Suppl 1):45-50 (2000).

Wang et al. Isolation of a High Affinity Inhibitor of Urokinase-Type Plasminogen Activator by Phage Display of Ecotin. *J. Biol. Chem.* 270, 12250-12256 (1995).

Watanabe et al. Gene Cloning of Chitinase A1 From Bacillus Circulans WL-12 Revealed its Evolutionary Relationship to Serratia Chintinaseand to the Type III Homology Units of Fibronectin. *J. Biol. Chem.* 265. 15659.15665 (1990).

Watanabe et al., Anti-Vascular Endothelial Growth Factor Receptor-2 (Flk-1/KDR) Antibody Suppresses Contact Hypersensitivity, *Exp. Dermatol.*, 13(11):671-681 (2004).

Wells, J.A., Additivity of Mutational Effects in Proteins, *Biochem.* 29, 509-517 (1990).

Williams et al. The Immunoglobulin Superfamily—Domains for Cell Surface Recognition, *Ann. Rev. Immunol.* 6, 381-405 (1988).

Williams et al., Solution Structures of Modular Proteins by Nuclear Magnetic Resonance, *Methods Enzymol.* 245, 451-469 (1994).

Wilson et al., The Use of mRNA Display to Select High-Affinity Protein-Binding Peptides, *PNAS* 98, No. 7, 3750-3755 (2001).

Xu et al., Directed Evolution of High- Affinity Antibody Mimics Using mRNA Display, *Chemistry & Biology*, 9:933-942 (2002).

Yoshiji H et al., Vascular Endothelial Growth Factor and Receptor Interaction is a Prerequisite for Murine Hepatic, *Gut*, 52(9):1347-1354 (2003).

Boder, et al., "Directed evolution of antibody fragments with monovalent femtomolar antigen-binding affinity," PNAS, vol. 97(20), pp. 10701-10705 (2000).

Kohler and Milstein, "Continuous Cultures of Fused Cells Secreting Antibody of Predefined Specificity", Nature, vol. 256, pp. 495-497 (1975).

Markland et al., "Iterative Optimization of High-Affinity Protease Inhibitors Using Phage Display", 2. Plasma Kallikrein and Thrombin. Biochemistry, vol. 35, pp. 8058-8067 (1996).

Parker et al., "Antibody mimics based on human fibronectin type three domain engineered for thermostability and high-affinity binding to vascular endothelial growth factor receptor two", Protein Engineering, Design & Selection, vol. 18(9), pp. 435-444 (2005).

Tang, L. et al., "Pharmacokinetic aspects of biotechnology products", J. Pharm Sci., vol. 93, pp. 2184-2204 (2004).

* cited by examiner

Figure 10
M5FL in 100 mM NaOAc, pH 4.5
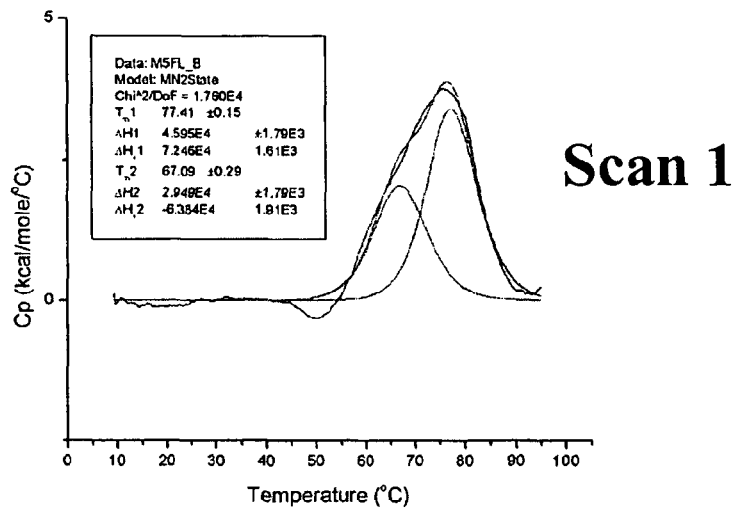
Scan 1
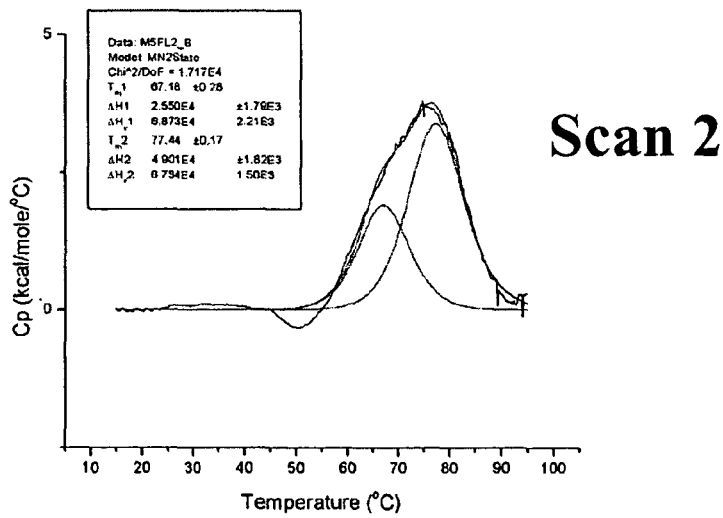
Scan 2
Scan 1: Tm = 67 deg (40%), 77 deg (60%)
Scan 2: Tm = 67 deg (34%), 77 deg (66%)
$\Delta H_{scan2}/\Delta H_{scan1} = 99\%$ Samples
M:     Marker
-:     Starting M5FL
20:    M5FL-PEG20
40:    M5FL-PEG40

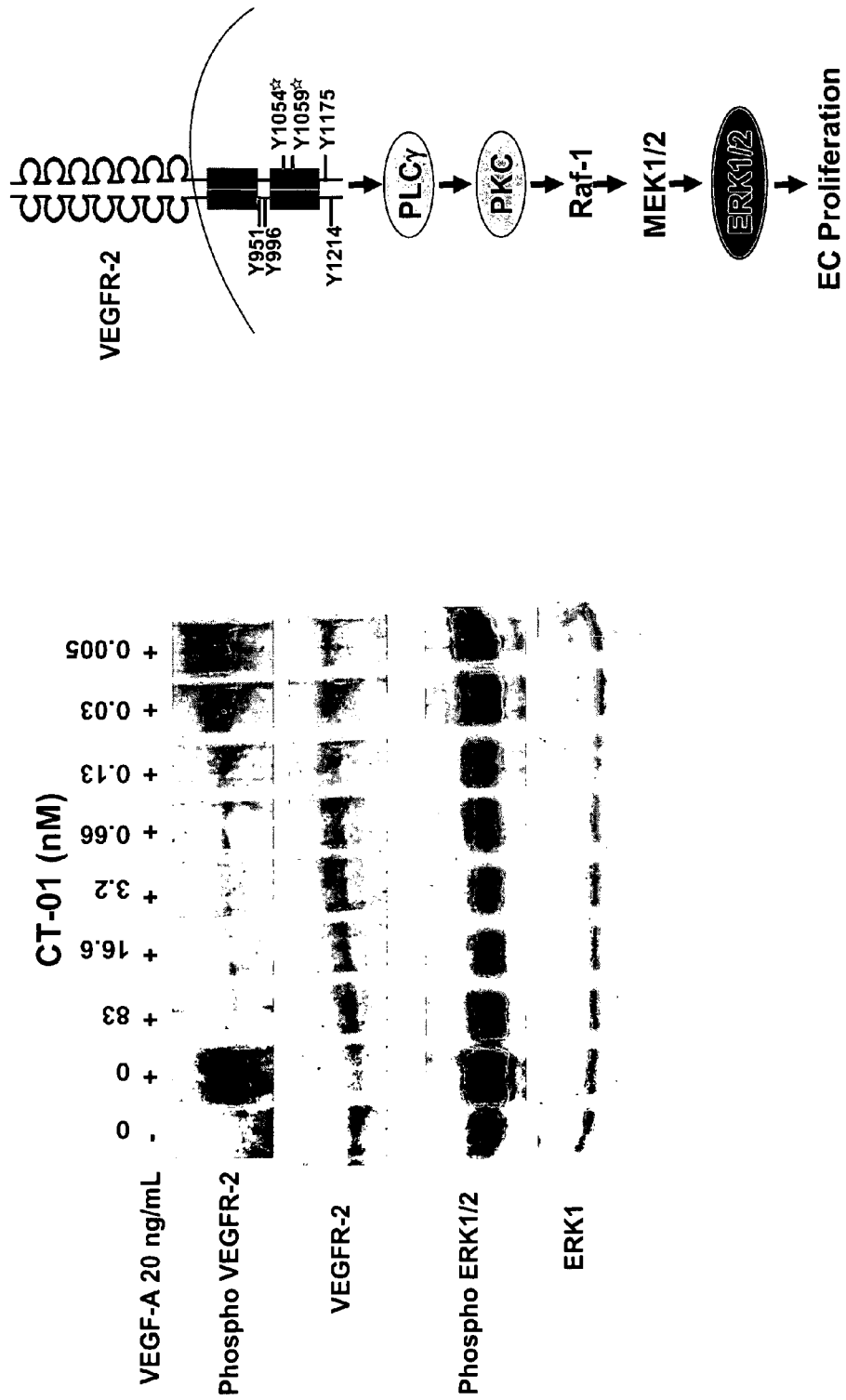
Figure 13. CT-01 Blocks VEGFR-2 Signaling in Human Endothelial Cells

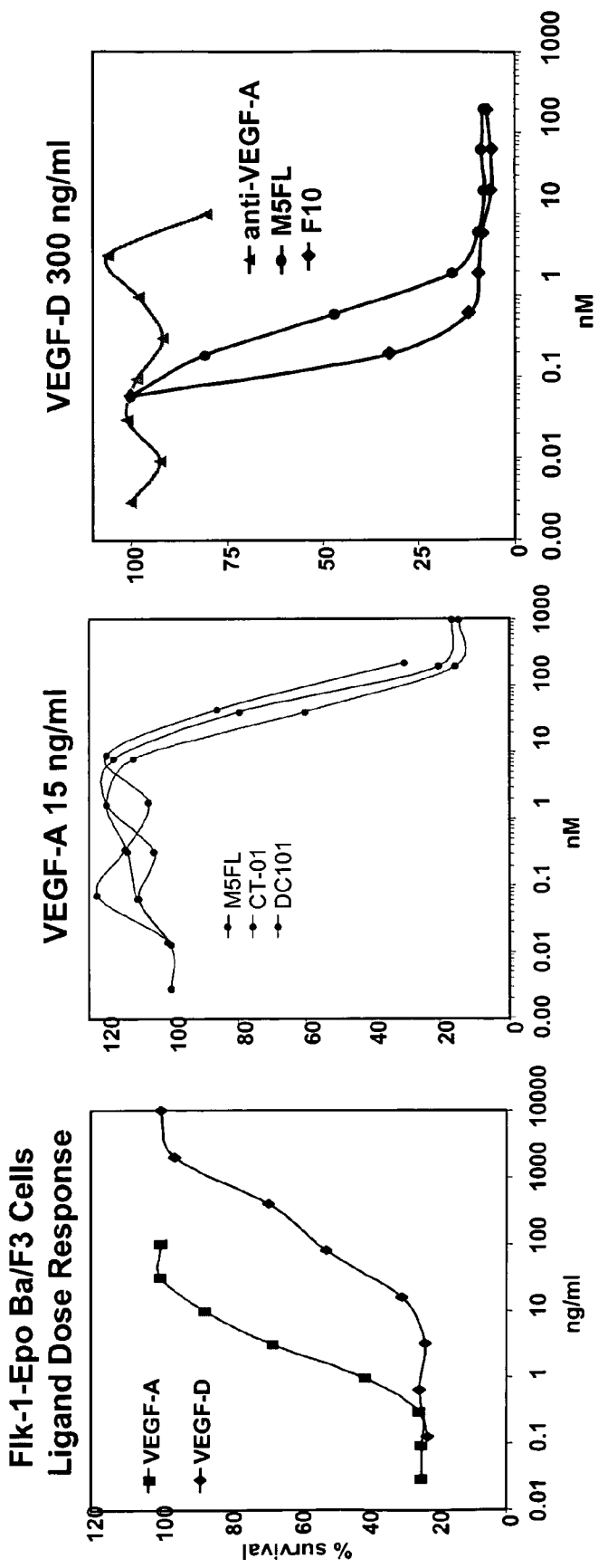
Figure 14. Blocking VEGF with Fibronectin-based KDR Binders (M5FL, F10, CT-01)

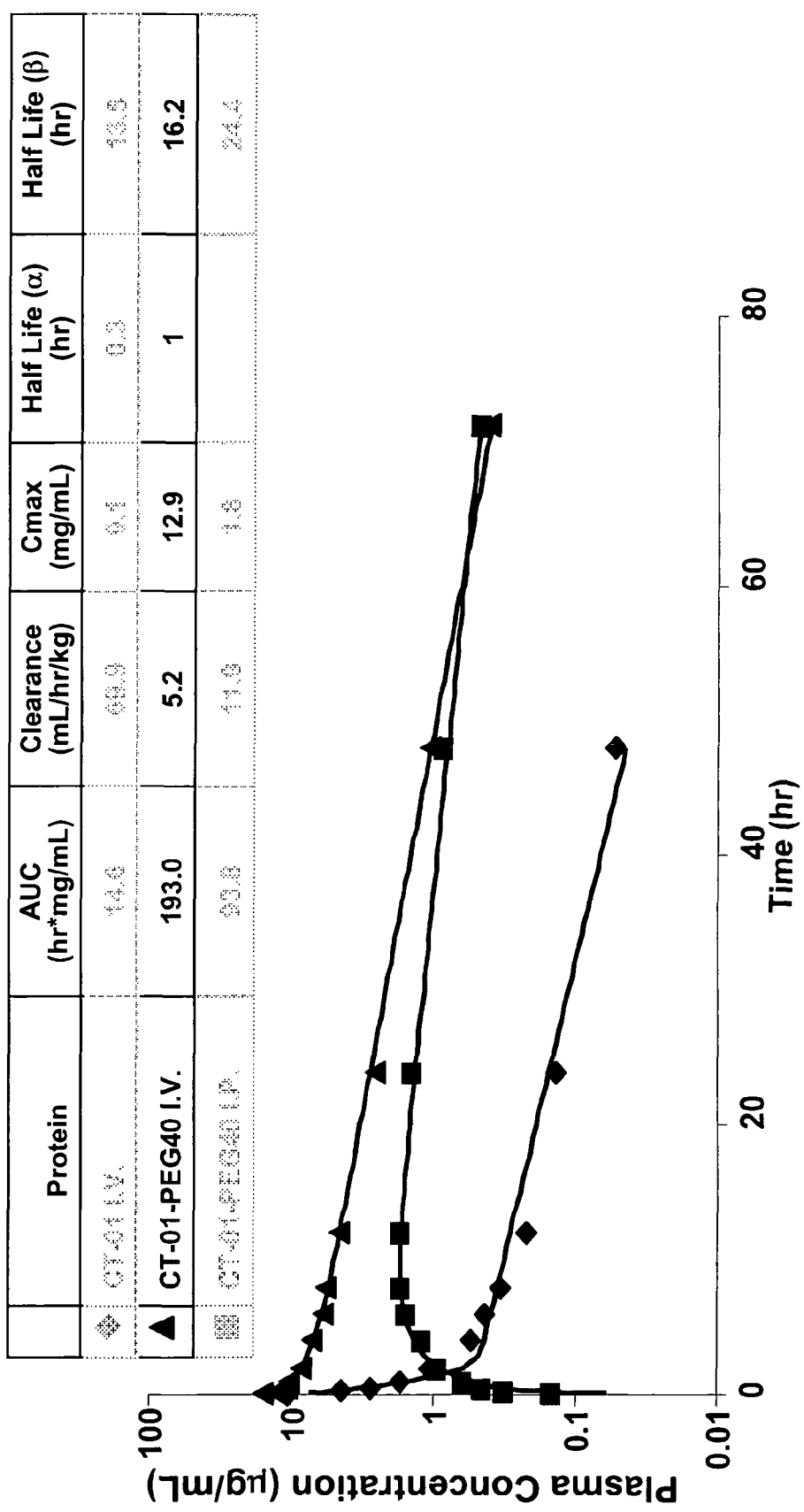
Figure 15. Comparison of $^{125}$I native, PEGylated CT-01 administered iv & ip.

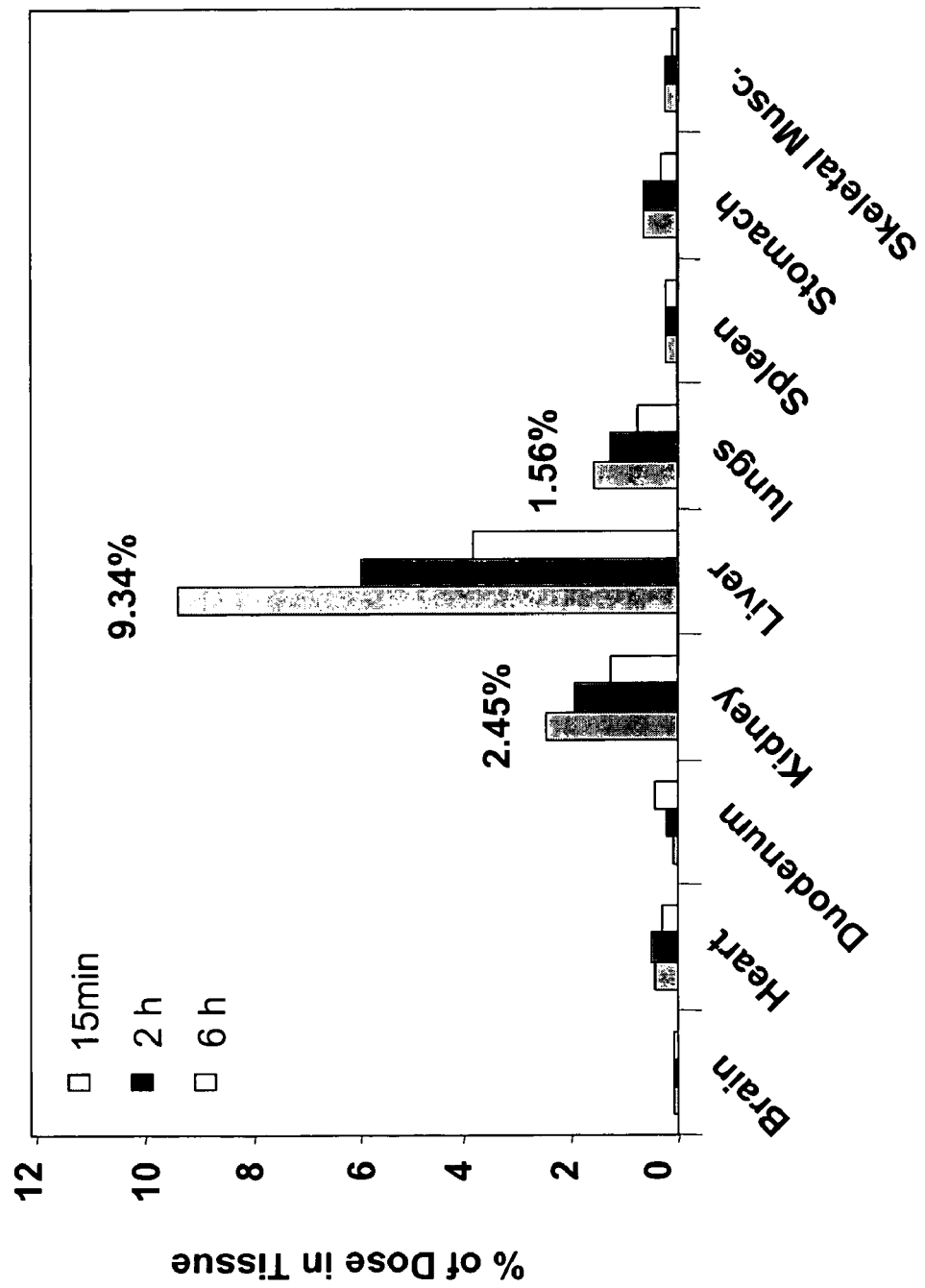
Figure 16. Pharmacokinetics of CT-01
Tissue distribution of $^{125}$I-CT01PEG40 in normal rats

Figure 17. Miles Assay Measures Vascular Permeability

1. Treat mice with test article i.p.
Treatment is hours prior to assessment of VEGF blocking activity

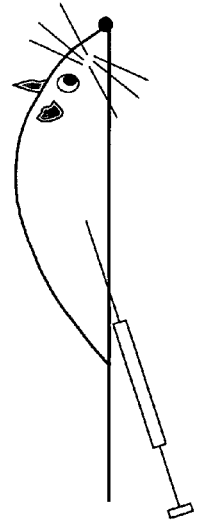

2. Inject Evans blue i.v.
Let it circulate for 10 min

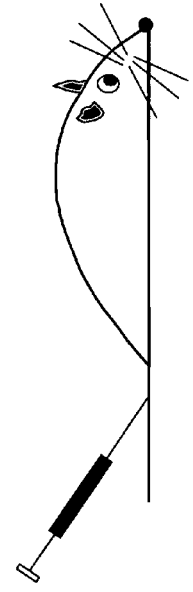

3. Inject VEGF$_{165}$ intradermally to induce vascular permeability

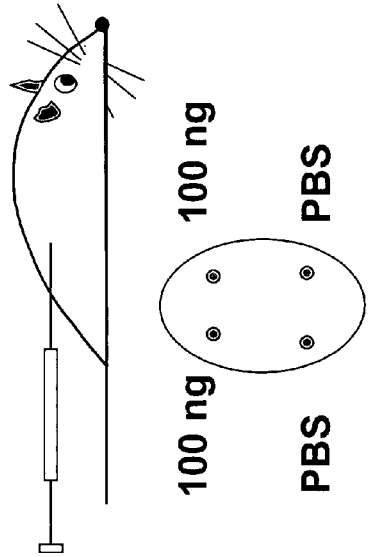

100 ng   100 ng
             PBS
100 ng   PBS
   PBS

4. Sacrifice mice and skin the back

Flipped back skin

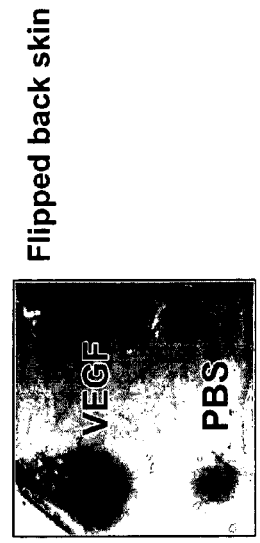

VEGF    PBS

5. Extract the Evans blue and quantify by A$_{620}$

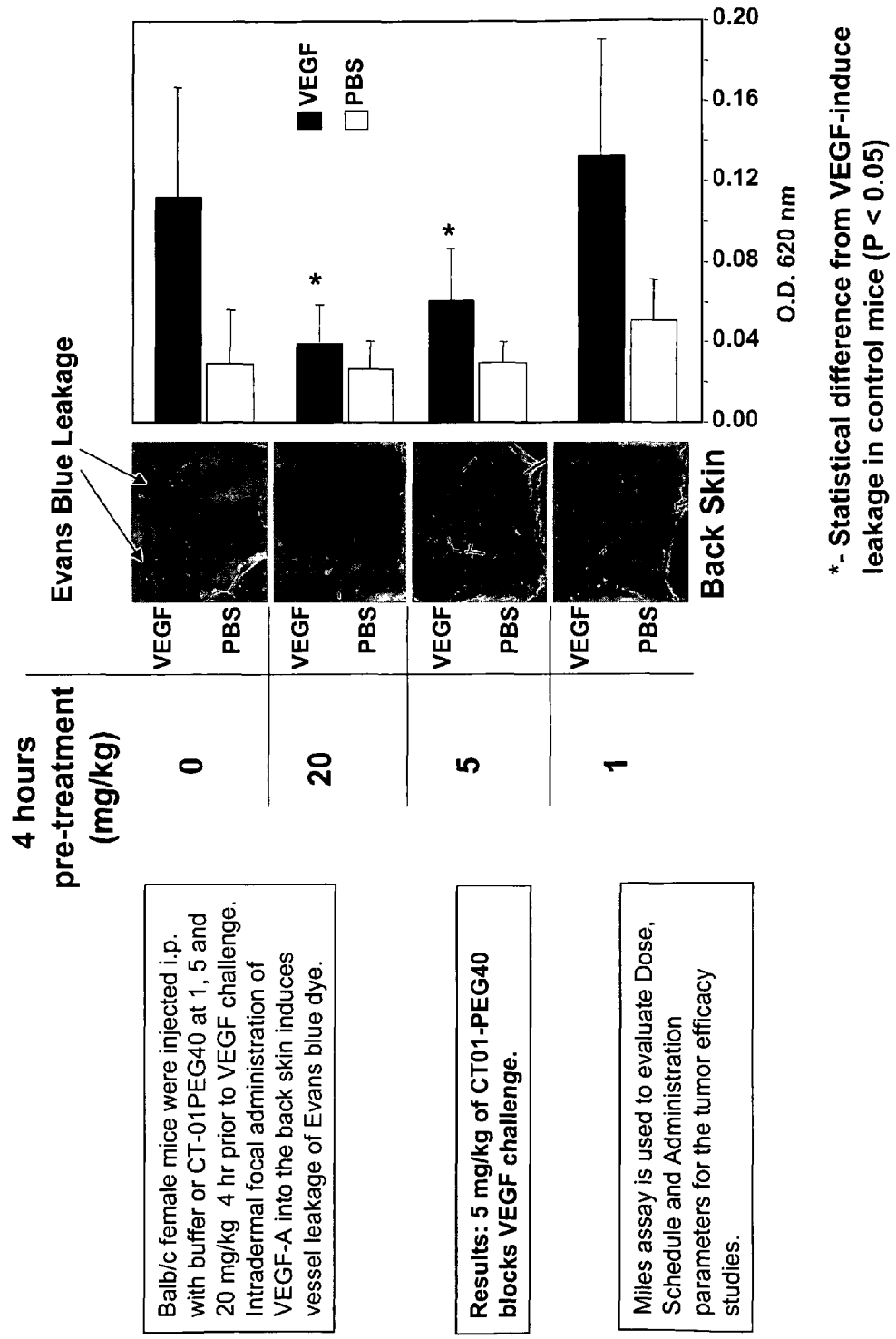
Figure 18. CT-01 Blocks VEGF In Vivo

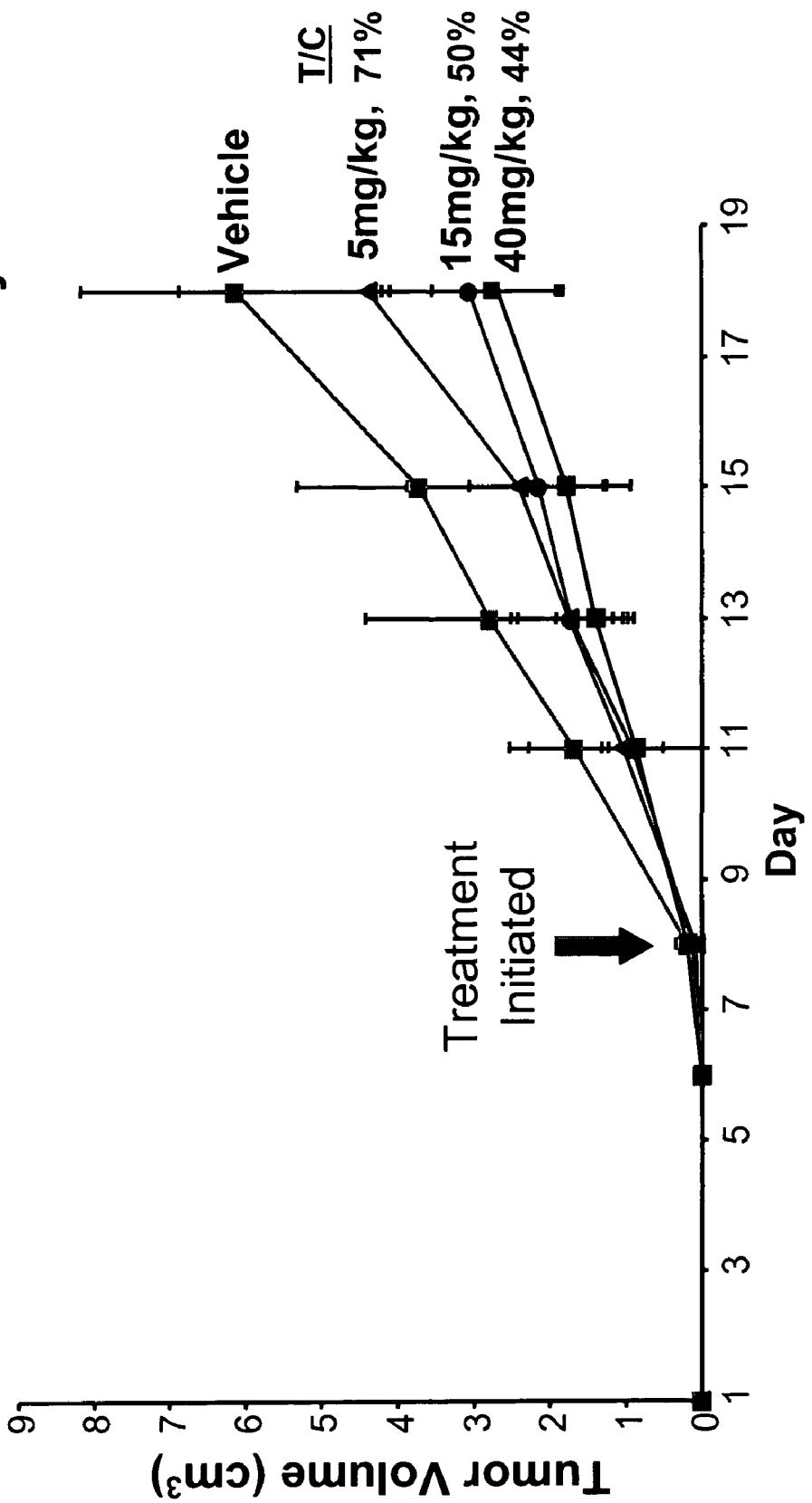
Figure 19. CT-01 Inhibits Tumor Growth
B16-F10 Murine Melanoma Tumor Assay

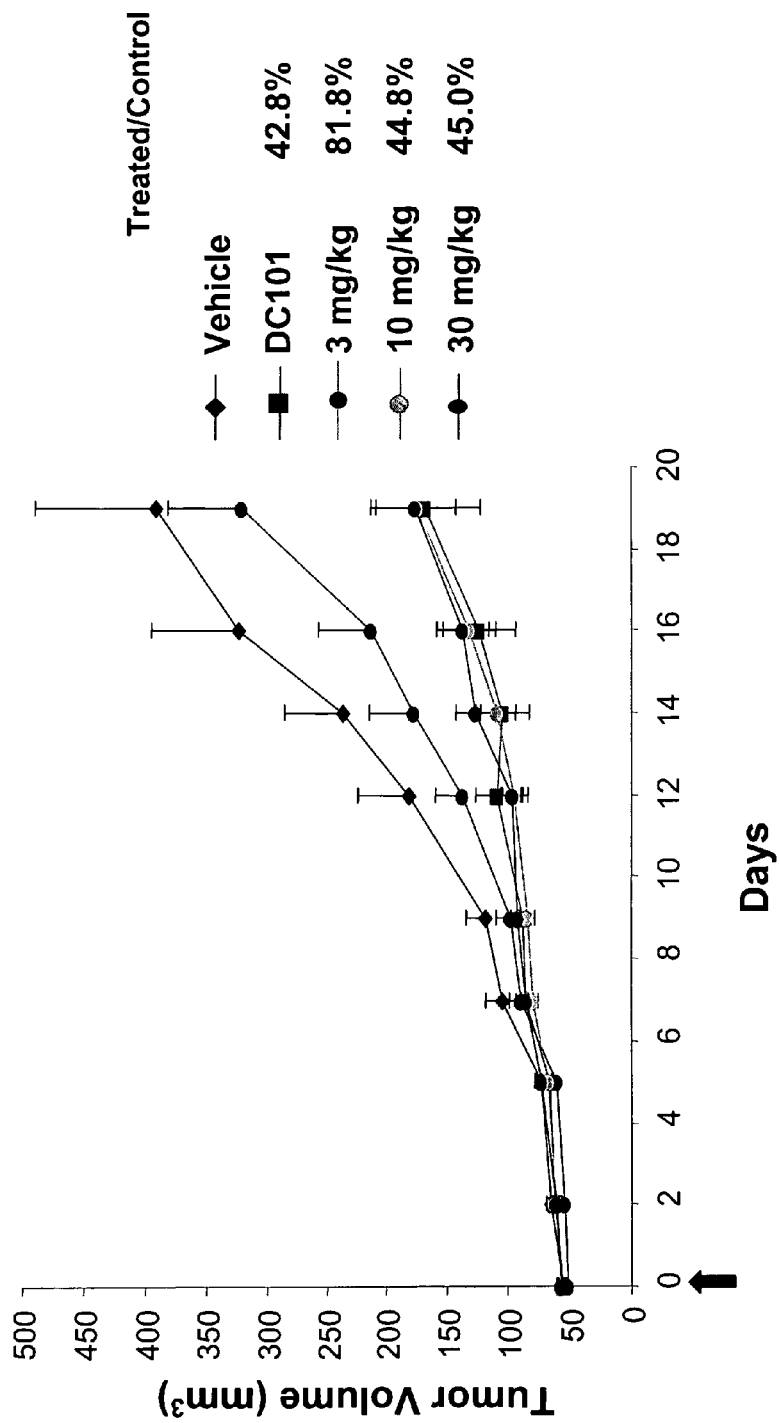

VL-KDR selection

PR7 VLE/KDR sequences

| SEQ ID NO: | | |
|---|---|---|
| 241 | A1-1 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 242 | C1-3 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YLDHWGQGTKVEIKADGSDYKDDDDKASA |
| 243 | H1-8 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YLDHWGQGTKVEIKADGSDYKDDDDKASA |
| 244 | F1-6 | EIVMTQSPGTLSLSPGERATLSCRASQS-VSSNS----VAWYRKKPGQAPRLLIYGASSRATGIPDRFSGSGSGTDFTLTISRLEPEDFAAYYCATIVAGDH-YFDHWGQGTKVEIIADGSDYKDDDDKASA |
| 245 | G1-7 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 246 | H4-32 | EIVMTQSPGTLSLSPGERATLSCRASQS-VSSNS----VAWYRKKPGQAPRLLIYGASSRAAGIPDRFSGSGSGTDFTLTISRLEPEDFAVYYCATIVAGDH-YFDHWGQGTKVEIKADGSDYKDDDDKASA |
| 247 | E2-13 | EIVLTQSPGTLSLSPGERATLSCRASQS-VGSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 248 | B2-10 | AIQMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 249 | H3-24 | AIQMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 250 | F4-30 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 251 | F2-14 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 252 | B3-18 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 253 | A2-9 | EIVMTQSPGTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 254 | C2-11 | EIVMTQSPGTLSLSPGERATLSCRTSQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 255 | D1-4 | EIVMTQSPDTLSLSPGERATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 256 | A4-25 | EIVMTQSPATLSVSPGGRATLSCRASQS-VSSNS----VAWYRKKPGQAPRLLIYGASSRATGIPDRFSGSGSGTDFTLTISRLEPEDFAVYYCATIVAGDH-YFDHWGQGTKVEIKADGSDYKDDDDKASA |
| 257 | B4-26 | EIVMTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 258 | C4-27 | EIVMTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 259 | G4-31 | EIVMTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 260 | H2-16 | EIVMTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 261 | E4-29 | EIVMTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIIADGSDYKDDDDKASA |
| 262 | F3-22 | EIVMTQSPGTLSLSPGDRATLSCRTSQS-VSSSS----LAWYQQKPGQAPRLLIYGASSRATGIPDRFSGSGPGTDFTLTVSRLEPEDFAVYYCAKLTYYG--SGRNWGQGTKVEIKADGSDYKDDDDKASA |
| 263 | G3-23 | EIVMTQSPGTLSVSPGGRASLPCRASQT-VTNNY----LAWYQQKSGQAPRLLIFGASNRATGIPERFSGSGSGTDFTLIISRLEAEDFAVYYCVSLKGRD------WGQGTKLEIKADGSDYKDDDDKASA |
| 264 | D3-20 | EIGMTQSPATLSVSPGKRATLSCRASQS-VGIK-----LAGYQQKLGQAPRLLIYEASTRATGVPTRFNGSGSGTEFTLTINSLQSEDFAVYYCTGGTGNYYGWFDPWGQGTKLEIKAYGSDYEDDDXASA |
| 265 | E1-5 | EIVLTQSPDFQSVTPKKKVTITCRASQS-IVTS-----LHWYQQKPGQAPSLLIYGASNRATGIPARFSGCGSGTEFTLTISGLQPEDAAVYYCAGDFGGQ--LPYWGQGTKLEIKADGSDYKDDDDKASA |
| 266 | A3-17 | QPVLTQ-PASVSGSPGQSITISCTGTSSDVGGYN---YVFWYQQHPGKAPKVMIYEDTERPSGVSNRFSGSKSGNTASLTISGLQAEDEAVYYCARRNYGSGSWIDYWGQGTKLTVLADGSDYKDDDDKASA |
| 267 | D4-28 | AIQMTQSPGTLSLSPGERATLSCRASQS-VRTK-----LAWYQQKPGQSPRLLIYDASTRATGVPARFSGSGSGTEFTLTISSLQSEDFAVYYCTGGTGNYYGWFDPWGQGTKVRSKQMAATTRTTTTRHPL |
| 268 | C3-19 | QSVLTQ-PPSVSGAPGQRVTISCTGSSSNIGAGY---DVHWYQQLPGTAPKLLIYGNSNRPSGVPDRFSGSKSGTSASLAITGLQAEDEAVYYCAS-AIPGTRILRDWGQGTKLTVLADGSDYRTTTTRHPL |
| 269 | E3-21 | EIVMTQSPATLSLSPGERATLSCRASQS-VSSN-----LAWYQQRPGQAPRLLIYGASIRATGIPDRFSGSESGTDFTLTISRLEPEDFAVYYCATEFRG---YAGYWGQGTKLEIKADGSDYKDDDDKASA |

PR8 VLE/KDR 5 nm pool sequences

| | | |
|---|---|---|
| 270 | A5-33 | EIVMTQSPGTLSLSPGRRATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 271 | C5-35 | GIVLTQSPGTLSLSPGERATLSCRASQS-VSSSS----LAWYRQKPGQAPRLLIYGASNRATGIPDRFSGSGSGTDFTLTISSLQPEDFAVYYCAKLTYYG--SGRNWGQGTKLEIKADGSDYKDDDDKASA |
| 272 | B5-34 | EIVMTQSPGTLSLSPGERATLSCRASQS-ISSSS----LAWYRQKPGQAPRLLIYGASTRATGIPDRFSGSGSGTDFSLTISSLQPEDAAVYYCAKLTYYG--SGRNWGQGTKLEIKADGSDYKDDDDKASA |

SEQUENCE LISTING

<160> NUMBER OF SEQ ID NOS: 528

<210> SEQ ID NO 1
<211> LENGTH: 11
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 1
<223> OTHER INFORMATION: Xaa = Leu or Met
<220> FEATURE:
<221> NAME/KEY: VARIANT
<222> LOCATION: 5
<223> OTHER INFORMATION: Xaa = Gly or Asp
<220> FEATURE:
<221> NAME/KEY: VARIANT
<222> LOCATION: 6
<223> OTHER INFORMATION: Xaa = His or Arg
<220> FEATURE:
<221> NAME/KEY: VARIANT
<222> LOCATION: 9
<223> OTHER INFORMATION: Xaa = Leu or Met

<400> SEQUENCE: 1

Xaa Gly Xaa Asn Xaa Xaa Glu Leu Xaa Thr Pro
 1               5                   10

<210> SEQ ID NO 2
<211> LENGTH: 11
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 1, 7
<223> OTHER INFORMATION: Xaa = Any Amino Acid
<220> FEATURE:
<221> NAME/KEY: VARIANT
<222> LOCATION: 9
<223> OTHER INFORMATION: Xaa = Leu, Met or Asn

<400> SEQUENCE: 2

Xaa Glu Arg Asn Gly Arg Xaa Leu Xaa Thr Pro
 1               5                   10

<210> SEQ ID NO 3
<211> LENGTH: 10
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 3, 5, 7, 8
<223> OTHER INFORMATION: Xaa = Any Amino Acid
<220> FEATURE:
<221> NAME/KEY: VARIANT
<222> LOCATION: 1
<223> OTHER INFORMATION: Xaa = Asp or Glu

<400> SEQUENCE: 3

Xaa Gly Xaa Asn Xaa Arg Xaa Xaa Ile Pro
 1               5                   10

```
<210> SEQ ID NO 4
<211> LENGTH: 10
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 3
<223> OTHER INFORMATION: Xaa = Arg or Pro
<220> FEATURE:
<221> NAME/KEY: VARIANT
<222> LOCATION: 5
<223> OTHER INFORMATION: Xaa = Gly or Glu
<220> FEATURE:
<221> NAME/KEY: VARIANT
<222> LOCATION: 7
<223> OTHER INFORMATION: Xaa = Ser or Leu
<220> FEATURE:
<221> NAME/KEY: VARIANT
<222> LOCATION: 8
<223> OTHER INFORMATION: Xaa = Ser or Phe

<400> SEQUENCE: 4

Xaa Gly Xaa Asn Xaa Arg Xaa Xaa Ile Pro
 1               5                  10

<210> SEQ ID NO 5
<211> LENGTH: 94
<212> TYPE: PRT
<213> ORGANISM: Homo sapiens

<400> SEQUENCE: 5

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Gly Tyr Ala Val Thr Gly Arg Gly Asp
 65                  70                  75                  80

Ser Pro Ala Ser Ser Lys Pro Ile Ser Ile Asn Tyr Arg Thr
                85                  90

<210> SEQ ID NO 6
<211> LENGTH: 86
<212> TYPE: PRT
<213> ORGANISM: Artificial Sequence
<220> FEATURE:
<223> OTHER INFORMATION: binding polypeptide

<400> SEQUENCE: 6

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
```

```
                50                  55                  60
Tyr Ala Val Thr Met Gly Leu Tyr Gly His Glu Leu Leu Thr Pro Ile
 65                  70                  75                  80

Ser Ile Asn Tyr Arg Thr
                85
```

<210> SEQ ID NO 7
<211> LENGTH: 86
<212> TYPE: PRT
<213> ORGANISM: Artificial Sequence
<220> FEATURE:
<223> OTHER INFORMATION: binding polypeptide

<400> SEQUENCE: 7

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Asp Gly Glu Asn Gly Gln Phe Leu Leu Val Pro Ile
 65                  70                  75                  80

Ser Ile Asn Tyr Arg Thr
                85
```

<210> SEQ ID NO 8
<211> LENGTH: 86
<212> TYPE: PRT
<213> ORGANISM: Artificial Sequence
<220> FEATURE:
<223> OTHER INFORMATION: binding polypeptide

<400> SEQUENCE: 8

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Gly Pro Asn Asp Asn Glu Leu Leu Thr Pro Ile
 65                  70                  75                  80

Ser Ile Asn Tyr Arg Thr
                85
```

<210> SEQ ID NO 9
<211> LENGTH: 86
<212> TYPE: PRT
<213> ORGANISM: Artificial Sequence
<220> FEATURE:
<223> OTHER INFORMATION: binding polypeptide

<400> SEQUENCE: 9

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30
```

```
Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Ala Gly Trp Asp Asp His Glu Leu Phe Ile Pro Ile
 65                  70                  75                  80

Ser Ile Asn Tyr Arg Thr
                85

<210> SEQ ID NO 10
<211> LENGTH: 86
<212> TYPE: PRT
<213> ORGANISM: Artificial Sequence
<220> FEATURE:
<223> OTHER INFORMATION: binding polypeptide

<400> SEQUENCE: 10

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Ser Gly His Asn Asp His Met Leu Met Ile Pro Ile
 65                  70                  75                  80

Ser Ile Asn Tyr Arg Thr
                85

<210> SEQ ID NO 11
<211> LENGTH: 86
<212> TYPE: PRT
<213> ORGANISM: Artificial Sequence
<220> FEATURE:
<223> OTHER INFORMATION: binding polypeptide

<400> SEQUENCE: 11

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Ala Gly Tyr Asn Asp Gln Ile Leu Met Thr Pro Ile
 65                  70                  75                  80

Ser Ile Asn Tyr Arg Thr
                85

<210> SEQ ID NO 12
<211> LENGTH: 86
<212> TYPE: PRT
<213> ORGANISM: Artificial Sequence
<220> FEATURE:
<223> OTHER INFORMATION: binding polypeptide

<400> SEQUENCE: 12
```

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Gly Leu Tyr Gly Lys Glu Leu Leu Ile Pro Ile
65                  70                  75                  80

Ser Ile Asn Tyr Arg Thr
                85
```

<210> SEQ ID NO 13
<211> LENGTH: 86
<212> TYPE: PRT
<213> ORGANISM: Artificial Sequence
<220> FEATURE:
<223> OTHER INFORMATION: binding polypeptide

<400> SEQUENCE: 13

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Thr Gly Pro Asn Asp Arg Leu Leu Phe Val Pro Ile
65                  70                  75                  80

Ser Ile Asn Tyr Arg Thr
                85
```

<210> SEQ ID NO 14
<211> LENGTH: 86
<212> TYPE: PRT
<213> ORGANISM: Artificial Sequence
<220> FEATURE:
<223> OTHER INFORMATION: binding polypeptide

<400> SEQUENCE: 14

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Val Tyr Asn Asp His Glu Ile Lys Thr Pro Ile
65                  70                  75                  80

Ser Ile Asn Tyr Arg Thr
                85
```

<210> SEQ ID NO 15
<211> LENGTH: 86
<212> TYPE: PRT
<213> ORGANISM: Artificial Sequence

```
<220> FEATURE:
<223> OTHER INFORMATION: binding polypeptide

<400> SEQUENCE: 15

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
     50                  55                  60

Tyr Ala Val Thr Asp Gly Lys Asp Gly Arg Val Leu Leu Thr Pro Ile
 65                  70                  75                  80

Ser Ile Asn Tyr Arg Thr
                 85

<210> SEQ ID NO 16
<211> LENGTH: 86
<212> TYPE: PRT
<213> ORGANISM: Artificial Sequence
<220> FEATURE:
<223> OTHER INFORMATION: binding polypeptide

<400> SEQUENCE: 16

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
     50                  55                  60

Tyr Ala Val Thr Glu Val His His Asp Arg Glu Ile Lys Thr Pro Ile
 65                  70                  75                  80

Ser Ile Asn Tyr Arg Thr
                 85

<210> SEQ ID NO 17
<211> LENGTH: 86
<212> TYPE: PRT
<213> ORGANISM: Artificial Sequence
<220> FEATURE:
<223> OTHER INFORMATION: binding polypeptide

<400> SEQUENCE: 17

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
     50                  55                  60

Tyr Ala Val Thr Gln Ala Pro Asn Asp Arg Val Leu Tyr Thr Pro Ile
 65                  70                  75                  80

Ser Ile Asn Tyr Arg Thr
                 85
```

<210> SEQ ID NO 18
<211> LENGTH: 86
<212> TYPE: PRT
<213> ORGANISM: Artificial Sequence
<220> FEATURE:
<223> OTHER INFORMATION: binding polypeptide

<400> SEQUENCE: 18

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Arg Glu Glu Asn Asp His Glu Leu Leu Ile Pro Ile
65                  70                  75                  80

Ser Ile Asn Tyr Arg Thr
                85

<210> SEQ ID NO 19
<211> LENGTH: 86
<212> TYPE: PRT
<213> ORGANISM: Artificial Sequence
<220> FEATURE:
<223> OTHER INFORMATION: binding polypeptide

<400> SEQUENCE: 19

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Thr His Asn Gly His Pro Leu Met Thr Pro Ile
65                  70                  75                  80

Ser Ile Asn Tyr Arg Thr
                85

<210> SEQ ID NO 20
<211> LENGTH: 86
<212> TYPE: PRT
<213> ORGANISM: Artificial Sequence
<220> FEATURE:
<223> OTHER INFORMATION: binding polypeptide

<400> SEQUENCE: 20

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Leu Lys Gly His Glu Leu Leu Thr Pro Ile

```
                65                  70                  75                  80
Ser Ile Asn Tyr Arg Thr
                85
```

```
<210> SEQ ID NO 21
<211> LENGTH: 94
<212> TYPE: PRT
<213> ORGANISM: Artificial Sequence
<220> FEATURE:
<223> OTHER INFORMATION: binding polypeptide

<400> SEQUENCE: 21

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Val Ala Gln Asn
65                  70                  75                  80

Asp His Glu Leu Ile Thr Pro Ile Ser Ile Asn Tyr Arg Thr
                85                  90
```

```
<210> SEQ ID NO 22
<211> LENGTH: 95
<212> TYPE: PRT
<213> ORGANISM: Artificial Sequence
<220> FEATURE:
<223> OTHER INFORMATION: binding polypeptide

<400> SEQUENCE: 22

Val Ser Asp Val Pro Arg Asp Leu Gln Glu Val Val Ala Ala Thr Pro
1               5                   10                  15

Thr Ser Leu Leu Ile Ser Trp Arg His Pro His Phe Pro Thr Arg Tyr
                20                  25                  30

Tyr Arg Ile Thr Tyr Gly Glu Thr Gly Gly Asn Ser Pro Val Gln Glu
            35                  40                  45

Phe Thr Val Pro Leu Gln Pro Pro Ala Ala Thr Ile Ser Gly Leu Lys
        50                  55                  60

Pro Gly Val Asp Tyr Thr Ile Thr Gly Tyr Ala Val Thr Met Ala Gln
65                  70                  75                  80

Ser Gly His Glu Leu Phe Thr Pro Ile Ser Ile Asn Tyr Arg Thr
                85                  90                  95
```

```
<210> SEQ ID NO 23
<211> LENGTH: 86
<212> TYPE: PRT
<213> ORGANISM: Artificial Sequence
<220> FEATURE:
<223> OTHER INFORMATION: binding polypeptide

<400> SEQUENCE: 23

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45
```

```
Ala Thr Ile Ser Gly Leu Lys Pro Gly Val Asp Tyr Thr Ile Thr Gly
        50                  55                  60

Tyr Ala Val Thr Val Glu Arg Asn Gly Arg Lys Leu Met Thr Pro Ile
65                  70                  75                  80

Ser Ile Asn Tyr Arg Thr
                85

<210> SEQ ID NO 24
<211> LENGTH: 86
<212> TYPE: PRT
<213> ORGANISM: Artificial Sequence
<220> FEATURE:
<223> OTHER INFORMATION: binding polypeptide

<400> SEQUENCE: 24

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Val Leu Met Thr Pro Ile
65                  70                  75                  80

Ser Ile Asn Tyr Arg Thr
                85

<210> SEQ ID NO 25
<211> LENGTH: 86
<212> TYPE: PRT
<213> ORGANISM: Artificial Sequence
<220> FEATURE:
<223> OTHER INFORMATION: binding polypeptide

<400> SEQUENCE: 25

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg His Leu Met Thr Pro Ile
65                  70                  75                  80

Ser Ile Asn Tyr Arg Thr
                85

<210> SEQ ID NO 26
<211> LENGTH: 86
<212> TYPE: PRT
<213> ORGANISM: Artificial Sequence
<220> FEATURE:
<223> OTHER INFORMATION: binding polypeptide

<400> SEQUENCE: 26

Glu Val Val Ala Ala Thr Pro Thr Ser Leu Leu Ile Ser Trp Arg His
1               5                   10                  15
```

-continued

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
            50                  55                  60

Tyr Ala Val Thr Val Glu Arg Asn Gly Arg Met Leu Met Thr Pro Ile
65                  70                  75                  80

Ser Ile Asn Tyr Arg Thr
                85

<210> SEQ ID NO 27
<211> LENGTH: 86
<212> TYPE: PRT
<213> ORGANISM: Artificial Sequence
<220> FEATURE:
<223> OTHER INFORMATION: binding polypeptide

<400> SEQUENCE: 27

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
            50                  55                  60

Tyr Ala Val Thr Leu Glu Arg Asn Gly Arg Val Leu Met Thr Pro Ile
65                  70                  75                  80

Ser Ile Asn Tyr Arg Thr
                85

<210> SEQ ID NO 28
<211> LENGTH: 86
<212> TYPE: PRT
<213> ORGANISM: Artificial Sequence
<220> FEATURE:
<223> OTHER INFORMATION: binding polypeptide

<400> SEQUENCE: 28

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
            50                  55                  60

Tyr Ala Val Thr Leu Glu Arg Asn Gly Arg Val Leu Asn Thr Pro Ile
65                  70                  75                  80

Ser Ile Asn Tyr Arg Thr
                85

<210> SEQ ID NO 29
<211> LENGTH: 86
<212> TYPE: PRT
<213> ORGANISM: Artificial Sequence
<220> FEATURE:
<223> OTHER INFORMATION: binding polypeptide

```
<400> SEQUENCE: 29

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Gln Leu Met Thr Pro Ile
65                  70                  75                  80

Ser Ile Asn Tyr Arg Thr
                85

<210> SEQ ID NO 30
<211> LENGTH: 86
<212> TYPE: PRT
<213> ORGANISM: Artificial Sequence
<220> FEATURE:
<223> OTHER INFORMATION: binding polypeptide

<400> SEQUENCE: 30

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Thr Leu Phe Thr Pro Ile
65                  70                  75                  80

Ser Ile Asn Tyr Arg Thr
                85

<210> SEQ ID NO 31
<211> LENGTH: 86
<212> TYPE: PRT
<213> ORGANISM: Artificial Sequence
<220> FEATURE:
<223> OTHER INFORMATION: binding polypeptide

<400> SEQUENCE: 31

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Glu Leu Met Thr Pro Ile
65                  70                  75                  80

Ser Ile Asn Tyr Arg Thr
                85

<210> SEQ ID NO 32
<211> LENGTH: 86
```

```
<212> TYPE: PRT
<213> ORGANISM: Artificial Sequence
<220> FEATURE:
<223> OTHER INFORMATION: binding polypeptide

<400> SEQUENCE: 32

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Leu Asn Thr Pro Ile
65                  70                  75                  80

Ser Ile Asn Tyr Arg Thr
                85

<210> SEQ ID NO 33
<211> LENGTH: 86
<212> TYPE: PRT
<213> ORGANISM: Artificial Sequence
<220> FEATURE:
<223> OTHER INFORMATION: binding polypeptide

<400> SEQUENCE: 33

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr His Glu Arg Asn Gly Arg Val Leu Met Thr Pro Ile
65                  70                  75                  80

Ser Ile Asn Tyr Arg Thr
                85

<210> SEQ ID NO 34
<211> LENGTH: 86
<212> TYPE: PRT
<213> ORGANISM: Artificial Sequence
<220> FEATURE:
<223> OTHER INFORMATION: binding polypeptide

<400> SEQUENCE: 34

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Glu Glu Arg Asn Gly Arg Val Leu Phe Thr Pro Ile
65                  70                  75                  80

Ser Ile Asn Tyr Arg Thr
```

<210> SEQ ID NO 35
<211> LENGTH: 86
<212> TYPE: PRT
<213> ORGANISM: Artificial Sequence
<220> FEATURE:
<223> OTHER INFORMATION: binding polypeptide

<400> SEQUENCE: 35

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Gln Leu Tyr Thr Pro Ile
65                  70                  75                  80

Ser Ile Asn Tyr Arg Thr
                85

<210> SEQ ID NO 36
<211> LENGTH: 86
<212> TYPE: PRT
<213> ORGANISM: Artificial Sequence
<220> FEATURE:
<223> OTHER INFORMATION: binding polypeptide

<400> SEQUENCE: 36

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Ala Leu Met Thr Pro Ile
65                  70                  75                  80

Ser Ile Asn Tyr Arg Thr
                85

<210> SEQ ID NO 37
<211> LENGTH: 86
<212> TYPE: PRT
<213> ORGANISM: Artificial Sequence
<220> FEATURE:
<223> OTHER INFORMATION: binding polypeptide

<400> SEQUENCE: 37

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Asn Leu Met Thr Pro Ile
65                  70                  75                  80

Ser Ile Asn Tyr Arg Thr
                85

<210> SEQ ID NO 38
<211> LENGTH: 86
<212> TYPE: PRT
<213> ORGANISM: Artificial Sequence
<220> FEATURE:
<223> OTHER INFORMATION: binding polypeptide

<400> SEQUENCE: 38

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Glu Arg Asn Gly Arg Val Leu Ile Thr Pro Ile
65                  70                  75                  80

Ser Ile Asn Tyr Arg Thr
                85

<210> SEQ ID NO 39
<211> LENGTH: 86
<212> TYPE: PRT
<213> ORGANISM: Artificial Sequence
<220> FEATURE:
<223> OTHER INFORMATION: binding polypeptide

<400> SEQUENCE: 39

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Val Leu Asn Thr Pro Ile
65                  70                  75                  80

Ser Ile Asn Tyr Arg Thr
                85

<210> SEQ ID NO 40
<211> LENGTH: 86
<212> TYPE: PRT
<213> ORGANISM: Artificial Sequence
<220> FEATURE:
<223> OTHER INFORMATION: binding polypeptide

<400> SEQUENCE: 40

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

```
Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Lys Val Leu Met Thr Pro Ile
 65                  70                  75                  80

Ser Ile Asn Tyr Arg Thr
                85

<210> SEQ ID NO 41
<211> LENGTH: 86
<212> TYPE: PRT
<213> ORGANISM: Artificial Sequence
<220> FEATURE:
<223> OTHER INFORMATION: binding polypeptide

<400> SEQUENCE: 41

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Thr Leu Met Met Pro Ile
 65                  70                  75                  80

Ser Ile Asn Tyr Arg Thr
                85

<210> SEQ ID NO 42
<211> LENGTH: 86
<212> TYPE: PRT
<213> ORGANISM: Artificial Sequence
<220> FEATURE:
<223> OTHER INFORMATION: binding polypeptide

<400> SEQUENCE: 42

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Glu Arg Asn Gly Arg Glu Leu Met Thr Pro Ile
 65                  70                  75                  80

Ser Ile Asn Tyr Arg Thr
                85

<210> SEQ ID NO 43
<211> LENGTH: 86
<212> TYPE: PRT
<213> ORGANISM: Artificial Sequence
<220> FEATURE:
<223> OTHER INFORMATION: binding polypeptide

<400> SEQUENCE: 43

Glu Val Val Ala Ala Thr Pro Thr Ser Leu Leu Ile Ser Trp Arg His
```

```
                 1               5                  10                 15
Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
            50                 55                 60

Tyr Ala Val Thr Glu Glu Arg Asn Gly Arg Thr Leu Arg Thr Pro Ile
 65                 70                 75                 80

Ser Ile Asn Tyr Arg Thr
                85
```

<210> SEQ ID NO 44
<211> LENGTH: 86
<212> TYPE: PRT
<213> ORGANISM: Artificial Sequence
<220> FEATURE:
<223> OTHER INFORMATION: binding polypeptide

<400> SEQUENCE: 44

```
Glu Val Val Ala Ala Thr Pro Thr Ser Leu Leu Ile Ser Trp Arg His
 1               5                  10                 15

Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
            50                 55                 60

Tyr Ala Val Thr Val Glu Arg Asn Gly Lys Thr Leu Met Thr Pro Ile
 65                 70                 75                 80

Ser Ile Asn Tyr Arg Thr
                85
```

<210> SEQ ID NO 45
<211> LENGTH: 86
<212> TYPE: PRT
<213> ORGANISM: Artificial Sequence
<220> FEATURE:
<223> OTHER INFORMATION: binding polypeptide

<400> SEQUENCE: 45

```
Glu Val Val Ala Ala Thr Pro Thr Ser Leu Leu Ile Ser Trp Arg His
 1               5                  10                 15

Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
            50                 55                 60

Tyr Ala Val Thr Leu Glu Arg Asn Asp Arg Val Leu Leu Thr Pro Ile
 65                 70                 75                 80

Ser Ile Asn Tyr Arg Thr
                85
```

<210> SEQ ID NO 46
<211> LENGTH: 86
<212> TYPE: PRT
<213> ORGANISM: Artificial Sequence
<220> FEATURE:

-continued

<223> OTHER INFORMATION: binding polypeptide

<400> SEQUENCE: 46

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Lys Leu Met Thr Pro Ile
65                  70                  75                  80

Ser Ile Asn Tyr Arg Thr
                85

<210> SEQ ID NO 47
<211> LENGTH: 86
<212> TYPE: PRT
<213> ORGANISM: Artificial Sequence
<220> FEATURE:
<223> OTHER INFORMATION: binding polypeptide

<400> SEQUENCE: 47

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Pro Asn Gly Arg Val Leu Asn Thr Pro Ile
65                  70                  75                  80

Ser Ile Asn Tyr Arg Thr
                85

<210> SEQ ID NO 48
<211> LENGTH: 86
<212> TYPE: PRT
<213> ORGANISM: Artificial Sequence
<220> FEATURE:
<223> OTHER INFORMATION: binding polypeptide

<400> SEQUENCE: 48

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Asp Arg Val Leu Phe Thr Pro Ile
65                  70                  75                  80

Ser Ile Asn Tyr Arg Thr
                85

```
<210> SEQ ID NO 49
<211> LENGTH: 86
<212> TYPE: PRT
<213> ORGANISM: Artificial Sequence
<220> FEATURE:
<223> OTHER INFORMATION: binding polypeptide

<400> SEQUENCE: 49

Glu Val Val Ala Ala Thr Pro Thr Ser Leu Leu Ile Ser Trp Arg His
 1               5                   10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Val Glu Arg Asn Gly Arg Glu Leu Lys Thr Pro Ile
 65                  70                  75                  80

Ser Ile Asn Tyr Arg Thr
                 85

<210> SEQ ID NO 50
<211> LENGTH: 86
<212> TYPE: PRT
<213> ORGANISM: Artificial Sequence
<220> FEATURE:
<223> OTHER INFORMATION: binding polypeptide

<400> SEQUENCE: 50

Glu Val Val Ala Ala Thr Pro Thr Ser Leu Leu Ile Ser Trp Arg His
 1               5                   10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Val Glu Arg Asn Gly Arg Glu Leu Arg Thr Pro Ile
 65                  70                  75                  80

Ser Ile Asn Tyr Arg Thr
                 85

<210> SEQ ID NO 51
<211> LENGTH: 86
<212> TYPE: PRT
<213> ORGANISM: Artificial Sequence
<220> FEATURE:
<223> OTHER INFORMATION: binding polypeptide

<400> SEQUENCE: 51

Glu Val Val Ala Ala Thr Pro Thr Ser Leu Leu Ile Ser Trp Arg His
 1               5                   10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Gln Glu Arg Asn Gly Arg Glu Leu Met Thr Pro Ile
 65                  70                  75                  80
```

```
Ser Ile Asn Tyr Arg Thr
                85

<210> SEQ ID NO 52
<211> LENGTH: 86
<212> TYPE: PRT
<213> ORGANISM: Artificial Sequence
<220> FEATURE:
<223> OTHER INFORMATION: binding polypeptide

<400> SEQUENCE: 52

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Val Glu Arg Asn Gly Arg Glu Leu Met Thr Pro Ile
 65                  70                  75                  80

Ser Ile Asn Tyr Arg Thr
                85

<210> SEQ ID NO 53
<211> LENGTH: 86
<212> TYPE: PRT
<213> ORGANISM: Artificial Sequence
<220> FEATURE:
<223> OTHER INFORMATION: binding polypeptide

<400> SEQUENCE: 53

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Val Glu Arg Asn Gly Arg Val Leu Ser Val Pro Ile
 65                  70                  75                  80

Ser Ile Asn Tyr Arg Thr
                85

<210> SEQ ID NO 54
<211> LENGTH: 86
<212> TYPE: PRT
<213> ORGANISM: Artificial Sequence
<220> FEATURE:
<223> OTHER INFORMATION: binding polypeptide

<400> SEQUENCE: 54

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45
```

```
Ala Thr Ile Ser Gly Leu Lys Pro Gly Val Asp Tyr Thr Ile Thr Gly
        50                  55                  60

Tyr Ala Val Thr Val Glu Arg Asp Gly Arg Thr Leu Arg Thr Pro Ile
65                  70                  75                  80

Ser Ile Asn Tyr Arg Thr
                85

<210> SEQ ID NO 55
<211> LENGTH: 86
<212> TYPE: PRT
<213> ORGANISM: Artificial Sequence
<220> FEATURE:
<223> OTHER INFORMATION: binding polypeptide

<400> SEQUENCE: 55

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Glu Leu Asn Thr Pro Ile
65                  70                  75                  80

Ser Ile Asn Tyr Arg Thr
                85

<210> SEQ ID NO 56
<211> LENGTH: 86
<212> TYPE: PRT
<213> ORGANISM: Artificial Sequence
<220> FEATURE:
<223> OTHER INFORMATION: binding polypeptide

<400> SEQUENCE: 56

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Val Leu Ile Val Pro Ile
65                  70                  75                  80

Ser Ile Asn Tyr Arg Thr
                85

<210> SEQ ID NO 57
<211> LENGTH: 86
<212> TYPE: PRT
<213> ORGANISM: Artificial Sequence
<220> FEATURE:
<223> OTHER INFORMATION: binding polypeptide

<400> SEQUENCE: 57

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
```

-continued

```
                    20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
            50                  55                  60

Tyr Ala Val Thr Leu Glu Arg Asn Gly Arg Glu Leu Met Val Pro Ile
65                  70                  75                  80

Ser Ile Asn Tyr Arg Thr
                85

<210> SEQ ID NO 58
<211> LENGTH: 86
<212> TYPE: PRT
<213> ORGANISM: Artificial Sequence
<220> FEATURE:
<223> OTHER INFORMATION: binding polypeptide

<400> SEQUENCE: 58

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
            50                  55                  60

Tyr Ala Val Thr Asp Gly Arg Asn Asp Arg Lys Leu Met Val Pro Ile
65                  70                  75                  80

Ser Ile Asn Tyr Arg Thr
                85

<210> SEQ ID NO 59
<211> LENGTH: 86
<212> TYPE: PRT
<213> ORGANISM: Artificial Sequence
<220> FEATURE:
<223> OTHER INFORMATION: binding polypeptide

<400> SEQUENCE: 59

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
            50                  55                  60

Tyr Ala Val Thr Val Glu His Asn Gly Arg Thr Ser Phe Thr Pro Ile
65                  70                  75                  80

Ser Ile Asn Tyr Arg Thr
                85

<210> SEQ ID NO 60
<211> LENGTH: 86
<212> TYPE: PRT
<213> ORGANISM: Artificial Sequence
<220> FEATURE:
<223> OTHER INFORMATION: binding polypeptide

<400> SEQUENCE: 60
```

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asp Gly Arg Lys Leu Tyr Thr Pro Ile
65                  70                  75                  80

Ser Ile Asn Tyr Arg Thr
                85
```

<210> SEQ ID NO 61
<211> LENGTH: 86
<212> TYPE: PRT
<213> ORGANISM: Artificial Sequence
<220> FEATURE:
<223> OTHER INFORMATION: binding polypeptide

<400> SEQUENCE: 61

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Glu Arg Asn Gly Arg Glu Leu Asn Thr Pro Ile
65                  70                  75                  80

Ser Ile Asn Tyr Arg Thr
                85
```

<210> SEQ ID NO 62
<211> LENGTH: 86
<212> TYPE: PRT
<213> ORGANISM: Artificial Sequence
<220> FEATURE:
<223> OTHER INFORMATION: binding polypeptide

<400> SEQUENCE: 62

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Asp Gly Trp Asn Gly Arg Leu Leu Ser Ile Pro Ile
65                  70                  75                  80

Ser Ile Asn Tyr Arg Thr
                85
```

<210> SEQ ID NO 63
<211> LENGTH: 86
<212> TYPE: PRT

```
<213> ORGANISM: Artificial Sequence
<220> FEATURE:
<223> OTHER INFORMATION: binding polypeptide

<400> SEQUENCE: 63

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Asp Gly Gln Asn Gly Arg Leu Leu Asn Val Pro Ile
65                  70                  75                  80

Ser Ile Asn Tyr Arg Thr
                85

<210> SEQ ID NO 64
<211> LENGTH: 86
<212> TYPE: PRT
<213> ORGANISM: Artificial Sequence
<220> FEATURE:
<223> OTHER INFORMATION: binding polypeptide

<400> SEQUENCE: 64

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Ile Glu Lys Asn Gly Arg His Leu Asn Ile Pro Ile
65                  70                  75                  80

Ser Ile Asn Tyr Arg Thr
                85

<210> SEQ ID NO 65
<211> LENGTH: 86
<212> TYPE: PRT
<213> ORGANISM: Artificial Sequence
<220> FEATURE:
<223> OTHER INFORMATION: binding polypeptide

<400> SEQUENCE: 65

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Asp Gly Trp Asn Gly Lys Met Leu Ser Val Pro Ile
65                  70                  75                  80

Ser Ile Asn Tyr Arg Thr
                85
```

<210> SEQ ID NO 66
<211> LENGTH: 86
<212> TYPE: PRT
<213> ORGANISM: Artificial Sequence
<220> FEATURE:
<223> OTHER INFORMATION: binding polypeptide

<400> SEQUENCE: 66

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Tyr Asn Asp Arg Leu Leu Phe Ile Pro Ile
65                  70                  75                  80

Ser Ile Asn Tyr Arg Thr
                85

<210> SEQ ID NO 67
<211> LENGTH: 86
<212> TYPE: PRT
<213> ORGANISM: Artificial Sequence
<220> FEATURE:
<223> OTHER INFORMATION: binding polypeptide

<400> SEQUENCE: 67

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Pro Asn Asp Arg Leu Leu Asn Ile Pro Ile
65                  70                  75                  80

Ser Ile Asn Tyr Arg Thr
                85

<210> SEQ ID NO 68
<211> LENGTH: 86
<212> TYPE: PRT
<213> ORGANISM: Artificial Sequence
<220> FEATURE:
<223> OTHER INFORMATION: binding polypeptide

<400> SEQUENCE: 68

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Pro Asn Asn Arg Glu Leu Ile Val Pro Ile
65                  70                  75                  80

Ser Ile Asn Tyr Arg Thr
                85

<210> SEQ ID NO 69
<211> LENGTH: 86
<212> TYPE: PRT
<213> ORGANISM: Artificial Sequence
<220> FEATURE:
<223> OTHER INFORMATION: binding polypeptide

<400> SEQUENCE: 69

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Asp Gly Leu Asn Gly Lys Tyr Leu Phe Val Pro Ile
65                  70                  75                  80

Ser Ile Asn Tyr Arg Thr
                85

<210> SEQ ID NO 70
<211> LENGTH: 86
<212> TYPE: PRT
<213> ORGANISM: Artificial Sequence
<220> FEATURE:
<223> OTHER INFORMATION: binding polypeptide

<400> SEQUENCE: 70

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Glu Gly Trp Asn Asp Arg Glu Leu Phe Val Pro Ile
65                  70                  75                  80

Ser Ile Asn Tyr Arg Thr
                85

<210> SEQ ID NO 71
<211> LENGTH: 86
<212> TYPE: PRT
<213> ORGANISM: Artificial Sequence
<220> FEATURE:
<223> OTHER INFORMATION: binding polypeptide

<400> SEQUENCE: 71

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr 35                  40                  45

Ala Thr Ile Ser Gly Leu Lys Pro Gly Val Asp Tyr Thr Ile Thr Gly
         50                  55                  60

Tyr Ala Val Thr Phe Gly Trp Asn Gly Arg Glu Leu Leu Thr Pro Ile
 65                  70                  75                  80

Ser Ile Asn Tyr Arg Thr
                 85

<210> SEQ ID NO 72
<211> LENGTH: 86
<212> TYPE: PRT
<213> ORGANISM: Artificial Sequence
<220> FEATURE:
<223> OTHER INFORMATION: binding polypeptide

<400> SEQUENCE: 72

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
         50                  55                  60

Tyr Ala Val Thr Phe Gly Trp Asn Asp Arg Glu Leu Leu Ile Pro Ile
 65                  70                  75                  80

Ser Ile Asn Tyr Arg Thr
                 85

<210> SEQ ID NO 73
<211> LENGTH: 86
<212> TYPE: PRT
<213> ORGANISM: Artificial Sequence
<220> FEATURE:
<223> OTHER INFORMATION: binding polypeptide

<400> SEQUENCE: 73

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
         50                  55                  60

Tyr Ala Val Thr Leu Glu Trp Asn Asn Arg Val Leu Met Thr Pro Ile
 65                  70                  75                  80

Ser Ile Asn Tyr Arg Thr
                 85

<210> SEQ ID NO 74
<211> LENGTH: 86
<212> TYPE: PRT
<213> ORGANISM: Artificial Sequence
<220> FEATURE:
<223> OTHER INFORMATION: binding polypeptide

<400> SEQUENCE: 74

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Trp Asn Gly Arg Val Leu Met Thr Pro Ile
65                  70                  75                  80

Ser Ile Asn Tyr Arg Thr
                85

<210> SEQ ID NO 75
<211> LENGTH: 86
<212> TYPE: PRT
<213> ORGANISM: Artificial Sequence
<220> FEATURE:
<223> OTHER INFORMATION: binding polypeptide

<400> SEQUENCE: 75

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asn Glu Arg Asn Gly Arg Glu Leu Met Thr Pro Ile
65                  70                  75                  80

Ser Ile Asn Tyr Arg Thr
                85

<210> SEQ ID NO 76
<211> LENGTH: 86
<212> TYPE: PRT
<213> ORGANISM: Artificial Sequence
<220> FEATURE:
<223> OTHER INFORMATION: binding polypeptide

<400> SEQUENCE: 76

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Lys Glu Leu Met Thr Pro Ile
65                  70                  75                  80

Ser Ile Asn Tyr Arg Thr
                85

<210> SEQ ID NO 77
<211> LENGTH: 86
<212> TYPE: PRT
<213> ORGANISM: Artificial Sequence
<220> FEATURE:
<223> OTHER INFORMATION: binding polypeptide

```
<400> SEQUENCE: 77

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Glu Leu Leu Thr Pro Ile
65                  70                  75                  80

Ser Ile Asn Tyr Arg Thr
                85

<210> SEQ ID NO 78
<211> LENGTH: 86
<212> TYPE: PRT
<213> ORGANISM: Artificial Sequence
<220> FEATURE:
<223> OTHER INFORMATION: binding polypeptide

<400> SEQUENCE: 78

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Glu Leu Lys Thr Pro Ile
65                  70                  75                  80

Ser Ile Asn Tyr Arg Thr
                85

<210> SEQ ID NO 79
<211> LENGTH: 86
<212> TYPE: PRT
<213> ORGANISM: Artificial Sequence
<220> FEATURE:
<223> OTHER INFORMATION: binding polypeptide

<400> SEQUENCE: 79

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Gln Glu Arg Asn Gly Arg Glu Leu Arg Thr Pro Ile
65                  70                  75                  80

Ser Ile Asn Tyr Arg Thr
                85

<210> SEQ ID NO 80
```

<211> LENGTH: 86
<212> TYPE: PRT
<213> ORGANISM: Artificial Sequence
<220> FEATURE:
<223> OTHER INFORMATION: binding polypeptide

<400> SEQUENCE: 80

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Glu Leu Leu Trp Pro Ile
65                  70                  75                  80

Ser Ile Asn Tyr Arg Thr
                85

<210> SEQ ID NO 81
<211> LENGTH: 86
<212> TYPE: PRT
<213> ORGANISM: Artificial Sequence
<220> FEATURE:
<223> OTHER INFORMATION: binding polypeptide

<400> SEQUENCE: 81

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Glu Leu Met Ile Pro Ile
65                  70                  75                  80

Ser Ile Asn Tyr Arg Thr
                85

<210> SEQ ID NO 82
<211> LENGTH: 86
<212> TYPE: PRT
<213> ORGANISM: Artificial Sequence
<220> FEATURE:
<223> OTHER INFORMATION: binding polypeptide

<400> SEQUENCE: 82

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Leu Val Leu Met Thr Pro Ile
65                  70                  75                  80

Ser Ile Asn Tyr Arg Thr
              85

<210> SEQ ID NO 83
<211> LENGTH: 86
<212> TYPE: PRT
<213> ORGANISM: Artificial Sequence
<220> FEATURE:
<223> OTHER INFORMATION: binding polypeptide

<400> SEQUENCE: 83

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Val Leu Ile Ile Pro Ile
65                  70                  75                  80

Ser Ile Asn Tyr Arg Thr
              85

<210> SEQ ID NO 84
<211> LENGTH: 86
<212> TYPE: PRT
<213> ORGANISM: Artificial Sequence
<220> FEATURE:
<223> OTHER INFORMATION: binding polypeptide

<400> SEQUENCE: 84

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly His Lys Leu Phe Thr Pro Ile
65                  70                  75                  80

Ser Ile Asn Tyr Arg Thr
              85

<210> SEQ ID NO 85
<211> LENGTH: 86
<212> TYPE: PRT
<213> ORGANISM: Artificial Sequence
<220> FEATURE:
<223> OTHER INFORMATION: binding polypeptide

<400> SEQUENCE: 85

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly

```
                    50                  55                  60
Tyr Ala Val Thr Val Glu Arg Asn Glu Arg Val Leu Met Thr Pro Ile
 65                  70                  75                  80

Ser Ile Asn Tyr Arg Thr
                85

<210> SEQ ID NO 86
<211> LENGTH: 86
<212> TYPE: PRT
<213> ORGANISM: Artificial Sequence
<220> FEATURE:
<223> OTHER INFORMATION: binding polypeptide

<400> SEQUENCE: 86

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Phe Gly Pro Asn Asp Arg Glu Leu Leu Thr Pro Ile
 65                  70                  75                  80

Ser Ile Asn Tyr Arg Thr
                85

<210> SEQ ID NO 87
<211> LENGTH: 86
<212> TYPE: PRT
<213> ORGANISM: Artificial Sequence
<220> FEATURE:
<223> OTHER INFORMATION: binding polypeptide

<400> SEQUENCE: 87

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Met Gly Pro Asn Asp Arg Glu Leu Leu Thr Pro Ile
 65                  70                  75                  80

Ser Ile Asn Tyr Arg Thr
                85

<210> SEQ ID NO 88
<211> LENGTH: 86
<212> TYPE: PRT
<213> ORGANISM: Artificial Sequence
<220> FEATURE:
<223> OTHER INFORMATION: binding polypeptide

<400> SEQUENCE: 88

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30
```

```
Gly Asn Ser Pro Val Gln Glu Phe Thr Val Pro Leu Gln Pro Thr
        35                  40                  45

Ala Thr Ile Ser Gly Leu Lys Pro Gly Val Asp Tyr Thr Ile Thr Gly
 50                  55                  60

Tyr Ala Val Thr Met Gly Lys Asn Asp Arg Glu Leu Leu Thr Pro Ile
 65                  70                  75                  80

Ser Ile Asn Tyr Arg Thr
                85

<210> SEQ ID NO 89
<211> LENGTH: 87
<212> TYPE: PRT
<213> ORGANISM: Artificial Sequence
<220> FEATURE:
<223> OTHER INFORMATION: binding polypeptide

<400> SEQUENCE: 89

Glu Val Val Ala Ala Thr Pro Thr Ser Leu Leu Ile Ser Trp Arg His
  1               5                  10                  15

His Pro His Phe Pro Thr Arg Tyr Tyr Arg Ile Thr Tyr Gly Glu Thr
                 20                  25                  30

Gly Gly Asn Ser Pro Val Gln Glu Phe Thr Val Pro Leu Gln Pro Pro
         35                  40                  45

Thr Ala Thr Ile Ser Gly Leu Lys Pro Gly Val Asp Tyr Thr Ile Thr
 50                  55                  60

Gly Tyr Ala Val Thr Val His Trp Asn Gly Arg Glu Leu Met Thr Pro
 65                  70                  75                  80

Ile Ser Ile Asn Tyr Arg Thr
                85

<210> SEQ ID NO 90
<211> LENGTH: 86
<212> TYPE: PRT
<213> ORGANISM: Artificial Sequence
<220> FEATURE:
<223> OTHER INFORMATION: binding polypeptide

<400> SEQUENCE: 90

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
 50                  55                  60

Tyr Ala Val Thr Glu Glu Trp Asn Gly Arg Val Leu Met Thr Pro Ile
 65                  70                  75                  80

Ser Ile Asn Tyr Arg Thr
                85

<210> SEQ ID NO 91
<211> LENGTH: 86
<212> TYPE: PRT
<213> ORGANISM: Artificial Sequence
<220> FEATURE:
<223> OTHER INFORMATION: binding polypeptide

<400> SEQUENCE: 91
```

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
 50                  55                  60

Tyr Ala Val Thr Val Glu Arg Asn Gly His Thr Leu Met Thr Pro Ile
 65                  70                  75                  80

Ser Ile Asn Tyr Arg Thr
                 85

<210> SEQ ID NO 92
<211> LENGTH: 86
<212> TYPE: PRT
<213> ORGANISM: Artificial Sequence
<220> FEATURE:
<223> OTHER INFORMATION: binding polypeptide

<400> SEQUENCE: 92

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
 50                  55                  60

Tyr Ala Val Thr Val Glu Asn Gly Arg Gln Leu Met Thr Pro Ile
 65                  70                  75                  80

Ser Ile Asn Tyr Arg Thr
                 85

<210> SEQ ID NO 93
<211> LENGTH: 86
<212> TYPE: PRT
<213> ORGANISM: Artificial Sequence
<220> FEATURE:
<223> OTHER INFORMATION: binding polypeptide

<400> SEQUENCE: 93

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
 50                  55                  60

Tyr Ala Val Thr Leu Glu Arg Asn Gly Gln Val Leu Phe Thr Pro Ile
 65                  70                  75                  80

Ser Ile Asn Tyr Arg Thr
                 85

<210> SEQ ID NO 94
<211> LENGTH: 86
<212> TYPE: PRT
<213> ORGANISM: Artificial Sequence
```

-continued

```
<220> FEATURE:
<223> OTHER INFORMATION: binding polypeptide

<400> SEQUENCE: 94

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Gln Val Leu Tyr Thr Pro Ile
65                  70                  75                  80

Ser Ile Asn Tyr Arg Thr
                85

<210> SEQ ID NO 95
<211> LENGTH: 86
<212> TYPE: PRT
<213> ORGANISM: Artificial Sequence
<220> FEATURE:
<223> OTHER INFORMATION: binding polypeptide

<400> SEQUENCE: 95

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Trp Gly Tyr Lys Asp His Glu Leu Leu Ile Pro Ile
65                  70                  75                  80

Ser Ile Asn Tyr Arg Thr
                85

<210> SEQ ID NO 96
<211> LENGTH: 86
<212> TYPE: PRT
<213> ORGANISM: Artificial Sequence
<220> FEATURE:
<223> OTHER INFORMATION: binding polypeptide

<400> SEQUENCE: 96

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly Arg Asn Asp Arg Glu Leu Leu Thr Pro Ile
65                  70                  75                  80

Ser Ile Asn Tyr Arg Thr
                85
```

<210> SEQ ID NO 97
<211> LENGTH: 86
<212> TYPE: PRT
<213> ORGANISM: Artificial Sequence
<220> FEATURE:
<223> OTHER INFORMATION: binding polypeptide

<400> SEQUENCE: 97

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Asp Gly Pro Asn Asp Arg Leu Leu Asn Ile Pro Ile
 65                  70                  75                  80

Ser Ile Asn Tyr Arg Thr
                 85
```

<210> SEQ ID NO 98
<211> LENGTH: 86
<212> TYPE: PRT
<213> ORGANISM: Artificial Sequence
<220> FEATURE:
<223> OTHER INFORMATION: binding polypeptide

<400> SEQUENCE: 98

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Phe Ala Arg Asp Gly His Glu Ile Leu Thr Pro Ile
 65                  70                  75                  80

Ser Ile Asn Tyr Arg Thr
                 85
```

<210> SEQ ID NO 99
<211> LENGTH: 86
<212> TYPE: PRT
<213> ORGANISM: Artificial Sequence
<220> FEATURE:
<223> OTHER INFORMATION: binding polypeptide

<400> SEQUENCE: 99

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Leu Glu Gln Asn Gly Arg Glu Leu Met Thr Pro Ile
```

```
65                  70                  75                  80

Ser Ile Asn Tyr Arg Thr
                85

<210> SEQ ID NO 100
<211> LENGTH: 86
<212> TYPE: PRT
<213> ORGANISM: Artificial Sequence
<220> FEATURE:
<223> OTHER INFORMATION: binding polypeptide

<400> SEQUENCE: 100

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Glu Asn Gly Arg Val Leu Asn Thr Pro Ile
65                  70                  75                  80

Ser Ile Asn Tyr Arg Thr
                85

<210> SEQ ID NO 101
<211> LENGTH: 86
<212> TYPE: PRT
<213> ORGANISM: Artificial Sequence
<220> FEATURE:
<223> OTHER INFORMATION: binding polypeptide

<400> SEQUENCE: 101

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Glu Pro Asn Gly Arg Tyr Leu Met Val Pro Ile
65                  70                  75                  80

Ser Ile Asn Tyr Arg Thr
                85

<210> SEQ ID NO 102
<211> LENGTH: 86
<212> TYPE: PRT
<213> ORGANISM: Artificial Sequence
<220> FEATURE:
<223> OTHER INFORMATION: binding polypeptide

<400> SEQUENCE: 102

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45
```

```
Ala Thr Ile Ser Gly Leu Lys Pro Gly Val Asp Tyr Thr Ile Thr Gly
    50                  55                  60

Tyr Ala Val Thr Glu Gly Arg Asn Gly Arg Glu Leu Phe Ile Pro Ile
65                  70                  75                  80

Ser Ile Asn Tyr Arg Thr
                85

<210> SEQ ID NO 103
<211> LENGTH: 86
<212> TYPE: PRT
<213> ORGANISM: Artificial Sequence
<220> FEATURE:
<223> OTHER INFORMATION: binding polypeptide

<400> SEQUENCE: 103

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Ser Gly Arg Asn Asp Arg Glu Leu Leu Val Pro Ile
65                  70                  75                  80

Ser Ile Asn Tyr Arg Thr
                85

<210> SEQ ID NO 104
<211> LENGTH: 86
<212> TYPE: PRT
<213> ORGANISM: Artificial Sequence
<220> FEATURE:
<223> OTHER INFORMATION: binding polypeptide

<400> SEQUENCE: 104

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Glu Arg Asp Gly Arg Glu Leu Asn Ile Pro Ile
65                  70                  75                  80

Ser Ile Asn Tyr Arg Thr
                85

<210> SEQ ID NO 105
<211> LENGTH: 86
<212> TYPE: PRT
<213> ORGANISM: Artificial Sequence
<220> FEATURE:
<223> OTHER INFORMATION: binding polypeptide

<400> SEQUENCE: 105

Glu Val Val Ala Ala Thr Pro Thr Ser Leu Leu Ile Ser Trp Arg His
1               5                   10                  15
```

-continued

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Glu Gln Asn Gly Arg Val Leu Met Thr Pro Ile
65                  70                  75                  80

Ser Ile Asn Tyr Arg Thr
                85

<210> SEQ ID NO 106
<211> LENGTH: 86
<212> TYPE: PRT
<213> ORGANISM: Artificial Sequence
<220> FEATURE:
<223> OTHER INFORMATION: binding polypeptide

<400> SEQUENCE: 106

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Glu His Asn Gly Arg Val Leu Asn Ile Pro Ile
65                  70                  75                  80

Ser Ile Asn Tyr Arg Thr
                85

<210> SEQ ID NO 107
<211> LENGTH: 86
<212> TYPE: PRT
<213> ORGANISM: Artificial Sequence
<220> FEATURE:
<223> OTHER INFORMATION: binding polypeptide

<400> SEQUENCE: 107

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Met Ala Pro Asn Gly Arg Glu Leu Leu Thr Pro Ile
65                  70                  75                  80

Ser Ile Asn Tyr Arg Thr
                85

<210> SEQ ID NO 108
<211> LENGTH: 86
<212> TYPE: PRT
<213> ORGANISM: Artificial Sequence
<220> FEATURE:
<223> OTHER INFORMATION: binding polypeptide

<400> SEQUENCE: 108

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Gln Asn Gly Arg Val Leu Asn Thr Pro Ile
65                  70                  75                  80

Ser Ile Asn Tyr Arg Thr
                85

<210> SEQ ID NO 109
<211> LENGTH: 86
<212> TYPE: PRT
<213> ORGANISM: Artificial Sequence
<220> FEATURE:
<223> OTHER INFORMATION: binding polypeptide

<400> SEQUENCE: 109

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Arg Asn Gly His Glu Leu Met Thr Pro Ile
65                  70                  75                  80

Ser Ile Asn Tyr Arg Thr
                85

<210> SEQ ID NO 110
<211> LENGTH: 86
<212> TYPE: PRT
<213> ORGANISM: Artificial Sequence
<220> FEATURE:
<223> OTHER INFORMATION: binding polypeptide

<400> SEQUENCE: 110

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Gly Arg Asn Gly Arg Glu Leu Met Val Pro Ile
65                  70                  75                  80

Ser Ile Asn Tyr Arg Thr
                85

<210> SEQ ID NO 111
<211> LENGTH: 86

```
<212> TYPE: PRT
<213> ORGANISM: Artificial Sequence
<220> FEATURE:
<223> OTHER INFORMATION: binding polypeptide

<400> SEQUENCE: 111

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Asn Arg Glu Leu Leu Thr Pro Ile
65                  70                  75                  80

Ser Ile Asn Tyr Arg Thr
                85

<210> SEQ ID NO 112
<211> LENGTH: 86
<212> TYPE: PRT
<213> ORGANISM: Artificial Sequence
<220> FEATURE:
<223> OTHER INFORMATION: binding polypeptide

<400> SEQUENCE: 112

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Glu Arg Ser Gly Arg Glu Leu Met Thr Pro Ile
65                  70                  75                  80

Ser Ile Asn Tyr Arg Thr
                85

<210> SEQ ID NO 113
<211> LENGTH: 94
<212> TYPE: PRT
<213> ORGANISM: Artificial Sequence
<220> FEATURE:
<223> OTHER INFORMATION: binding polypeptide

<400> SEQUENCE: 113

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Arg Ala Leu Leu
65                  70                  75                  80

Ser Ile Glu Leu Phe Thr Pro Ile Ser Ile Asn Tyr Arg Thr
```

```
                          85                  90

<210> SEQ ID NO 114
<211> LENGTH: 94
<212> TYPE: PRT
<213> ORGANISM: Artificial Sequence
<220> FEATURE:
<223> OTHER INFORMATION: binding polypeptide

<400> SEQUENCE: 114

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Phe Ala Arg Lys
65                  70                  75                  80

Gly Thr Glu Leu Phe Thr Pro Ile Ser Ile Asn Tyr Arg Thr
                85                  90

<210> SEQ ID NO 115
<211> LENGTH: 94
<212> TYPE: PRT
<213> ORGANISM: Artificial Sequence
<220> FEATURE:
<223> OTHER INFORMATION: binding polypeptide

<400> SEQUENCE: 115

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Glu Arg Cys
65                  70                  75                  80

Gly Arg Glu Leu Phe Thr Pro Ile Ser Ile Asn Tyr Arg Thr
                85                  90

<210> SEQ ID NO 116
<211> LENGTH: 94
<212> TYPE: PRT
<213> ORGANISM: Artificial Sequence
<220> FEATURE:
<223> OTHER INFORMATION: binding polypeptide

<400> SEQUENCE: 116

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60
```

```
Gly Val Asp Tyr Thr Ile Thr Gly Tyr Ala Val Thr Arg Glu Arg Asn
65                  70                  75                  80

Gly Arg Glu Leu Phe Thr Pro Ile Ser Ile Asn Tyr Arg Thr
                85                  90
```

<210> SEQ ID NO 117
<211> LENGTH: 94
<212> TYPE: PRT
<213> ORGANISM: Artificial Sequence
<220> FEATURE:
<223> OTHER INFORMATION: binding polypeptide

<400> SEQUENCE: 117

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Lys Glu Arg Asn
65                  70                  75                  80

Gly Arg Glu Leu Phe Thr Pro Ile Ser Ile Asn Tyr Arg Thr
                85                  90
```

<210> SEQ ID NO 118
<211> LENGTH: 94
<212> TYPE: PRT
<213> ORGANISM: Artificial Sequence
<220> FEATURE:
<223> OTHER INFORMATION: binding polypeptide

<400> SEQUENCE: 118

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Cys Glu Arg Asn
65                  70                  75                  80

Gly Arg Glu Leu Phe Thr Pro Ile Ser Ile Asn Tyr Arg Thr
                85                  90
```

<210> SEQ ID NO 119
<211> LENGTH: 94
<212> TYPE: PRT
<213> ORGANISM: Artificial Sequence
<220> FEATURE:
<223> OTHER INFORMATION: binding polypeptide

<400> SEQUENCE: 119

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30
```

```
Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Leu Glu Arg Thr
 65                  70                  75                  80

Gly Arg Glu Leu Phe Thr Pro Ile Ser Ile Asn Tyr Arg Thr
                 85                  90
```

<210> SEQ ID NO 120
<211> LENGTH: 94
<212> TYPE: PRT
<213> ORGANISM: Artificial Sequence
<220> FEATURE:
<223> OTHER INFORMATION: binding polypeptide

<400> SEQUENCE: 120

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Trp Glu Arg Thr
 65                  70                  75                  80

Gly Lys Glu Leu Phe Thr Pro Ile Ser Ile Asn Tyr Arg Thr
                 85                  90
```

<210> SEQ ID NO 121
<211> LENGTH: 94
<212> TYPE: PRT
<213> ORGANISM: Artificial Sequence
<220> FEATURE:
<223> OTHER INFORMATION: binding polypeptide

<400> SEQUENCE: 121

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Ile Glu Arg Thr
 65                  70                  75                  80

Cys Arg Glu Leu Phe Thr Pro Ile Ser Ile Asn Tyr Arg Thr
                 85                  90
```

<210> SEQ ID NO 122
<211> LENGTH: 94
<212> TYPE: PRT
<213> ORGANISM: Artificial Sequence
<220> FEATURE:
<223> OTHER INFORMATION: binding polypeptide

<400> SEQUENCE: 122

```
Val Ser Asp Val Pro Arg Asp Leu Glu Val Val Ala Ala Thr Pro Thr
```

```
                1               5                  10                 15
Ser Leu Leu Ile Ser Trp Arg His Pro His Phe Pro Thr Arg Tyr Tyr
                    20                 25                 30

Arg Ile Thr Tyr Gly Glu Thr Gly Gly Asn Ser Pro Val Gln Glu Phe
                    35                 40                 45

Thr Val Pro Leu Gln Pro Pro Ala Ala Thr Ile Ser Gly Leu Lys Pro
                    50                 55                 60

Gly Val Asp Tyr Thr Ile Thr Gly Tyr Ala Val Thr Gly Gly Met Ile
 65                      70                 75                 80

Val Arg Glu Leu Phe Thr Pro Ile Ser Ile Asn Tyr Arg Thr
                    85                 90
```

<210> SEQ ID NO 123
<211> LENGTH: 94
<212> TYPE: PRT
<213> ORGANISM: Artificial Sequence
<220> FEATURE:
<223> OTHER INFORMATION: binding polypeptide

<400> SEQUENCE: 123

```
Val Ser Asp Val Pro Arg Asp Leu Glu Val Val Ala Ala Thr Pro Thr
 1               5                  10                 15

Ser Leu Leu Ile Ser Trp Arg His Pro His Phe Pro Thr Arg Tyr Tyr
                    20                 25                 30

Arg Ile Thr Tyr Gly Glu Thr Gly Gly Asn Ser Pro Val Gln Glu Phe
                    35                 40                 45

Thr Val Pro Leu Gln Pro Pro Ala Ala Thr Ile Ser Gly Leu Lys Pro
                    50                 55                 60

Gly Val Asp Tyr Thr Ile Thr Gly Tyr Ala Val Thr Phe Gly Arg Ser
 65                      70                 75                 80

Ser Arg Glu Leu Phe Thr Pro Ile Ser Ile Asn Tyr Arg Thr
                    85                 90
```

<210> SEQ ID NO 124
<211> LENGTH: 94
<212> TYPE: PRT
<213> ORGANISM: Artificial Sequence
<220> FEATURE:
<223> OTHER INFORMATION: binding polypeptide

<400> SEQUENCE: 124

```
Val Ser Asp Val Pro Arg Asp Leu Glu Val Val Ala Ala Thr Pro Thr
 1               5                  10                 15

Ser Leu Leu Ile Ser Trp Arg His Pro His Phe Pro Thr Arg Tyr Tyr
                    20                 25                 30

Arg Ile Thr Tyr Gly Glu Thr Gly Gly Asn Ser Pro Val Gln Glu Phe
                    35                 40                 45

Thr Val Pro Leu Gln Pro Pro Ala Ala Thr Ile Ser Gly Leu Lys Pro
                    50                 55                 60

Gly Val Asp Tyr Thr Ile Thr Gly Tyr Ala Val Thr Arg His Lys Ser
 65                      70                 75                 80

Arg Gly Glu Leu Phe Thr Pro Ile Ser Ile Asn Tyr Arg Thr
                    85                 90
```

<210> SEQ ID NO 125
<211> LENGTH: 94
<212> TYPE: PRT
<213> ORGANISM: Artificial Sequence
<220> FEATURE:

<223> OTHER INFORMATION: binding polypeptide

<400> SEQUENCE: 125

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Arg His Arg Asp
65                  70                  75                  80

Lys Arg Glu Leu Phe Thr Pro Ile Ser Ile Asn Tyr Arg Thr
                85                  90

<210> SEQ ID NO 126
<211> LENGTH: 94
<212> TYPE: PRT
<213> ORGANISM: Artificial Sequence
<220> FEATURE:
<223> OTHER INFORMATION: binding polypeptide

<400> SEQUENCE: 126

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Tyr His Arg Gly
65                  70                  75                  80

Arg Gly Glu Leu Phe Thr Pro Ile Ser Ile Asn Tyr Arg Thr
                85                  90

<210> SEQ ID NO 127
<211> LENGTH: 94
<212> TYPE: PRT
<213> ORGANISM: Artificial Sequence
<220> FEATURE:
<223> OTHER INFORMATION: binding polypeptide

<400> SEQUENCE: 127

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Arg His Arg Gly
65                  70                  75                  80

Cys Arg Glu Leu Phe Thr Pro Ile Ser Ile Asn Tyr Arg Thr
                85                  90

```
<210> SEQ ID NO 128
<211> LENGTH: 94
<212> TYPE: PRT
<213> ORGANISM: Artificial Sequence
<220> FEATURE:
<223> OTHER INFORMATION: binding polypeptide

<400> SEQUENCE: 128

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Ser His Arg Leu
65                  70                  75                  80

Arg Lys Glu Leu Phe Thr Pro Ile Ser Ile Asn Tyr Arg Thr
                85                  90

<210> SEQ ID NO 129
<211> LENGTH: 94
<212> TYPE: PRT
<213> ORGANISM: Artificial Sequence
<220> FEATURE:
<223> OTHER INFORMATION: binding polypeptide

<400> SEQUENCE: 129

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Met His Arg Gln
65                  70                  75                  80

Arg Gly Glu Leu Phe Thr Pro Ile Ser Ile Asn Tyr Arg Thr
                85                  90

<210> SEQ ID NO 130
<211> LENGTH: 94
<212> TYPE: PRT
<213> ORGANISM: Artificial Sequence
<220> FEATURE:
<223> OTHER INFORMATION: binding polypeptide

<400> SEQUENCE: 130

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Phe His Arg Arg
65                  70                  75                  80
```

Arg Gly Glu Leu Phe Thr Pro Ile Ser Ile Asn Tyr Arg Thr
                85                  90

<210> SEQ ID NO 131
<211> LENGTH: 94
<212> TYPE: PRT
<213> ORGANISM: Artificial Sequence
<220> FEATURE:
<223> OTHER INFORMATION: binding polypeptide

<400> SEQUENCE: 131

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Phe His Arg Arg
65                  70                  75                  80

Arg Gly Glu Leu Phe Thr Pro Ile Ser Ile Asn Tyr Arg Thr
                85                  90

<210> SEQ ID NO 132
<211> LENGTH: 94
<212> TYPE: PRT
<213> ORGANISM: Artificial Sequence
<220> FEATURE:
<223> OTHER INFORMATION: binding polypeptide

<400> SEQUENCE: 132

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Ser His Arg Arg
65                  70                  75                  80

Arg Asn Glu Leu Phe Thr Pro Ile Ser Ile Asn Tyr Arg Thr
                85                  90

<210> SEQ ID NO 133
<211> LENGTH: 94
<212> TYPE: PRT
<213> ORGANISM: Artificial Sequence
<220> FEATURE:
<223> OTHER INFORMATION: binding polypeptide

<400> SEQUENCE: 133

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

```
Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu His Arg Arg
 65                  70                  75                  80

Val Arg Glu Leu Phe Thr Pro Ile Ser Ile Asn Tyr Arg Thr
                85                  90
```

<210> SEQ ID NO 134
<211> LENGTH: 94
<212> TYPE: PRT
<213> ORGANISM: Artificial Sequence
<220> FEATURE:
<223> OTHER INFORMATION: binding polypeptide

<400> SEQUENCE: 134

```
Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Arg His Arg Arg
 65                  70                  75                  80

Arg Gly Glu Leu Phe Thr Pro Ile Ser Ile Asn Tyr Arg Thr
                85                  90
```

<210> SEQ ID NO 135
<211> LENGTH: 94
<212> TYPE: PRT
<213> ORGANISM: Artificial Sequence
<220> FEATURE:
<223> OTHER INFORMATION: binding polypeptide

<400> SEQUENCE: 135

```
Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Trp His Arg Ser
 65                  70                  75                  80

Arg Lys Glu Leu Phe Thr Pro Ile Ser Ile Asn Tyr Arg Thr
                85                  90
```

<210> SEQ ID NO 136
<211> LENGTH: 94
<212> TYPE: PRT
<213> ORGANISM: Artificial Sequence
<220> FEATURE:
<223> OTHER INFORMATION: binding polypeptide

<400> SEQUENCE: 136

```
Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
```

-continued

```
                20                  25                  30
Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
         50                  55                  60

Gly Val Asp Tyr Thr Ile Thr Gly Tyr Ala Val Thr Arg His Arg Ser
 65                  70                  75                  80

Arg Gly Glu Leu Phe Thr Pro Ile Ser Ile Asn Tyr Arg Thr
                 85                  90
```

<210> SEQ ID NO 137
<211> LENGTH: 94
<212> TYPE: PRT
<213> ORGANISM: Artificial Sequence
<220> FEATURE:
<223> OTHER INFORMATION: binding polypeptide

<400> SEQUENCE: 137

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
         35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Val His Arg Thr
 65                  70                  75                  80

Gly Arg Glu Leu Phe Thr Pro Ile Ser Ile Asn Tyr Arg Thr
                 85                  90
```

<210> SEQ ID NO 138
<211> LENGTH: 94
<212> TYPE: PRT
<213> ORGANISM: Artificial Sequence
<220> FEATURE:
<223> OTHER INFORMATION: binding polypeptide

<400> SEQUENCE: 138

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
         35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Trp His Arg Val
 65                  70                  75                  80

Arg Gly Glu Leu Phe Thr Pro Ile Ser Ile Asn Tyr Arg Thr
                 85                  90
```

<210> SEQ ID NO 139
<211> LENGTH: 94
<212> TYPE: PRT
<213> ORGANISM: Artificial Sequence
<220> FEATURE:
<223> OTHER INFORMATION: binding polypeptide

<400> SEQUENCE: 139

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp His Arg Val
65                  70                  75                  80

Arg Gly Glu Leu Phe Thr Pro Ile Ser Ile Asn Tyr Arg Thr
                85                  90
```

```
<210> SEQ ID NO 140
<211> LENGTH: 94
<212> TYPE: PRT
<213> ORGANISM: Artificial Sequence
<220> FEATURE:
<223> OTHER INFORMATION: binding polypeptide

<400> SEQUENCE: 140

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp His Arg Trp
65                  70                  75                  80

Arg Gly Glu Leu Phe Thr Pro Ile Ser Ile Asn Tyr Arg Thr
                85                  90
```

```
<210> SEQ ID NO 141
<211> LENGTH: 94
<212> TYPE: PRT
<213> ORGANISM: Artificial Sequence
<220> FEATURE:
<223> OTHER INFORMATION: binding polypeptide

<400> SEQUENCE: 141

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp Lys Arg Ser
65                  70                  75                  80

Gly Gly Glu Leu Phe Thr Pro Ile Ser Ile Asn Tyr Arg Thr
                85                  90
```

```
<210> SEQ ID NO 142
<211> LENGTH: 94
<212> TYPE: PRT
```

```
<213> ORGANISM: Artificial Sequence
<220> FEATURE:
<223> OTHER INFORMATION: binding polypeptide
<220> FEATURE:
<221> NAME/KEY: VARIANT
<222> LOCATION: 79, 81
<223> OTHER INFORMATION: Xaa = Any Amino Acid

<400> SEQUENCE: 142

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Arg Leu Xaa Asn
65                  70                  75                  80

Xaa Val Glu Leu Phe Thr Pro Ile Ser Ile Asn Tyr Arg Thr
                85                  90

<210> SEQ ID NO 143
<211> LENGTH: 94
<212> TYPE: PRT
<213> ORGANISM: Artificial Sequence
<220> FEATURE:
<223> OTHER INFORMATION: binding polypeptide

<400> SEQUENCE: 143

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Trp Arg Thr Pro
65                  70                  75                  80

His Ala Glu Leu Phe Thr Pro Ile Ser Ile Asn Tyr Arg Thr
                85                  90

<210> SEQ ID NO 144
<211> LENGTH: 94
<212> TYPE: PRT
<213> ORGANISM: Artificial Sequence
<220> FEATURE:
<223> OTHER INFORMATION: binding polypeptide

<400> SEQUENCE: 144

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Ser Pro His
```

```
                65                  70                  75                  80
Ser Val Glu Leu Phe Thr Pro Ile Ser Ile Asn Tyr Arg Thr
                    85                  90

<210> SEQ ID NO 145
<211> LENGTH: 94
<212> TYPE: PRT
<213> ORGANISM: Artificial Sequence
<220> FEATURE:
<223> OTHER INFORMATION: binding polypeptide

<400> SEQUENCE: 145

Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Val Ser Arg Gln
 65                  70                  75                  80

Lys Ala Glu Leu Phe Thr Pro Ile Ser Ile Asn Tyr Arg Thr
                    85                  90

<210> SEQ ID NO 146
<211> LENGTH: 94
<212> TYPE: PRT
<213> ORGANISM: Artificial Sequence
<220> FEATURE:
<223> OTHER INFORMATION: binding polypeptide

<400> SEQUENCE: 146

Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Ser Ser Tyr Ser
 65                  70                  75                  80

Lys Leu Glu Leu Phe Thr Pro Ile Ser Ile Asn Tyr Arg Thr
                    85                  90

<210> SEQ ID NO 147
<211> LENGTH: 94
<212> TYPE: PRT
<213> ORGANISM: Artificial Sequence
<220> FEATURE:
<223> OTHER INFORMATION: binding polypeptide

<400> SEQUENCE: 147

Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45
```

```
Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Leu Thr Asp Arg
 65                  70                  75                  80

Gly Ser Glu Leu Phe Thr Pro Ile Ser Ile Asn Tyr Arg Thr
                 85                  90

<210> SEQ ID NO 148
<211> LENGTH: 94
<212> TYPE: PRT
<213> ORGANISM: Artificial Sequence
<220> FEATURE:
<223> OTHER INFORMATION: binding polypeptide

<400> SEQUENCE: 148

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Gly Thr Arg Thr
 65                  70                  75                  80

Arg Ser Glu Leu Phe Thr Pro Ile Ser Ile Asn Tyr Arg Thr
                 85                  90

<210> SEQ ID NO 149
<211> LENGTH: 94
<212> TYPE: PRT
<213> ORGANISM: Artificial Sequence
<220> FEATURE:
<223> OTHER INFORMATION: binding polypeptide

<400> SEQUENCE: 149

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Pro Val Ala Gly
 65                  70                  75                  80

Cys Ser Glu Leu Phe Thr Pro Ile Ser Ile Asn Tyr Arg Thr
                 85                  90

<210> SEQ ID NO 150
<211> LENGTH: 94
<212> TYPE: PRT
<213> ORGANISM: Artificial Sequence
<220> FEATURE:
<223> OTHER INFORMATION: binding polypeptide

<400> SEQUENCE: 150

Val Ser Asp Val Pro Arg Asp Leu Glu Val Val Ala Ala Thr Pro Thr
 1               5                  10                  15
```

```
Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp Trp Gln Thr
65                  70                  75                  80

Pro Arg Glu Leu Phe Thr Pro Ile Ser Ile Asn Tyr Arg Thr
                85                  90
```

<210> SEQ ID NO 151
<211> LENGTH: 94
<212> TYPE: PRT
<213> ORGANISM: Artificial Sequence
<220> FEATURE:
<223> OTHER INFORMATION: binding polypeptide

<400> SEQUENCE: 151

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp Trp Gln Thr
65                  70                  75                  80

Pro Arg Glu Leu Phe Thr Pro Ile Ser Ile Asn Tyr Arg Thr
                85                  90
```

<210> SEQ ID NO 152
<211> LENGTH: 94
<212> TYPE: PRT
<213> ORGANISM: Artificial Sequence
<220> FEATURE:
<223> OTHER INFORMATION: binding polypeptide

<400> SEQUENCE: 152

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp Glu Arg Asn
65                  70                  75                  80

Gly Arg Glu Leu Phe Thr Pro Ile Ser Ile Asn Tyr Arg Thr
                85                  90
```

<210> SEQ ID NO 153
<211> LENGTH: 94
<212> TYPE: PRT
<213> ORGANISM: Artificial Sequence
<220> FEATURE:
<223> OTHER INFORMATION: binding polypeptide

```
<400> SEQUENCE: 153

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Trp Glu Trp Asn
65                  70                  75                  80

Gly Arg Glu Leu Phe Thr Pro Ile Ser Ile Asn Tyr Arg Thr
                85                  90

<210> SEQ ID NO 154
<211> LENGTH: 94
<212> TYPE: PRT
<213> ORGANISM: Artificial Sequence
<220> FEATURE:
<223> OTHER INFORMATION: binding polypeptide

<400> SEQUENCE: 154

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Lys Glu Arg Asn
65                  70                  75                  80

Gly Arg Glu Leu Phe Thr Pro Ile Ser Ile Asn Tyr Arg Thr
                85                  90

<210> SEQ ID NO 155
<211> LENGTH: 94
<212> TYPE: PRT
<213> ORGANISM: Artificial Sequence
<220> FEATURE:
<223> OTHER INFORMATION: binding polypeptide

<400> SEQUENCE: 155

Val Ser Asp Val Pro Arg Asp Leu Glu Val Val Ala Ala Thr Pro Thr
1               5                   10                  15

Ser Leu Leu Ile Ser Trp Leu His Pro His Phe Pro Thr His Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ala Ala Thr Ile Ser Gly Leu Lys Pro
        50                  55                  60

Gly Val Asp Tyr Thr Ile Thr Gly Tyr Ala Val Thr Gly Ala Leu Asn
65                  70                  75                  80

Thr Ser Glu Leu Phe Thr Pro Ile Ser Ile Asn Tyr Arg Thr
                85                  90

<210> SEQ ID NO 156
<211> LENGTH: 94
```

```
<212> TYPE: PRT
<213> ORGANISM: Artificial Sequence
<220> FEATURE:
<223> OTHER INFORMATION: binding polypeptide

<400> SEQUENCE: 156

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Phe Gly Arg Glu
65                  70                  75                  80

Arg Arg Glu Leu Phe Thr Pro Ile Ser Ile Asn Tyr Arg Thr
                85                  90

<210> SEQ ID NO 157
<211> LENGTH: 94
<212> TYPE: PRT
<213> ORGANISM: Artificial Sequence
<220> FEATURE:
<223> OTHER INFORMATION: binding polypeptide

<400> SEQUENCE: 157

Val Ser Asp Val Pro Arg Asp Leu Glu Val Val Ala Ala Thr Pro Thr
1               5                   10                  15

Ser Leu Leu Ile Ser Trp Leu His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Ser Gly Arg Val
65                  70                  75                  80

Ser Phe Glu Leu Phe Thr Pro Ile Ser Ile Asn Tyr Arg Thr
                85                  90

<210> SEQ ID NO 158
<211> LENGTH: 94
<212> TYPE: PRT
<213> ORGANISM: Artificial Sequence
<220> FEATURE:
<223> OTHER INFORMATION: binding polypeptide

<400> SEQUENCE: 158

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Phe His Arg Arg
65                  70                  75                  80

Arg Gly Glu Leu Phe Thr Pro Ile Ser Ile Asn Tyr Arg Thr
```

<210> SEQ ID NO 159
<211> LENGTH: 94
<212> TYPE: PRT
<213> ORGANISM: Artificial Sequence
<220> FEATURE:
<223> OTHER INFORMATION: binding polypeptide

<400> SEQUENCE: 159

Val Ser Asp Val Pro Arg Asp Leu Glu Val Val Ala Ala Thr Pro Thr
1               5                   10                  15

Ser Leu Leu Ile Ser Trp Leu His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Ile Arg Met
65                  70                  75                  80

Asn Thr Glu Leu Phe Thr Pro Ile Ser Ile Asn Tyr Arg Thr
                85                  90

<210> SEQ ID NO 160
<211> LENGTH: 94
<212> TYPE: PRT
<213> ORGANISM: Artificial Sequence
<220> FEATURE:
<223> OTHER INFORMATION: binding polypeptide

<400> SEQUENCE: 160

Val Ser Asp Val Pro Arg Asp Leu Glu Val Val Ala Ala Thr Pro Thr
1               5                   10                  15

Ser Leu Leu Ile Ser Trp Leu His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Cys Leu His Leu
65                  70                  75                  80

Ile Thr Glu Leu Phe Thr Pro Ile Ser Ile Asn Tyr Arg Thr
                85                  90

<210> SEQ ID NO 161
<211> LENGTH: 94
<212> TYPE: PRT
<213> ORGANISM: Artificial Sequence
<220> FEATURE:
<223> OTHER INFORMATION: binding polypeptide

<400> SEQUENCE: 161

Val Ser Asp Val Pro Arg Asp Leu Glu Val Val Ala Ala Thr Pro Thr
1               5                   10                  15

Ser Leu Leu Ile Ser Trp Leu His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

```
Gly Val Asp Tyr Thr Ile Thr Gly Tyr Ala Val Thr Val Leu Lys Leu
 65                  70                  75                  80

Thr Leu Glu Leu Phe Thr Pro Ile Ser Ile Asn Tyr Arg Thr
                 85                  90

<210> SEQ ID NO 162
<211> LENGTH: 94
<212> TYPE: PRT
<213> ORGANISM: Artificial Sequence
<220> FEATURE:
<223> OTHER INFORMATION: binding polypeptide

<400> SEQUENCE: 162

Val Ser Asp Val Pro Arg Asp Leu Glu Val Val Ala Ala Thr Pro Thr
  1               5                  10                  15

Ser Leu Leu Ile Ser Trp Leu His Pro His Phe Pro Thr His Tyr Tyr
                 20                  25                  30

Arg Ile Thr Tyr Gly Glu Thr Gly Gly Asn Ser Pro Val Gln Glu Phe
             35                  40                  45

Thr Val Pro Leu Gln Pro Pro Ala Ala Thr Ile Ser Gly Leu Lys Pro
         50                  55                  60

Gly Val Asp Tyr Thr Ile Thr Gly Tyr Ala Val Thr Val Leu Lys Leu
 65                  70                  75                  80

Thr Leu Glu Leu Phe Thr Pro Ile Ser Ile Asn Tyr Arg Thr
                 85                  90

<210> SEQ ID NO 163
<211> LENGTH: 94
<212> TYPE: PRT
<213> ORGANISM: Artificial Sequence
<220> FEATURE:
<223> OTHER INFORMATION: binding polypeptide

<400> SEQUENCE: 163

Val Ser Asp Val Pro Arg Asp Leu Glu Val Val Ala Ala Thr Pro Thr
  1               5                  10                  15

Ser Leu Leu Ile Ser Trp Phe His Pro His Phe Pro Thr His Tyr Tyr
                 20                  25                  30

Arg Ile Thr Tyr Gly Glu Thr Gly Gly Asn Ser Pro Val Gln Glu Phe
             35                  40                  45

Thr Val Pro Leu Gln Pro Pro Ala Ala Thr Ile Ser Gly Leu Lys Pro
         50                  55                  60

Gly Val Asp Tyr Thr Ile Thr Gly Tyr Ala Val Thr Val Leu Lys Leu
 65                  70                  75                  80

Thr Leu Glu Leu Phe Thr Pro Ile Ser Ile Asn Tyr Arg Thr
                 85                  90

<210> SEQ ID NO 164
<211> LENGTH: 94
<212> TYPE: PRT
<213> ORGANISM: Artificial Sequence
<220> FEATURE:
<223> OTHER INFORMATION: binding polypeptide

<400> SEQUENCE: 164

Val Ser Asp Val Pro Arg Asp Leu Glu Val Val Ala Ala Thr Pro Thr
  1               5                  10                  15

Ser Leu Leu Ile Ser Trp Leu His Pro His Phe Pro Thr His Tyr Tyr
                 20                  25                  30
```

```
Arg Ile Thr Tyr Gly Glu Thr Gly Asn Ser Pro Val Gln Glu Phe
            35                  40                  45

Thr Val Pro Leu Gln Pro Pro Ala Ala Thr Ile Ser Gly Leu Lys Pro
 50                  55                  60

Gly Val Asp Tyr Thr Ile Thr Gly Tyr Ala Val Thr Ala Leu Met Ala
 65                  70                  75                  80

Ser Gly Glu Leu Phe Thr Pro Ile Ser Ile Asn Tyr Arg Thr
                85                  90
```

<210> SEQ ID NO 165
<211> LENGTH: 94
<212> TYPE: PRT
<213> ORGANISM: Artificial Sequence
<220> FEATURE:
<223> OTHER INFORMATION: binding polypeptide

<400> SEQUENCE: 165

```
Val Ser Asp Val Pro Arg Asp Leu Glu Val Val Ala Ala Thr Pro Thr
 1               5                  10                  15

Ser Leu Leu Ile Ser Trp Leu His Pro His Phe Pro Thr His Tyr Tyr
                20                  25                  30

Arg Ile Thr Tyr Gly Glu Thr Gly Asn Ser Pro Val Gln Glu Phe
            35                  40                  45

Thr Val Pro Leu Gln Pro Pro Ala Ala Thr Ile Ser Gly Leu Lys Pro
 50                  55                  60

Gly Val Asp Tyr Thr Ile Thr Gly Tyr Ala Val Thr Ser Met Lys Asn
 65                  70                  75                  80

Arg Leu Glu Leu Phe Thr Pro Ile Ser Ile Asn Tyr Arg Thr
                85                  90
```

<210> SEQ ID NO 166
<211> LENGTH: 94
<212> TYPE: PRT
<213> ORGANISM: Artificial Sequence
<220> FEATURE:
<223> OTHER INFORMATION: binding polypeptide

<400> SEQUENCE: 166

```
Val Ser Asp Val Pro Arg Asp Leu Glu Val Val Ala Ala Thr Pro Thr
 1               5                  10                  15

Ser Leu Leu Ile Ser Trp Phe His Pro His Phe Pro Thr His Tyr Tyr
                20                  25                  30

Arg Ile Thr Tyr Gly Glu Thr Gly Asn Ser Pro Val Gln Glu Phe
            35                  40                  45

Thr Val Pro Leu Gln Pro Pro Ala Ala Thr Ile Ser Gly Leu Lys Pro
 50                  55                  60

Gly Val Asp Tyr Thr Ile Thr Gly Tyr Ala Val Thr Leu Arg Cys Leu
 65                  70                  75                  80

Ile Pro Glu Leu Phe Thr Pro Ile Ser Ile Asn Tyr Arg Thr
                85                  90
```

<210> SEQ ID NO 167
<211> LENGTH: 94
<212> TYPE: PRT
<213> ORGANISM: Artificial Sequence
<220> FEATURE:
<223> OTHER INFORMATION: binding polypeptide

<400> SEQUENCE: 167

```
Val Ser Asp Val Pro Arg Asp Leu Glu Val Val Ala Ala Thr Pro Thr
```

```
                1               5                  10                 15
Ser Leu Leu Ile Ser Trp Leu His Pro His Phe Pro Thr His Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Ala Ala Thr Ile Ser Gly Leu Lys Pro
                50                 55                 60

Gly Val Asp Tyr Thr Ile Thr Gly Tyr Ala Val Thr Val Ser Arg Gln
 65                 70                 75                 80

Lys Ala Glu Leu Phe Thr Pro Ile Ser Ile Asn Tyr Arg Thr
                85                 90

<210> SEQ ID NO 168
<211> LENGTH: 94
<212> TYPE: PRT
<213> ORGANISM: Artificial Sequence
<220> FEATURE:
<223> OTHER INFORMATION: binding polypeptide

<400> SEQUENCE: 168

Val Ser Asp Val Pro Arg Asp Leu Glu Val Val Ala Ala Thr Pro Thr
 1               5                  10                 15

Ser Leu Leu Ile Ser Trp Arg His Pro His Phe Pro Thr His Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Ala Ala Thr Ile Ser Gly Leu Lys Pro
                50                 55                 60

Gly Val Asp Tyr Thr Ile Thr Gly Tyr Ala Val Thr Trp Ser Arg Thr
 65                 70                 75                 80

Gly Arg Glu Leu Phe Thr Pro Ile Ser Ile Asn Tyr Arg Thr
                85                 90

<210> SEQ ID NO 169
<211> LENGTH: 94
<212> TYPE: PRT
<213> ORGANISM: Artificial Sequence
<220> FEATURE:
<223> OTHER INFORMATION: binding polypeptide

<400> SEQUENCE: 169

Val Ser Asp Val Pro Arg Asp Leu Glu Val Val Ala Ala Thr Pro Thr
 1               5                  10                 15

Ser Leu Leu Ile Ser Trp Arg His Pro His Phe Pro Thr His Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Ala Ala Thr Ile Ser Gly Leu Lys Pro
                50                 55                 60

Gly Val Asp Tyr Thr Ile Thr Gly Tyr Ala Val Thr Val Trp Arg Thr
 65                 70                 75                 80

Gly Arg Glu Leu Phe Thr Pro Ile Ser Ile Asn Tyr Arg Thr
                85                 90

<210> SEQ ID NO 170
<211> LENGTH: 94
<212> TYPE: PRT
<213> ORGANISM: Artificial Sequence
<220> FEATURE:
```

<223> OTHER INFORMATION: binding polypeptide

<400> SEQUENCE: 170

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Thr Glu Arg Thr
65                  70                  75                  80

Gly Arg Glu Leu Phe Thr Pro Ile Ser Ile Asn Tyr Arg Thr
                85                  90
```

<210> SEQ ID NO 171
<211> LENGTH: 94
<212> TYPE: PRT
<213> ORGANISM: Artificial Sequence
<220> FEATURE:
<223> OTHER INFORMATION: binding polypeptide

<400> SEQUENCE: 171

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Lys Glu Arg Ser
65                  70                  75                  80

Gly Arg Glu Leu Phe Thr Pro Ile Ser Ile Asn Tyr Arg Thr
                85                  90
```

<210> SEQ ID NO 172
<211> LENGTH: 94
<212> TYPE: PRT
<213> ORGANISM: Artificial Sequence
<220> FEATURE:
<223> OTHER INFORMATION: binding polypeptide

<400> SEQUENCE: 172

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Glu Arg Asn
65                  70                  75                  80

Asp Arg Glu Leu Phe Thr Pro Ile Ser Ile Asn Tyr Arg Thr
                85                  90
```

```
<210> SEQ ID NO 173
<211> LENGTH: 94
<212> TYPE: PRT
<213> ORGANISM: Artificial Sequence
<220> FEATURE:
<223> OTHER INFORMATION: binding polypeptide

<400> SEQUENCE: 173

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr His Tyr Tyr
             20                  25                  30

Arg Ile Thr Tyr Gly Glu Thr Gly Gly Asn Ser Pro Val Gln Glu Phe
         35                  40                  45

Thr Val Pro Leu Gln Pro Pro Ala Ala Thr Ile Ser Gly Leu Lys Pro
     50                  55                  60

Gly Val Asp Tyr Thr Ile Thr Gly Tyr Ala Val Thr Leu Glu Arg Asp
 65                  70                  75                  80

Gly Arg Glu Leu Phe Thr Pro Ile Ser Ile Asn Tyr Arg Thr
                 85                  90

<210> SEQ ID NO 174
<211> LENGTH: 94
<212> TYPE: PRT
<213> ORGANISM: Artificial Sequence
<220> FEATURE:
<223> OTHER INFORMATION: binding polypeptide

<400> SEQUENCE: 174

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
         35                  40                  45

Thr Val Pro Leu Gln Pro Pro Thr Ala Thr Ile Ser Gly Leu Lys Pro
     50                  55                  60

Gly Val Asp Tyr Thr Ile Thr Gly Tyr Ala Val Thr Gln Gly Arg His
 65                  70                  75                  80

Lys Arg Glu Leu Phe Thr Pro Ile Ser Ile Asn Tyr Arg Thr
                 85                  90

<210> SEQ ID NO 175
<211> LENGTH: 94
<212> TYPE: PRT
<213> ORGANISM: Artificial Sequence
<220> FEATURE:
<223> OTHER INFORMATION: binding polypeptide

<400> SEQUENCE: 175

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
         35                  40                  45

Thr Val Pro Leu Gln Pro Pro Leu Ala Thr Ile Ser Gly Leu Lys Pro
     50                  55                  60

Gly Val Asp Tyr Thr Ile Thr Gly Tyr Ala Val Thr Lys Glu Arg Asn
 65                  70                  75                  80
```

Gly Arg Glu Leu Phe Thr Pro Ile Ser Ile Asn Tyr Arg Thr
                85                  90

<210> SEQ ID NO 176
<211> LENGTH: 94
<212> TYPE: PRT
<213> ORGANISM: Artificial Sequence
<220> FEATURE:
<223> OTHER INFORMATION: binding polypeptide

<400> SEQUENCE: 176

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ile Ala Thr Ile Ser Gly Leu Lys Pro
    50                  55                  60

Gly Val Asp Tyr Thr Ile Thr Gly Tyr Ala Val Thr Met Ala Gln Asn
65                  70                  75                  80

Asp His Glu Leu Ile Thr Pro Ile Ser Ile Asn Tyr Arg Thr
                85                  90

<210> SEQ ID NO 177
<211> LENGTH: 94
<212> TYPE: PRT
<213> ORGANISM: Artificial Sequence
<220> FEATURE:
<223> OTHER INFORMATION: binding polypeptide

<400> SEQUENCE: 177

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ile Ala Thr Ile Ser Gly Leu Lys Pro
    50                  55                  60

Gly Val Asp Tyr Thr Ile Thr Gly Tyr Ala Val Thr Met Ala Gln Asn
65                  70                  75                  80

Asp His Glu Leu Ile Thr Pro Ile Ser Ile Asn Tyr Arg Thr
                85                  90

<210> SEQ ID NO 178
<211> LENGTH: 94
<212> TYPE: PRT
<213> ORGANISM: Artificial Sequence
<220> FEATURE:
<223> OTHER INFORMATION: binding polypeptide

<400> SEQUENCE: 178

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Thr Thr Ala Thr Ile Ser Gly Leu Lys Pro
 50                 55                  60

Gly Val Asp Tyr Thr Ile Thr Gly Tyr Ala Val Thr Trp Glu Arg Asn
 65                 70                  75                  80

Gly Arg Glu Leu Phe Thr Pro Ile Ser Ile Asn Tyr Arg Thr
                 85                  90

<210> SEQ ID NO 179
<211> LENGTH: 94
<212> TYPE: PRT
<213> ORGANISM: Artificial Sequence
<220> FEATURE:
<223> OTHER INFORMATION: binding polypeptide

<400> SEQUENCE: 179

Val Ser Asp Val Pro Arg Asp Leu Glu Val Val Ala Ala Thr Pro Thr
 1               5                   10                  15

Ser Leu Leu Ile Ser Trp Arg His Pro His Phe Pro Thr Arg Tyr Tyr
                 20                  25                  30

Arg Ile Thr Tyr Gly Glu Thr Gly Gly Asn Ser Pro Val Gln Glu Phe
             35                  40                  45

Thr Val Pro Leu Gln Pro Thr Val Ala Thr Ile Ser Gly Leu Lys Pro
 50                 55                  60

Gly Val Asp Tyr Thr Ile Thr Gly Tyr Ala Val Thr Leu Glu Arg Asn
 65                 70                  75                  80

Asp Arg Glu Leu Phe Thr Pro Ile Ser Ile Asn Tyr Arg Thr
                 85                  90

<210> SEQ ID NO 180
<211> LENGTH: 94
<212> TYPE: PRT
<213> ORGANISM: Artificial Sequence
<220> FEATURE:
<223> OTHER INFORMATION: binding polypeptide

<400> SEQUENCE: 180

Val Ser Asp Val Pro Arg Asp Leu Glu Val Val Ala Ala Thr Pro Thr
 1               5                   10                  15

Ser Leu Leu Ile Ser Trp Arg Pro Pro His Phe Pro Thr Arg Tyr Tyr
                 20                  25                  30

Arg Ile Thr Tyr Gly Glu Thr Gly Gly Asn Ser Pro Val Gln Glu Phe
             35                  40                  45

Thr Val Pro Leu Gln Pro Thr Val Ala Thr Ile Ser Gly Leu Lys Pro
 50                 55                  60

Gly Val Asp Tyr Thr Ile Thr Gly Tyr Ala Val Thr Leu Glu Arg Asn
 65                 70                  75                  80

Asp Arg Glu Leu Phe Thr Pro Ile Ser Ile Asn Tyr Arg Thr
                 85                  90

<210> SEQ ID NO 181
<211> LENGTH: 94
<212> TYPE: PRT
<213> ORGANISM: Artificial Sequence
<220> FEATURE:
<223> OTHER INFORMATION: binding polypeptide

<400> SEQUENCE: 181

Val Ser Asp Val Pro Arg Asp Leu Glu Val Val Ala Ala Thr Pro Thr
 1               5                   10                  15

Ser Leu Leu Ile Ser Trp Arg His Pro His Phe Pro Thr Arg Tyr Tyr

-continued

```
                20                  25                  30
Arg Ile Thr Tyr Gly Glu Thr Gly Asn Ser Pro Val Gln Glu Phe
            35                  40                  45

Thr Val Pro Pro Gln Pro Pro Ala Ala Thr Ile Ser Gly Leu Lys Pro
        50                  55                  60

Gly Val Asp Tyr Thr Ile Thr Gly Tyr Ala Val Thr Lys Glu Arg Ser
65                  70                  75                  80

Gly Arg Glu Leu Phe Thr Pro Ile Ser Ile Asn Tyr Arg Thr
                85                  90
```

<210> SEQ ID NO 182
<211> LENGTH: 94
<212> TYPE: PRT
<213> ORGANISM: Artificial Sequence
<220> FEATURE:
<223> OTHER INFORMATION: binding polypeptide

<400> SEQUENCE: 182

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Pro Gln Pro Pro Ala Ala Thr Ile Ser Gly Leu Lys Pro
        50                  55                  60

Gly Val Asp Tyr Thr Ile Thr Gly Tyr Ala Val Thr Leu Glu Arg Asn
65                  70                  75                  80

Asp Arg Glu Leu Phe Thr Pro Ile Ser Ile Asn Tyr Arg Thr
                85                  90
```

<210> SEQ ID NO 183
<211> LENGTH: 94
<212> TYPE: PRT
<213> ORGANISM: Artificial Sequence
<220> FEATURE:
<223> OTHER INFORMATION: binding polypeptide

<400> SEQUENCE: 183

```
Val Ser Asp Val Pro Arg Asp Leu Glu Val Val Ala Ala Thr Pro Thr
1               5                   10                  15

Ser Leu Leu Ile Ser Trp Cys His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Ile Ala Thr Ile Ser Gly Leu Lys Pro
        50                  55                  60

Gly Val Asp Tyr Thr Ile Thr Gly Tyr Ala Val Thr Met Ala Gln Asn
65                  70                  75                  80

Asp His Glu Leu Ile Thr Pro Ile Ser Ile Asn Tyr Arg Thr
                85                  90
```

<210> SEQ ID NO 184
<211> LENGTH: 285
<212> TYPE: DNA
<213> ORGANISM: Artificial Sequence
<220> FEATURE:
<223> OTHER INFORMATION: binding polypeptide

<400> SEQUENCE: 184

```
atgggcgaag ttgttgctgc gacccccacc agcctactga tcagctggcg ccacccgcac    60
ttcccgacta gatattacag gatcacttac ggagaaacag gaggaaatag ccctgtccag   120
gagttcactg tgcctctgca gccccccaca gctaccatca gcggccttaa acctggagtt   180
gattatacca tcactgtgta tgctgtcact gacggccgga acgggcgcct cctgagcatc   240
ccaatttcca ttaattaccg cacagaaatt gacaaaccat gccag                    285
```

<210> SEQ ID NO 185
<211> LENGTH: 264
<212> TYPE: DNA
<213> ORGANISM: Artificial Sequence
<220> FEATURE:
<223> OTHER INFORMATION: binding polypeptide

<400> SEQUENCE: 185

```
atgggcgaag ttgttgctgc gacccccacc agcctactga tcagctggcg ccacccgcac    60
ttcccgacta gatattacag gatcacttac ggagaaacag gaggaaatag ccctgtccag   120
gagttcactg tgcctctgca gccccccaca gctaccatca gcggccttaa acctggagtt   180
gattatacca tcactgtgta tgctgtcact gacggccgga acgggcgcct cctgagcatc   240
ccaatttcca ttaattaccg caca                                           264
```

<210> SEQ ID NO 186
<211> LENGTH: 95
<212> TYPE: PRT
<213> ORGANISM: Artificial Sequence
<220> FEATURE:
<223> OTHER INFORMATION: binding polypeptide

<400> SEQUENCE: 186

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
    50                  55                  60

Thr Val Tyr Ala Val Thr Asp Gly Arg Asn Gly Arg Leu Leu Ser Ile
65                  70                  75                  80

Pro Ile Ser Ile Asn Tyr Arg Thr Glu Ile Asp Lys Pro Ser Gln
                85                  90                  95

<210> SEQ ID NO 187
<211> LENGTH: 95
<212> TYPE: PRT
<213> ORGANISM: Artificial Sequence
<220> FEATURE:
<223> OTHER INFORMATION: binding polypeptide

<400> SEQUENCE: 187

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile

-continued

```
                    50                  55                  60
Thr Val Tyr Ala Val Thr Asp Gly Arg Asn Gly Arg Leu Leu Ser Ile
 65                  70                  75                  80

Pro Ile Ser Ile Asn Tyr Arg Thr Glu Ile Asp Lys Pro Cys Gln
                 85                  90                  95

<210> SEQ ID NO 188
<211> LENGTH: 102
<212> TYPE: PRT
<213> ORGANISM: Artificial Sequence
<220> FEATURE:
<223> OTHER INFORMATION: binding polypeptide

<400> SEQUENCE: 188

Met Val Ser Asp Val Pro Arg Asp Leu Glu Val Val Ala Ala Thr Pro
 1               5                  10                  15

Thr Ser Leu Leu Ile Ser Trp Arg His Pro His Phe Pro Thr Arg Tyr
             20                  25                  30

Tyr Arg Ile Thr Tyr Gly Glu Thr Gly Gly Asn Ser Pro Val Gln Glu
         35                  40                  45

Phe Thr Val Pro Leu Gln Pro Pro Thr Ala Thr Ile Ser Gly Leu Lys
     50                  55                  60

Pro Gly Val Asp Tyr Thr Ile Thr Val Tyr Ala Val Thr Asp Gly Arg
 65                  70                  75                  80

Asn Gly Arg Leu Leu Ser Ile Pro Ile Ser Asn Tyr Arg Thr Glu
                 85                  90                  95

Ile Asp Lys Pro Ser Gln
            100

<210> SEQ ID NO 189
<211> LENGTH: 88
<212> TYPE: PRT
<213> ORGANISM: Artificial Sequence
<220> FEATURE:
<223> OTHER INFORMATION: binding polypeptide

<400> SEQUENCE: 189

Met Gly Glu Val Val Ala Ala Thr Pro Thr Ser Leu Leu Ile Ser Trp
 1               5                  10                  15

Arg His Pro His Phe Pro Thr Arg Tyr Tyr Arg Ile Thr Tyr Gly Glu
             20                  25                  30

Thr Gly Gly Asn Ser Pro Val Gln Glu Phe Thr Val Pro Leu Gln Pro
         35                  40                  45

Pro Thr Ala Thr Ile Ser Gly Leu Lys Pro Gly Val Asp Tyr Thr Ile
     50                  55                  60

Thr Val Tyr Ala Val Thr Asp Gly Trp Asn Gly Arg Leu Leu Ser Ile
 65                  70                  75                  80

Pro Ile Ser Ile Asn Tyr Arg Thr
                 85

<210> SEQ ID NO 190
<211> LENGTH: 88
<212> TYPE: PRT
<213> ORGANISM: Artificial Sequence
<220> FEATURE:
<223> OTHER INFORMATION: binding polypeptide

<400> SEQUENCE: 190

Met Gly Glu Val Val Ala Ala Thr Pro Thr Ser Leu Leu Ile Ser Trp
 1               5                  10                  15
```

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
    50                  55                  60

Thr Val Tyr Ala Val Thr Glu Gly Pro Asn Glu Arg Ser Leu Phe Ile
65                  70                  75                  80

Pro Ile Ser Ile Asn Tyr Arg Thr
                85

<210> SEQ ID NO 191
<211> LENGTH: 95
<212> TYPE: PRT
<213> ORGANISM: Artificial Sequence
<220> FEATURE:
<223> OTHER INFORMATION: binding polypeptide

<400> SEQUENCE: 191

Met Val Ser Asp Val Pro Arg Asp Leu Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
        35                  40                  45

Phe Thr Val Pro Leu Gln Pro Pro Thr Ala Thr Ile Ser Gly Leu Lys
    50                  55                  60

Pro Gly Val Asp Tyr Thr Ile Thr Val Tyr Ala Val Thr Glu Gly Pro
65                  70                  75                  80

Asn Glu Arg Ser Leu Phe Ile Pro Ile Ser Ile Asn Tyr Arg Thr
                85                  90                  95

<210> SEQ ID NO 192
<211> LENGTH: 86
<212> TYPE: PRT
<213> ORGANISM: Artificial Sequence
<220> FEATURE:
<223> OTHER INFORMATION: binding polypeptide

<400> SEQUENCE: 192

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
    50                  55                  60

Tyr Ala Val Thr Asp Gly Arg Asn Gly Arg Leu Leu Ser Ile Pro Ile
65                  70                  75                  80

Ser Ile Asn Tyr Arg Thr
                85

<210> SEQ ID NO 193
<211> LENGTH: 94
<212> TYPE: PRT
<213> ORGANISM: Artificial Sequence
<220> FEATURE:
<223> OTHER INFORMATION: binding polypeptide

<400> SEQUENCE: 193

Val Ser Asp Val Pro Arg Asp Leu Glu Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Val Tyr Ala Val Thr Asp Gly Arg Asn
65              70                  75                  80

Gly Arg Leu Leu Ser Ile Pro Ile Ser Ile Asn Tyr Arg Thr
                85                  90

<210> SEQ ID NO 194
<211> LENGTH: 94
<212> TYPE: PRT
<213> ORGANISM: Artificial Sequence
<220> FEATURE:
<223> OTHER INFORMATION: binding polypeptide

<400> SEQUENCE: 194

Gly Glu Val Val Ala Ala Thr Pro Thr Ser Leu Leu Ile Ser Trp Arg
1               5                   10                  15

His Pro His Phe Pro Thr Arg Tyr Tyr Arg Ile Thr Tyr Gly Glu Thr
            20                  25                  30

Gly Gly Asn Ser Pro Val Gln Glu Phe Thr Val Pro Leu Gln Pro Pro
            35                  40                  45

Thr Ala Thr Ile Ser Gly Leu Lys Pro Gly Val Asp Tyr Thr Ile Thr
        50                  55                  60

Val Tyr Ala Val Thr Asp Gly Arg Asn Gly Arg Leu Leu Ser Ile Pro
65              70                  75                  80

Ile Ser Ile Asn Tyr Arg Thr Glu Ile Asp Lys Pro Cys Gln
                85                  90

<210> SEQ ID NO 195
<211> LENGTH: 94
<212> TYPE: PRT
<213> ORGANISM: Artificial Sequence
<220> FEATURE:
<223> OTHER INFORMATION: binding polypeptide

<400> SEQUENCE: 195

Gly Glu Val Val Ala Ala Thr Pro Thr Ser Leu Leu Ile Ser Trp Arg
1               5                   10                  15

His Pro His Phe Pro Thr Arg Tyr Tyr Arg Ile Thr Tyr Gly Glu Thr
            20                  25                  30

Gly Gly Asn Ser Pro Val Gln Glu Phe Thr Val Pro Leu Gln Pro Pro
            35                  40                  45

Thr Ala Thr Ile Ser Gly Leu Lys Pro Gly Val Asp Tyr Thr Ile Thr
        50                  55                  60

Val Tyr Ala Val Thr Asp Gly Arg Asn Gly Arg Leu Leu Ser Ile Pro
65              70                  75                  80

Ile Ser Ile Asn Tyr Arg Thr Glu Ile Asp Lys Pro Ser Gln
                85                  90

<210> SEQ ID NO 196

```
<211> LENGTH: 86
<212> TYPE: PRT
<213> ORGANISM: Artificial Sequence
<220> FEATURE:
<223> OTHER INFORMATION: binding polypeptide

<400> SEQUENCE: 196

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
    50                  55                  60

Tyr Ala Val Thr Glu Gly Pro Asn Glu Arg Ser Leu Phe Ile Pro Ile
65                  70                  75                  80

Ser Ile Asn Tyr Arg Thr
                85

<210> SEQ ID NO 197
<211> LENGTH: 94
<212> TYPE: PRT
<213> ORGANISM: Artificial Sequence
<220> FEATURE:
<223> OTHER INFORMATION: binding polypeptide

<400> SEQUENCE: 197

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Val Tyr Ala Val Thr Glu Gly Pro Asn
65                  70                  75                  80

Glu Arg Ser Leu Phe Ile Pro Ile Ser Ile Asn Tyr Arg Thr
                85                  90

<210> SEQ ID NO 198
<211> LENGTH: 10
<212> TYPE: PRT
<213> ORGANISM: Artificial Sequence
<220> FEATURE:
<223> OTHER INFORMATION: binding polypeptide

<400> SEQUENCE: 198

Val Ala Gln Asn Asp His Glu Leu Ile Thr
 1               5                  10

<210> SEQ ID NO 199
<211> LENGTH: 109
<212> TYPE: PRT
<213> ORGANISM: Artificial Sequence
<220> FEATURE:
<223> OTHER INFORMATION: binding polypeptide

<400> SEQUENCE: 199

Met Gly Val Ser Asp Val Pro Arg Asp Leu Glu Val Val Ala Ala Thr
 1               5                  10                  15
```

Pro Thr Ser Leu Leu Ile Ser Trp Arg His Pro His Phe Pro Thr Arg
        20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Leu Ala Thr Ile Ser Gly Leu
        50                  55                  60

Lys Pro Gly Val Asp Tyr Thr Ile Thr Val Tyr Ala Val Thr Lys Glu
 65                  70                  75                  80

Arg Asn Gly Arg Glu Leu Phe Thr Pro Ile Ser Ile Asn Tyr Arg Thr
                85                  90                  95

Glu Ile Asp Lys Pro Cys Gln His His His His His
               100                 105

<210> SEQ ID NO 200
<211> LENGTH: 87
<212> TYPE: PRT
<213> ORGANISM: Artificial Sequence
<220> FEATURE:
<223> OTHER INFORMATION: binding polypeptide

<400> SEQUENCE: 200

Gly Glu Val Val Ala Ala Thr Pro Thr Ser Leu Leu Ile Ser Trp Arg
 1               5                  10                  15

His Pro His Phe Pro Thr Arg Tyr Tyr Arg Ile Thr Tyr Gly Glu Thr
                20                  25                  30

Gly Gly Asn Ser Pro Val Gln Glu Phe Thr Val Pro Leu Gln Pro Pro
        35                  40                  45

Thr Ala Thr Ile Ser Gly Leu Lys Pro Gly Val Asp Tyr Thr Ile Thr
        50                  55                  60

Val Tyr Ala Val Thr Asp Gly Trp Asn Gly Arg Leu Leu Ser Ile Pro
 65                  70                  75                  80

Ile Ser Ile Asn Tyr Arg Thr
                85

<210> SEQ ID NO 201
<211> LENGTH: 66
<212> TYPE: DNA
<213> ORGANISM: Artificial Sequence
<220> FEATURE:
<223> OTHER INFORMATION: binding polypeptide

<400> SEQUENCE: 201
gcgtaatacg actcactata gggacaatta ctatttacaa ttacaatggt ttctgatgtt      60
ccgagg                                                                66

<210> SEQ ID NO 202
<211> LENGTH: 78
<212> TYPE: DNA
<213> ORGANISM: Artificial Sequence
<220> FEATURE:
<223> OTHER INFORMATION: binding polypeptide

<400> SEQUENCE: 202
gcgtaatacg actcactata gggacaatta ctatttacaa ttacaatgga agttgttgct      60
gcgaccccca ccagccta                                                   78

<210> SEQ ID NO 203
<211> LENGTH: 57
<212> TYPE: DNA

<213> ORGANISM: Artificial Sequence
<220> FEATURE:
<223> OTHER INFORMATION: binding polypeptide

<400> SEQUENCE: 203
tttttttttt tttttttttt aaatagcgga tgccttgtcg tcgtcgtcct tgtagtc      57

<210> SEQ ID NO 204
<211> LENGTH: 69
<212> TYPE: DNA
<213> ORGANISM: Artificial Sequence
<220> FEATURE:
<223> OTHER INFORMATION: binding polypeptide

<400> SEQUENCE: 204
atggtttctg atgttccgag ggacctggaa gttgttgctg cgaccccac cagcctactg      60 atcagctgg                                                             69

<210> SEQ ID NO 205
<211> LENGTH: 66
<212> TYPE: DNA
<213> ORGANISM: Artificial Sequence
<220> FEATURE:
<223> OTHER INFORMATION: binding polypeptide

<400> SEQUENCE: 205
aggcacagtg aactcctgga cagggctatt tcctcctgtt tctccgtaag tgatcctgta     60
atatct                                                                66

<210> SEQ ID NO 206
<211> LENGTH: 66
<212> TYPE: DNA
<213> ORGANISM: Artificial Sequence
<220> FEATURE:
<223> OTHER INFORMATION: binding polypeptide

<400> SEQUENCE: 206
agatattaca ggatcactta cggagaaaca ggaggaaata gccctgtcca ggagttcact     60
gtgcct                                                                66

<210> SEQ ID NO 207
<211> LENGTH: 63
<212> TYPE: DNA
<213> ORGANISM: Artificial Sequence
<220> FEATURE:
<223> OTHER INFORMATION: binding polypeptide

<400> SEQUENCE: 207
agtgacagca tacacagtga tggtataatc aactccaggt ttaaggccgc tgatggtagc     60
tgt                                                                   63

<210> SEQ ID NO 208
<211> LENGTH: 63
<212> TYPE: DNA
<213> ORGANISM: Artificial Sequence
<220> FEATURE:
<223> OTHER INFORMATION: binding polypeptide

<400> SEQUENCE: 208
acagctacca tcagcggcct taaacctgga gttgattata ccatcactgt gtatgctgtc     60
act                                                                   63

<210> SEQ ID NO 209
<211> LENGTH: 77
<212> TYPE: DNA
<213> ORGANISM: Artificial Sequence
<220> FEATURE:
<223> OTHER INFORMATION: binding polypeptide

<400> SEQUENCE: 209

```
tttttttttt tttttttta aatagcggat gccttgtcgt cgtcgtcctt gtagtctgtt      60
cggtaattaa tggaaat                                                    77
```

<210> SEQ ID NO 210
<211> LENGTH: 58
<212> TYPE: DNA
<213> ORGANISM: Artificial Sequence
<220> FEATURE:
<223> OTHER INFORMATION: binding polypeptide

<400> SEQUENCE: 210

```
ttttaaatag cggatgcctt gtcgtcgtcg tccttgtagt ctgttcggta attaatgg       58
```

<210> SEQ ID NO 211
<211> LENGTH: 30
<212> TYPE: DNA
<213> ORGANISM: Artificial Sequence
<220> FEATURE:
<223> OTHER INFORMATION: binding polypeptide

<400> SEQUENCE: 211

```
gtgtatgctg tcactatttc cattaattac                                      30
```

<210> SEQ ID NO 212
<211> LENGTH: 68
<212> TYPE: DNA
<213> ORGANISM: Artificial Sequence
<220> FEATURE:
<223> OTHER INFORMATION: binding polypeptide

<400> SEQUENCE: 212

```
taatacgact cactataggg acaattacta tttacaattc tatcaataca atggtgtctg     60
atgtgccg                                                              68
```

<210> SEQ ID NO 213
<211> LENGTH: 72
<212> TYPE: DNA
<213> ORGANISM: Artificial Sequence
<220> FEATURE:
<223> OTHER INFORMATION: binding polypeptide

<400> SEQUENCE: 213

```
ccaggagatc agcagggagg tcggggtggc agccaccact tccaggtcgc gcggcacatc     60
agacaccatt gt                                                         72
```

<210> SEQ ID NO 214
<211> LENGTH: 64
<212> TYPE: DNA
<213> ORGANISM: Artificial Sequence
<220> FEATURE:
<223> OTHER INFORMATION: binding polypeptide

<400> SEQUENCE: 214

```
acctccctgc tgatctcctg gcgccatccg cattttccga cccgctatta ccgcatcact     60
tacg                                                                  64
```

<210> SEQ ID NO 215
<211> LENGTH: 63
<212> TYPE: DNA
<213> ORGANISM: Artificial Sequence
<220> FEATURE:
<223> OTHER INFORMATION: binding polypeptide

<400> SEQUENCE: 215
cacagtgaac tcctggaccg ggctattgcc tcctgtttcg ccgtaagtga tgcggtaata    60
gcg                                                                 63

<210> SEQ ID NO 216
<211> LENGTH: 61
<212> TYPE: DNA
<213> ORGANISM: Artificial Sequence
<220> FEATURE:
<223> OTHER INFORMATION: binding polypeptide

<400> SEQUENCE: 216
cggtccagga gttcactgtg ccgctgcagc cgccggcggc taccatcagc ggccttaaac    60
c                                                                   61

<210> SEQ ID NO 217
<211> LENGTH: 61
<212> TYPE: DNA
<213> ORGANISM: Artificial Sequence
<220> FEATURE:
<223> OTHER INFORMATION: binding polypeptide
<220> FEATURE:
<221> NAME/KEY: misc_feature
<222> LOCATION: 24, 25, 27, 28, 30, 31, 33, 34, 36, 37
<223> OTHER INFORMATION: n = A,T,C or G

<400> SEQUENCE: 217
cggtccagga gttcactgtg ccgnnsnnsn nsnnsnnsgc taccatcagc ggccttaaac    60
c                                                                   61

<210> SEQ ID NO 218
<211> LENGTH: 59
<212> TYPE: DNA
<213> ORGANISM: Artificial Sequence
<220> FEATURE:
<223> OTHER INFORMATION: binding polypeptide

<400> SEQUENCE: 218
agtgacagca tacacagtga tggtataatc aacgccaggt ttaaggccgc tgatggtag     59

<210> SEQ ID NO 219
<211> LENGTH: 87
<212> TYPE: DNA
<213> ORGANISM: Artificial Sequence
<220> FEATURE:
<223> OTHER INFORMATION: binding polypeptide
<220> FEATURE:
<221> NAME/KEY: misc_feature
<222> LOCATION: 25, 26, 28, 29, 31, 32, 34, 35, 37, 38, 40, 41
<223> OTHER INFORMATION: n = A,T,C or G

<400> SEQUENCE: 219
accatcactg tgtatgctgt cactnnsnns nnsnnsnnsn nsgaactgtt taccccaatt    60
tccatcaact accgcacaga ctacaag                                       87

<210> SEQ ID NO 220
<211> LENGTH: 97

<212> TYPE: DNA
<213> ORGANISM: Artificial Sequence
<220> FEATURE:
<223> OTHER INFORMATION: binding polypeptide

<400> SEQUENCE: 220
aaatagcgga tgcgcgtttg ttctgatctt ccttatttat gtgatgatgg tggtgatgct    60
tgtcgtcgtc gtccttgtag tctgtgcggt agttgat    97

<210> SEQ ID NO 221
<211> LENGTH: 51
<212> TYPE: DNA
<213> ORGANISM: Artificial Sequence
<220> FEATURE:
<223> OTHER INFORMATION: binding polypeptide

<400> SEQUENCE: 221
tttttttttt tttttttttt aaatagcgga tgcgcgtttg ttctgatctt c    51

<210> SEQ ID NO 222
<211> LENGTH: 21
<212> TYPE: DNA
<213> ORGANISM: Artificial Sequence
<220> FEATURE:
<223> OTHER INFORMATION: binding polypeptide

<400> SEQUENCE: 222
gcgcgtttgt tctgatcttc c    21

<210> SEQ ID NO 223
<211> LENGTH: 73
<212> TYPE: DNA
<213> ORGANISM: Artificial Sequence
<220> FEATURE:
<223> OTHER INFORMATION: binding polypeptide
<220> FEATURE:
<221> NAME/KEY: misc_feature
<222> LOCATION: 39, 40, 42, 43, 45, 46, 48, 49, 51, 52, 54, 55, 57, 58
<223> OTHER INFORMATION: n = A,T,C or G

<400> SEQUENCE: 223
tgcctcctgt ttcgccgtaa gtgatgcggt aatagcgsnn snnsnnsnns nnsnnsnncc    60
agctgatcag cag    73

<210> SEQ ID NO 224
<211> LENGTH: 69
<212> TYPE: DNA
<213> ORGANISM: Artificial Sequence
<220> FEATURE:
<223> OTHER INFORMATION: binding polypeptide
<220> FEATURE:
<221> NAME/KEY: misc_feature
<222> LOCATION: 14, 15, 17, 18, 20, 21, 23, 24
<223> OTHER INFORMATION: n = A,T,C or G

<400> SEQUENCE: 224
gatggtagct gtsnnsnnsn nsnnaggcac agtgaactcc tggacagggc tattgcctcc    60
tgtttcgcc    69

<210> SEQ ID NO 225
<211> LENGTH: 68
<212> TYPE: DNA
<213> ORGANISM: Artificial Sequence
<220> FEATURE:
<223> OTHER INFORMATION: binding polypeptide
<220> FEATURE:

```
<221> NAME/KEY: misc_feature
<222> LOCATION: 25, 26, 28, 29, 31, 32, 34, 35, 37, 38, 40, 41, 43, 44,
      46, 47, 49, 50, 52, 53
<223> OTHER INFORMATION: n = A,T,C or G

<400> SEQUENCE: 225
gtgcggtaat taatggaaat tggsnnsnns nnsnnsnnsn nsnnsnnsnn snnagtgaca    60
gcatacac                                                            68

<210> SEQ ID NO 226
<211> LENGTH: 21
<212> TYPE: DNA
<213> ORGANISM: Artificial Sequence
<220> FEATURE:
<223> OTHER INFORMATION: binding polypeptide

<400> SEQUENCE: 226
cctcctgttt ctccgtaagt g                                             21

<210> SEQ ID NO 227
<211> LENGTH: 21
<212> TYPE: DNA
<213> ORGANISM: Artificial Sequence
<220> FEATURE:
<223> OTHER INFORMATION: binding polypeptide

<400> SEQUENCE: 227
cacttacgga gaaacaggag g                                             21

<210> SEQ ID NO 228
<211> LENGTH: 63
<212> TYPE: DNA
<213> ORGANISM: Artificial Sequence
<220> FEATURE:
<223> OTHER INFORMATION: binding polypeptide

<400> SEQUENCE: 228
acagctacca tcagcggcct taaacctggc gttgattata ccatcactgt gtatgctgtc    60
act                                                                 63

<210> SEQ ID NO 229
<211> LENGTH: 18
<212> TYPE: DNA
<213> ORGANISM: Artificial Sequence
<220> FEATURE:
<223> OTHER INFORMATION: binding polypeptide

<400> SEQUENCE: 229
agtgacagca tacacagt                                                 18

<210> SEQ ID NO 230
<211> LENGTH: 75
<212> TYPE: DNA
<213> ORGANISM: Artificial Sequence
<220> FEATURE:
<223> OTHER INFORMATION: binding polypeptide

<400> SEQUENCE: 230
tttttttttt tttttttttt aaatagcgga tgccttgtcg tcgtcgtcct tgtagtctgt    60
gcggtaatta atgga                                                    75

<210> SEQ ID NO 231
<211> LENGTH: 28
<212> TYPE: DNA
```

```
<213> ORGANISM: Artificial Sequence
<220> FEATURE:
<223> OTHER INFORMATION: binding polypeptide

<400> SEQUENCE: 231
tagagaattc atggagagca aggtgctg                                      28

<210> SEQ ID NO 232
<211> LENGTH: 39
<212> TYPE: DNA
<213> ORGANISM: Artificial Sequence
<220> FEATURE:
<223> OTHER INFORMATION: binding polypeptide

<400> SEQUENCE: 232
agggagagcg tcaggatgag ttccaagttc gtcttttcc                          39

<210> SEQ ID NO 233
<211> LENGTH: 28
<212> TYPE: DNA
<213> ORGANISM: Artificial Sequence
<220> FEATURE:
<223> OTHER INFORMATION: binding polypeptide

<400> SEQUENCE: 233
tagagaattc atggagagca aggcgctg                                      28

<210> SEQ ID NO 234
<211> LENGTH: 39
<212> TYPE: DNA
<213> ORGANISM: Artificial Sequence
<220> FEATURE:
<223> OTHER INFORMATION: binding polypeptide

<400> SEQUENCE: 234
agggagagcg tcaggatgag ttccaagttg gtcttttcc                          39

<210> SEQ ID NO 235
<211> LENGTH: 32
<212> TYPE: DNA
<213> ORGANISM: Artificial Sequence
<220> FEATURE:
<223> OTHER INFORMATION: binding polypeptide

<400> SEQUENCE: 235
tagagaattc atgatgtcgt cctggataag gt                                 32

<210> SEQ ID NO 236
<211> LENGTH: 39
<212> TYPE: DNA
<213> ORGANISM: Artificial Sequence
<220> FEATURE:
<223> OTHER INFORMATION: binding polypeptide

<400> SEQUENCE: 236
agggagagcg tcaggatgag atgttcccga ccggtttta                          39

<210> SEQ ID NO 237
<211> LENGTH: 39
<212> TYPE: DNA
<213> ORGANISM: Artificial Sequence
<220> FEATURE:
<223> OTHER INFORMATION: binding polypeptide

<400> SEQUENCE: 237
ggaaaagacg aacttggaac tcatcctgac gctctccct                          39
```

<210> SEQ ID NO 238
<211> LENGTH: 39
<212> TYPE: DNA
<213> ORGANISM: Artificial Sequence
<220> FEATURE:
<223> OTHER INFORMATION: binding polypeptide

<400> SEQUENCE: 238
ggaaaagacc aacttggaac tcatcctgac gctctccct                                      39

<210> SEQ ID NO 239
<211> LENGTH: 31
<212> TYPE: DNA
<213> ORGANISM: Artificial Sequence
<220> FEATURE:
<223> OTHER INFORMATION: binding polypeptide

<400> SEQUENCE: 239
tagactcgag tcaagagcaa gccacatagc t                                              31

<210> SEQ ID NO 240
<211> LENGTH: 39
<212> TYPE: DNA
<213> ORGANISM: Artificial Sequence
<220> FEATURE:
<223> OTHER INFORMATION: binding polypeptide

<400> SEQUENCE: 240
taaaaccggt cgggaacatc tcatcctgac gctctccct                                      39

<210> SEQ ID NO 241
<211> LENGTH: 126
<212> TYPE: PRT
<213> ORGANISM: Artificial Sequence
<220> FEATURE:
<223> OTHER INFORMATION: binding polypeptide

<400> SEQUENCE: 241

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 242
<211> LENGTH: 126
<212> TYPE: PRT
<213> ORGANISM: Artificial Sequence
<220> FEATURE:
<223> OTHER INFORMATION: binding polypeptide

```
<400> SEQUENCE: 242

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Leu Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 243
<211> LENGTH: 126
<212> TYPE: PRT
<213> ORGANISM: Artificial Sequence
<220> FEATURE:
<223> OTHER INFORMATION: binding polypeptide

<400> SEQUENCE: 243

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Leu Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 244
<211> LENGTH: 126
<212> TYPE: PRT
<213> ORGANISM: Artificial Sequence
<220> FEATURE:
<223> OTHER INFORMATION: binding polypeptide

<400> SEQUENCE: 244

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45
```

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Ala Tyr Tyr Cys Ala Thr Ile Val Ala Gly Asp
                85                  90                  95

His Tyr Phe Asp His Trp Gly Gln Gly Thr Lys Val Glu Ile Ile Ala
            100                 105                 110

Asp Gly Ser Asp Tyr Lys Asp Asp Asp Lys Ala Ser Ala
        115                 120                 125

<210> SEQ ID NO 245
<211> LENGTH: 126
<212> TYPE: PRT
<213> ORGANISM: Artificial Sequence
<220> FEATURE:
<223> OTHER INFORMATION: binding polypeptide

<400> SEQUENCE: 245

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asn
                20                  25                  30

Ser Val Ala Trp Tyr Arg Lys Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 246
<211> LENGTH: 126
<212> TYPE: PRT
<213> ORGANISM: Artificial Sequence
<220> FEATURE:
<223> OTHER INFORMATION: binding polypeptide

<400> SEQUENCE: 246

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asn
                20                  25                  30

Ser Val Ala Trp Tyr Arg Lys Lys Pro Gly Gln Ala Pro Arg Leu Leu
            35                  40                  45

Ile Tyr Gly Ala Ser Ser Arg Ala Ala Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

```
Asp Gly Ser Asp Tyr Lys Asp Asp Asp Lys Ala Ser Ala
        115                 120                 125

<210> SEQ ID NO 247
<211> LENGTH: 126
<212> TYPE: PRT
<213> ORGANISM: Artificial Sequence
<220> FEATURE:
<223> OTHER INFORMATION: binding polypeptide

<400> SEQUENCE: 247

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Gly Ser Asn
             20                  25                  30

Ser Val Ala Trp Tyr Arg Lys Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 248
<211> LENGTH: 126
<212> TYPE: PRT
<213> ORGANISM: Artificial Sequence
<220> FEATURE:
<223> OTHER INFORMATION: binding polypeptide

<400> SEQUENCE: 248

Ala Ile Gln Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Ser Val Ala Trp Tyr Arg Lys Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 249
<211> LENGTH: 126
<212> TYPE: PRT
<213> ORGANISM: Artificial Sequence
<220> FEATURE:
<223> OTHER INFORMATION: binding polypeptide
```

<400> SEQUENCE: 249

Ala Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
            115                 120                 125

<210> SEQ ID NO 250
<211> LENGTH: 126
<212> TYPE: PRT
<213> ORGANISM: Artificial Sequence
<220> FEATURE:
<223> OTHER INFORMATION: binding polypeptide

<400> SEQUENCE: 250

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
            115                 120                 125

<210> SEQ ID NO 251
<211> LENGTH: 126
<212> TYPE: PRT
<213> ORGANISM: Artificial Sequence
<220> FEATURE:
<223> OTHER INFORMATION: binding polypeptide

<400> SEQUENCE: 251

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
            115                 120                 125

<210> SEQ ID NO 252
<211> LENGTH: 126
<212> TYPE: PRT
<213> ORGANISM: Artificial Sequence
<220> FEATURE:
<223> OTHER INFORMATION: binding polypeptide

<400> SEQUENCE: 252

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Ser Val Ala Trp Tyr Arg Lys Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
            115                 120                 125

<210> SEQ ID NO 253
<211> LENGTH: 126
<212> TYPE: PRT
<213> ORGANISM: Artificial Sequence
<220> FEATURE:
<223> OTHER INFORMATION: binding polypeptide

<400> SEQUENCE: 253

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Ser Val Ala Trp Tyr Arg Lys Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
```

-continued

```
              100                 105                 110
Asp Gly Ser Asp Tyr Lys Asp Asp Asp Lys Ala Ser Ala
        115                 120                 125

<210> SEQ ID NO 254
<211> LENGTH: 126
<212> TYPE: PRT
<213> ORGANISM: Artificial Sequence
<220> FEATURE:
<223> OTHER INFORMATION: binding polypeptide

<400> SEQUENCE: 254

Glu Ile Val Met Thr Gln Ser Pro Gly Thr Leu Ser Leu Ser Pro Gly
1               5                   10                  15

Glu Arg Ala Thr Leu Ser Cys Arg Thr Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 255
<211> LENGTH: 126
<212> TYPE: PRT
<213> ORGANISM: Artificial Sequence
<220> FEATURE:
<223> OTHER INFORMATION: binding polypeptide

<400> SEQUENCE: 255

Glu Ile Val Met Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 256
<211> LENGTH: 126
<212> TYPE: PRT
<213> ORGANISM: Artificial Sequence
<220> FEATURE:
```

<223> OTHER INFORMATION: binding polypeptide

<400> SEQUENCE: 256

Glu Ile Val Met Thr Gln Ser Pro Ala Thr Leu Ser Val Ser Pro Gly
1               5                   10                  15

Gly Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 257
<211> LENGTH: 125
<212> TYPE: PRT
<213> ORGANISM: Artificial Sequence
<220> FEATURE:
<223> OTHER INFORMATION: binding polypeptide

<400> SEQUENCE: 257

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
        115                 120                 125

<210> SEQ ID NO 258
<211> LENGTH: 125
<212> TYPE: PRT
<213> ORGANISM: Artificial Sequence
<220> FEATURE:
<223> OTHER INFORMATION: binding polypeptide

<400> SEQUENCE: 258

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu

```
                35                  40                  45
Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95

Ser Gly Arg Asn Trp Gly Gln Gly Thr Lys Leu Glu Ile Lys Ala Asp
                100                 105                 110

Gly Ser Asp Tyr Lys Asp Asp Asp Lys Ala Ser Ala
                115                 120                 125

<210> SEQ ID NO 259
<211> LENGTH: 125
<212> TYPE: PRT
<213> ORGANISM: Artificial Sequence
<220> FEATURE:
<223> OTHER INFORMATION: binding polypeptide

<400> SEQUENCE: 259

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Ser Leu Ala Trp Tyr Arg Gln Lys Pro Gly Gln Ala Pro Arg Leu Leu
             35                  40                  45

Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95

Ser Gly Arg Asn Trp Gly Gln Gly Thr Lys Leu Glu Ile Lys Ala Asp
                100                 105                 110

Gly Ser Asp Tyr Lys Asp Asp Asp Lys Ala Ser Ala
                115                 120                 125

<210> SEQ ID NO 260
<211> LENGTH: 125
<212> TYPE: PRT
<213> ORGANISM: Artificial Sequence
<220> FEATURE:
<223> OTHER INFORMATION: binding polypeptide

<400> SEQUENCE: 260

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Ser Leu Ala Trp Tyr Arg Gln Lys Pro Gly Gln Ala Pro Arg Leu Leu
             35                  40                  45

Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95
```

-continued

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
        115                 120                 125

<210> SEQ ID NO 261
<211> LENGTH: 125
<212> TYPE: PRT
<213> ORGANISM: Artificial Sequence
<220> FEATURE:
<223> OTHER INFORMATION: binding polypeptide

<400> SEQUENCE: 261

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Ile Ala Asp
            100                 105                 110

Gly Ser Asp Tyr Lys Asp Asp Asp Lys Ala Ser Ala
        115                 120                 125

<210> SEQ ID NO 262
<211> LENGTH: 125
<212> TYPE: PRT
<213> ORGANISM: Artificial Sequence
<220> FEATURE:
<223> OTHER INFORMATION: binding polypeptide

<400> SEQUENCE: 262

Glu Ile Val Met Thr Gln Ser Pro Gly Thr Leu Ser Leu Ser Pro Gly
1               5                   10                  15

Asp Arg Ala Thr Leu Ser Cys Arg Thr Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Pro Gly Thr Asp Phe Thr Leu Thr Val Ser Arg Leu Glu
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Val Glu Ile Lys Ala Asp
            100                 105                 110

Gly Ser Asp Tyr Lys Asp Asp Asp Lys Ala Ser Ala
        115                 120                 125

<210> SEQ ID NO 263
<211> LENGTH: 121
<212> TYPE: PRT
<213> ORGANISM: Artificial Sequence

```
<220> FEATURE:
<223> OTHER INFORMATION: binding polypeptide

<400> SEQUENCE: 263

Glu Ile Val Met Thr Gln Ser Pro Gly Thr Leu Ser Val Ser Pro Gly
 1               5                  10                  15

Gly Arg Ala Ser Leu Pro Cys Arg Ala Ser Gln Thr Val Thr Asn Asn
                20                  25                  30

Tyr Leu Ala Trp Tyr Gln Gln Lys Ser Gly Gln Ala Pro Arg Leu Leu
            35                  40                  45

Ile Phe Gly Ala Ser Asn Arg Ala Thr Gly Ile Pro Glu Arg Phe Ser
        50                  55                  60

Gly Ser Gly Ser Gly Thr Asp Phe Thr Leu Ile Ile Ser Arg Leu Glu
65                  70                  75                  80

Ala Glu Asp Phe Ala Val Tyr Tyr Cys Val Ser Leu Lys Gly Arg Asp
                85                  90                  95

Trp Gly Gln Gly Thr Lys Leu Glu Ile Lys Ala Asp Gly Ser Asp Tyr
            100                 105                 110

Lys Asp Asp Asp Asp Lys Ala Ser Ala
        115                 120

<210> SEQ ID NO 264
<211> LENGTH: 126
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 123
<223> OTHER INFORMATION: Xaa = Any Amino Acid

<400> SEQUENCE: 264

Glu Ile Gly Met Thr Gln Ser Pro Ala Thr Leu Ser Val Ser Pro Gly
 1               5                  10                  15

Lys Arg Ala Thr Leu Ser Cys Arg Ala Ser Gln Ser Val Gly Ile Lys
                20                  25                  30

Leu Ala Gly Tyr Gln Gln Lys Leu Gly Gln Ala Pro Arg Leu Leu Ile
            35                  40                  45

Tyr Glu Ala Ser Thr Arg Ala Thr Gly Val Pro Thr Arg Phe Asn Gly
        50                  55                  60

Ser Gly Ser Gly Thr Glu Phe Thr Leu Thr Ile Asn Ser Leu Gln Ser
65                  70                  75                  80

Glu Asp Phe Ala Val Tyr Tyr Cys Thr Gly Thr Gly Asn Tyr Tyr
                85                  90                  95

Gly Trp Phe Asp Pro Trp Gly Gln Gly Thr Lys Leu Glu Ile Lys Ala
            100                 105                 110

Tyr Gly Ser Asp Tyr Glu Asp Asp Asp Xaa Ala Ser Ala
        115                 120                 125

<210> SEQ ID NO 265
<211> LENGTH: 123
<212> TYPE: PRT
<213> ORGANISM: Artificial Sequence
<220> FEATURE:
<223> OTHER INFORMATION: binding polypeptide

<400> SEQUENCE: 265

Glu Ile Val Leu Thr Gln Ser Pro Asp Phe Gln Ser Val Thr Pro Lys
 1               5                  10                  15
```

```
Lys Lys Val Thr Ile Thr Cys Arg Ala Ser Gln Ser Ile Val Thr Ser
                20                  25                  30

Leu His Trp Tyr Gln Gln Lys Pro Gly Gln Ala Pro Ser Leu Leu Ile
            35                  40                  45

Tyr Gly Ala Ser Asn Arg Ala Thr Gly Ile Pro Ala Arg Phe Ser Gly
        50                  55                  60

Cys Gly Ser Gly Thr Glu Phe Thr Leu Thr Ile Ser Gly Leu Gln Pro
65                  70                  75                  80

Glu Asp Ala Ala Val Tyr Tyr Cys Ala Gly Asp Phe Gly Gly Gln Leu
                85                  90                  95

Pro Tyr Trp Gly Gln Gly Thr Lys Leu Glu Ile Lys Ala Asp Gly Ser
            100                 105                 110

Asp Tyr Lys Asp Asp Asp Lys Ala Ser Ala
        115                 120

<210> SEQ ID NO 266
<211> LENGTH: 128
<212> TYPE: PRT
<213> ORGANISM: Artificial Sequence
<220> FEATURE:
<223> OTHER INFORMATION: binding polypeptide

<400> SEQUENCE: 266

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Phe Trp Tyr Gln Gln His Pro Gly Lys Ala Pro Lys Val
            35                  40                  45

Met Ile Tyr Glu Asp Thr Glu Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Val Tyr Tyr Cys Ala Arg Arg Asn Tyr Gly
                85                  90                  95

Ser Gly Ser Trp Ile Asp Tyr Trp Gly Gln Gly Thr Lys Leu Thr Val
            100                 105                 110

Leu Ala Asp Gly Ser Asp Tyr Lys Asp Asp Asp Lys Ala Ser Ala
        115                 120                 125

<210> SEQ ID NO 267
<211> LENGTH: 126
<212> TYPE: PRT
<213> ORGANISM: Artificial Sequence
<220> FEATURE:
<223> OTHER INFORMATION: binding polypeptide

<400> SEQUENCE: 267

Ala Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Arg Thr Lys
                20                  25                  30

Leu Ala Trp Tyr Gln Gln Lys Pro Gly Gln Ser Pro Arg Leu Leu Ile
            35                  40                  45

Tyr Asp Ala Ser Thr Arg Ala Thr Gly Val Pro Ala Arg Phe Ser Gly
        50                  55                  60

Ser Gly Ser Gly Thr Glu Phe Thr Leu Thr Ile Ser Ser Leu Gln Ser
```

```
             65                  70                  75                  80
Glu Asp Phe Ala Val Tyr Tyr Cys Thr Gly Gly Thr Gly Asn Tyr Tyr
                    85                  90                  95

Gly Trp Phe Asp Pro Trp Gly Gln Gly Thr Lys Val Arg Ser Lys Gln
                100                 105                 110

Met Ala Ala Thr Thr Arg Thr Thr Thr Arg His Pro Leu
                115                 120                 125

<210> SEQ ID NO 268
<211> LENGTH: 127
<212> TYPE: PRT
<213> ORGANISM: Artificial Sequence
<220> FEATURE:
<223> OTHER INFORMATION: binding polypeptide

<400> SEQUENCE: 268

Gln Ser Val Leu Thr Gln Pro Pro Ser Val Ser Gly Ala Pro Gly Gln
  1               5                  10                  15

Arg Val Thr Ile Ser Cys Thr Gly Ser Ser Asn Ile Gly Ala Gly
                 20                  25                  30

Tyr Asp Val His Trp Tyr Gln Gln Leu Pro Gly Thr Ala Pro Lys Leu
                 35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Val Tyr Tyr Cys Ala Ser Ala Ile Pro Gly
                 85                  90                  95

Thr Arg Ile Leu Arg Asp Trp Gly Gln Gly Thr Lys Leu Thr Val Leu
                100                 105                 110

Ala Asp Gly Ser Asp Tyr Arg Thr Thr Thr Arg His Pro Leu
                115                 120                 125

<210> SEQ ID NO 269
<211> LENGTH: 123
<212> TYPE: PRT
<213> ORGANISM: Artificial Sequence
<220> FEATURE:
<223> OTHER INFORMATION: binding polypeptide

<400> SEQUENCE: 269

Glu Ile Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Arg Pro Gly Gln Ala Pro Arg Leu Leu Ile
                 35                  40                  45

Tyr Gly Ala Ser Ile Arg Ala Thr Gly Ile Pro Asp Arg Phe Ser Gly
     50                  55                  60

Ser Glu Ser Gly Thr Asp Phe Thr Leu Thr Ile Ser Arg Leu Glu Pro
 65                  70                  75                  80

Glu Asp Phe Ala Val Tyr Tyr Cys Ala Thr Glu Phe Arg Gly Tyr Ala
                 85                  90                  95

Gly Tyr Trp Gly Gln Gly Thr Lys Leu Glu Ile Lys Ala Asp Gly Ser
                100                 105                 110

Asp Tyr Lys Asp Asp Asp Lys Ala Ser Ala
                115                 120
```

<210> SEQ ID NO 270
<211> LENGTH: 125
<212> TYPE: PRT
<213> ORGANISM: Artificial Sequence
<220> FEATURE:
<223> OTHER INFORMATION: binding polypeptide

<400> SEQUENCE: 270

```
Glu Ile Val Met Thr Gln Ser Pro Gly Thr Leu Ser Leu Ser Pro Gly
 1               5                  10                  15

Arg Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
        115                 120             125
```

<210> SEQ ID NO 271
<211> LENGTH: 125
<212> TYPE: PRT
<213> ORGANISM: Artificial Sequence
<220> FEATURE:
<223> OTHER INFORMATION: binding polypeptide

<400> SEQUENCE: 271

```
Gly Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
        115                 120             125
```

<210> SEQ ID NO 272
<211> LENGTH: 125
<212> TYPE: PRT
<213> ORGANISM: Artificial Sequence
<220> FEATURE:
<223> OTHER INFORMATION: binding polypeptide

<400> SEQUENCE: 272

```
Glu Ile Val Met Thr Gln Ser Pro Gly Thr Leu Ser Leu Ser Pro Gly
```

```
                1               5                   10                  15
Glu Arg Ala Thr Leu Ser Cys Arg Ala Ser Gln Ser Ile Ser Ser Ser
                    20                  25                  30

Ser Leu Ala Trp Tyr Arg Gln Lys Pro Gly Gln Ala Pro Arg Leu Leu
                    35                  40                  45

Ile Tyr Gly Ala Ser Thr Arg Ala Thr Gly Ile Pro Asp Arg Phe Ser
            50                  55                  60

Gly Ser Gly Ser Gly Thr Asp Phe Ser Leu Thr Ile Ser Ser Leu Gln
65                  70                  75                  80

Pro Glu Asp Ala Ala Val Tyr Tyr Cys Ala Lys Leu Thr Tyr Tyr Gly
                    85                  90                  95

Ser Gly Arg Asn Trp Gly Gln Gly Thr Lys Leu Glu Ile Lys Ala Asp
                100                 105                 110

Gly Ser Asp Tyr Lys Asp Asp Asp Asp Lys Ala Ser Ala
            115                 120                 125
```

<210> SEQ ID NO 273
<211> LENGTH: 126
<212> TYPE: PRT
<213> ORGANISM: Artificial Sequence
<220> FEATURE:
<223> OTHER INFORMATION: binding polypeptide

<400> SEQUENCE: 273

```
Glu Ile Val Met Thr Gln Ser Pro Gly Ala Leu Ser Leu Ser Pro Gly
1               5                   10                  15

Glu Gly Ala Thr Leu Ser Cys Arg Ala Ser Gln Ser Val Ser Ser Asn
                    20                  25                  30

Ser Val Ala Trp Tyr Arg Lys Lys Pro Gly Gln Ala Pro Arg Leu Leu
                    35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                    85                  90                  95

His Tyr Phe Asp His Trp Gly Gln Gly Thr Lys Val Glu Ile Lys Glu
                100                 105                 110

Asp Gly Ser Asp Tyr Lys Asp Asp Asp Asp Lys Ala Ser Ala
            115                 120                 125
```

<210> SEQ ID NO 274
<211> LENGTH: 126
<212> TYPE: PRT
<213> ORGANISM: Artificial Sequence
<220> FEATURE:
<223> OTHER INFORMATION: binding polypeptide

<400> SEQUENCE: 274

```
Glu Ile Val Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
                    20                  25                  30

Ser Val Ala Trp Tyr Arg Lys Lys Pro Gly Gln Ala Pro Arg Leu Leu
                    35                  40                  45

Ile Tyr Gly Ala Ser Ser Arg Ala Thr Gly Ile Pro Asp Arg Phe Ser
            50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125
```

<210> SEQ ID NO 275
<211> LENGTH: 126
<212> TYPE: PRT
<213> ORGANISM: Artificial Sequence
<220> FEATURE:
<223> OTHER INFORMATION: binding polypeptide

<400> SEQUENCE: 275

```
Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Ser Val Ala Trp Tyr Arg Lys Lys Pro Gly Leu Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125
```

<210> SEQ ID NO 276
<211> LENGTH: 126
<212> TYPE: PRT
<213> ORGANISM: Artificial Sequence
<220> FEATURE:
<223> OTHER INFORMATION: binding polypeptide

<400> SEQUENCE: 276

```
Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Ser Val Ala Trp Tyr Arg Lys Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125
```

<210> SEQ ID NO 277
<211> LENGTH: 126
<212> TYPE: PRT
<213> ORGANISM: Artificial Sequence
<220> FEATURE:
<223> OTHER INFORMATION: binding polypeptide

<400> SEQUENCE: 277

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Ser Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Ile Ala
            100                 105                 110

Asp Gly Ser Asp Tyr Lys Asp Asp Asp Lys Ala Ser Ala
        115                 120                 125
```

<210> SEQ ID NO 278
<211> LENGTH: 126
<212> TYPE: PRT
<213> ORGANISM: Artificial Sequence
<220> FEATURE:
<223> OTHER INFORMATION: binding polypeptide

<400> SEQUENCE: 278

```
Ala Ile Gln Met Thr Gln Ser Pro Gly Thr Leu Ser Leu Ser Pro Gly
1               5                   10                  15

Gly Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125
```

<210> SEQ ID NO 279
<211> LENGTH: 126
<212> TYPE: PRT
<213> ORGANISM: Artificial Sequence
<220> FEATURE:
<223> OTHER INFORMATION: binding polypeptide

<400> SEQUENCE: 279

```
Lys Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Ser Val Ala Trp Tyr Arg Lys Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
                100                 105                 110

Asp Gly Ser Asp Tyr Lys Asp Asp Asp Lys Ala Ser Ala
            115                 120                 125
```

<210> SEQ ID NO 280
<211> LENGTH: 126
<212> TYPE: PRT
<213> ORGANISM: Artificial Sequence
<220> FEATURE:
<223> OTHER INFORMATION: binding polypeptide

<400> SEQUENCE: 280

```
Asp Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Ser Val Ala Trp Tyr Arg Lys Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
                100                 105                 110

Asp Gly Ser Asp Tyr Lys Asp Asp Asp Lys Ala Ser Ala
            115                 120                 125
```

<210> SEQ ID NO 281
<211> LENGTH: 126
<212> TYPE: PRT
<213> ORGANISM: Artificial Sequence
<220> FEATURE:
<223> OTHER INFORMATION: binding polypeptide

<400> SEQUENCE: 281

```
Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Ser Val Ala Trp Tyr Arg Lys Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
                100                 105                 110

Asp Gly Ser Asp Tyr Lys Asp Asp Asp Lys Ala Ser Ala
            115                 120                 125

<210> SEQ ID NO 282
<211> LENGTH: 126
<212> TYPE: PRT
<213> ORGANISM: Artificial Sequence
<220> FEATURE:
<223> OTHER INFORMATION: binding polypeptide

<400> SEQUENCE: 282

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Ser Val Ala Trp Tyr Arg Lys Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
                100                 105                 110

Asp Gly Ser Asp Tyr Lys Asp Asp Asp Lys Ala Ser Ala
            115                 120                 125

<210> SEQ ID NO 283
<211> LENGTH: 126
<212> TYPE: PRT
<213> ORGANISM: Artificial Sequence
<220> FEATURE:
<223> OTHER INFORMATION: binding polypeptide

<400> SEQUENCE: 283

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Ser Val Ala Trp Tyr Arg Lys Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Ala Thr Ile Val Ala Gly Asp
                 85                  90                  95

His Tyr Phe Asp His Trp Gly Gln Gly Thr Lys Val Glu Ile Lys Ala
                100                 105                 110

Asp Gly Ser Asp Tyr Lys Asp Asp Asp Lys Ala Ser Ala
```

```
            115                 120                 125

<210> SEQ ID NO 284
<211> LENGTH: 126
<212> TYPE: PRT
<213> ORGANISM: Artificial Sequence
<220> FEATURE:
<223> OTHER INFORMATION: binding polypeptide

<400> SEQUENCE: 284

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 285
<211> LENGTH: 126
<212> TYPE: PRT
<213> ORGANISM: Artificial Sequence
<220> FEATURE:
<223> OTHER INFORMATION: binding polypeptide

<400> SEQUENCE: 285

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
            20                  25                  30

Ser Val Ala Trp Tyr Arg Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Ala Thr Ile Val Ala Gly Asp
                85                  90                  95

His Tyr Phe Asp His Trp Gly Gln Gly Thr Lys Val Glu Ile Lys Ala
            100                 105                 110

Asp Gly Ser Asp Tyr Lys Asp Asp Asp Lys Ala Ser Ala
        115                 120                 125

<210> SEQ ID NO 286
<211> LENGTH: 125
<212> TYPE: PRT
<213> ORGANISM: Artificial Sequence
<220> FEATURE:
<223> OTHER INFORMATION: binding polypeptide

<400> SEQUENCE: 286
```

-continued

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
            35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
            115                 120                 125

<210> SEQ ID NO 287
<211> LENGTH: 125
<212> TYPE: PRT
<213> ORGANISM: Artificial Sequence
<220> FEATURE:
<223> OTHER INFORMATION: binding polypeptide

<400> SEQUENCE: 287

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
            35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
                85                  90                  95

Ser Gly Arg Asn Trp Gly Gln Gly Thr Lys Leu Glu Ile Lys Ala Asp
            100                 105                 110

Gly Ser Asp Tyr Lys Asp Asp Asp Lys Ala Ser Ala
            115                 120                 125

<210> SEQ ID NO 288
<211> LENGTH: 125
<212> TYPE: PRT
<213> ORGANISM: Artificial Sequence
<220> FEATURE:
<223> OTHER INFORMATION: binding polypeptide

<400> SEQUENCE: 288

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
            35                  40                  45

Ile Tyr Gly Ala Ser Asn Arg Ala Thr Gly Ile Pro Asp Arg Phe Ser

```
                50                  55                  60
Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95

Ser Gly Arg Asn Trp Gly Gln Gly Thr Lys Leu Glu Ile Lys Ala Asp
                100                 105                 110

Gly Ser Asp Tyr Lys Asp Asp Asp Lys Ala Ser Ala
            115                 120                 125

<210> SEQ ID NO 289
<211> LENGTH: 125
<212> TYPE: PRT
<213> ORGANISM: Artificial Sequence
<220> FEATURE:
<223> OTHER INFORMATION: binding polypeptide

<400> SEQUENCE: 289

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Ser Leu Ala Trp Tyr Arg Gln Lys Pro Gly Gln Ala Pro Arg Leu Leu
             35                  40                  45

Ile Tyr Gly Ala Ser Asn Arg Ala Thr Gly Ile Pro Asp Arg Phe Ser
         50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95

Ser Gly Arg Asn Trp Gly Gln Gly Thr Lys Leu Glu Ile Lys Glu Asp
                100                 105                 110

Gly Ser Asp Tyr Lys Asp Asp Asp Lys Ala Ser Ala
            115                 120                 125

<210> SEQ ID NO 290
<211> LENGTH: 125
<212> TYPE: PRT
<213> ORGANISM: Artificial Sequence
<220> FEATURE:
<223> OTHER INFORMATION: binding polypeptide

<400> SEQUENCE: 290

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Ser Leu Ala Trp Tyr Arg Gln Lys Pro Gly Gln Ala Pro Arg Leu Leu
             35                  40                  45

Ile Tyr Gly Ala Ser Asn Arg Ala Thr Gly Ile Pro Asp Arg Phe Ser
         50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Ala Lys Leu Thr Tyr Tyr Gly
                 85                  90                  95

Ser Gly Arg Asn Trp Gly Gln Gly Thr Lys Leu Glu Ile Lys Ala Asp
                100                 105                 110
```

Gly Ser Asp Tyr Lys Asp Asp Asp Lys Ala Ser Ala
        115                 120                 125

<210> SEQ ID NO 291
<211> LENGTH: 125
<212> TYPE: PRT
<213> ORGANISM: Artificial Sequence
<220> FEATURE:
<223> OTHER INFORMATION: binding polypeptide

<400> SEQUENCE: 291

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Tyr Tyr Gly
            85                  90                  95

Ser Gly Arg Asn Trp Gly Gln Gly Thr Lys Leu Glu Ile Lys Ala Asp
        100                 105                 110

Gly Ser Asp Tyr Lys Asp Asp Asp Lys Ala Ser Ala
        115                 120                 125

<210> SEQ ID NO 292
<211> LENGTH: 125
<212> TYPE: PRT
<213> ORGANISM: Artificial Sequence
<220> FEATURE:
<223> OTHER INFORMATION: binding polypeptide
<220> FEATURE:
<221> NAME/KEY: VARIANT
<222> LOCATION: 94
<223> OTHER INFORMATION: Xaa = Any Amino Acid

<400> SEQUENCE: 292

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Arg Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Ala Lys Leu Thr Xaa Tyr Gly
            85                  90                  95

Ser Gly Arg Asn Trp Gly Gln Gly Thr Lys Leu Glu Ile Lys Ala Asp
        100                 105                 110

Gly Ser Asp Tyr Lys Asp Asp Asp Lys Ala Ser Ala
        115                 120                 125

<210> SEQ ID NO 293
<211> LENGTH: 125
<212> TYPE: PRT

<213> ORGANISM: Artificial Sequence
<220> FEATURE:
<223> OTHER INFORMATION: binding polypeptide

<400> SEQUENCE: 293

```
Glu Ile Val Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Ser Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Ala Lys Leu Thr Tyr Tyr Gly
                85                  90                  95
Ser Gly Arg Asn Trp Gly Gln Gly Thr Lys Leu Glu Ile Lys Ala Asp
            100                 105                 110
Gly Ser Asp Tyr Lys Asp Asp Asp Lys Ala Ser Ala
        115                 120                 125
```

<210> SEQ ID NO 294
<211> LENGTH: 126
<212> TYPE: PRT
<213> ORGANISM: Artificial Sequence
<220> FEATURE:
<223> OTHER INFORMATION: binding polypeptide

<400> SEQUENCE: 294

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Gly Ile Lys
            20                  25                  30
Leu Ala Trp Tyr Gln Gln Lys Leu Gly Gln Ala Pro Arg Leu Leu Ile
        35                  40                  45
Tyr Asp Ala Ser Thr Arg Ala Thr Gly Val Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Thr Gly Gly Thr Gly Asn Tyr Tyr
                85                  90                  95
Gly Trp Phe Asp Pro Trp Gly Gln Gly Thr Lys Leu Glu Ile Lys Ala
            100                 105                 110
Asp Gly Ser Asp Tyr Lys Asp Asp Asp Lys Ala Ser Ala
        115                 120                 125
```

<210> SEQ ID NO 295
<211> LENGTH: 126
<212> TYPE: PRT
<213> ORGANISM: Artificial Sequence
<220> FEATURE:
<223> OTHER INFORMATION: binding polypeptide

<400> SEQUENCE: 295

```
Ala Ile Gln Met Thr Gln Ser Pro Gly Thr Leu Ser Leu Ser Pro Gly
1               5                   10                  15
Glu Arg Ala Thr Leu Ser Cys Arg Ala Ser Gln Ser Val Arg Thr Lys
            20                  25                  30
```

```
Leu Ala Trp Tyr Gln Gln Lys Pro Gly Gln Ser Pro Arg Leu Leu Ile
            35                  40                  45

Tyr Asp Ala Ser Thr Arg Ala Thr Gly Val Pro Ala Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Val Tyr Tyr Cys Thr Gly Thr Gly Asn Tyr Tyr
                85                  90                  95

Gly Trp Phe Asp Pro Trp Gly Gln Gly Thr Lys Val Glu Ile Lys Ala
                100                 105                 110

Asp Gly Ser Asp Tyr Lys Asp Asp Asp Lys Ala Ser Ala
            115                 120                 125

<210> SEQ ID NO 296
<211> LENGTH: 125
<212> TYPE: PRT
<213> ORGANISM: Artificial Sequence
<220> FEATURE:
<223> OTHER INFORMATION: binding polypeptide

<400> SEQUENCE: 296

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
            20                  25                  30

Leu Asn Trp Tyr Gln Leu Lys Pro Gly Glu Ala Pro Lys Arg Leu Ile
            35                  40                  45

Tyr Ala Ala Ser Asn Leu Glu Ser Gly Val Pro Ser Arg Phe Ser Gly
        50                  55                  60

Ser Gly Ser Gly Thr Glu Phe Thr Leu Thr Ile Asn Ser Leu Gln Pro
 65                  70                  75                  80

Glu Asp Phe Ala Val Tyr Tyr Cys Ala Gly Ser Phe Ile Ala Arg Gly
                85                  90                  95

Pro Leu Asn Tyr Trp Gly Gln Gly Thr Lys Val Glu Ile Lys Ala Asp
                100                 105                 110

Gly Ser Asp Tyr Lys Asp Asp Asp Lys Ala Ser Ala
            115                 120                 125

<210> SEQ ID NO 297
<211> LENGTH: 125
<212> TYPE: PRT
<213> ORGANISM: Artificial Sequence
<220> FEATURE:
<223> OTHER INFORMATION: binding polypeptide

<400> SEQUENCE: 297

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
            20                  25                  30

Leu Asn Trp Tyr Gln Leu Lys Pro Gly Glu Ala Pro Lys Arg Leu Ile
            35                  40                  45

Tyr Ala Ala Ser Asn Leu Glu Ser Gly Val Pro Ser Arg Phe Ser Gly
        50                  55                  60

Ser Gly Ser Gly Thr Glu Phe Thr Leu Thr Ile Asn Ser Leu Gln Pro
 65                  70                  75                  80

Glu Asp Phe Ala Val Tyr Tyr Cys Ala Gly Ser Phe Ile Ala Arg Gly
```

-continued

```
                    85                  90                  95
Pro Leu Asn Tyr Trp Gly Gln Gly Thr Lys Val Glu Ile Lys Ala Asp
                100                 105                 110
Gly Ser Asp Tyr Lys Asp Asp Asp Lys Ala Ser Ala
            115                 120                 125

<210> SEQ ID NO 298
<211> LENGTH: 128
<212> TYPE: PRT
<213> ORGANISM: Artificial Sequence
<220> FEATURE:
<223> OTHER INFORMATION: binding polypeptide

<400> SEQUENCE: 298

Ser Tyr Glu Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asp His Val Phe Trp Tyr Gln Gln His Pro Gly Lys Ala Pro Lys Leu
             35                  40                  45

Met Ile Tyr Glu Asp Ser Lys Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Asp Glu Asp Glu Ala Val Tyr Tyr Cys Ala Lys Arg Arg Tyr Val
                 85                  90                  95

Asn Ala Gly Trp Phe Asp Tyr Trp Gly Gln Gly Thr Lys Leu Thr Val
                100                 105                 110

Leu Ala Asp Gly Ser Asp Tyr Lys Asp Asp Asp Lys Ala Ser Ala
            115                 120                 125

<210> SEQ ID NO 299
<211> LENGTH: 128
<212> TYPE: PRT
<213> ORGANISM: Artificial Sequence
<220> FEATURE:
<223> OTHER INFORMATION: binding polypeptide

<400> SEQUENCE: 299

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asp His Val Phe Trp Tyr Gln Gln His Pro Gly Lys Ala Pro Lys Leu
             35                  40                  45

Met Ile Tyr Glu Asp Ser Lys Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Val Tyr Tyr Cys Ala Lys Arg Arg Tyr Val
                 85                  90                  95

Asn Ala Gly Trp Phe Asp Tyr Trp Gly Gln Gly Thr Lys Leu Thr Val
                100                 105                 110

Leu Ala Asp Gly Ser Asp Tyr Lys Asp Asp Asp Lys Ala Ser Ala
            115                 120                 125

<210> SEQ ID NO 300
<211> LENGTH: 128
```

```
<212> TYPE: PRT
<213> ORGANISM: Artificial Sequence
<220> FEATURE:
<223> OTHER INFORMATION: binding polypeptide

<400> SEQUENCE: 300

Gln Ser Val Leu Thr Gln Pro Arg Ser Val Ser Gly Ser Pro Gly Gln
1               5                   10                  15

Ser Val Ala Ile Ser Cys Thr Gly Thr Ser Ser Asp Val Gly Gly Tyr
            20                  25                  30

Asn Tyr Val Phe Trp Tyr Gln Arg His Pro Gly Lys Ala Pro Lys Leu
        35                  40                  45

Ile Ile Tyr Glu Asp Asn Lys Arg Pro Ser Gly Val Pro Asp Arg Phe
    50                  55                  60

Ser Gly Ser Lys Phe Gly Asn Thr Ala Ser Leu Thr Ile Ser Gly Leu
65                  70                  75                  80

His Thr Glu Asp Glu Ala Val Tyr Tyr Cys Ala Lys Arg Arg Tyr Val
                85                  90                  95

Asn Ala Gly Trp Phe Asp Tyr Trp Gly Gln Gly Thr Lys Val Thr Val
            100                 105                 110

Leu Ala Asp Gly Ser Asp Tyr Lys Asp Asp Asp Lys Ala Ser Ala
        115                 120                 125

<210> SEQ ID NO 301
<211> LENGTH: 128
<212> TYPE: PRT
<213> ORGANISM: Artificial Sequence
<220> FEATURE:
<223> OTHER INFORMATION: binding polypeptide

<400> SEQUENCE: 301

Gln Ser Val Leu Thr Gln Pro Arg Ser Val Ser Gly Ser Pro Gly Gln
1               5                   10                  15

Ser Val Ala Ile Ser Cys Thr Gly Thr Ser Ser Asp Val Gly Gly Tyr
            20                  25                  30

Asn Tyr Val Phe Trp Tyr Gln Arg His Pro Gly Lys Ala Pro Lys Leu
        35                  40                  45

Ile Ile Tyr Glu Asp Asn Lys Arg Pro Ser Gly Val Pro Asp Arg Phe
    50                  55                  60

Ser Gly Ser Lys Phe Gly Asn Thr Ala Ser Leu Thr Ile Ser Gly Leu
65                  70                  75                  80

His Thr Glu Asp Glu Ala Val Tyr Tyr Cys Ala Lys Arg Arg Tyr Val
                85                  90                  95

Asn Ala Gly Trp Phe Asp Tyr Trp Gly Gln Gly Thr Lys Val Thr Val
            100                 105                 110

Leu Ala Asp Gly Ser Asp Tyr Lys Asp Asp Asp Lys Ala Ser Ala
        115                 120                 125

<210> SEQ ID NO 302
<211> LENGTH: 128
<212> TYPE: PRT
<213> ORGANISM: Artificial Sequence
<220> FEATURE:
<223> OTHER INFORMATION: binding polypeptide

<400> SEQUENCE: 302

Gln Ser Val Leu Thr Gln Pro Arg Ser Val Ser Gly Ser Pro Gly Gln
1               5                   10                  15

Ser Val Ala Ile Ser Cys Thr Gly Thr Ser Ser Asp Val Gly Gly Tyr
```

-continued

```
                    20                  25                  30

Asn Tyr Val Phe Trp Tyr Gln Arg His Pro Gly Lys Ala Pro Lys Leu
                35                  40                  45

Ile Ile Tyr Glu Asp Asn Lys Arg Pro Ser Gly Val Pro Asp Arg Phe
 50                  55                  60

Ser Gly Ser Lys Phe Gly Asn Thr Ala Ser Leu Thr Ile Ser Gly Leu
 65                  70                  75                  80

His Thr Glu Asp Glu Ala Val Tyr Tyr Cys Ala Lys Arg Arg Tyr Val
                85                  90                  95

Asn Ala Gly Trp Phe Asp Tyr Trp Gly Gln Gly Thr Lys Val Thr Val
                100                 105                 110

Leu Ala Asp Gly Ser Asp Tyr Lys Asp Asp Asp Lys Ala Ser Ala
                115                 120                 125
```

<210> SEQ ID NO 303
<211> LENGTH: 128
<212> TYPE: PRT
<213> ORGANISM: Artificial Sequence
<220> FEATURE:
<223> OTHER INFORMATION: binding polypeptide

<400> SEQUENCE: 303

```
Gln Ser Val Leu Thr Gln Pro Arg Ser Val Ser Gly Ser Pro Gly Gln
 1                   5                  10                  15

Ser Val Ala Ile Ser Cys Thr Gly Thr Ser Ser Asp Val Gly Gly Tyr
                20                  25                  30

Asn Tyr Val Phe Trp Tyr Gln Arg His Pro Gly Lys Ala Pro Lys Leu
                35                  40                  45

Ile Ile Tyr Glu Asp Asn Lys Arg Pro Ser Gly Val Pro Asp Arg Phe
 50                  55                  60

Ser Gly Ser Lys Phe Gly Asn Thr Ala Ser Leu Thr Ile Ser Gly Leu
 65                  70                  75                  80

His Thr Glu Asp Glu Ala Val Tyr Tyr Cys Ala Lys Arg Arg Tyr Val
                85                  90                  95

Asn Ala Gly Trp Phe Asp Tyr Trp Gly Gln Gly Thr Lys Val Thr Val
                100                 105                 110

Leu Ala Asp Gly Ser Asp Tyr Lys Asp Asp Asp Lys Ala Ser Ala
                115                 120                 125
```

<210> SEQ ID NO 304
<211> LENGTH: 128
<212> TYPE: PRT
<213> ORGANISM: Artificial Sequence
<220> FEATURE:
<223> OTHER INFORMATION: binding polypeptide

<400> SEQUENCE: 304

```
Ser Tyr Glu Leu Thr Gln Pro Ala Ser Val Ser Gly Ser Pro Gly Gln
 1                   5                  10                  15

Ser Val Ala Ile Ser Cys Thr Gly Thr Ser Ser Asp Val Gly Gly Tyr
                20                  25                  30

Asn Tyr Val Phe Trp Tyr Gln Arg His Pro Gly Lys Ala Pro Lys Leu
                35                  40                  45

Ile Ile Tyr Glu Asp Asn Lys Arg Pro Ser Gly Val Pro Asp Arg Phe
 50                  55                  60

Ser Gly Ser Lys Phe Gly Asn Thr Ala Ser Leu Thr Ile Ser Gly Leu
 65                  70                  75                  80
```

```
His Thr Glu Asp Glu Ala Val Tyr Tyr Cys Ala Lys Arg Arg Tyr Val
                85                  90                  95

Asn Ala Gly Trp Phe Asp Tyr Trp Gly Gln Gly Thr Lys Val Thr Val
            100                 105                 110

Leu Ala Asp Gly Ser Asp Tyr Lys Asp Asp Asp Lys Ala Ser Ala
            115                 120                 125

<210> SEQ ID NO 305
<211> LENGTH: 127
<212> TYPE: PRT
<213> ORGANISM: Artificial Sequence
<220> FEATURE:
<223> OTHER INFORMATION: binding polypeptide

<400> SEQUENCE: 305

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Ala Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Val Tyr Tyr Cys Ala Ser Ala Ile Pro Gly
                85                  90                  95

Thr Arg Ile Leu Arg Asp Trp Gly Gln Gly Thr Lys Leu Thr Val Leu
            100                 105                 110

Ala Asp Gly Ser Asp Tyr Lys Asp Asp Asp Lys Ala Ser Ala
            115                 120                 125

<210> SEQ ID NO 306
<211> LENGTH: 123
<212> TYPE: PRT
<213> ORGANISM: Artificial Sequence
<220> FEATURE:
<223> OTHER INFORMATION: binding polypeptide

<400> SEQUENCE: 306

Glu Ile Val Met Thr Gln Ser Pro Ala Thr Leu Ser Val Ser Pro Gly
 1               5                  10                  15

Glu Arg Ala Ala Leu Ser Cys Arg Ala Ser Gln Ser Val Ser Asp Lys
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ala Thr Glu Phe Arg Gly Tyr Ala
                85                  90                  95

Gly Tyr Trp Gly Gln Gly Thr Lys Leu Glu Ile Lys Ala Asp Gly Ser
            100                 105                 110

Asp Tyr Lys Asp Asp Asp Lys Ala Ser Ala
            115                 120

<210> SEQ ID NO 307
```

<211> LENGTH: 123
<212> TYPE: PRT
<213> ORGANISM: Artificial Sequence
<220> FEATURE:
<223> OTHER INFORMATION: binding polypeptide

<400> SEQUENCE: 307

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Ala Gly Phe Asp Pro Tyr Gln Pro
                85                  90                  95

Pro Arg Trp Gly Gln Gly Thr Lys Leu Glu Ile Lys Ala Asp Gly Ser
            100                 105                 110

Asp Tyr Lys Asp Asp Asp Asp Lys Ala Ser Ala
        115                 120
```

<210> SEQ ID NO 308
<211> LENGTH: 123
<212> TYPE: PRT
<213> ORGANISM: Artificial Sequence
<220> FEATURE:
<223> OTHER INFORMATION: binding polypeptide

<400> SEQUENCE: 308

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Val Thr Ser
            20                  25                  30

Leu His Trp Tyr Gln Gln Lys Pro Gly Gln Ala Pro Ser Leu Leu Ile
        35                  40                  45

Tyr Gly Ala Ser Asn Arg Ala Thr Gly Ile Pro Ala Arg Phe Ser Gly
 50                  55                  60

Ser Gly Ser Gly Thr Glu Phe Thr Leu Thr Ile Ser Gly Leu Gln Pro
65                  70                  75                  80

Glu Asp Ala Ala Val Tyr Tyr Cys Ala Gly Asp Phe Gly Gly Gln Leu
                85                  90                  95

Pro Tyr Trp Gly Gln Gly Thr Lys Leu Glu Ile Lys Ala Asp Gly Ser
            100                 105                 110

Asp Tyr Lys Asp Asp Asp Asp Lys Ala Ser Ala
        115                 120
```

<210> SEQ ID NO 309
<211> LENGTH: 129
<212> TYPE: PRT
<213> ORGANISM: Artificial Sequence
<220> FEATURE:
<223> OTHER INFORMATION: binding polypeptide

<400> SEQUENCE: 309

```
Asp Ile Val Met Thr Gln Ser Pro Leu Ser Leu Pro Val Thr Leu Gly
 1               5                  10                  15
```

```
Gln Pro Ala Ser Ile Ser Cys Arg Ser Ser Gln Ser Leu Leu Tyr Ser
                20                  25                  30

Asp Gly Asn Thr Tyr Leu Asn Trp Phe Gln Gln Arg Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Ala Val Tyr Tyr Cys Ala Arg Ala
                85                  90                  95

Gly Ser Ser Trp Lys Phe Asp Tyr Trp Gly Gln Gly Thr Lys Val Glu
                100                 105                 110

Ile Lys Ala Asp Gly Ser Asp Tyr Lys Asp Asp Asp Lys Ala Ser
                115                 120                 125

Ala
```

<210> SEQ ID NO 310
<211> LENGTH: 129
<212> TYPE: PRT
<213> ORGANISM: Artificial Sequence
<220> FEATURE:
<223> OTHER INFORMATION: binding polypeptide

<400> SEQUENCE: 310

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Leu Thr
                20                  25                  30

Ser Gly Asp Asn Tyr Leu Asn Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Arg Met
                85                  90                  95

Gly Ala Val Ala Gly Tyr Asp Tyr Trp Gly Gln Gly Thr Lys Val Glu
                100                 105                 110

Ile Lys Ala Asp Gly Ser Asp Tyr Lys Asp Asp Asp Lys Ala Ser
                115                 120                 125

Ala
```

<210> SEQ ID NO 311
<211> LENGTH: 86
<212> TYPE: PRT
<213> ORGANISM: Artificial Sequence
<220> FEATURE:
<223> OTHER INFORMATION: binding polypeptide

<400> SEQUENCE: 311

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
```

```
                50                  55                  60
Tyr Ala Val Thr Val Glu Gln Asp Gly His Val Leu Tyr Ile Pro Ile
 65                  70                  75                  80

Ser Ile Asn Tyr Arg Thr
                 85

<210> SEQ ID NO 312
<211> LENGTH: 86
<212> TYPE: PRT
<213> ORGANISM: Artificial Sequence
<220> FEATURE:
<223> OTHER INFORMATION: binding polypeptide

<400> SEQUENCE: 312

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Met Gly Lys Asn Gly His Glu Leu Leu Thr Pro Ile
 65                  70                  75                  80

Ser Ile Asn Tyr Arg Thr
                 85

<210> SEQ ID NO 313
<211> LENGTH: 86
<212> TYPE: PRT
<213> ORGANISM: Artificial Sequence
<220> FEATURE:
<223> OTHER INFORMATION: binding polypeptide

<400> SEQUENCE: 313

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Pro Gly Pro Gly Asp Arg Glu Leu Ile Thr Pro Ile
 65                  70                  75                  80

Ser Ile Asn Tyr Arg Thr
                 85

<210> SEQ ID NO 314
<211> LENGTH: 86
<212> TYPE: PRT
<213> ORGANISM: Artificial Sequence
<220> FEATURE:
<223> OTHER INFORMATION: binding polypeptide

<400> SEQUENCE: 314

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30
```

-continued

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
 50                  55                  60

Tyr Ala Val Thr Ala Gly Pro Gly Ala His Glu Leu Leu Thr Pro Ile
 65                  70                  75                  80

Ser Ile Asn Tyr Arg Thr
                85

<210> SEQ ID NO 315
<211> LENGTH: 86
<212> TYPE: PRT
<213> ORGANISM: Artificial Sequence
<220> FEATURE:
<223> OTHER INFORMATION: binding polypeptide

<400> SEQUENCE: 315

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
 50                  55                  60

Tyr Ala Val Thr Met Ala Gln Asn Asn Arg Glu Leu Leu Thr Pro Ile
 65                  70                  75                  80

Ser Ile Asn Tyr Arg Thr
                85

<210> SEQ ID NO 316
<211> LENGTH: 86
<212> TYPE: PRT
<213> ORGANISM: Artificial Sequence
<220> FEATURE:
<223> OTHER INFORMATION: binding polypeptide

<400> SEQUENCE: 316

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
 50                  55                  60

Tyr Ala Val Thr Met Ala Gln Tyr Gly Arg Glu Leu Leu Thr Pro Ile
 65                  70                  75                  80

Ser Ile Asn Tyr Arg Thr
                85

<210> SEQ ID NO 317
<211> LENGTH: 86
<212> TYPE: PRT
<213> ORGANISM: Artificial Sequence
<220> FEATURE:
<223> OTHER INFORMATION: binding polypeptide

<400> SEQUENCE: 317

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala His Asn Gly Asn Glu Leu Leu Thr Pro Ile
65              70                  75                  80

Ser Ile Asn Tyr Arg Thr
                85
```

<210> SEQ ID NO 318
<211> LENGTH: 86
<212> TYPE: PRT
<213> ORGANISM: Artificial Sequence
<220> FEATURE:
<223> OTHER INFORMATION: binding polypeptide

<400> SEQUENCE: 318

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Trp Asn Gly His Glu Leu Met Thr Pro Ile
65              70                  75                  80

Ser Ile Asn Tyr Arg Thr
                85
```

<210> SEQ ID NO 319
<211> LENGTH: 86
<212> TYPE: PRT
<213> ORGANISM: Artificial Sequence
<220> FEATURE:
<223> OTHER INFORMATION: binding polypeptide

<400> SEQUENCE: 319

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Leu Arg Asp Arg Glu Leu Phe Val Pro Ile
65              70                  75                  80

Ser Ile Asn Tyr Arg Thr
                85
```

<210> SEQ ID NO 320
<211> LENGTH: 86
<212> TYPE: PRT
<213> ORGANISM: Artificial Sequence -continued

```
<220> FEATURE:
<223> OTHER INFORMATION: binding polypeptide

<400> SEQUENCE: 320

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ser Gly Leu Asn Asp Arg Val Leu Phe Ile Pro Ile
65                  70                  75                  80

Ser Ile Asn Tyr Arg Thr
                85

<210> SEQ ID NO 321
<211> LENGTH: 86
<212> TYPE: PRT
<213> ORGANISM: Artificial Sequence
<220> FEATURE:
<223> OTHER INFORMATION: binding polypeptide

<400> SEQUENCE: 321

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Gly Pro Asn Asp Arg Glu Leu Leu Thr Pro Ile
65                  70                  75                  80

Ser Ile Asn Tyr Arg Thr
                85

<210> SEQ ID NO 322
<211> LENGTH: 86
<212> TYPE: PRT
<213> ORGANISM: Artificial Sequence
<220> FEATURE:
<223> OTHER INFORMATION: binding polypeptide

<400> SEQUENCE: 322

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly His Asn Asp Arg Glu Leu Leu Thr Pro Ile
65                  70                  75                  80

Ser Ile Asn Tyr Arg Thr
                85
```

```
<210> SEQ ID NO 323
<211> LENGTH: 86
<212> TYPE: PRT
<213> ORGANISM: Artificial Sequence
<220> FEATURE:
<223> OTHER INFORMATION: binding polypeptide

<400> SEQUENCE: 323

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Leu Asn Asp Arg Glu Leu Met Thr Pro Ile
65                  70                  75                  80

Ser Ile Asn Tyr Arg Thr
                85

<210> SEQ ID NO 324
<211> LENGTH: 86
<212> TYPE: PRT
<213> ORGANISM: Artificial Sequence
<220> FEATURE:
<223> OTHER INFORMATION: binding polypeptide

<400> SEQUENCE: 324

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Gly His Lys Leu Met Thr Pro Ile
65                  70                  75                  80

Ser Ile Asn Tyr Arg Thr
                85

<210> SEQ ID NO 325
<211> LENGTH: 86
<212> TYPE: PRT
<213> ORGANISM: Artificial Sequence
<220> FEATURE:
<223> OTHER INFORMATION: binding polypeptide

<400> SEQUENCE: 325

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val His Trp Asn Gly His Glu Leu Met Thr Pro Ile
```

```
65                  70                  75                  80

Ser Ile Asn Tyr Arg Thr
                85

<210> SEQ ID NO 326
<211> LENGTH: 86
<212> TYPE: PRT
<213> ORGANISM: Artificial Sequence
<220> FEATURE:
<223> OTHER INFORMATION: binding polypeptide

<400> SEQUENCE: 326

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Gly Phe Met Ala His Glu Leu Met Val Pro Ile
 65                 70                  75                  80

Ser Ile Asn Tyr Arg Thr
                85

<210> SEQ ID NO 327
<211> LENGTH: 86
<212> TYPE: PRT
<213> ORGANISM: Artificial Sequence
<220> FEATURE:
<223> OTHER INFORMATION: binding polypeptide

<400> SEQUENCE: 327

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ala Gly Leu Asn Glu His Glu Leu Leu Ile Pro Ile
 65                 70                  75                  80

Ser Ile Asn Tyr Arg Thr
                85

<210> SEQ ID NO 328
<211> LENGTH: 86
<212> TYPE: PRT
<213> ORGANISM: Artificial Sequence
<220> FEATURE:
<223> OTHER INFORMATION: binding polypeptide

<400> SEQUENCE: 328

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45
```

```
Ala Thr Ile Ser Gly Leu Lys Pro Gly Val Asp Tyr Thr Ile Thr Gly
        50                  55                  60

Tyr Ala Val Thr Leu Ala Asp Asn Ala Arg Glu Leu Leu Thr Pro Ile
65                  70                  75                  80

Ser Ile Asn Tyr Arg Thr
                85

<210> SEQ ID NO 329
<211> LENGTH: 86
<212> TYPE: PRT
<213> ORGANISM: Artificial Sequence
<220> FEATURE:
<223> OTHER INFORMATION: binding polypeptide

<400> SEQUENCE: 329

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly Lys Asp Val Arg Glu Leu Leu Thr Pro Ile
65                  70                  75                  80

Ser Ile Asn Tyr Arg Thr
                85

<210> SEQ ID NO 330
<211> LENGTH: 86
<212> TYPE: PRT
<213> ORGANISM: Artificial Sequence
<220> FEATURE:
<223> OTHER INFORMATION: binding polypeptide

<400> SEQUENCE: 330

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Ser Asp Ser Gly His Ala Leu Phe Thr Pro Ile
65                  70                  75                  80

Ser Ile Asn Tyr Arg Thr
                85

<210> SEQ ID NO 331
<211> LENGTH: 86
<212> TYPE: PRT
<213> ORGANISM: Artificial Sequence
<220> FEATURE:
<223> OTHER INFORMATION: binding polypeptide

<400> SEQUENCE: 331

Glu Val Val Ala Ala Thr Pro Thr Ser Leu Leu Ile Ser Trp Arg His
1               5                   10                  15
```

-continued

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly Pro Tyr Glu His Glu Leu Leu Thr Pro Ile
65                  70                  75                  80

Ser Ile Asn Tyr Arg Thr
                85

<210> SEQ ID NO 332
<211> LENGTH: 86
<212> TYPE: PRT
<213> ORGANISM: Artificial Sequence
<220> FEATURE:
<223> OTHER INFORMATION: binding polypeptide

<400> SEQUENCE: 332

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ala Gly Arg His Asp His Glu Leu Ile Ile Pro Ile
65                  70                  75                  80

Ser Ile Asn Tyr Arg Thr
                85

<210> SEQ ID NO 333
<211> LENGTH: 86
<212> TYPE: PRT
<213> ORGANISM: Artificial Sequence
<220> FEATURE:
<223> OTHER INFORMATION: binding polypeptide

<400> SEQUENCE: 333

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ile Gly Pro Asn Asn His Glu Leu Leu Thr Pro Ile
65                  70                  75                  80

Ser Ile Asn Tyr Arg Thr
                85

<210> SEQ ID NO 334
<211> LENGTH: 86
<212> TYPE: PRT
<213> ORGANISM: Artificial Sequence
<220> FEATURE:
<223> OTHER INFORMATION: binding polypeptide -continued

```
<400> SEQUENCE: 334

Glu Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Gln Asn Gly Arg Glu Leu Ile Ile Pro Ile
65                  70                  75                  80

Ser Ile Asn Tyr Arg Thr
                85

<210> SEQ ID NO 335
<211> LENGTH: 86
<212> TYPE: PRT
<213> ORGANISM: Artificial Sequence
<220> FEATURE:
<223> OTHER INFORMATION: binding polypeptide

<400> SEQUENCE: 335

Glu Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ala Gly Leu Asp Glu His Glu Leu Leu Ile Pro Ile
65                  70                  75                  80

Ser Ile Asn Tyr Arg Thr
                85

<210> SEQ ID NO 336
<211> LENGTH: 86
<212> TYPE: PRT
<213> ORGANISM: Artificial Sequence
<220> FEATURE:
<223> OTHER INFORMATION: binding polypeptide

<400> SEQUENCE: 336

Glu Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Pro Asn Gly His Glu Leu Phe Thr Pro Ile
65                  70                  75                  80

Ser Ile Asn Tyr Arg Thr
                85

<210> SEQ ID NO 337
<211> LENGTH: 86
```

```
<212> TYPE: PRT
<213> ORGANISM: Artificial Sequence
<220> FEATURE:
<223> OTHER INFORMATION: binding polypeptide

<400> SEQUENCE: 337

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Gly His Ala Leu Phe Thr Pro Ile
65                  70                  75                  80

Ser Ile Asn Tyr Arg Thr
                85

<210> SEQ ID NO 338
<211> LENGTH: 86
<212> TYPE: PRT
<213> ORGANISM: Artificial Sequence
<220> FEATURE:
<223> OTHER INFORMATION: binding polypeptide

<400> SEQUENCE: 338

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Gly Tyr Asn Asn Arg Glu Leu Leu Thr Pro Ile
65                  70                  75                  80

Ser Ile Asn Tyr Arg Thr
                85

<210> SEQ ID NO 339
<211> LENGTH: 86
<212> TYPE: PRT
<213> ORGANISM: Artificial Sequence
<220> FEATURE:
<223> OTHER INFORMATION: binding polypeptide

<400> SEQUENCE: 339

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asp Gly His Phe Leu Tyr Thr Pro Ile
65                  70                  75                  80

Ser Ile Asn Tyr Arg Thr
```

<210> SEQ ID NO 340
<211> LENGTH: 86
<212> TYPE: PRT
<213> ORGANISM: Artificial Sequence
<220> FEATURE:
<223> OTHER INFORMATION: binding polypeptide

<400> SEQUENCE: 340

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ser Gly His Asn Gly His Glu Val Met Thr Pro Ile
65                  70                  75                  80

Ser Ile Asn Tyr Arg Thr
                85

<210> SEQ ID NO 341
<211> LENGTH: 86
<212> TYPE: PRT
<213> ORGANISM: Artificial Sequence
<220> FEATURE:
<223> OTHER INFORMATION: binding polypeptide

<400> SEQUENCE: 341

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Asp Gln Ser Asp His Glu Leu Leu Thr Pro Ile
65                  70                  75                  80

Ser Ile Asn Tyr Arg Thr
                85

<210> SEQ ID NO 342
<211> LENGTH: 86
<212> TYPE: PRT
<213> ORGANISM: Artificial Sequence
<220> FEATURE:
<223> OTHER INFORMATION: binding polypeptide

<400> SEQUENCE: 342

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

-continued

Tyr Ala Val Thr Val Gly Pro Asn Glu Arg Met Leu Met Thr Pro Ile
65                  70                  75                  80

Ser Ile Asn Tyr Arg Thr
                85

<210> SEQ ID NO 343
<211> LENGTH: 86
<212> TYPE: PRT
<213> ORGANISM: Artificial Sequence
<220> FEATURE:
<223> OTHER INFORMATION: binding polypeptide

<400> SEQUENCE: 343

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Gly Tyr Tyr Asn Asp Arg Glu Leu Leu Thr Pro Ile
65                  70                  75                  80

Ser Ile Asn Tyr Arg Thr
                85

<210> SEQ ID NO 344
<211> LENGTH: 86
<212> TYPE: PRT
<213> ORGANISM: Artificial Sequence
<220> FEATURE:
<223> OTHER INFORMATION: binding polypeptide

<400> SEQUENCE: 344

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Thr His Asn Asp His Glu Leu Leu Thr Pro Ile
65                  70                  75                  80

Ser Ile Asn Tyr Arg Thr
                85

<210> SEQ ID NO 345
<211> LENGTH: 86
<212> TYPE: PRT
<213> ORGANISM: Artificial Sequence
<220> FEATURE:
<223> OTHER INFORMATION: binding polypeptide

<400> SEQUENCE: 345

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

-continued

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Val Gly Arg Asn Asp Arg Glu Leu Leu Thr Pro Ile
65                  70                  75                  80

Ser Ile Asn Tyr Arg Thr
                85

<210> SEQ ID NO 346
<211> LENGTH: 86
<212> TYPE: PRT
<213> ORGANISM: Artificial Sequence
<220> FEATURE:
<223> OTHER INFORMATION: binding polypeptide

<400> SEQUENCE: 346

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Trp Ala Gln Asn Gly Arg Glu Leu Leu Thr Pro Ile
65                  70                  75                  80

Ser Ile Asn Tyr Arg Thr
                85

<210> SEQ ID NO 347
<211> LENGTH: 86
<212> TYPE: PRT
<213> ORGANISM: Artificial Sequence
<220> FEATURE:
<223> OTHER INFORMATION: binding polypeptide

<400> SEQUENCE: 347

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Leu Gly Lys Asn Asp His Glu Leu Leu Thr Pro Ile
65                  70                  75                  80

Ser Ile Asn Tyr Arg Thr
                85

<210> SEQ ID NO 348
<211> LENGTH: 86
<212> TYPE: PRT
<213> ORGANISM: Artificial Sequence
<220> FEATURE:
<223> OTHER INFORMATION: binding polypeptide

<400> SEQUENCE: 348

Glu Val Val Ala Ala Thr Pro Thr Ser Leu Leu Ile Ser Trp Arg His

-continued

```
                1               5                  10                 15
Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
         50                 55                 60

Tyr Ala Val Thr Leu Gly Pro Asn Asp His Glu Leu Met Thr Pro Ile
 65                 70                 75                 80

Ser Ile Asn Tyr Arg Thr
                85

<210> SEQ ID NO 349
<211> LENGTH: 86
<212> TYPE: PRT
<213> ORGANISM: Artificial Sequence
<220> FEATURE:
<223> OTHER INFORMATION: binding polypeptide

<400> SEQUENCE: 349

Glu Val Val Ala Ala Thr Pro Thr Ser Leu Leu Ile Ser Trp Arg His
 1               5                  10                 15

Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
         50                 55                 60

Tyr Ala Val Thr Thr Gly Trp Asn Gly Asn Glu Leu Phe Thr Pro Ile
 65                 70                 75                 80

Ser Ile Asn Tyr Arg Thr
                85

<210> SEQ ID NO 350
<211> LENGTH: 86
<212> TYPE: PRT
<213> ORGANISM: Artificial Sequence
<220> FEATURE:
<223> OTHER INFORMATION: binding polypeptide

<400> SEQUENCE: 350

Glu Val Val Ala Ala Thr Pro Thr Ser Leu Leu Ile Ser Trp Arg His
 1               5                  10                 15

Pro His Phe Pro Thr Arg Tyr Tyr Arg Ile Thr Tyr Gly Glu Thr Gly
                20                 25                 30

Gly Asn Ser Pro Val Gln Glu Phe Thr Val Pro Leu Gln Pro Pro Thr
                35                 40                 45

Ala Thr Ile Ser Gly Leu Lys Pro Gly Val Asp Tyr Thr Ile Thr Gly
         50                 55                 60

Tyr Ala Val Thr Leu Ala His Asn Asp His Glu Leu Leu Thr Pro Ile
 65                 70                 75                 80

Ser Ile Asn Tyr Arg Thr
                85

<210> SEQ ID NO 351
<211> LENGTH: 86
<212> TYPE: PRT
<213> ORGANISM: Artificial Sequence
<220> FEATURE:
```

<223> OTHER INFORMATION: binding polypeptide

<400> SEQUENCE: 351

Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Leu Glu Gln Asn Asp Arg Val Leu Leu Thr Pro Ile
65                  70                  75                  80
Ser Ile Asn Tyr Arg Thr
                85

<210> SEQ ID NO 352
<211> LENGTH: 86
<212> TYPE: PRT
<213> ORGANISM: Artificial Sequence
<220> FEATURE:
<223> OTHER INFORMATION: binding polypeptide

<400> SEQUENCE: 352

Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Thr Gly His His Asp His Glu Leu Ile Ile Pro Ile
65                  70                  75                  80
Ser Ile Asn Tyr Arg Thr
                85

<210> SEQ ID NO 353
<211> LENGTH: 86
<212> TYPE: PRT
<213> ORGANISM: Artificial Sequence
<220> FEATURE:
<223> OTHER INFORMATION: binding polypeptide

<400> SEQUENCE: 353

Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Val Ala His Glu Asn Arg Glu Leu Leu Thr Pro Ile
65                  70                  75                  80
Ser Ile Asn Tyr Arg Thr
                85

```
<210> SEQ ID NO 354
<211> LENGTH: 86
<212> TYPE: PRT
<213> ORGANISM: Artificial Sequence
<220> FEATURE:
<223> OTHER INFORMATION: binding polypeptide

<400> SEQUENCE: 354

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly Leu Asn Asp His Glu Leu Ile Thr Pro Ile
65                  70                  75                  80

Ser Ile Asn Tyr Arg Thr
                85

<210> SEQ ID NO 355
<211> LENGTH: 86
<212> TYPE: PRT
<213> ORGANISM: Artificial Sequence
<220> FEATURE:
<223> OTHER INFORMATION: binding polypeptide

<400> SEQUENCE: 355

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ala Gly Pro Asn Asp His Gln Leu Phe Thr Pro Ile
65                  70                  75                  80

Ser Ile Asn Tyr Arg Thr
                85

<210> SEQ ID NO 356
<211> LENGTH: 86
<212> TYPE: PRT
<213> ORGANISM: Artificial Sequence
<220> FEATURE:
<223> OTHER INFORMATION: binding polypeptide

<400> SEQUENCE: 356

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Asp Ala Met Tyr Gly Arg Glu Leu Met Thr Pro Ile
65                  70                  75                  80
```

Ser Ile Asn Tyr Arg Thr
            85

<210> SEQ ID NO 357
<211> LENGTH: 86
<212> TYPE: PRT
<213> ORGANISM: Artificial Sequence
<220> FEATURE:
<223> OTHER INFORMATION: binding polypeptide

<400> SEQUENCE: 357

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Trp Asp Asp His Glu Leu Leu Thr Pro Ile
65                  70                  75                  80

Ser Ile Asn Tyr Arg Thr
            85

<210> SEQ ID NO 358
<211> LENGTH: 86
<212> TYPE: PRT
<213> ORGANISM: Artificial Sequence
<220> FEATURE:
<223> OTHER INFORMATION: binding polypeptide

<400> SEQUENCE: 358

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Gly Gln Asn Asp Lys Glu Leu Ile Thr Pro Ile
65                  70                  75                  80

Ser Ile Asn Tyr Arg Thr
            85

<210> SEQ ID NO 359
<211> LENGTH: 86
<212> TYPE: PRT
<213> ORGANISM: Artificial Sequence
<220> FEATURE:
<223> OTHER INFORMATION: binding polypeptide

<400> SEQUENCE: 359

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

```
Ala Thr Ile Ser Gly Leu Lys Pro Gly Val Asp Tyr Thr Ile Thr Gly
        50                  55                  60

Tyr Ala Val Thr Leu Ala Gln Asn Gly His Glu Leu Tyr Thr Pro Ile
 65                  70                  75                  80

Ser Ile Asn Tyr Arg Thr
                85

<210> SEQ ID NO 360
<211> LENGTH: 86
<212> TYPE: PRT
<213> ORGANISM: Artificial Sequence
<220> FEATURE:
<223> OTHER INFORMATION: binding polypeptide

<400> SEQUENCE: 360

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
        50                  55                  60

Tyr Ala Val Thr Pro Gly His Asn Asp His Glu Leu Met Val Pro Ile
 65                  70                  75                  80

Ser Ile Asn Tyr Arg Thr
                85

<210> SEQ ID NO 361
<211> LENGTH: 86
<212> TYPE: PRT
<213> ORGANISM: Artificial Sequence
<220> FEATURE:
<223> OTHER INFORMATION: binding polypeptide

<400> SEQUENCE: 361

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
        50                  55                  60

Tyr Ala Val Thr Glu Ala Arg Asn Gly Arg Glu Leu Leu Thr Pro Ile
 65                  70                  75                  80

Ser Ile Asn Tyr Arg Thr
                85

<210> SEQ ID NO 362
<211> LENGTH: 86
<212> TYPE: PRT
<213> ORGANISM: Artificial Sequence
<220> FEATURE:
<223> OTHER INFORMATION: binding polypeptide

<400> SEQUENCE: 362

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
```

```
                    20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Leu Ala His Asn Asp Arg Glu Leu Leu Thr Pro Ile
 65                  70                  75                  80

Ser Ile Asn Tyr Arg Thr
                85

<210> SEQ ID NO 363
<211> LENGTH: 86
<212> TYPE: PRT
<213> ORGANISM: Artificial Sequence
<220> FEATURE:
<223> OTHER INFORMATION: binding polypeptide

<400> SEQUENCE: 363

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Met Ala His Asn Asp His Glu Leu Leu Thr Pro Ile
 65                  70                  75                  80

Ser Ile Asn Tyr Arg Thr
                85

<210> SEQ ID NO 364
<211> LENGTH: 86
<212> TYPE: PRT
<213> ORGANISM: Artificial Sequence
<220> FEATURE:
<223> OTHER INFORMATION: binding polypeptide

<400> SEQUENCE: 364

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Leu Gly Gln Asn Asp Arg Gln Leu Leu Val Pro Ile
 65                  70                  75                  80

Ser Ile Asn Tyr Arg Thr
                85

<210> SEQ ID NO 365
<211> LENGTH: 86
<212> TYPE: PRT
<213> ORGANISM: Artificial Sequence
<220> FEATURE:
<223> OTHER INFORMATION: binding polypeptide

<400> SEQUENCE: 365
```

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ala Gly Gly Asn Gly His Glu Leu Leu Thr Pro Ile
65                  70                  75                  80

Ser Ile Asn Tyr Arg Thr
                85

<210> SEQ ID NO 366
<211> LENGTH: 86
<212> TYPE: PRT
<213> ORGANISM: Artificial Sequence
<220> FEATURE:
<223> OTHER INFORMATION: binding polypeptide

<400> SEQUENCE: 366

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr His Gly Pro Tyr Asp Gln Val Leu Leu Thr Pro Ile
65                  70                  75                  80

Ser Ile Asn Tyr Arg Thr
                85

<210> SEQ ID NO 367
<211> LENGTH: 86
<212> TYPE: PRT
<213> ORGANISM: Artificial Sequence
<220> FEATURE:
<223> OTHER INFORMATION: binding polypeptide

<400> SEQUENCE: 367

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Ile Glu Gln Ser Gly Leu Gln Leu Met Thr Pro Ile
65                  70                  75                  80

Ser Ile Asn Tyr Arg Thr
                85

<210> SEQ ID NO 368
<211> LENGTH: 86
<212> TYPE: PRT

```
<213> ORGANISM: Artificial Sequence
<220> FEATURE:
<223> OTHER INFORMATION: binding polypeptide

<400> SEQUENCE: 368

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp Arg Glu Leu Leu Thr Pro Ile
65                  70                  75                  80

Ser Ile Asn Tyr Arg Thr
                85

<210> SEQ ID NO 369
<211> LENGTH: 86
<212> TYPE: PRT
<213> ORGANISM: Artificial Sequence
<220> FEATURE:
<223> OTHER INFORMATION: binding polypeptide

<400> SEQUENCE: 369

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Ala Trp Asp Gly Arg Glu Leu Phe Thr Pro Ile
65                  70                  75                  80

Ser Ile Asn Tyr Arg Thr
                85

<210> SEQ ID NO 370
<211> LENGTH: 86
<212> TYPE: PRT
<213> ORGANISM: Artificial Sequence
<220> FEATURE:
<223> OTHER INFORMATION: binding polypeptide

<400> SEQUENCE: 370

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Tyr Asn Gly Arg Glu Ile Ile Thr Pro Ile
65                  70                  75                  80

Ser Ile Asn Tyr Arg Thr
                85
```

<210> SEQ ID NO 371
<211> LENGTH: 86
<212> TYPE: PRT
<213> ORGANISM: Artificial Sequence
<220> FEATURE:
<223> OTHER INFORMATION: binding polypeptide

<400> SEQUENCE: 371

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Trp Ser Gln Asn Asn Arg Glu Leu Phe Thr Pro Ile
65                  70                  75                  80

Ser Ile Asn Tyr Arg Thr
                85
```

<210> SEQ ID NO 372
<211> LENGTH: 86
<212> TYPE: PRT
<213> ORGANISM: Artificial Sequence
<220> FEATURE:
<223> OTHER INFORMATION: binding polypeptide

<400> SEQUENCE: 372

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Thr Trp Asn Asp His Glu Ile Arg Thr Pro Ile
65                  70                  75                  80

Ser Ile Asn Tyr Arg Thr
                85
```

<210> SEQ ID NO 373
<211> LENGTH: 86
<212> TYPE: PRT
<213> ORGANISM: Artificial Sequence
<220> FEATURE:
<223> OTHER INFORMATION: binding polypeptide

<400> SEQUENCE: 373

```
Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60
```

-continued

Tyr Ala Val Thr Val Ala Gln Asn Gly His Gln Leu Phe Thr Pro Ile
65                  70                  75                  80

Ser Ile Asn Tyr Arg Thr
                85

<210> SEQ ID NO 374
<211> LENGTH: 94
<212> TYPE: PRT
<213> ORGANISM: Artificial Sequence
<220> FEATURE:
<223> OTHER INFORMATION: binding polypeptide

<400> SEQUENCE: 374

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Val Thr His Asn
65                  70                  75                  80

Gly His Pro Leu Met Thr Pro Ile Ser Ile Asn Tyr Arg Thr
                85                  90

<210> SEQ ID NO 375
<211> LENGTH: 107
<212> TYPE: PRT
<213> ORGANISM: Artificial Sequence
<220> FEATURE:
<223> OTHER INFORMATION: binding polypeptide

<400> SEQUENCE: 375

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Tyr Tyr Arg Ile Thr
            35                  40                  45

Tyr Gly Glu Thr Gly Gly Asn Ser Pro Val Gln Glu Phe Thr Val Pro
        50                  55                  60

Leu Gln Pro Pro Thr Ala Thr Ile Ser Gly Leu Lys Pro Gly Val Asp
65                  70                  75                  80

Tyr Thr Ile Thr Gly Tyr Ala Val Thr Phe Ala Gln Asn Asp His Gln
                85                  90                  95

Leu Phe Thr Pro Ile Ser Ile Asn Tyr Arg Thr
                100                 105

<210> SEQ ID NO 376
<211> LENGTH: 107
<212> TYPE: PRT
<213> ORGANISM: Artificial Sequence
<220> FEATURE:
<223> OTHER INFORMATION: binding polypeptide

<400> SEQUENCE: 376

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly

```
                    20                  25                  30
Gly Asn Ser Pro Val Gln Glu Phe Thr Val Pro Tyr Tyr Arg Ile Thr
            35                  40                  45
Tyr Gly Glu Thr Gly Gly Asn Ser Pro Val Gln Glu Phe Thr Val Pro
        50                  55                  60
Leu Gln Pro Pro Thr Ala Thr Ile Ser Gly Leu Lys Pro Gly Val Asp
65                  70                  75                  80
Tyr Thr Ile Thr Gly Tyr Ala Val Thr Gly Gln Met Asn Arg Val
                85                  90                  95
Leu Met Thr Pro Ile Ser Ile Asn Tyr Arg Thr
            100                 105

<210> SEQ ID NO 377
<211> LENGTH: 107
<212> TYPE: PRT
<213> ORGANISM: Artificial Sequence
<220> FEATURE:
<223> OTHER INFORMATION: binding polypeptide

<400> SEQUENCE: 377

Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Tyr Tyr Arg Ile Thr
            35                  40                  45
Tyr Gly Glu Thr Gly Gly Asn Ser Pro Val Gln Glu Phe Thr Val Pro
        50                  55                  60
Leu Gln Pro Pro Thr Ala Thr Ile Ser Gly Leu Lys Pro Gly Val Asp
65                  70                  75                  80
Tyr Thr Ile Thr Gly Tyr Ala Val Thr Leu Val His Asn Asp Arg Glu
                85                  90                  95
Leu Leu Thr Pro Ile Ser Ile Asn Tyr Arg Thr
            100                 105

<210> SEQ ID NO 378
<211> LENGTH: 107
<212> TYPE: PRT
<213> ORGANISM: Artificial Sequence
<220> FEATURE:
<223> OTHER INFORMATION: binding polypeptide

<400> SEQUENCE: 378

Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Tyr Tyr Arg Ile Thr
            35                  40                  45
Tyr Gly Glu Thr Gly Gly Asn Ser Pro Val Gln Glu Phe Thr Val Pro
        50                  55                  60
Leu Gln Pro Pro Thr Ala Thr Ile Ser Gly Leu Lys Pro Gly Val Asp
65                  70                  75                  80
Tyr Thr Ile Thr Gly Tyr Ala Val Thr Val Ala Gln Asn Gly His Glu
                85                  90                  95
Leu Phe Thr Pro Ile Ser Ile Asn Tyr Arg Thr
            100                 105
```

```
<210> SEQ ID NO 379
<211> LENGTH: 115
<212> TYPE: PRT
<213> ORGANISM: Artificial Sequence
<220> FEATURE:
<223> OTHER INFORMATION: binding polypeptide

<400> SEQUENCE: 379

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Tyr Arg Ile Thr Tyr Gly Glu Thr Gly Gly Asn Ser
    50                  55                  60

Pro Val Gln Glu Phe Thr Val Pro Leu Gln Pro Pro Thr Ala Thr Ile
65                  70                  75                  80

Ser Gly Leu Lys Pro Gly Val Asp Tyr Thr Ile Thr Gly Tyr Ala Val
                85                  90                  95

Thr Val His Trp Asn Gly His Glu Leu Met Thr Pro Ile Ser Ile Asn
            100                 105                 110

Tyr Arg Thr
        115

<210> SEQ ID NO 380
<211> LENGTH: 107
<212> TYPE: PRT
<213> ORGANISM: Artificial Sequence
<220> FEATURE:
<223> OTHER INFORMATION: binding polypeptide

<400> SEQUENCE: 380

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Tyr Tyr Arg Ile Thr
        35                  40                  45

Tyr Gly Glu Thr Gly Gly Asn Ser Pro Val Gln Glu Phe Thr Val Pro
    50                  55                  60

Leu Gln Pro Pro Thr Ala Thr Ile Ser Gly Leu Lys Pro Gly Val Asp
65                  70                  75                  80

Tyr Thr Ile Thr Gly Tyr Ala Val Thr Leu Gly Trp Asn Asp His Glu
                85                  90                  95

Leu Tyr Ile Pro Ile Ser Ile Asn Tyr Arg Thr
            100                 105

<210> SEQ ID NO 381
<211> LENGTH: 86
<212> TYPE: PRT
<213> ORGANISM: Artificial Sequence
<220> FEATURE:
<223> OTHER INFORMATION: binding polypeptide

<400> SEQUENCE: 381

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
```

-continued

```
                    20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Ala Gly His Lys Asp Gln Glu Leu Leu Thr Pro Ile
 65                  70                  75                  80

Ser Ile Asn Tyr Arg Thr
                85

<210> SEQ ID NO 382
<211> LENGTH: 86
<212> TYPE: PRT
<213> ORGANISM: Artificial Sequence
<220> FEATURE:
<223> OTHER INFORMATION: binding polypeptide

<400> SEQUENCE: 382

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Leu Ala Gln Asn Asn His Glu Leu Leu Thr Pro Ile
 65                  70                  75                  80

Ser Ile Asn Tyr Arg Thr
                85

<210> SEQ ID NO 383
<211> LENGTH: 86
<212> TYPE: PRT
<213> ORGANISM: Artificial Sequence
<220> FEATURE:
<223> OTHER INFORMATION: binding polypeptide

<400> SEQUENCE: 383

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Thr
            35                  40                  45

Ala Thr Ile Ser Gly Leu Lys Pro Gly Val Asp Tyr Thr Ile Thr Gly
 50                  55                  60

Tyr Ala Val Thr Val Ala Trp Asn Asp His Glu Ile Tyr Thr Pro Ile
 65                  70                  75                  80

Ser Ile Asn Tyr Arg Thr
                85

<210> SEQ ID NO 384
<211> LENGTH: 86
<212> TYPE: PRT
<213> ORGANISM: Artificial Sequence
<220> FEATURE:
<223> OTHER INFORMATION: binding polypeptide

<400> SEQUENCE: 384
```

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Gln Thr Gly Arg Glu Leu Leu Thr Pro Ile
65                  70                  75                  80

Ser Ile Asn Tyr Arg Thr
                85

<210> SEQ ID NO 385
<211> LENGTH: 86
<212> TYPE: PRT
<213> ORGANISM: Artificial Sequence
<220> FEATURE:
<223> OTHER INFORMATION: binding polypeptide

<400> SEQUENCE: 385

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Gly Trp Ser Gly His Glu Leu Phe Val Pro Ile
65                  70                  75                  80

Ser Ile Asn Tyr Arg Thr
                85

<210> SEQ ID NO 386
<211> LENGTH: 86
<212> TYPE: PRT
<213> ORGANISM: Artificial Sequence
<220> FEATURE:
<223> OTHER INFORMATION: binding polypeptide

<400> SEQUENCE: 386

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Gly His Asn Asp Arg Glu Leu Ile Thr Pro Ile
65                  70                  75                  80

Ser Ile Asn Tyr Arg Thr
                85

<210> SEQ ID NO 387
<211> LENGTH: 86
<212> TYPE: PRT

<213> ORGANISM: Artificial Sequence
<220> FEATURE:
<223> OTHER INFORMATION: binding polypeptide

<400> SEQUENCE: 387

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Trp Asn Gln Asn Gly Gln Glu Leu Phe Thr Pro Ile
65                  70                  75                  80

Ser Ile Asn Tyr Arg Thr
                85

<210> SEQ ID NO 388
<211> LENGTH: 86
<212> TYPE: PRT
<213> ORGANISM: Artificial Sequence
<220> FEATURE:
<223> OTHER INFORMATION: binding polypeptide

<400> SEQUENCE: 388

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Gly Gln Asn Gly His Ala Leu Leu Thr Pro Ile
65                  70                  75                  80

Ser Ile Asn Tyr Arg Thr
                85

<210> SEQ ID NO 389
<211> LENGTH: 86
<212> TYPE: PRT
<213> ORGANISM: Artificial Sequence
<220> FEATURE:
<223> OTHER INFORMATION: binding polypeptide

<400> SEQUENCE: 389

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Arg Gly Leu Asn Asp Gly Glu Leu Leu Thr Pro Ile
65                  70                  75                  80

Ser Ile Asn Tyr Arg Thr
                85

<210> SEQ ID NO 390
<211> LENGTH: 86
<212> TYPE: PRT
<213> ORGANISM: Artificial Sequence
<220> FEATURE:
<223> OTHER INFORMATION: binding polypeptide

<400> SEQUENCE: 390

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Phe Gly Pro Ser Asp His Val Leu Leu Thr Pro Ile
 65                  70                  75                  80

Ser Ile Asn Tyr Arg Thr
                 85
```

<210> SEQ ID NO 391
<211> LENGTH: 86
<212> TYPE: PRT
<213> ORGANISM: Artificial Sequence
<220> FEATURE:
<223> OTHER INFORMATION: binding polypeptide

<400> SEQUENCE: 391

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Leu Ala Gln Asn Asn His Glu Leu Leu Thr Pro Ile
 65                  70                  75                  80

Ser Ile Asn Tyr Arg Thr
                 85
```

<210> SEQ ID NO 392
<211> LENGTH: 86
<212> TYPE: PRT
<213> ORGANISM: Artificial Sequence
<220> FEATURE:
<223> OTHER INFORMATION: binding polypeptide

<400> SEQUENCE: 392

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60
```

```
Tyr Ala Val Thr Val Ala Gln Asn Asp His Lys Leu Phe Ile Pro Ile
 65                  70                  75                  80

Ser Ile Asn Tyr Arg Thr
                 85
```

<210> SEQ ID NO 393
<211> LENGTH: 86
<212> TYPE: PRT
<213> ORGANISM: Artificial Sequence
<220> FEATURE:
<223> OTHER INFORMATION: binding polypeptide

<400> SEQUENCE: 393

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Arg Asp Gln Tyr Glu His Glu Leu Leu Thr Pro Ile
 65                  70                  75                  80

Ser Ile Asn Tyr Arg Thr
                 85
```

<210> SEQ ID NO 394
<211> LENGTH: 86
<212> TYPE: PRT
<213> ORGANISM: Artificial Sequence
<220> FEATURE:
<223> OTHER INFORMATION: binding polypeptide

<400> SEQUENCE: 394

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Leu Ala Leu Asn Gly His Glu Leu Phe Thr Pro Ile
 65                  70                  75                  80

Ser Ile Asn Tyr Arg Thr
                 85
```

<210> SEQ ID NO 395
<211> LENGTH: 86
<212> TYPE: PRT
<213> ORGANISM: Artificial Sequence
<220> FEATURE:
<223> OTHER INFORMATION: binding polypeptide

<400> SEQUENCE: 395

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
```

-continued

```
                35                  40                  45
Ala Thr Ile Ser Gly Leu Lys Pro Gly Val Asp Tyr Thr Ile Thr Gly
         50                  55                  60

Tyr Ala Val Thr Val Glu Ser Asn Gly His Ala Leu Phe Val Pro Ile
 65                  70                  75                  80

Ser Ile Asn Tyr Arg Thr
                 85

<210> SEQ ID NO 396
<211> LENGTH: 86
<212> TYPE: PRT
<213> ORGANISM: Artificial Sequence
<220> FEATURE:
<223> OTHER INFORMATION: binding polypeptide

<400> SEQUENCE: 396

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Val Gly Gln Asn Asn His Glu Leu Leu Thr Pro Ile
 65                  70                  75                  80

Ser Ile Asn Tyr Arg Thr
                 85

<210> SEQ ID NO 397
<211> LENGTH: 86
<212> TYPE: PRT
<213> ORGANISM: Artificial Sequence
<220> FEATURE:
<223> OTHER INFORMATION: binding polypeptide

<400> SEQUENCE: 397

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Trp Asp Gln Asn Gly His Val Leu Leu Thr Pro Ile
 65                  70                  75                  80

Ser Ile Asn Tyr Arg Thr
                 85

<210> SEQ ID NO 398
<211> LENGTH: 86
<212> TYPE: PRT
<213> ORGANISM: Artificial Sequence
<220> FEATURE:
<223> OTHER INFORMATION: binding polypeptide

<400> SEQUENCE: 398

Glu Val Val Ala Ala Thr Pro Thr Ser Leu Leu Ile Ser Trp Arg His
 1               5                  10                  15
```

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Gly Leu Asn Asp His Glu Leu Ile Ile Pro Ile
65                  70                  75                  80

Ser Ile Asn Tyr Arg Thr
                85

<210> SEQ ID NO 399
<211> LENGTH: 86
<212> TYPE: PRT
<213> ORGANISM: Artificial Sequence
<220> FEATURE:
<223> OTHER INFORMATION: binding polypeptide

<400> SEQUENCE: 399

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Gly Leu Asn Asp His Glu Leu Met Ile Pro Ile
65                  70                  75                  80

Ser Ile Asn Tyr Arg Thr
                85

<210> SEQ ID NO 400
<211> LENGTH: 86
<212> TYPE: PRT
<213> ORGANISM: Artificial Sequence
<220> FEATURE:
<223> OTHER INFORMATION: binding polypeptide

<400> SEQUENCE: 400

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Gly Gln Asn Asp Gln Leu Leu Phe Ile Pro Ile
65                  70                  75                  80

Ser Ile Asn Tyr Arg Thr
                85

<210> SEQ ID NO 401
<211> LENGTH: 86
<212> TYPE: PRT
<213> ORGANISM: Artificial Sequence
<220> FEATURE:
<223> OTHER INFORMATION: binding polypeptide

<400> SEQUENCE: 401

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Gly His Glu Leu Leu Thr Pro Ile
65                  70                  75                  80

Ser Ile Asn Tyr Arg Thr
                85

<210> SEQ ID NO 402
<211> LENGTH: 86
<212> TYPE: PRT
<213> ORGANISM: Artificial Sequence
<220> FEATURE:
<223> OTHER INFORMATION: binding polypeptide

<400> SEQUENCE: 402

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp Arg Glu Leu Leu Thr Pro Ile
65                  70                  75                  80

Ser Ile Asn Tyr Arg Thr
                85

<210> SEQ ID NO 403
<211> LENGTH: 86
<212> TYPE: PRT
<213> ORGANISM: Artificial Sequence
<220> FEATURE:
<223> OTHER INFORMATION: binding polypeptide

<400> SEQUENCE: 403

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Gly His Glu Leu Phe Thr Pro Ile
65                  70                  75                  80

Ser Ile Asn Tyr Arg Thr
                85

<210> SEQ ID NO 404

<211> LENGTH: 86
<212> TYPE: PRT
<213> ORGANISM: Artificial Sequence
<220> FEATURE:
<223> OTHER INFORMATION: binding polypeptide

<400> SEQUENCE: 404

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Glu Arg Glu Leu Phe Thr Pro Ile
65                  70                  75                  80

Ser Ile Asn Tyr Arg Thr
                85
```

<210> SEQ ID NO 405
<211> LENGTH: 86
<212> TYPE: PRT
<213> ORGANISM: Artificial Sequence
<220> FEATURE:
<223> OTHER INFORMATION: binding polypeptide

<400> SEQUENCE: 405

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Ala Trp Asn Asp His Met Leu Met Thr Pro Ile
65                  70                  75                  80

Ser Ile Asn Tyr Arg Thr
                85
```

<210> SEQ ID NO 406
<211> LENGTH: 86
<212> TYPE: PRT
<213> ORGANISM: Artificial Sequence
<220> FEATURE:
<223> OTHER INFORMATION: binding polypeptide

<400> SEQUENCE: 406

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Gly Pro Asn Asp Arg Glu Leu Met Thr Pro Ile
65                  70                  75                  80
```

Ser Ile Asn Tyr Arg Thr
                85

<210> SEQ ID NO 407
<211> LENGTH: 94
<212> TYPE: PRT
<213> ORGANISM: Artificial Sequence
<220> FEATURE:
<223> OTHER INFORMATION: binding polypeptide

<400> SEQUENCE: 407

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Val Gly Pro Asn
65                  70                  75                  80

Glu Arg Met Leu Met Thr Pro Ile Ser Ile Asn Tyr Arg Thr
                85                  90

<210> SEQ ID NO 408
<211> LENGTH: 86
<212> TYPE: PRT
<213> ORGANISM: Artificial Sequence
<220> FEATURE:
<223> OTHER INFORMATION: binding polypeptide

<400> SEQUENCE: 408

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala His Asn Asp His Glu Leu Leu Thr Pro Ile
65                  70                  75                  80

Ser Ile Asn Tyr Arg Thr
                85

<210> SEQ ID NO 409
<211> LENGTH: 86
<212> TYPE: PRT
<213> ORGANISM: Artificial Sequence
<220> FEATURE:
<223> OTHER INFORMATION: binding polypeptide

<400> SEQUENCE: 409

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly

```
                50                  55                  60
Tyr Ala Val Thr Val Ala Lys Asn Asp His Glu Leu Leu Thr Pro Ile
 65                  70                  75                  80

Ser Ile Asn Tyr Arg Thr
                 85
```

<210> SEQ ID NO 410
<211> LENGTH: 86
<212> TYPE: PRT
<213> ORGANISM: Artificial Sequence
<220> FEATURE:
<223> OTHER INFORMATION: binding polypeptide

<400> SEQUENCE: 410

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Trp Ala Gln Asn Asp His Glu Leu Leu Thr Pro Ile
 65                  70                  75                  80

Ser Ile Asn Tyr Arg Thr
                 85
```

<210> SEQ ID NO 411
<211> LENGTH: 86
<212> TYPE: PRT
<213> ORGANISM: Artificial Sequence
<220> FEATURE:
<223> OTHER INFORMATION: binding polypeptide

<400> SEQUENCE: 411

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Phe Ala Gln Asn Asp His Glu Leu Leu Thr Pro Ile
 65                  70                  75                  80

Ser Ile Asn Tyr Arg Thr
                 85
```

<210> SEQ ID NO 412
<211> LENGTH: 86
<212> TYPE: PRT
<213> ORGANISM: Artificial Sequence
<220> FEATURE:
<223> OTHER INFORMATION: binding polypeptide

<400> SEQUENCE: 412

```
Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30
```

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
         50                  55                  60

Tyr Ala Val Thr Met Glu Gln Asn Gly His Glu Leu Phe Thr Pro Ile
65                  70                  75                  80

Ser Ile Asn Tyr Arg Thr
                85

<210> SEQ ID NO 413
<211> LENGTH: 86
<212> TYPE: PRT
<213> ORGANISM: Artificial Sequence
<220> FEATURE:
<223> OTHER INFORMATION: binding polypeptide

<400> SEQUENCE: 413

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
         50                  55                  60

Tyr Ala Val Thr Asp Ala Pro Asn Gly Arg Glu Leu Met Val Pro Ile
65                  70                  75                  80

Ser Ile Asn Tyr Arg Thr
                85

<210> SEQ ID NO 414
<211> LENGTH: 86
<212> TYPE: PRT
<213> ORGANISM: Artificial Sequence
<220> FEATURE:
<223> OTHER INFORMATION: binding polypeptide

<400> SEQUENCE: 414

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
         50                  55                  60

Tyr Ala Val Thr Gly Gly Arg Asn Gly His Thr Leu Leu Thr Pro Ile
65                  70                  75                  80

Ser Ile Asn Tyr Arg Thr
                85

<210> SEQ ID NO 415
<211> LENGTH: 86
<212> TYPE: PRT
<213> ORGANISM: Artificial Sequence
<220> FEATURE:
<223> OTHER INFORMATION: binding polypeptide

<400> SEQUENCE: 415

```
Glu Val Val Ala Ala Thr Pro Thr Ser Leu Leu Ile Ser Trp Arg His
 1               5                   10                  15
Pro His Phe Pro Thr Arg Tyr Tyr Arg Ile Thr Tyr Gly Glu Thr Gly
                20                  25                  30
Gly Asn Ser Pro Val Gln Glu Phe Thr Val Pro Leu Gln Pro Pro Thr
            35                  40                  45
Ala Thr Ile Ser Gly Leu Lys Pro Gly Val Asp Tyr Thr Ile Thr Gly
        50                  55                  60
Tyr Ala Val Thr Leu Ser Gln Thr Asp His Glu Leu Leu Thr Pro Ile
 65                 70                  75                  80
Ser Ile Asn Tyr Arg Thr
                85
```

<210> SEQ ID NO 416
<211> LENGTH: 86
<212> TYPE: PRT
<213> ORGANISM: Artificial Sequence
<220> FEATURE:
<223> OTHER INFORMATION: binding polypeptide

<400> SEQUENCE: 416

```
Glu Val Val Ala Ala Thr Pro Thr Ser Leu Leu Ile Ser Trp Arg His
 1               5                   10                  15
Pro His Phe Pro Thr Arg Tyr Tyr Arg Ile Thr Tyr Gly Glu Thr Gly
                20                  25                  30
Gly Asn Ser Pro Val Gln Glu Phe Thr Val Pro Leu Gln Pro Pro Thr
            35                  40                  45
Ala Thr Ile Ser Gly Leu Lys Pro Gly Val Asp Tyr Thr Ile Thr Gly
        50                  55                  60
Tyr Ala Val Thr Val Gly Gln Asn Glu His Glu Leu Leu Thr Pro Ile
 65                 70                  75                  80
Ser Ile Asn Tyr Arg Thr
                85
```

<210> SEQ ID NO 417
<211> LENGTH: 86
<212> TYPE: PRT
<213> ORGANISM: Artificial Sequence
<220> FEATURE:
<223> OTHER INFORMATION: binding polypeptide

<400> SEQUENCE: 417

```
Glu Val Val Ala Ala Thr Pro Thr Ser Leu Leu Ile Ser Trp Arg His
 1               5                   10                  15
Pro His Phe Pro Thr Arg Tyr Tyr Arg Ile Thr Tyr Gly Glu Thr Gly
                20                  25                  30
Gly Asn Ser Pro Val Gln Glu Phe Thr Val Pro Leu Gln Pro Pro Thr
            35                  40                  45
Ala Thr Ile Ser Gly Leu Lys Pro Gly Val Asp Tyr Thr Ile Thr Gly
        50                  55                  60
Tyr Ala Val Thr Val Ala Gln Asn Gly His Glu Leu Lys Thr Pro Ile
 65                 70                  75                  80
Ser Ile Asn Tyr Arg Thr
                85
```

<210> SEQ ID NO 418
<211> LENGTH: 86
<212> TYPE: PRT
<213> ORGANISM: Artificial Sequence

```
<220> FEATURE:
<223> OTHER INFORMATION: binding polypeptide

<400> SEQUENCE: 418

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp Arg Glu Leu Phe Thr Pro Ile
65                  70                  75                  80

Ser Ile Asn Tyr Arg Thr
                85

<210> SEQ ID NO 419
<211> LENGTH: 86
<212> TYPE: PRT
<213> ORGANISM: Artificial Sequence
<220> FEATURE:
<223> OTHER INFORMATION: binding polypeptide

<400> SEQUENCE: 419

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Gly Gln Asn His His Glu Leu Phe Thr Pro Ile
65                  70                  75                  80

Ser Ile Asn Tyr Arg Thr
                85

<210> SEQ ID NO 420
<211> LENGTH: 86
<212> TYPE: PRT
<213> ORGANISM: Artificial Sequence
<220> FEATURE:
<223> OTHER INFORMATION: binding polypeptide

<400> SEQUENCE: 420

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Gly Pro His Asp Arg Glu Leu Leu Thr Pro Ile
65                  70                  75                  80

Ser Ile Asn Tyr Arg Thr
                85
```

```
<210> SEQ ID NO 421
<211> LENGTH: 94
<212> TYPE: PRT
<213> ORGANISM: Artificial Sequence
<220> FEATURE:
<223> OTHER INFORMATION: binding polypeptide

<400> SEQUENCE: 421

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Met Gly Phe Met
65                  70                  75                  80

Ala His Glu Leu Met Val Pro Ile Ser Ile Asn Tyr Arg Thr
                85                  90

<210> SEQ ID NO 422
<211> LENGTH: 86
<212> TYPE: PRT
<213> ORGANISM: Artificial Sequence
<220> FEATURE:
<223> OTHER INFORMATION: binding polypeptide

<400> SEQUENCE: 422

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp His Glu Leu Leu Thr Pro Ile
65                  70                  75                  80

Ser Ile Asn Tyr Arg Thr
                85

<210> SEQ ID NO 423
<211> LENGTH: 86
<212> TYPE: PRT
<213> ORGANISM: Artificial Sequence
<220> FEATURE:
<223> OTHER INFORMATION: binding polypeptide

<400> SEQUENCE: 423

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Leu Val Arg Asn Asp His Glu Leu Leu Thr Pro Ile
```

```
                 65                  70                  75                  80

Ser Ile Asn Tyr Arg Thr
                85

<210> SEQ ID NO 424
<211> LENGTH: 86
<212> TYPE: PRT
<213> ORGANISM: Artificial Sequence
<220> FEATURE:
<223> OTHER INFORMATION: binding polypeptide

<400> SEQUENCE: 424

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Leu Ala Gln Asp Asp His Glu Leu Leu Thr Pro Ile
 65                  70                  75                  80

Ser Ile Asn Tyr Arg Thr
                85

<210> SEQ ID NO 425
<211> LENGTH: 86
<212> TYPE: PRT
<213> ORGANISM: Artificial Sequence
<220> FEATURE:
<223> OTHER INFORMATION: binding polypeptide

<400> SEQUENCE: 425

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Glu Asp Ile Arg Val Leu Trp Leu Asn Thr Thr Ile
 65                  70                  75                  80

Ser Ile Asn Tyr Arg Thr
                85

<210> SEQ ID NO 426
<211> LENGTH: 86
<212> TYPE: PRT
<213> ORGANISM: Artificial Sequence
<220> FEATURE:
<223> OTHER INFORMATION: binding polypeptide

<400> SEQUENCE: 426

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45
```

```
Ala Thr Ile Ser Gly Leu Lys Pro Gly Val Asp Tyr Thr Ile Thr Gly
    50                  55                  60

Tyr Ala Val Thr Val Thr Gln Asn Asp His Glu Leu Leu Thr Pro Ile
65                  70                  75                  80

Ser Ile Asn Tyr Arg Thr
                85

<210> SEQ ID NO 427
<211> LENGTH: 86
<212> TYPE: PRT
<213> ORGANISM: Artificial Sequence
<220> FEATURE:
<223> OTHER INFORMATION: binding polypeptide

<400> SEQUENCE: 427

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Val Gly Gln Asn Asp His Glu Leu Leu Thr Pro Ile
65                  70                  75                  80

Ser Ile Asn Tyr Arg Thr
                85

<210> SEQ ID NO 428
<211> LENGTH: 86
<212> TYPE: PRT
<213> ORGANISM: Artificial Sequence
<220> FEATURE:
<223> OTHER INFORMATION: binding polypeptide

<400> SEQUENCE: 428

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Asp His Lys Leu Phe Thr Pro Ile
65                  70                  75                  80

Ser Ile Asn Tyr Arg Thr
                85

<210> SEQ ID NO 429
<211> LENGTH: 86
<212> TYPE: PRT
<213> ORGANISM: Artificial Sequence
<220> FEATURE:
<223> OTHER INFORMATION: binding polypeptide

<400> SEQUENCE: 429

Glu Val Val Ala Ala Thr Pro Thr Ser Leu Leu Ile Ser Trp Arg His
1               5                   10                  15
```

```
Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp His Glu Leu Leu Thr Pro Ile
65                  70                  75                  80

Ser Ile Asn Tyr Arg Thr
                85
```

<210> SEQ ID NO 430
<211> LENGTH: 86
<212> TYPE: PRT
<213> ORGANISM: Artificial Sequence
<220> FEATURE:
<223> OTHER INFORMATION: binding polypeptide

<400> SEQUENCE: 430

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Asp His Glu Leu Leu Thr Pro Ile
65                  70                  75                  80

Ser Ile Asn Tyr Arg Thr
                85
```

<210> SEQ ID NO 431
<211> LENGTH: 86
<212> TYPE: PRT
<213> ORGANISM: Artificial Sequence
<220> FEATURE:
<223> OTHER INFORMATION: binding polypeptide

<400> SEQUENCE: 431

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asn His Glu Leu Leu Thr Pro Ile
65                  70                  75                  80

Ser Ile Asn Tyr Arg Thr
                85
```

<210> SEQ ID NO 432
<211> LENGTH: 86
<212> TYPE: PRT
<213> ORGANISM: Artificial Sequence
<220> FEATURE:
<223> OTHER INFORMATION: binding polypeptide

```
<400> SEQUENCE: 432

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp Arg Glu Leu Ile Thr Pro Ile
65                  70                  75                  80

Ser Ile Asn Tyr Arg Thr
                85

<210> SEQ ID NO 433
<211> LENGTH: 86
<212> TYPE: PRT
<213> ORGANISM: Artificial Sequence
<220> FEATURE:
<223> OTHER INFORMATION: binding polypeptide

<400> SEQUENCE: 433

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Gly Gln Asn Asn His Glu Leu Ile Thr Pro Ile
65                  70                  75                  80

Ser Ile Asn Tyr Arg Thr
                85

<210> SEQ ID NO 434
<211> LENGTH: 86
<212> TYPE: PRT
<213> ORGANISM: Artificial Sequence
<220> FEATURE:
<223> OTHER INFORMATION: binding polypeptide

<400> SEQUENCE: 434

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Gly His Glu Leu Ile Thr Pro Ile
65                  70                  75                  80

Ser Ile Asn Tyr Arg Thr
                85

<210> SEQ ID NO 435
<211> LENGTH: 86
```

```
<212> TYPE: PRT
<213> ORGANISM: Artificial Sequence
<220> FEATURE:
<223> OTHER INFORMATION: binding polypeptide

<400> SEQUENCE: 435

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Thr Ala His Asn Gly His Glu Leu Leu Thr Pro Ile
65                  70                  75                  80

Ser Ile Asn Tyr Arg Thr
            85

<210> SEQ ID NO 436
<211> LENGTH: 86
<212> TYPE: PRT
<213> ORGANISM: Artificial Sequence
<220> FEATURE:
<223> OTHER INFORMATION: binding polypeptide

<400> SEQUENCE: 436

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Tyr His Asp His Ala Leu Phe Thr Pro Ile
65                  70                  75                  80

Ser Ile Asn Tyr Arg Thr
            85

<210> SEQ ID NO 437
<211> LENGTH: 86
<212> TYPE: PRT
<213> ORGANISM: Artificial Sequence
<220> FEATURE:
<223> OTHER INFORMATION: binding polypeptide

<400> SEQUENCE: 437

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Trp Ala Trp Asn Asp His Glu Leu Met Thr Pro Ile
65                  70                  75                  80

Ser Ile Asn Tyr Arg Thr
```

<210> SEQ ID NO 438
<211> LENGTH: 86
<212> TYPE: PRT
<213> ORGANISM: Artificial Sequence
<220> FEATURE:
<223> OTHER INFORMATION: binding polypeptide

<400> SEQUENCE: 438

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp His Glu Leu Leu Thr Pro Ile
65                  70                  75                  80

Ser Ile Asn Tyr Arg Thr
            85

<210> SEQ ID NO 439
<211> LENGTH: 86
<212> TYPE: PRT
<213> ORGANISM: Artificial Sequence
<220> FEATURE:
<223> OTHER INFORMATION: binding polypeptide

<400> SEQUENCE: 439

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Asp His Glu Leu Met Thr Pro Ile
65                  70                  75                  80

Ser Ile Asn Tyr Arg Thr
            85

<210> SEQ ID NO 440
<211> LENGTH: 86
<212> TYPE: PRT
<213> ORGANISM: Artificial Sequence
<220> FEATURE:
<223> OTHER INFORMATION: binding polypeptide

<400> SEQUENCE: 440

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

-continued

Tyr Ala Val Thr Met Ala Gln Asn Asp His Glu Leu Leu Thr Pro Ile
65                  70                  75                  80

Ser Ile Asn Tyr Arg Thr
                85

<210> SEQ ID NO 441
<211> LENGTH: 86
<212> TYPE: PRT
<213> ORGANISM: Artificial Sequence
<220> FEATURE:
<223> OTHER INFORMATION: binding polypeptide

<400> SEQUENCE: 441

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Gly His Glu Leu Ile Thr Pro Ile
65                  70                  75                  80

Ser Ile Asn Tyr Arg Thr
                85

<210> SEQ ID NO 442
<211> LENGTH: 94
<212> TYPE: PRT
<213> ORGANISM: Artificial Sequence
<220> FEATURE:
<223> OTHER INFORMATION: binding polypeptide

<400> SEQUENCE: 442

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Glu Gly Trp Ile
65                  70                  75                  80

Asp His Glu Ile Met Ile Pro Ile Ser Ile Asn Tyr Arg Thr
                85                  90

<210> SEQ ID NO 443
<211> LENGTH: 86
<212> TYPE: PRT
<213> ORGANISM: Artificial Sequence
<220> FEATURE:
<223> OTHER INFORMATION: binding polypeptide

<400> SEQUENCE: 443

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

```
Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Glu Gly Gln Asn Gly Ser Glu Leu Ile Val Pro Ile
 65                  70                  75                  80

Ser Ile Asn Tyr Arg Thr
                85

<210> SEQ ID NO 444
<211> LENGTH: 86
<212> TYPE: PRT
<213> ORGANISM: Artificial Sequence
<220> FEATURE:
<223> OTHER INFORMATION: binding polypeptide

<400> SEQUENCE: 444

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Met Ala Gln Asn Asp Arg Glu Leu Ile Thr Pro Ile
 65                  70                  75                  80

Ser Ile Asn Tyr Arg Thr
                85

<210> SEQ ID NO 445
<211> LENGTH: 86
<212> TYPE: PRT
<213> ORGANISM: Artificial Sequence
<220> FEATURE:
<223> OTHER INFORMATION: binding polypeptide

<400> SEQUENCE: 445

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Val Gly Gln Asn Asp His Glu Leu Phe Thr Pro Ile
 65                  70                  75                  80

Ser Ile Asn Tyr Arg Thr
                85

<210> SEQ ID NO 446
<211> LENGTH: 86
<212> TYPE: PRT
<213> ORGANISM: Artificial Sequence
<220> FEATURE:
<223> OTHER INFORMATION: binding polypeptide

<400> SEQUENCE: 446

Glu Val Val Ala Ala Thr Pro Thr Ser Leu Leu Ile Ser Trp Arg His
```

-continued

```
                 1               5              10              15
Pro His Phe Pro Thr Arg Tyr Tyr Arg Ile Thr Tyr Gly Glu Thr Gly
                20              25              30

Gly Asn Ser Pro Val Gln Glu Phe Thr Val Pro Leu Gln Pro Pro Thr
                35              40              45

Ala Thr Ile Ser Gly Leu Lys Pro Gly Val Asp Tyr Thr Ile Thr Gly
                50              55              60

Tyr Ala Val Thr Val Ala Gln Ser Asp His Glu Leu Phe Thr Pro Ile
 65              70              75              80

Ser Ile Asn Tyr Arg Thr
                85
```

<210> SEQ ID NO 447
<211> LENGTH: 86
<212> TYPE: PRT
<213> ORGANISM: Artificial Sequence
<220> FEATURE:
<223> OTHER INFORMATION: binding polypeptide

<400> SEQUENCE: 447

```
Glu Val Val Ala Ala Thr Pro Thr Ser Leu Leu Ile Ser Trp Arg His
 1               5              10              15

Pro His Phe Pro Thr Arg Tyr Tyr Arg Ile Thr Tyr Gly Glu Thr Gly
                20              25              30

Gly Asn Ser Pro Val Gln Glu Phe Thr Val Pro Leu Gln Pro Pro Thr
                35              40              45

Ala Thr Ile Ser Gly Leu Lys Pro Gly Val Asp Tyr Thr Ile Thr Gly
                50              55              60

Tyr Ala Val Thr Val Asp Arg Asn Asp His Glu Leu Phe Thr Pro Ile
 65              70              75              80

Ser Ile Asn Tyr Arg Thr
                85
```

<210> SEQ ID NO 448
<211> LENGTH: 86
<212> TYPE: PRT
<213> ORGANISM: Artificial Sequence
<220> FEATURE:
<223> OTHER INFORMATION: binding polypeptide

<400> SEQUENCE: 448

```
Glu Val Val Ala Ala Thr Pro Thr Ser Leu Leu Ile Ser Trp Arg His
 1               5              10              15

Pro His Phe Pro Thr Arg Tyr Tyr Arg Ile Thr Tyr Gly Glu Thr Gly
                20              25              30

Gly Asn Ser Pro Val Gln Glu Phe Thr Val Pro Leu Gln Pro Pro Thr
                35              40              45

Ala Thr Ile Ser Gly Leu Lys Pro Gly Val Asp Tyr Thr Ile Thr Gly
                50              55              60

Tyr Ala Val Thr Leu Ala Gln Asn Asp His Glu Leu Met Thr Pro Ile
 65              70              75              80

Ser Ile Asn Tyr Arg Thr
                85
```

<210> SEQ ID NO 449
<211> LENGTH: 86
<212> TYPE: PRT
<213> ORGANISM: Artificial Sequence
<220> FEATURE:

<223> OTHER INFORMATION: binding polypeptide

<400> SEQUENCE: 449

```
Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Val Ala Gln Asn Asp His Glu Leu Phe Thr Pro Ile
65                  70                  75                  80
Ser Ile Asn Tyr Arg Thr
                85
```

<210> SEQ ID NO 450
<211> LENGTH: 86
<212> TYPE: PRT
<213> ORGANISM: Artificial Sequence
<220> FEATURE:
<223> OTHER INFORMATION: binding polypeptide

<400> SEQUENCE: 450

```
Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Leu Gly Glu Asn Asp Arg Lys Leu Ile Thr Pro Ile
65                  70                  75                  80
Ser Ile Asn Tyr Arg Thr
                85
```

<210> SEQ ID NO 451
<211> LENGTH: 86
<212> TYPE: PRT
<213> ORGANISM: Artificial Sequence
<220> FEATURE:
<223> OTHER INFORMATION: binding polypeptide

<400> SEQUENCE: 451

```
Glu Val Val Ala Ala Thr Pro Thr Ser Leu Leu Ile Ser Trp Arg His
1               5                   10                  15
Pro His Phe Pro Thr Arg Tyr Tyr Arg Ile Thr Tyr Gly Glu Thr Gly
            20                  25                  30
Gly Asn Ser Pro Val Gln Glu Phe Thr Val Pro Leu Gln Pro Pro Thr
        35                  40                  45
Ala Thr Ile Ser Gly Leu Lys Pro Gly Val Asp Tyr Thr Ile Thr Gly
    50                  55                  60
Tyr Ala Val Thr Val Ala Gln Asn Asp His Glu Leu Leu Thr Pro Ile
65                  70                  75                  80
Ser Ile Asn Tyr Arg Thr
                85
```

<210> SEQ ID NO 452
<211> LENGTH: 86
<212> TYPE: PRT
<213> ORGANISM: Artificial Sequence
<220> FEATURE:
<223> OTHER INFORMATION: binding polypeptide

<400> SEQUENCE: 452

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Gly Pro Asn Gly His Glu Leu Ile Thr Pro Ile
65                  70                  75                  80

Ser Ile Asn Tyr Arg Thr
                85

<210> SEQ ID NO 453
<211> LENGTH: 86
<212> TYPE: PRT
<213> ORGANISM: Artificial Sequence
<220> FEATURE:
<223> OTHER INFORMATION: binding polypeptide

<400> SEQUENCE: 453

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Ala Gln Asn Val Arg Glu Leu Leu Thr Pro Ile
65                  70                  75                  80

Ser Ile Asn Tyr Arg Thr
                85

<210> SEQ ID NO 454
<211> LENGTH: 86
<212> TYPE: PRT
<213> ORGANISM: Artificial Sequence
<220> FEATURE:
<223> OTHER INFORMATION: binding polypeptide

<400> SEQUENCE: 454

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Thr Gln Asn Gly His Glu Leu Ile Thr Pro Ile
65                  70                  75                  80

Ser Ile Asn Tyr Arg Thr
            85

<210> SEQ ID NO 455
<211> LENGTH: 86
<212> TYPE: PRT
<213> ORGANISM: Artificial Sequence
<220> FEATURE:
<223> OTHER INFORMATION: binding polypeptide

<400> SEQUENCE: 455

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Thr Gln Asn Asp His Glu Leu Phe Thr Pro Ile
65                  70                  75                  80

Ser Ile Asn Tyr Arg Thr
            85

<210> SEQ ID NO 456
<211> LENGTH: 86
<212> TYPE: PRT
<213> ORGANISM: Artificial Sequence
<220> FEATURE:
<223> OTHER INFORMATION: binding polypeptide

<400> SEQUENCE: 456

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Gly His Glu Leu Leu Thr Pro Ile
65                  70                  75                  80

Ser Ile Asn Tyr Arg Thr
            85

<210> SEQ ID NO 457
<211> LENGTH: 86
<212> TYPE: PRT
<213> ORGANISM: Artificial Sequence
<220> FEATURE:
<223> OTHER INFORMATION: binding polypeptide

<400> SEQUENCE: 457

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

```
Ala Thr Ile Ser Gly Leu Lys Pro Gly Val Asp Tyr Thr Ile Thr Gly
        50                  55                  60

Tyr Ala Val Thr Val Ala Gln Asn Asp Arg Gln Leu Phe Thr Pro Ile
65                  70                  75                  80

Ser Ile Asn Tyr Arg Thr
                85

<210> SEQ ID NO 458
<211> LENGTH: 86
<212> TYPE: PRT
<213> ORGANISM: Artificial Sequence
<220> FEATURE:
<223> OTHER INFORMATION: binding polypeptide

<400> SEQUENCE: 458

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
        50                  55                  60

Tyr Ala Val Thr Val Gly Pro Asn Asp Arg Glu Leu Ile Val Pro Ile
65                  70                  75                  80

Ser Ile Asn Tyr Arg Thr
                85

<210> SEQ ID NO 459
<211> LENGTH: 86
<212> TYPE: PRT
<213> ORGANISM: Artificial Sequence
<220> FEATURE:
<223> OTHER INFORMATION: binding polypeptide

<400> SEQUENCE: 459

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
        50                  55                  60

Tyr Ala Val Thr Val Ala Gln Asn Glu His Glu Leu Leu Thr Pro Ile
65                  70                  75                  80

Ser Ile Asn Tyr Arg Thr
                85

<210> SEQ ID NO 460
<211> LENGTH: 86
<212> TYPE: PRT
<213> ORGANISM: Artificial Sequence
<220> FEATURE:
<223> OTHER INFORMATION: binding polypeptide

<400> SEQUENCE: 460

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
```

-continued

```
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Ala Gln Asn Asn His Glu Leu Ile Thr Pro Ile
65                  70                  75                  80

Ser Ile Asn Tyr Arg Thr
                85

<210> SEQ ID NO 461
<211> LENGTH: 86
<212> TYPE: PRT
<213> ORGANISM: Artificial Sequence
<220> FEATURE:
<223> OTHER INFORMATION: binding polypeptide

<400> SEQUENCE: 461

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Glu Ala His His Gly His Glu Leu Met Ile Pro Ile
65                  70                  75                  80

Ser Ile Asn Tyr Arg Thr
                85

<210> SEQ ID NO 462
<211> LENGTH: 86
<212> TYPE: PRT
<213> ORGANISM: Artificial Sequence
<220> FEATURE:
<223> OTHER INFORMATION: binding polypeptide

<400> SEQUENCE: 462

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Gly Asp His Asn Asp Arg Glu Leu Met Thr Pro Ile
65                  70                  75                  80

Ser Ile Asn Tyr Arg Thr
                85

<210> SEQ ID NO 463
<211> LENGTH: 94
<212> TYPE: PRT
<213> ORGANISM: Artificial Sequence
<220> FEATURE:
<223> OTHER INFORMATION: binding polypeptide

<400> SEQUENCE: 463
```

```
Val Ser Asp Val Pro Arg Asp Leu Glu Val Val Ala Ala Thr Pro Thr
1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
                35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Gly Gly Gln Met
65                  70                  75                  80

Asn Arg Val Leu Met Thr Pro Ile Ser Ile Asn Tyr Arg Thr
                85                  90

<210> SEQ ID NO 464
<211> LENGTH: 86
<212> TYPE: PRT
<213> ORGANISM: Artificial Sequence
<220> FEATURE:
<223> OTHER INFORMATION: binding polypeptide

<400> SEQUENCE: 464

Glu Val Val Ala Ala Thr Pro Thr Ser Leu Leu Ile Ser Trp Arg His
1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Ala His Asn Asp Arg Glu Leu Ile Thr Pro Ile
65                  70                  75                  80

Ser Ile Asn Tyr Arg Thr
                85

<210> SEQ ID NO 465
<211> LENGTH: 86
<212> TYPE: PRT
<213> ORGANISM: Artificial Sequence
<220> FEATURE:
<223> OTHER INFORMATION: binding polypeptide

<400> SEQUENCE: 465

Glu Val Val Ala Ala Thr Pro Thr Ser Leu Leu Ile Ser Trp Arg His
1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Pro Gln Asn Gly His Glu Leu Ile Thr Met Ile
65                  70                  75                  80

Ser Ile Asn Tyr Arg Thr
                85

<210> SEQ ID NO 466
<211> LENGTH: 86
<212> TYPE: PRT
```

```
<213> ORGANISM: Artificial Sequence
<220> FEATURE:
<223> OTHER INFORMATION: binding polypeptide

<400> SEQUENCE: 466

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp His Glu Leu Phe Thr Pro Ile
65                  70                  75                  80

Ser Ile Asn Tyr Arg Thr
                85

<210> SEQ ID NO 467
<211> LENGTH: 86
<212> TYPE: PRT
<213> ORGANISM: Artificial Sequence
<220> FEATURE:
<223> OTHER INFORMATION: binding polypeptide

<400> SEQUENCE: 467

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Asp Gln Asn Asp His Glu Leu Phe Thr Pro Ile
65                  70                  75                  80

Ser Ile Asn Tyr Arg Thr
                85

<210> SEQ ID NO 468
<211> LENGTH: 94
<212> TYPE: PRT
<213> ORGANISM: Artificial Sequence
<220> FEATURE:
<223> OTHER INFORMATION: binding polypeptide

<400> SEQUENCE: 468

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Val Ala Trp Asn
65                  70                  75                  80

Asp His Met Leu Met Thr Pro Ile Ser Ile Asn Tyr Arg Thr
                85                  90
```

```
<210> SEQ ID NO 469
<211> LENGTH: 94
<212> TYPE: PRT
<213> ORGANISM: Artificial Sequence
<220> FEATURE:
<223> OTHER INFORMATION: binding polypeptide

<400> SEQUENCE: 469

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Ser Gly His Asn
65                  70                  75                  80

Asp His Met Leu Met Ile Pro Ile Ser Ile Asn Tyr Arg Thr
                85                  90

<210> SEQ ID NO 470
<211> LENGTH: 86
<212> TYPE: PRT
<213> ORGANISM: Artificial Sequence
<220> FEATURE:
<223> OTHER INFORMATION: binding polypeptide

<400> SEQUENCE: 470

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Gly His Val Leu Ile Thr Pro Ile
65                  70                  75                  80

Ser Ile Asn Tyr Arg Thr
                85

<210> SEQ ID NO 471
<211> LENGTH: 86
<212> TYPE: PRT
<213> ORGANISM: Artificial Sequence
<220> FEATURE:
<223> OTHER INFORMATION: binding polypeptide

<400> SEQUENCE: 471

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60
```

-continued

Tyr Ala Val Thr Val Thr His Asn Asp His Glu Leu Leu Thr Pro Ile
65                  70                  75                  80

Ser Ile Asn Tyr Arg Thr
                85

<210> SEQ ID NO 472
<211> LENGTH: 86
<212> TYPE: PRT
<213> ORGANISM: Artificial Sequence
<220> FEATURE:
<223> OTHER INFORMATION: binding polypeptide

<400> SEQUENCE: 472

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Gly Gln Asn Asp His Glu Leu Met Thr Pro Ile
65                  70                  75                  80

Ser Ile Asn Tyr Arg Thr
                85

<210> SEQ ID NO 473
<211> LENGTH: 86
<212> TYPE: PRT
<213> ORGANISM: Artificial Sequence
<220> FEATURE:
<223> OTHER INFORMATION: binding polypeptide

<400> SEQUENCE: 473

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Ala Gln Asn Asp His Glu Ile Met Thr Pro Ile
65                  70                  75                  80

Ser Ile Asn Tyr Arg Thr
                85

<210> SEQ ID NO 474
<211> LENGTH: 86
<212> TYPE: PRT
<213> ORGANISM: Artificial Sequence
<220> FEATURE:
<223> OTHER INFORMATION: binding polypeptide

<400> SEQUENCE: 474

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr

```
                35                  40                  45

Ala Thr Ile Ser Gly Leu Lys Pro Gly Val Asp Tyr Thr Ile Thr Gly
         50                  55                  60

Tyr Ala Val Thr Leu Ala Gln Asn Asp His Glu Leu Ile Thr Pro Ile
 65                  70                  75                  80

Ser Ile Asn Tyr Arg Thr
                 85

<210> SEQ ID NO 475
<211> LENGTH: 86
<212> TYPE: PRT
<213> ORGANISM: Artificial Sequence
<220> FEATURE:
<223> OTHER INFORMATION: binding polypeptide

<400> SEQUENCE: 475

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Val Ser Gln Gln Asn His Glu Leu Leu Thr Pro Ile
 65                  70                  75                  80

Ser Ile Asn Tyr Arg Thr
                 85

<210> SEQ ID NO 476
<211> LENGTH: 86
<212> TYPE: PRT
<213> ORGANISM: Artificial Sequence
<220> FEATURE:
<223> OTHER INFORMATION: binding polypeptide

<400> SEQUENCE: 476

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Val Ala Gln Asn Asp His Glu Leu Met Thr Pro Ile
 65                  70                  75                  80

Ser Ile Asn Tyr Arg Thr
                 85

<210> SEQ ID NO 477
<211> LENGTH: 86
<212> TYPE: PRT
<213> ORGANISM: Artificial Sequence
<220> FEATURE:
<223> OTHER INFORMATION: binding polypeptide

<400> SEQUENCE: 477

Glu Val Val Ala Ala Thr Pro Thr Ser Leu Leu Ile Ser Trp Arg His
 1               5                  10                  15
```

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
     50                  55                  60

Tyr Ala Val Thr Val Ala Tyr Asn Glu His Glu Leu Tyr Thr Pro Ile
 65                  70                  75                  80

Ser Ile Asn Tyr Arg Thr
                85

<210> SEQ ID NO 478
<211> LENGTH: 86
<212> TYPE: PRT
<213> ORGANISM: Artificial Sequence
<220> FEATURE:
<223> OTHER INFORMATION: binding polypeptide

<400> SEQUENCE: 478

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
     50                  55                  60

Tyr Ala Val Thr Val Ala Gln His Asp His Glu Leu Leu Thr Pro Ile
 65                  70                  75                  80

Ser Ile Asn Tyr Arg Thr
                85

<210> SEQ ID NO 479
<211> LENGTH: 86
<212> TYPE: PRT
<213> ORGANISM: Artificial Sequence
<220> FEATURE:
<223> OTHER INFORMATION: binding polypeptide

<400> SEQUENCE: 479

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
                35                  40                  45

Ala Thr Ile Ser Gly Leu Lys Pro Gly Val Asp Tyr Thr Ile Thr Gly
     50                  55                  60

Tyr Ala Val Thr Val Gly Gln Asn Asp Gln Glu Leu Leu Thr Pro Ile
 65                  70                  75                  80

Ser Ile Asn Tyr Arg Thr
                85

<210> SEQ ID NO 480
<211> LENGTH: 86
<212> TYPE: PRT
<213> ORGANISM: Artificial Sequence
<220> FEATURE:
<223> OTHER INFORMATION: binding polypeptide

<400> SEQUENCE: 480

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Ala Arg Asn Asp His Glu Leu Met Thr Pro Ile
65                  70                  75                  80

Ser Ile Asn Tyr Arg Thr
                85

<210> SEQ ID NO 481
<211> LENGTH: 86
<212> TYPE: PRT
<213> ORGANISM: Artificial Sequence
<220> FEATURE:
<223> OTHER INFORMATION: binding polypeptide

<400> SEQUENCE: 481

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Gly Pro Thr Asp His Glu Leu Leu Thr Pro Ile
65                  70                  75                  80

Ser Ile Asn Tyr Arg Thr
                85

<210> SEQ ID NO 482
<211> LENGTH: 86
<212> TYPE: PRT
<213> ORGANISM: Artificial Sequence
<220> FEATURE:
<223> OTHER INFORMATION: binding polypeptide

<400> SEQUENCE: 482

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Gly Leu Thr Asp His Val Leu Leu Thr Pro Ile
65                  70                  75                  80

Ser Ile Asn Tyr Arg Thr
                85

<210> SEQ ID NO 483

```
<211> LENGTH: 86
<212> TYPE: PRT
<213> ORGANISM: Artificial Sequence
<220> FEATURE:
<223> OTHER INFORMATION: binding polypeptide

<400> SEQUENCE: 483

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asp Asp His Glu Leu Phe Thr Pro Ile
65                  70                  75                  80

Ser Ile Asn Tyr Arg Thr
                85

<210> SEQ ID NO 484
<211> LENGTH: 86
<212> TYPE: PRT
<213> ORGANISM: Artificial Sequence
<220> FEATURE:
<223> OTHER INFORMATION: binding polypeptide

<400> SEQUENCE: 484

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Gln Asn Asp His Glu Leu Phe Thr Pro Ile
65                  70                  75                  80

Ser Ile Asn Tyr Arg Thr
                85

<210> SEQ ID NO 485
<211> LENGTH: 86
<212> TYPE: PRT
<213> ORGANISM: Artificial Sequence
<220> FEATURE:
<223> OTHER INFORMATION: binding polypeptide

<400> SEQUENCE: 485

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Gly Trp Asn Asp His Glu Leu Ile Thr Pro Ile
65                  70                  75                  80
```

-continued

Ser Ile Asn Tyr Arg Thr
                85

<210> SEQ ID NO 486
<211> LENGTH: 86
<212> TYPE: PRT
<213> ORGANISM: Artificial Sequence
<220> FEATURE:
<223> OTHER INFORMATION: binding polypeptide

<400> SEQUENCE: 486

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp His Glu Leu Phe Thr Pro Ile
65                  70                  75                  80

Ser Ile Asn Tyr Arg Thr
                85

<210> SEQ ID NO 487
<211> LENGTH: 86
<212> TYPE: PRT
<213> ORGANISM: Artificial Sequence
<220> FEATURE:
<223> OTHER INFORMATION: binding polypeptide

<400> SEQUENCE: 487

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Gln Glu Asn Gln Glu Leu Ile Thr Pro Ile
65                  70                  75                  80

Ser Ile Asn Tyr Arg Thr
                85

<210> SEQ ID NO 488
<211> LENGTH: 94
<212> TYPE: PRT
<213> ORGANISM: Artificial Sequence
<220> FEATURE:
<223> OTHER INFORMATION: binding polypeptide

<400> SEQUENCE: 488

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro

```
                50                  55                  60
Gly Val Asp Tyr Thr Ile Thr Gly Tyr Ala Val Thr Leu Ala Pro Ser
 65                  70                  75                  80

Ala Arg Glu Leu Met Thr Pro Ile Ser Ile Asn Tyr Arg Thr
                 85                  90

<210> SEQ ID NO 489
<211> LENGTH: 86
<212> TYPE: PRT
<213> ORGANISM: Artificial Sequence
<220> FEATURE:
<223> OTHER INFORMATION: binding polypeptide

<400> SEQUENCE: 489

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Val Val His Asn Gly His Glu Ile Leu Thr Pro Ile
 65                  70                  75                  80

Ser Ile Asn Tyr Arg Thr
                 85

<210> SEQ ID NO 490
<211> LENGTH: 86
<212> TYPE: PRT
<213> ORGANISM: Artificial Sequence
<220> FEATURE:
<223> OTHER INFORMATION: binding polypeptide

<400> SEQUENCE: 490

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Met Gly Tyr Glu Asp His Glu Leu Ile Thr Pro Ile
 65                  70                  75                  80

Ser Ile Asn Tyr Arg Thr
                 85

<210> SEQ ID NO 491
<211> LENGTH: 94
<212> TYPE: PRT
<213> ORGANISM: Artificial Sequence
<220> FEATURE:
<223> OTHER INFORMATION: binding polypeptide

<400> SEQUENCE: 491

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30
```

-continued

Arg Ile Thr Tyr Gly Glu Thr Gly Gly Asn Ser Pro Val Gln Glu Phe
                35                  40                  45

Thr Val Pro Leu Gln Pro Pro Thr Ala Thr Ile Ser Gly Leu Lys Pro
 50                  55                  60

Gly Val Asp Tyr Thr Ile Thr Gly Tyr Ala Val Thr Glu Gly Tyr Gln
 65                  70                  75                  80

Asn His Glu Leu Ser Val Pro Ile Ser Ile Asn Tyr Arg Thr
                 85                  90

<210> SEQ ID NO 492
<211> LENGTH: 86
<212> TYPE: PRT
<213> ORGANISM: Artificial Sequence
<220> FEATURE:
<223> OTHER INFORMATION: binding polypeptide

<400> SEQUENCE: 492

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
     50                  55                  60

Tyr Ala Val Thr Val Asp Gln Asn Asp His Glu Leu Phe Thr Pro Ile
 65                  70                  75                  80

Ser Ile Asn Tyr Arg Thr
                 85

<210> SEQ ID NO 493
<211> LENGTH: 86
<212> TYPE: PRT
<213> ORGANISM: Artificial Sequence
<220> FEATURE:
<223> OTHER INFORMATION: binding polypeptide

<400> SEQUENCE: 493

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
     50                  55                  60

Tyr Ala Val Thr Val Ala Gln Ser Asp His Glu Leu Met Thr Pro Ile
 65                  70                  75                  80

Ser Ile Asn Tyr Arg Thr
                 85

<210> SEQ ID NO 494
<211> LENGTH: 86
<212> TYPE: PRT
<213> ORGANISM: Artificial Sequence
<220> FEATURE:
<223> OTHER INFORMATION: binding polypeptide

<400> SEQUENCE: 494

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Gly Gln Asn Asp His Glu Leu Ile Thr Pro Ile
65                  70                  75                  80

Ser Ile Asn Tyr Arg Thr
                85

<210> SEQ ID NO 495
<211> LENGTH: 86
<212> TYPE: PRT
<213> ORGANISM: Artificial Sequence
<220> FEATURE:
<223> OTHER INFORMATION: binding polypeptide

<400> SEQUENCE: 495

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp His Glu Leu Met Thr Pro Ile
65                  70                  75                  80

Ser Ile Asn Tyr Arg Thr
                85

<210> SEQ ID NO 496
<211> LENGTH: 86
<212> TYPE: PRT
<213> ORGANISM: Artificial Sequence
<220> FEATURE:
<223> OTHER INFORMATION: binding polypeptide

<400> SEQUENCE: 496

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Gly His Glu Leu Ile Thr Pro Ile
65                  70                  75                  80

Ser Ile Asn Tyr Arg Thr
                85

<210> SEQ ID NO 497
<211> LENGTH: 86
<212> TYPE: PRT
<213> ORGANISM: Artificial Sequence -continued

```
<220> FEATURE:
<223> OTHER INFORMATION: binding polypeptide

<400> SEQUENCE: 497

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Arg Ala Gln Asn Asp His Glu Leu Ile Thr Pro Ile
65                  70                  75                  80

Ser Ile Asn Tyr Arg Thr
                85

<210> SEQ ID NO 498
<211> LENGTH: 86
<212> TYPE: PRT
<213> ORGANISM: Artificial Sequence
<220> FEATURE:
<223> OTHER INFORMATION: binding polypeptide

<400> SEQUENCE: 498

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Ala Gln Ser Asn His Glu Leu Met Thr Pro Ile
65                  70                  75                  80

Ser Ile Asn Tyr Arg Thr
                85

<210> SEQ ID NO 499
<211> LENGTH: 86
<212> TYPE: PRT
<213> ORGANISM: Artificial Sequence
<220> FEATURE:
<223> OTHER INFORMATION: binding polypeptide

<400> SEQUENCE: 499

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Ala Gln Asn Asp Arg Glu Leu Ile Thr Pro Ile
65                  70                  75                  80

Ser Ile Asn Tyr Arg Thr
                85
```

-continued

<210> SEQ ID NO 500
<211> LENGTH: 86
<212> TYPE: PRT
<213> ORGANISM: Artificial Sequence
<220> FEATURE:
<223> OTHER INFORMATION: binding polypeptide

<400> SEQUENCE: 500

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Thr His Asn Glu Gln Tyr Leu Phe Thr Pro Ile
65                  70                  75                  80

Ser Ile Asn Tyr Arg Thr
                85

<210> SEQ ID NO 501
<211> LENGTH: 94
<212> TYPE: PRT
<213> ORGANISM: Artificial Sequence
<220> FEATURE:
<223> OTHER INFORMATION: binding polypeptide

<400> SEQUENCE: 501

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Glu Ile Tyr Asn
65                  70                  75                  80

Asp His Glu Leu Met Thr Pro Ile Ser Ile Asn Tyr Arg Thr
                85                  90

<210> SEQ ID NO 502
<211> LENGTH: 86
<212> TYPE: PRT
<213> ORGANISM: Artificial Sequence
<220> FEATURE:
<223> OTHER INFORMATION: binding polypeptide

<400> SEQUENCE: 502

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Ala Gln Asn Asp His Glu Leu Ile Thr Pro Ile

-continued

```
                65                  70                  75                  80
Ser Ile Asn Tyr Arg Thr
                85

<210> SEQ ID NO 503
<211> LENGTH: 86
<212> TYPE: PRT
<213> ORGANISM: Artificial Sequence
<220> FEATURE:
<223> OTHER INFORMATION: binding polypeptide

<400> SEQUENCE: 503

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Ser Gln Tyr Gly His Glu Leu Ile Thr Pro Ile
65                  70                  75                  80

Ser Ile Asn Tyr Arg Thr
                85

<210> SEQ ID NO 504
<211> LENGTH: 86
<212> TYPE: PRT
<213> ORGANISM: Artificial Sequence
<220> FEATURE:
<223> OTHER INFORMATION: binding polypeptide

<400> SEQUENCE: 504

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Ala Lys Asn Asp His Glu Leu Ile Thr Pro Ile
65                  70                  75                  80

Ser Ile Asn Tyr Arg Thr
                85

<210> SEQ ID NO 505
<211> LENGTH: 86
<212> TYPE: PRT
<213> ORGANISM: Artificial Sequence
<220> FEATURE:
<223> OTHER INFORMATION: binding polypeptide

<400> SEQUENCE: 505

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45
```

```
Ala Thr Ile Ser Gly Leu Lys Pro Gly Val Asp Tyr Thr Ile Thr Gly
     50                  55                  60

Tyr Ala Val Thr Val Ala Gln Asn Asn His Glu Leu Ile Thr Pro Ile
65                  70                  75                  80

Ser Ile Asn Tyr Arg Thr
                85

<210> SEQ ID NO 506
<211> LENGTH: 86
<212> TYPE: PRT
<213> ORGANISM: Artificial Sequence
<220> FEATURE:
<223> OTHER INFORMATION: binding polypeptide

<400> SEQUENCE: 506

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Val Ala Gln His Asp His Glu Leu Leu Thr Pro Ile
65                  70                  75                  80

Ser Ile Asn Tyr Arg Thr
                85

<210> SEQ ID NO 507
<211> LENGTH: 94
<212> TYPE: PRT
<213> ORGANISM: Artificial Sequence
<220> FEATURE:
<223> OTHER INFORMATION: binding polypeptide

<400> SEQUENCE: 507

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
     50                  55                  60

Gly Val Asp Tyr Thr Ile Thr Gly Tyr Ala Val Thr Leu Ser His Tyr
65                  70                  75                  80

Gly Lys Glu Leu Arg Thr Pro Ile Ser Ile Asn Tyr Arg Thr
                85                  90

<210> SEQ ID NO 508
<211> LENGTH: 86
<212> TYPE: PRT
<213> ORGANISM: Artificial Sequence
<220> FEATURE:
<223> OTHER INFORMATION: binding polypeptide

<400> SEQUENCE: 508

Glu Val Val Ala Ala Thr Pro Thr Ser Leu Leu Ile Ser Trp Arg His
1               5                   10                  15
```

-continued

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Ala His Glu Leu Met Thr Pro Ile
65                  70                  75                  80

Ser Ile Asn Tyr Arg Thr
                85

<210> SEQ ID NO 509
<211> LENGTH: 86
<212> TYPE: PRT
<213> ORGANISM: Artificial Sequence
<220> FEATURE:
<223> OTHER INFORMATION: binding polypeptide

<400> SEQUENCE: 509

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Gln Asn Asp His Glu Leu Leu Thr Pro Ile
65                  70                  75                  80

Ser Ile Asn Tyr Arg Thr
                85

<210> SEQ ID NO 510
<211> LENGTH: 86
<212> TYPE: PRT
<213> ORGANISM: Artificial Sequence
<220> FEATURE:
<223> OTHER INFORMATION: binding polypeptide

<400> SEQUENCE: 510

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asn Asp His Glu Leu Lys Thr Pro Ile
65                  70                  75                  80

Ser Ile Asn Tyr Arg Thr
                85

<210> SEQ ID NO 511
<211> LENGTH: 86
<212> TYPE: PRT
<213> ORGANISM: Artificial Sequence
<220> FEATURE:
<223> OTHER INFORMATION: binding polypeptide

```
<400> SEQUENCE: 511

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Gly Glu Gln Asn Asp Tyr Glu Leu Leu Val Pro Ile
65                  70                  75                  80

Ser Ile Asn Tyr Arg Thr
                85

<210> SEQ ID NO 512
<211> LENGTH: 86
<212> TYPE: PRT
<213> ORGANISM: Artificial Sequence
<220> FEATURE:
<223> OTHER INFORMATION: binding polypeptide

<400> SEQUENCE: 512

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Leu Thr Gln His Asp His Glu Leu Leu Thr Pro Ile
65                  70                  75                  80

Ser Ile Asn Tyr Arg Thr
                85

<210> SEQ ID NO 513
<211> LENGTH: 86
<212> TYPE: PRT
<213> ORGANISM: Artificial Sequence
<220> FEATURE:
<223> OTHER INFORMATION: binding polypeptide

<400> SEQUENCE: 513

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Met Ala Gln Asn Asp His Glu Leu Ile Thr Pro Ile
65                  70                  75                  80

Ser Ile Asn Tyr Arg Thr
                85

<210> SEQ ID NO 514
<211> LENGTH: 94
```

```
<212> TYPE: PRT
<213> ORGANISM: Artificial Sequence
<220> FEATURE:
<223> OTHER INFORMATION: binding polypeptide

<400> SEQUENCE: 514

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Glu Ala Pro Asn
65                  70                  75                  80

Gly Arg Glu Leu Arg Thr Pro Ile Ser Ile Asn Tyr Arg Thr
                85                  90

<210> SEQ ID NO 515
<211> LENGTH: 94
<212> TYPE: PRT
<213> ORGANISM: Artificial Sequence
<220> FEATURE:
<223> OTHER INFORMATION: binding polypeptide

<400> SEQUENCE: 515

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Val Gly Pro Thr
65                  70                  75                  80

Asp His Glu Leu Leu Thr Pro Ile Ser Ile Asn Tyr Arg Thr
                85                  90

<210> SEQ ID NO 516
<211> LENGTH: 86
<212> TYPE: PRT
<213> ORGANISM: Artificial Sequence
<220> FEATURE:
<223> OTHER INFORMATION: binding polypeptide

<400> SEQUENCE: 516

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Gly Gln Tyr Asp His Glu Leu Ile Thr Pro Ile
65                  70                  75                  80

Ser Ile Asn Tyr Arg Thr
```

-continued

<210> SEQ ID NO 517
<211> LENGTH: 86
<212> TYPE: PRT
<213> ORGANISM: Artificial Sequence
<220> FEATURE:
<223> OTHER INFORMATION: binding polypeptide

<400> SEQUENCE: 517

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Ala Gln Asp Glu His Glu Leu Ile Thr Pro Ile
65                  70                  75                  80

Ser Ile Asn Tyr Arg Thr
                85

<210> SEQ ID NO 518
<211> LENGTH: 94
<212> TYPE: PRT
<213> ORGANISM: Artificial Sequence
<220> FEATURE:
<223> OTHER INFORMATION: binding polypeptide

<400> SEQUENCE: 518

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Asp Ala Gln Asn
65                  70                  75                  80

Val Gln Ala Pro Ile Ala Gln Ile Ser Ile Asn Tyr Arg Thr
                85                  90

<210> SEQ ID NO 519
<211> LENGTH: 94
<212> TYPE: PRT
<213> ORGANISM: Artificial Sequence
<220> FEATURE:
<223> OTHER INFORMATION: binding polypeptide

<400> SEQUENCE: 519

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

-continued

Gly Val Asp Tyr Thr Ile Thr Gly Tyr Ala Val Thr Ser Gly Gln Asn
65                  70                  75                  80

Asp His Ala Leu Leu Ile Pro Ile Ser Ile Asn Tyr Arg Thr
                85                  90

<210> SEQ ID NO 520
<211> LENGTH: 94
<212> TYPE: PRT
<213> ORGANISM: Artificial Sequence
<220> FEATURE:
<223> OTHER INFORMATION: binding polypeptide

<400> SEQUENCE: 520

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Glu Asp Ile Arg
65                  70                  75                  80

Val Leu Trp Leu Asn Thr Thr Ile Ser Ile Asn Tyr Arg Thr
                85                  90

<210> SEQ ID NO 521
<211> LENGTH: 94
<212> TYPE: PRT
<213> ORGANISM: Artificial Sequence
<220> FEATURE:
<223> OTHER INFORMATION: binding polypeptide

<400> SEQUENCE: 521

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Trp Asp Gln Asn
65                  70                  75                  80

Gly His Val Leu Leu Thr Pro Ile Ser Ile Asn Tyr Arg Thr
                85                  90

<210> SEQ ID NO 522
<211> LENGTH: 94
<212> TYPE: PRT
<213> ORGANISM: Artificial Sequence
<220> FEATURE:
<223> OTHER INFORMATION: binding polypeptide

<400> SEQUENCE: 522

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

```
Arg Ile Thr Tyr Gly Glu Thr Gly Asn Ser Pro Val Gln Glu Phe
            35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Leu Gly Leu Arg
65                  70                  75                  80

Asp Arg Glu Leu Phe Val Pro Ile Ser Ile Asn Tyr Arg Thr
                85                  90
```

<210> SEQ ID NO 523
<211> LENGTH: 94
<212> TYPE: PRT
<213> ORGANISM: Artificial Sequence
<220> FEATURE:
<223> OTHER INFORMATION: binding polypeptide

<400> SEQUENCE: 523

```
Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Asn Ser Pro Val Gln Glu Phe
            35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Val Glu Pro Asn
65                  70                  75                  80

Gly His Lys Leu Ala Ile Pro Ile Ser Ile Asn Tyr Arg Thr
                85                  90
```

<210> SEQ ID NO 524
<211> LENGTH: 86
<212> TYPE: PRT
<213> ORGANISM: Artificial Sequence
<220> FEATURE:
<223> OTHER INFORMATION: binding polypeptide

<400> SEQUENCE: 524

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
    50                  55                  60

Tyr Ala Val Thr Phe Gly Gln Asn Gly Lys Glu Phe Arg Ile Pro Ile
65                  70                  75                  80

Ser Ile Asn Tyr Arg Thr
                85
```

<210> SEQ ID NO 525
<211> LENGTH: 94
<212> TYPE: PRT
<213> ORGANISM: Artificial Sequence
<220> FEATURE:
<223> OTHER INFORMATION: binding polypeptide

<400> SEQUENCE: 525

```
Val Ser Asp Val Pro Arg Asp Leu Glu Val Val Ala Ala Thr Pro Thr
```

```
                1               5                  10                 15
Ser Leu Leu Ile Ser Trp Arg His Pro His Phe Pro Thr Arg Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Thr Ala Thr Ile Ser Gly Leu Lys Pro
        50                 55                 60

Gly Val Asp Tyr Thr Ile Thr Gly Tyr Ala Val Thr Ser Gly His Asn
65                  70                 75                  80

Gly His Glu Val Met Thr Pro Ile Ser Ile Asn Tyr Arg Thr
                85                 90

<210> SEQ ID NO 526
<211> LENGTH: 94
<212> TYPE: PRT
<213> ORGANISM: Artificial Sequence
<220> FEATURE:
<223> OTHER INFORMATION: binding polypeptide

<400> SEQUENCE: 526

Val Ser Asp Val Pro Arg Asp Leu Glu Val Val Ala Ala Thr Pro Thr
1               5                  10                 15

Ser Leu Leu Ile Ser Trp Arg His Pro His Phe Pro Thr Arg Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Thr Ala Thr Ile Ser Gly Leu Lys Pro
        50                 55                 60

Gly Val Asp Tyr Thr Ile Thr Gly Tyr Ala Val Thr Leu Gly Trp Asn
65                  70                 75                  80

Asp His Glu Leu Tyr Ile Pro Ile Ser Ile Asn Tyr Arg Thr
                85                 90

<210> SEQ ID NO 527
<211> LENGTH: 94
<212> TYPE: PRT
<213> ORGANISM: Artificial Sequence
<220> FEATURE:
<223> OTHER INFORMATION: binding polypeptide

<400> SEQUENCE: 527

Val Ser Asp Val Pro Arg Asp Leu Glu Val Val Ala Ala Thr Pro Thr
1               5                  10                 15

Ser Leu Leu Ile Ser Trp Arg His Pro His Phe Pro Thr Arg Tyr Tyr
                20                 25                 30

Arg Ile Thr Tyr Gly Glu Thr Gly Gly Asn Ser Pro Val Gln Glu Phe
                35                 40                 45

Thr Val Pro Leu Gln Pro Pro Thr Ala Thr Ile Ser Gly Leu Lys Pro
        50                 55                 60

Gly Val Asp Tyr Thr Ile Thr Gly Tyr Ala Val Thr Leu Gly Lys Asp
65                  70                 75                  80

Val Arg Glu Leu Leu Thr Pro Ile Ser Ile Asn Tyr Arg Thr
                85                 90

<210> SEQ ID NO 528
<211> LENGTH: 94
<212> TYPE: PRT
<213> ORGANISM: Artificial Sequence
<220> FEATURE:
```

-continued

```
<223> OTHER INFORMATION: binding polypeptide

<400> SEQUENCE: 528

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
        50                  55                  60

Gly Val Asp Tyr Thr Ile Thr Gly Tyr Ala Val Thr Leu Ala Leu Phe
65              70                  75                      80

Asp His Glu Leu Leu Thr Pro Ile Ser Ile Asn Tyr Arg Thr
                85                  90
```

PHARMACOKINETIC MODULATION AND COMPOSITIONS FOR MODIFIED FN3 POLYPEPTIDES

RELATED APPLICATIONS

This application is a continuation of U.S. patent application Ser. No. 11/448,171, entitled "Inhibitors of Type 2 Vascular Endothelial Growth Factor Receptors," filed Jun. 5, 2006, which is a continuation of International Application PCT/US04/40885, entitled "Inhibitors of Type 2 Vascular Endothelial Growth Factor Receptors," filed Dec. 6, 2004 which claims the benefit of U.S. Provisional Application No. 60/527,886, entitled "Inhibitors of Vascular Endothelial Growth Factor Receptors," filed Dec. 5, 2003. All of the teachings of the above-referenced applications are incorporated herein by reference.

BACKGROUND OF THE INVENTION

The present disclosure relates to novel vascular endothelial growth factor receptor (VEGFR)-binding polypeptides and methods for using these polypeptides to inhibit biological activities mediated by vascular endothelial growth factors (VEGFs).

Angiogenesis is the process by which new blood vessels are formed from pre-existing capillaries or post capillary venules; it is an important component of many physiological processes including ovulation, embryonic development, wound repair, and collateral vascular generation in the myocardium. Angiogenesis is also central to a number of pathological conditions such as tumor growth and metastasis, diabetic retinopathy, and macular degeneration. In many instances, the process begins with the activation of existing vascular endothelial cells in response to a variety of cytokines and growth factors. In cancer, tumor released cytokines or angiogenic factors stimulate vascular endothelial cells by interacting with specific cell surface receptors. The activated endothelial cells secrete enzymes that degrade the basement membrane of the vessels, allowing invasion of the endothelial cells into the tumor tissue. Once situated, the endothelial cells differentiate to form new vessel offshoots of pre-existing vessels. The new blood vessels provide nutrients to the tumor, facilitating further growth, and also provide a route for metastasis.

To date, numerous angiogenic factors have been identified, including the particularly potent factor VEGF. VEGF was initially purified from the conditioned media of folliculostellate cells and from a variety of cell lines. More recently a number of structural homologs and alternatively spliced forms of VEGF have been identified. The various forms of VEGF bind as high affinity ligands to a suite of VEGF receptors (VEGFRs). VEGFRs are tyrosine kinase receptors, many of which are important regulators of angiogenesis. The VEGFR family includes 3 major subtypes: VEGFR-1, VEGFR-2 (also known as Kinase Insert Domain Receptor, "KDR", in humans), and VEGFR-3. Among VEGF forms, VEGF-A, VEGF-C and VEGF-D are known to bind and activate VEGFR-2.

VEGF, acting through its cognate receptors, can function as an endothelial specific mitogen during angiogenesis. In addition, there is substantial evidence that VEGF and VEGFRs are up-regulated in conditions characterized by inappropriate angiogenesis, such as cancer. As a result, a great deal of research has focused on the identification of therapeutics that target and inhibit VEGF or VEGFR.

Current therapeutic approaches that target or inhibit VEGF or VEGFR include antibodies, peptides, and small molecule kinase inhibitors. Of these, antibodies are the most widely used for in vivo recognition and inhibition of ligands and cellular receptors. Highly specific antibodies have been used to block receptor-ligand interaction, thereby neutralizing the biological activity of the components, and also to specifically deliver toxic agents to cells expressing the cognate receptor on its surface. Although effective, antibodies are large, complex molecules that rely on expression in recombinant mammalian cells for production. Antibodies also cause a variety of side effects that are often undesirable, including activation of complement pathways and antibody-directed cellular cytotoxicity. As a result, there remains a need for effective therapeutics that can specifically inhibit VEGF/VEGFR pathways as a treatment for disorders characterized by inappropriate angiogenesis, such as cancer.

SUMMARY OF THE INVENTION

In part, this disclosure provides novel, single domain polypeptides that bind to VEGFR-2 receptors, particularly human VEGFR-2 (also known as KDR) and mouse VEGFR-2 (also known as Flk-1). VEGFR-2 binding proteins described herein may be used, for example, to detect VEGFR-2 in vivo or in vitro. Additionally, certain VEGFR-2 binding proteins described herein may be used to treat diseases associated with VEGFR-2-mediated biological activity. For example, KDR mediates pro-angiogenic effects of VEGF, and accordingly, certain KDR binding proteins of the disclosure may be used to inhibit angiogenesis in a human patient. Certain VEGFR-2 binding proteins of the disclosure may be used to treat disorders such as cancers, inflammatory diseases, autoimmune diseases and retinopathies. Many disorders related to the hyperproliferation of cells of a tissue will include an angiogenic component, and thus it is expected that certain VEGFR-2 binding proteins described herein can be used to treat such disorders.

A single domain polypeptide described herein will generally be a polypeptide that binds to a target, such as VEGFR-2, and where target binding activity situated within a single structural domain, as differentiated from, for example, antibodies and single chain antibodies, where antigen binding activity is generally contributed by both a heavy chain variable domain and a light chain variable domain. The disclosure also provides larger proteins that may comprise single domain polypeptides that bind to target. For example, a plurality of single domain polypeptides may be connected to create a composite molecule with increased avidity. Likewise, a single domain polypeptide may be attached (e.g., as a fusion protein) to any number of other polypeptides. In certain aspects a single domain polypeptide may comprise at least five to seven beta or beta-like strands distributed among at least two beta sheets, as exemplified by immunoglobulin and immunoglobulin-like domains. A beta-like strand is a string of amino acids that participates in the stabilization of a single domain polypeptide but does not necessarily adopt a beta strand conformation. Whether a beta-like strand participates in the stabilization of the protein may be assessed by deleting the string or altering the sequence of the string and analyzing whether protein stability is diminished. Stability may be assessed by, for example, thermal denaturation and renaturation studies. Preferably, a single domain polypeptide will include no more than two beta-like strands. A beta-like strand will not usually adopt an alpha-helical conformation but may adopt a random coil structure. In the context of an immunoglobulin domain or an immunoglobulin-like domain, a beta-like strand will most often occur at the position in the structure that would otherwise be occupied by the most N-terminal beta strand or the most C-terminal beta strand. An amino acid string which, if situated in the interior of a protein sequence would normally form a beta strand, may, when situated at a position closer to an N- or C-terminus, adopt a conformation that is not clearly a beta strand and is referred to herein as a beta-like strand.

In certain embodiments, the disclosure provides single domain polypeptides that bind to VEGFR-2. Preferably the single domain polypeptides bind to human KDR, mouse Flk-1, or both. A single domain polypeptide may comprise between about 80 and about 150 amino acids that have a structural organization comprising: at least seven beta strands or beta-like strands distributed between at least two beta sheets, and at least one loop portion connecting two beta strands or beta-like strands, which loop portion participates in binding to VEGFR-2. In other words a loop portion may link two beta strands, two beta-like strands or one beta strand and one beta-like strand. Typically, one or more of the loop portions will participate in VEGFR-2 binding, although it is possible that one or more of the beta or beta-like strand portions will also participate in VEGFR-2 binding, particularly those beta or beta-like strand portions that are situated closest to the loop portions. A single domain polypeptide may comprise a structural unit that is an immunoglobulin domain or an immunoglobulin-like domain. A single domain polypeptide may bind to any part of VEGFR-2, although polypeptides that bind to an extracellular domain of a VEGFR-2 are preferred. Binding may be assessed in terms of equilibrium constants (e.g., dissociation, $K_D$) and in terms of kinetic constants (e.g., on rate constant, $k_{on}$ and off rate constant, $k_{off}$). A single domain polypeptide will typically be selected to bind to VEGFR-2 with a $K_D$ of less than $10^{-6}$ M, or less than $10^{-7}$M, $5 \times 10^{-8}$M, $10^{-8}$M or less than $10^{-9}$M. VEGFR-2 binding polypeptides may compete for binding with one, two or more members of the VEGF family, particularly VEGF-A, VEGF-C and VEGF-D and may inhibit one or more VEGFR-2-mediated biological events, such as proliferation of endothelial cells, permeabilization of blood vessels and increased motility in endothelial cells. VEGFR-2 binding polypeptides may be used for therapeutic purposes as well as for any purpose involving the detection or binding of VEGFR-2. Polypeptides for therapeutic use will generally have a $K_D$ of less than $5 \times 10^{-8}$M, less than $10^{-8}$M or less than $10^{-9}$M, although higher $K_D$ values may be tolerated where the $k_{off}$ is sufficiently low or the $k_{on}$ is sufficiently high. In certain embodiments, a single domain polypeptide that binds to VEGFR-2 will comprise a consensus VEGFR-2 binding sequence selected from the group consisting of: SEQ ID NO:1, SEQ ID NO:2, SEQ ID NO:3 and SEQ ID NO:4. Preferably, such sequence will be situated in a loop, particularly the FG loop.

In certain embodiments, the single domain polypeptide comprises an immunoglobulin (Ig) variable domain. The Ig variable domain may, for example, be selected from the group consisting of: a human $V_L$ domain, a human $V_H$ domain and a camelid $V_{HH}$ domain. One, two, three or more loops of the Ig variable domain may participate in binding to VEGFR-2, and typically any of the loops known as CDR1, CDR2 or CDR3 will participate in VEGFR-2 binding.

In certain embodiments, the single domain polypeptide comprises an immunoglobulin-like domain. One, two, three or more loops of the immunoglobulin-like domain may participate in binding to VEGFR-2. A preferred immunoglobulin-like domain is a fibronectin type III (Fn3) domain. Such domain may comprise, in order from N-terminus to C-terminus, a beta or beta-like strand, A; a loop, AB; a beta strand, B; a loop, BC; a beta strand C; a loop CD; a beta strand D; a loop DE; a beta strand F; a loop FG; and a beta or beta-like strand G. See FIG. 22 for an example of the structural organization. Optionally, any or all of loops AB, BC, CD, DE, EF and FG may participate in VEGFR-2 binding, although preferred loops are BC, DE and FG. A preferred Fn3 domain is an Fn3 domain derived from human fibronectin, particularly the $10^{th}$ Fn3 domain of fibronectin, referred to as $^{10}$Fn3. It should be noted that none of VEGFR-2 binding polypeptides disclosed herein have an amino acid sequence that is identical to native $^{10}$Fn3; the sequence has been modified to obtain VEGFR-2 binding proteins, but proteins having the basic structural features of $^{10}$Fn3, and particularly those retaining recognizable sequence homology to the native $^{10}$Fn3 are nonetheless referred to herein as "$^{10}$Fn3 polypeptides". This nomenclature is similar to that found in the antibody field where, for example, a recombinant antibody $V_L$ domain generated against a particular target protein may not be identical to any naturally occurring $V_L$ domain but nonetheless the protein is recognizably a $V_L$ protein. A $^{10}$Fn3 polypeptide may be at least 60%, 65%, 70%, 75%, 80%, 85%, or 90% identical to the human $^{10}$Fn3 domain, shown in SEQ ID NO:5. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 5, provided that such variation does not disrupt the stability of the polypeptide in physiological conditions. A $^{10}$Fn3 polypeptide may have a sequence in each of the loops AB, CD, and EF that consists essentially of an amino acid sequence that is at least 80%, 85%, 90%, 95% or 100% identical to the sequence of a corresponding loop of SEQ ID NO:5. In many instances, any or all of loops BC, DE, and FG will be poorly conserved relative to SEQ ID NO:5. For example, all of loops BC, DE, and FG may be less than 20%, 10%, or 0% identical to their corresponding loops in SEQ ID NO:5.

In certain embodiments, the disclosure provides a non-antibody polypeptide comprising a domain having an immunoglobulin-like fold that binds to VEGFR-2. The non-antibody polypeptide may have a molecular weight of less than 20 kDa, or less than 15 kDa and will generally be derived (by, for example, alteration of the amino acid sequence) from a reference, or "scaffold", protein, such as an Fn3 scaffold. The non-antibody polypeptide may bind VEGFR-2 with a $K_D$ less than $10^{-6}$M, or less than $10^{-7}$M, less than $5 \times 10^{-8}$M, less than $10^{-8}$M or less than $10^{-9}$M. The unaltered reference protein either will not meaningfully bind to VEGFR-2 or will bind with a $K_D$ of greater than $10^{-6}$M. The non-antibody polypeptide may inhibit VEGF signaling, particularly where the non-antibody polypeptide has a $K_D$ of less than $5 \times 10^{-8}$M, less than $10^{-8}$M or less than $10^{-9}$M, although higher $K_D$ values may be tolerated where the $k_{off}$ is sufficiently low (e.g., less than $5 \times 10^{-4}$ s$^{-1}$). The immunoglobulin-like fold may be a $^{10}$Fn3 polypeptide.

In certain embodiments, the disclosure provides a polypeptide comprising a single domain having an immunoglobulin fold that binds to VEGFR-2. The polypeptide may have a molecular weight of less than 20 kDa, or less than 15 kDa and will generally be derived (by, for example, alteration of the amino acid sequence) from a variable domain of an immunoglobulin. The polypeptide may bind VEGFR-2 with a $K_D$ less than $10^{-6}$M, or less than $10^{-7}$M, less than $5 \times 10^{-8}$M, less than $10^{-8}$M or less than $10^{-9}$M. The polypeptide may inhibit VEGF signaling, particularly where the polypeptide has a $K_D$ of less than $5\times10^{-8}$M, less than $10^{-8}$M or less than $10^{-9}$M, although higher $K_D$ values may be tolerated where the $k_{off}$ is sufficiently low or where the $k_{on}$ is sufficiently high. In certain preferred embodiments, a single domain polypeptide having an immunoglobulin fold derived from an immunoglobulin light chain variable domain and capable of binding to VEGFR-2 may comprise an amino acid sequence selected from the group consisting of: SEQ ID NOs:241-310.

In certain preferred embodiments, the disclosure provides VEGFR-2 binding polypeptides comprising the amino acid sequence of any of SEQ ID NOs:192-194. In the case of a polypeptide comprising the amino acid sequence of SEQ ID NO:194, a PEG moiety or other moiety of interest, may be covalently bound to the cysteine at position 93. The PEG moiety may also be covalently bonded to an amine moiety in the polypeptide. The amine moiety may be, for example, a primary amine found at the N-terminus of a polypeptide or an amine group present in an amino acid, such as lysine or arginine. In certain embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

In certain aspects, the disclosure provides short peptide sequences that mediate VEGFR-2 binding. Such sequences may mediate VEGFR-2 binding in an isolated form or when inserted into a particular protein structure, such as an immunoglobulin or immunoglobulin-like domain. Examples of such sequences include those disclosed as SEQ ID NOs:1-4 and other sequences that are at least 85%, 90%, or 95% identical to SEQ ID NOs:1-4 and retain VEGFR-2 binding activity. Accordingly, the disclosure provides substantially pure polypeptides comprising an amino acid sequence that is at least 85% identical to the sequence of any of SEQ ID NOs:1-4, wherein said polypeptide binds to a VEGFR-2 and competes with a VEGF species for binding to VEGFR-2. Examples of such polypeptides include a polypeptide comprising an amino acid sequence that is at least 80%, 85%, 90%, 95% or 100% identical to an amino acid sequence at least 85% identical to the sequence of any of SEQ ID NOs: 6-183, 186-197, 199 and 311-528. Preferably such polypeptide will inhibit a biological activity of VEGF and may bind to VEGFR-2 with a $K_D$ less than $10^{-6}$M, or less than $10^{-7}$M, less than $5\times10^{-8}$M, less than $10^{-8}$M or less than $10^{-9}$M.

In certain embodiments, any of the VEGFR-2 binding polypeptides described herein may be bound to one or more additional moieties, including, for example, a moiety that also binds to VEGFR-2 (e.g., a second identical or different VEGFR-2 binding polypeptide), a moiety that binds to a different target (e.g., to create a dual-specificity binding agent), a labeling moiety, a moiety that facilitates protein purification or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). Moieties that tend to slow clearance of a protein from the blood include polyethylene glycol, sugars (e.g. sialic acid), and well-tolerated protein moieties (e.g., Fc fragment or serum albumin). The single domain polypeptide may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety. Where polyethylene glycol is employed, one or more PEG molecules may be attached at different positions in the protein, and such attachment may be achieved by reaction with amines, thiols or other suitable reactive groups. Pegylation may be achieved by site-directed pegylation, wherein a suitable reactive group is introduced into the protein to create a site where pegylation preferentially occurs. In a preferred embodiment, the protein is modified so as to have a cysteine residue at a desired position, permitting site directed pegylation on the cysteine. PEG may vary widely in molecular weight and may be branched or linear. Notably, the present disclosure establishes that pegylation is compatible with target binding activity of $^{10}$Fn3 polypeptides and, further, that pegylation does improve the pharmacokinetics of such polypeptides. Accordingly, in one embodiment, the disclosure provides pegylated forms of $^{10}$Fn3 polypeptides, regardless of the target that can be bound by such polypeptides.

In certain embodiments, the disclosure provides a formulation comprising any of the VEGFR-2 binding polypeptides disclosed herein. A formulation may be a therapeutic formulation comprising a VEGFR-2 binding polypeptide and a pharmaceutically acceptable carrier. A formulation may also be a combination formulation, comprising an additional active agent, such as an anti-cancer agent or an anti-angiogenic agent.

In certain aspects, the disclosure provides methods for using a VEGFR-2 binding protein to inhibit a VEGF biological activity in a cell or to inhibit a biological activity mediated by VEGFR-2. The cell may be situated in vivo or ex vivo, and may be, for example, a cell of a living organism, a cultured cell or a cell in a tissue sample. The method may comprise contacting said cell with any of the VEGFR-2-inhibiting polypeptides disclosed herein, in an amount and for a time sufficient to inhibit such biological activity.

In certain aspects, the disclosure provides methods for treating a subject having a condition which responds to the inhibition of VEGF or VEGFR-2. Such a method may comprise administering to said subject an effective amount of any of the VEGFR-2 inhibiting polypeptides described herein. A condition may be one that is characterized by inappropriate angiogenesis. A condition may be a hyperproliferative condition. Examples of conditions (or disorders) suitable for treatment include autoimmune disorders, inflammatory disorders, retinopathies (particularly proliferative retinopathies), and cancers. Any of the VEGFR-2 inhibiting polypeptides described herein may be used for the preparation of a medicament for the treatment of a disorder, particularly a disorder selected from the group consisting of: an autoimmune disorder, an inflammatory disorder, a retinopathy, and a cancer.

In certain aspects, the disclosure provides methods for detecting VEGFR-2 in a sample. A method may comprise contacting the sample with a VEGFR-2 binding polypeptide described herein, wherein said contacting is carried out under conditions that allow polypeptide-VEGFR-2 complex formation; and detecting said complex, thereby detecting said VEGFR-2 in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, a suspected tumor or a tissue suspected of undergoing unwanted angiogenesis. The sample may be from a human or other mammal. The VEGFR-2 binding polypeptide may be labeled with a labeling moiety, such as a radioactive moiety, a fluorescent moiety, a chromogenic moiety, a chemiluminescent moiety, or a hapten moiety. The VEGFR-2 binding polypeptide may be immobilized on a solid support.

Another aspect of the disclosure relates to a nucleic acid comprising a nucleic acid sequence encoding a polypeptide disclosed herein. In certain embodiments, a nucleic acid may comprise a nucleic acid sequence encoding a polypeptide selected from the group consisting of any of SEQ ID Nos. 6-183, 186-197, 199 and 241-528. In certain embodiments, a nucleic acid comprises a nucleic acid sequence that hybridizes in stringent conditions to a nucleic acid sequence of SEQ ID NO:184 and encodes a polypeptide that binds to human KDR with a KD of less than $1 \times 10^{-6}$M. In particular embodiments, nucleic acid may comprise a nucleic acid sequence selected from the group consisting of SEQ ID NO:184 and SEQ ID NO:185.

A further aspect of the disclosure relates to an expression vector comprising a nucleic acid operably linked with a promoter, wherein the nucleic acid encodes a polypeptide disclosed herein. Another aspect of the disclosure relates to a cell comprising a nucleic acid disclosed herein. Also provided is a method of producing the polypeptide that binds VEGFR-2, e.g., KDR, comprising: expressing a nucleic acid encoding a polypeptide of the disclosure. In certain embodiments, the nucleic acid may comprise a sequence that encodes a polypeptide selected from the group consisting of any of SEQ ID Nos. 6-183, 186-197, 199 and 241-528. In certain embodiments, the nucleic acid comprises a sequence that hybridizes in stringent conditions to a nucleic acid sequence of SEQ ID NO:184. In certain embodiments, the nucleic acid comprises a nucleic acid sequence selected from the group consisting of SEQ ID NO:184 and SEQ ID NO:185. In certain embodiments, the nucleic acid is expressed in a cell. Alternatively, the nucleic acid is expressed in a cell-free system.

In certain aspects, the disclosure provides discoveries that may be applicable to any $^{10}$Fn3 polypeptide, regardless of which target the polypeptide is engineered to bind. As noted above, the disclosure demonstrates that PEG can be used successfully to improve the pharmacokinetics of a $^{10}$Fn3 polypeptide, while not interfering meaningfully with target binding. Accordingly, the disclosure provides pegylated $^{10}$Fn3 polypeptides that bind to target and have improved pharmacokinetics relative to the non-pegylated polypeptide. In a further embodiment, the disclosure demonstrates that a deletion of the first eight amino acids of a $^{10}$Fn3 polypeptide can increase target binding affinity. Accordingly, the disclosure provides $^{10}$Fn3 polypeptides lacking the initial eight amino acids (amino acids numbered in reference to the sequence of SEQ ID No:5). It is understood that one or two amino acids may be added back to the deleted form of the polypeptide so as to facilitate translation and proper processing. The disclosure demonstrates that subcutaneous administration of a $^{10}$Fn3 polypeptide results in a delayed release of polypeptide into the bloodstream and a decreased maximum serum concentration of the $^{10}$Fn3 polypeptide. Accordingly, the disclosure provides methods for administering a $^{10}$Fn3 polypeptide to a patient by a subcutaneous administration. This route of administration may be useful to achieve a delayed release relative to intravenous administration, and/or to decrease the maximum serum concentration of the $^{10}$Fn3 polypeptide by at least 25% or at least 50% relative to the maximum serum concentration achieved by intravenous administration of an equal dosage. The administered $^{10}$Fn3 polypeptide may be attached to a moiety that increases the serum half-life (or decreases clearance rate, or similarly affects another pharmacokinetic parameter) of the $^{10}$Fn3 polypeptide, such as a polyethylene glycol moiety. Preferably, the administered $^{10}$Fn3 polypeptide comprises an amino acid sequence that is at least 60%, 65%, 70%, 75%, 80%, 85%, 90% identical to SEQ ID NO:5.

In certain aspects, the disclosure provides single domain polypeptides that bind to a preselected target protein from a first mammal and to a homolog thereof from a second mammal. Such single domain polypeptides are particularly useful where the first mammal is a human and the second mammal is a desirable mammal in which to conduct preclinical testing, such as a mouse, rat, guinea pig, dog, or non-human primate. The disclosure demonstrates that single domain polypeptides can be engineered to have such dual specificity, and that the dual specificity simplifies drug development by allowing testing of the same polypeptide in human cells, human subjects and animal models. Preferably, the preselected target protein of the first mammal and the homolog thereof from the second mammal are sufficiently similar in amino acid sequence to allow generation of dual specificity polypeptides. For example, the preselected target protein and the homolog from the second mammal may share at least 80%, 90%, or 95% identity across a region of at least 50 amino acids, and optionally may share at least 80%, 90%, or 95% identity across the entire protein sequence or across the sequence of the extracellular domain, in the case of a membrane protein. A single domain polypeptide with this type of dual specificity binding characteristic may comprise an immunoglobulin or immunoglobulin-like domain, and will preferably bind to both the preselected human target protein and to the homolog thereof with a dissociation constant of less than $1 \times 10^{-6}$M, $1 \times 10^{-7}$M, $5 \times 10^{-8}$M, $1 \times 10^{-8}$M or $1 \times 10^{-9}$M.

BRIEF DESCRIPTION OF THE DRAWINGS

FIG. 1A is a graph showing the specific binding of fibronectin-based binding proteins to 25 nM of KDR-Fc analyzed in radioactive equilibrium binding assay. FIG. 1B is a graph showing the inhibition of specific binding of KDR-Fc and selected fibronectin based binding proteins in the presence of 100-fold excess of $VEGF_{165}$. As shown in this figure, certain binding proteins bound KDR-Fc competitively with $VEGF_{165}$ while others, exemplified by clone 8, did not compete with $VEGF_{165}$. FIG. 1C is a graph showing the inhibition of KDR-Fc interaction with immobilized $VEGF_{165}$ in presence of selected fibronectin based binding proteins analyzed in BIAcore. FIG. 1D is an image showing binding of VR28 to KDR-expressing and control cells detected by immunofluorescence.

FIG. 3A shows the saturation binding of VR28 (-■-) and affinity matured K1 (-▲-), K6 (-▼-), K9 (-◆-), K10 (-●-), K12 (-□-), K13 (-Δ-), K14 (-∇-), K15 (-◇-) to KDR-Fc in radioactive equilibrium binding assay FIG. 3B shows the binding of clones with and without N-terminal deletion to KDR-Fc. Deletion Δ 1-8 in the N-terminus of fibronectin-based binding proteins improved binding to KDR-Fc. The data represents an average KDR-Fc binding of 23 independent clones with and without N-terminal deletion.

FIG. 6A shows the importance of arginine at positions 79 and 82 in binders with dual specificity to human and mouse VEGFR-2 for binding to mouse VEGFR-2 (Flk1). When either of these positions was replaced by amino acid other than R (X79=E, Q, W, P; X82=L, K), binding to Flk1 but not to KDR significantly decreased. FIG. 6B shows the importance of all three variable loops (BC, DE and FG) of KDR fibronectin-based binding proteins for binding to the target in these proteins. Substitution of each loop at a time by NNS sequence affected binding to KDR and Flk1. The binding data is an average from E6 and E26 clones.

FIG. 10 is a set of graphs showing the reversible refolding of M5FL in optimized buffer.

FIG. 13 shows western analysis of VEGFR-2 signaling in endothelial cells. Phospho VEGFR-2—Visualization of phosphorylated VEGFR-2. VEGFR-2—Sample loading control. Phospho ERK1/2—Visualization of phosphorylated ERK1/2 (MAPK). ERK1—Sample loading control. The results demonstrated that 130 pM CT-01 blocks VEGFR-2 activation and signaling by VEGF-A.

FIG. 14 shows that various $^{10}$Fn3-derived molecules (e.g. M5FL, F10, CT-01) can block VEGF-A and VEGF-D signaling.

FIG. 15 shows a comparison of $^{125}$I native, pegylated CT-01 administered i.v. & i.p. CT-01 is a 12 kDa protein. It is rapidly cleared from the blood. Addition of a 40 kDa PEG reduces its clearance rate and increases the AUC by 10 fold. Half life of 16 hr in rats is equivalent to 2× dosing per week in humans. Administration route: i.p. CT-01-PEG40 has an AUC that is only 50% of an i.v. administration.

FIG. 16 shows the tissue distribution of $^{125}$I-CT01PEG40 in normal rats. Tissue distribution of $^{125}$I-CT01PEG40 indicates secretion primarily via the liver and secondarily via the kidney. This is expected for the high molecular weight PEG form. No long term accumulation of CT-01PEG40 is detected.

FIG. 17 is a schematic view of the Miles Assay that measures vascular permeability.

FIG. 18 shows that CT-01 blocks VEGF in vivo using the Miles Assay. The results indicate that 5 mg/kg of CT01-PEG40 blocks VEGF challenge.

FIG. 19 shows that CT-01 inhibits tumor growth using the B16-F10 Murine Melanoma Tumor Assay.

FIG. 20 shows that CT-01 inhibits tumor growth using U87 Human Glioblastoma.

FIGS. 21A and 21B show the sequences of VEGFR binding polypeptides that are based on an antibody light chain framework/scaffold (SEQ ID NOs:241-310).

DETAILED DESCRIPTION OF THE INVENTION

1. Overview

Figures 1A, 1B, 1C, 1D:
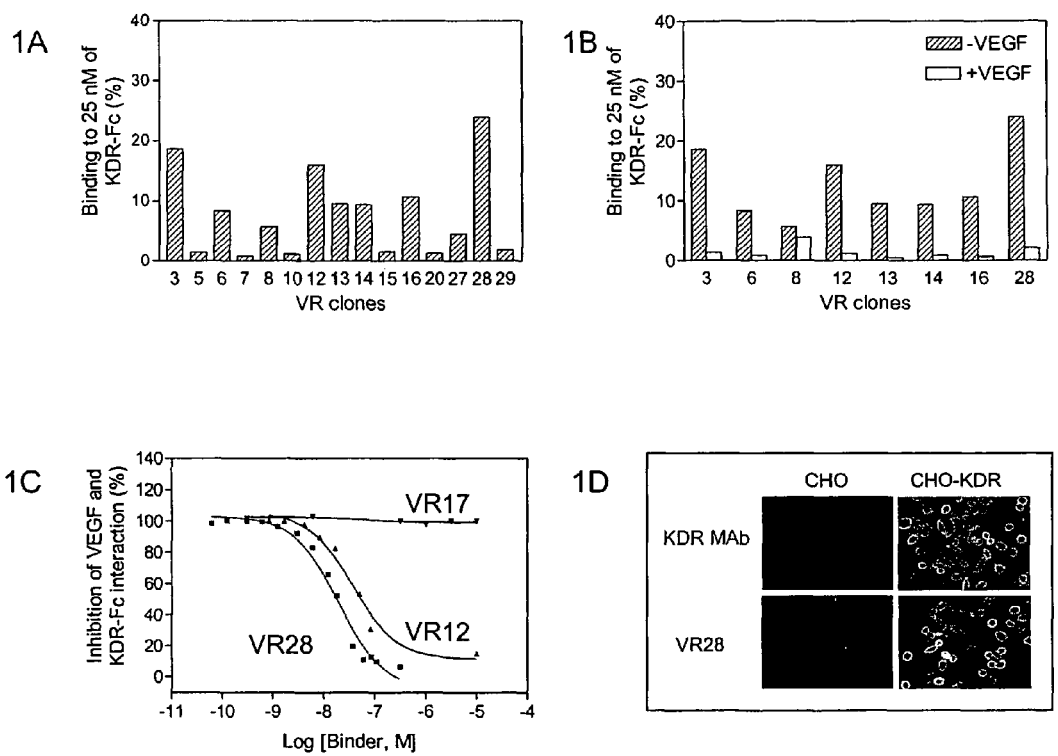
FIGS. 1A-1D are graphs and images depicting the characterization of KDR-binding single clones from Round 6 of KDR selection.

This specification describes, inter alia, the identification and production of novel, single domain polypeptides that bind to VEGFR-2 receptors. VEGFR-2, also called KDR in humans and Flk-1 in mice, is the primary mediator for the pro-angiogenic effects of VEGF signaling. VEGFR-2 is bound and activated by VEGF-A, VEGF-C and VEGF-D. In endothelial cells, VEGFR-2 activation stimulates cell proliferation and migration, and in vivo, VEGFR-2 activation triggers angiogenesis and increases the permeability of the vasculature. Increased angiogenesis is well-established as an important feature of tumor growth and various retinopathies, while increased permeability of the vasculature is a significant event in many inflammatory responses.

The present disclosure provides hundreds of single domain polypeptides that bind to VEGFR-2, many of which exhibit in vitro and/or in vivo VEGF antagonist activity. Single domain polypeptides having VEGF antagonist activity will be useful in numerous therapeutic applications. Anti-KDR antibodies have been established as having in vivo utility against diseases and conditions ranging from cancers and complications resulting from cancers to proliferative retinopathies, inflammatory disorders and fibrosis. Based on the in vivo and in vitro data presented here, it is expected that the single domain polypeptides will be useful in treating the same spectrum of disorders.

In addition to therapeutic applications, VEGFR-2-binding single domain polypeptides may be used in any circumstance where it is desirable to detect VEGFR-2. For example, many stem cells express VEGFR-2, including particularly useful cells of hematopoietic lineages. KDR-binding polypeptides may be used, particularly in a labeled format, to detect stem cells and facilitate cell sorting. In vivo, labeled VEGFR-2-binding polypeptides may be used to image tissues in which VEGFR-2 is expressed. Elevated VEGFR-2 expression may be characteristic of tissues experiencing particularly high levels of angiogenic or inflammatory activity. Histological analyses of tissue samples may also benefit from detection of VEGFR-2. For example, it may be desirable to detect VEGFR-2 expression in a tumor biopsy in order to assess the likely effectiveness of an anti-VEGFR-2 or anti-VEGF therapy. Interestingly, many of the VEGFR-2 binding proteins disclosed herein bind to VEGFR-2 with nanomolar dissociation constants and yet fail to have a significant effect on VEGFR-2 mediated biological events. Accordingly, such binding proteins, may be useful for in vivo visualization techniques or cell-labeling techniques, where it will often be desirable to selectively label cells that express a VEGFR-2 without causing a significant perturbation of VEGFR-2 mediated events.

This disclosure describes the use of an in vitro display technology, termed PROfusion™, that exploits nucleic acid-protein fusions (RNA- and DNA-protein fusions) to identify novel single domain polypeptides and amino acid motifs that are important for binding to VEGFR-2. Nucleic acid-protein fusion technology is a display technology that covalently couples a protein to its encoding genetic information. PROfusion™ technology was used to screen collections of nucleic acids encoding single domain polypeptides constructed using a scaffold based on the human fibronectin type three domain ($^{10}$Fn3) or constructed from the variable domains of antibody light chains. The expressed polypeptides, termed a "library" of scaffold proteins, was screened for polypeptides that could bind VEGFR-2 with high affinity. We isolated from this library of scaffold proteins novel single domain polypeptides that bind to VEGFR-2 and that, in some instances, inhibit VEGF biological activities. Furthermore, it was discovered that many independently randomized loops situated in immunoglobulin or immunoglobulin-like scaffolds tended to converge to a related set of consensus sequences that participated in VEGFR-2 binding. Therefore, it is expected that polypeptides having these consensus sequences will be useful as VEGFR-2 binding agents even when separated from the protein context in which they were identified. See, for example, SEQ ID Nos. 1-4. Such polypeptides may be used as independent, small peptide VEGFR-2 binding agents or may be situated in other proteins, particularly proteins that share an immunoglobulin or immunoglobulin-like fold.

As discussed above, the present disclosure demonstrates that single domain polypeptides having certain desirable properties, such as high affinity binding to VEGFR-2, antagonist effects with respect to one or more of VEGF-A, -C or -D and improved pharmacokinetics, can be used as effective anti-cancer agents. While it is expected that the effectiveness of such polypeptides as anti-cancer agents is related to the role of angiogenesis in cancer, we do not wish to be bound to any particular mechanism. It is formally possible that the present single domain polypeptides are effective against cancers for reasons unrelated to angiogenic processes.

To our knowledge, the present disclosure represents the first successful effort to use an Fn3-based polypeptide to achieve a therapeutic effect in vivo. Many of the improvements and discoveries made in achieving in vivo effectiveness will be broadly applicable to other Fn3-based polypeptides. In other words, although ligand binding properties of an Fn3-based polypeptide will generally be determined by a relatively small number of amino acids situated in solvent accessible loop regions, other features, such as pharmacokinetic features, of Fn3-based polypeptides will tend to be determined by the majority of the protein that is not directly involved in ligand binding and that is conserved from protein to protein regardless of the target protein. This has been the case with antibodies, where a few loops, called CDR regions, mediate antigen binding, while other features of in vivo antibody behavior are largely dictated by the conserved framework regions and constant domains.

By "inhibit" is meant a measurable reduction in a phenomenon, often used herein in reference to any of the following: the interaction of VEGF with a VEGFR, VEGF- or VEGFR-mediated angiogenesis, angiogenesis, symptoms of angiogenesis, the viability of VEGFR-containing cells, the viability of VEGF-dependent Ba/F3 cells, or VEGF- or VEGFR-mediated cellular proliferation as compared to a control sample not treated with the polypeptide. A polypeptide will inhibit a VEGF- or VEGFR-2 mediated activity if the reduction in activity or interaction is at least 10%, preferably 20%, 30%, 40%, or 50%, and more preferably 60%, 70%, 80%, 90% or more.

By "VEGF biological activity" is meant any function of any VEGF family member acting through any VEGF receptor, but particularly signaling through a VEGFR-2 receptor. The VEGF family includes VEGF-A, VEGF-B, VEGF-C, VEGF-D, and placental growth factor (PlGF), as well as various alternatively spliced forms of VEGF including VEGF121, VEGF145, VEGF165, VEGF189, and VEGF206 (Tischer et al., J. Biol. Chem, 266:11947-11954, 1991). The VEGFR family of tyrosine kinase receptors includes VEGFR-1 (also known as Flt-1), VEGFR-2 (also known as KDR (human form) or Flk-1 (mouse form)), and VEGFR-3 (also known as Flt-4). VEGF ligands bind to the VEGF receptors to induce, for example, angiogenesis, vasculogenesis, endothelial cell proliferation, vasodilation, and cell migration. VEGF ligands can also inhibit apoptosis through binding to their cognate receptors. VEGFR-2 is believed to be the VEGFR most involved in angiogenesis. A VEGFR-2 or KDR-mediated biological activity is any biological function in which VEGFR-2 or KDR participates in significantly, such that antagonism of VEGFR-2 or KDR causes a measurable decrease in the biological activity. The biological activity of VEGF and VEGFR can be measured by standard assays known in the art. Examples include ligand binding assays and Scatchard plot analysis; receptor dimerization assays; cellular phosphorylation assays; tyrosine kinase phosphorylation assays (see for example Meyer et al., Ann. N.Y. Acad. Sci. 995:200-207, 2003); endothelial cell proliferation assays such as BrdU labeling and cell counting experiments; VEGF-dependent cell proliferation assays; and angiogenesis assays. Methods for measuring angiogenesis are standard, and are described, for example, in Jain et al. (Nat. Rev. Cancer 2:266-276, 2002). Angiogenesis can be assayed by measuring the number of non-branching blood vessel segments (number of segments per unit area), the functional vascular density (total length of perfused blood vessel per unit area), the vessel diameter, the formation of vascular channels, or the vessel volume density (total of calculated blood vessel volume based on length and diameter of each segment per unit area). Exemplary assays for VEGF-mediated proliferation and angiogenesis can be found in U.S. Pat. No. 6,559,126, Lyden et al, Nature Medicine 7:1194 (2001), Jacob et al, Exp. Pathol. 15:1234 (1978) and Bae et al, J. Biol. Chem. 275: 13588 (2000). These assays can be performed using either purified receptor or ligand or both, and can be performed in vitro or in vivo. These assays can also be performed in cells using a genetically introduced or the naturally-occurring ligand or receptor or both. A polypeptide that inhibits the biological activity of VEGF will cause a decrease of at least 10%, preferably 20%, 30%, 40%, or 50%, and more preferably 60%, 70%, 80%, 90% or greater decrease in the biological activity of VEGF. The inhibition of biological activity can also be measured by the IC50. Preferably, a polypeptide that inhibits the biological activity of VEGF or VEGFR-2 will have an IC50 of less than 100 nM, more preferably less than 10 nM and most preferably less than 1 nM.

2. Polypeptides

The methodology described herein has been successfully used to develop single domain VEGFR-2 binding polypeptides derived from two related groups of protein structures: those proteins having an immunoglobulin fold and those proteins having an immunoglobulin-like fold. By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D). The term "single domain polypeptide" is used to indicate that the target binding activity (e.g., VEGFR-2 binding activity) of the subject polypeptide is situated within a single structural domain, as differentiated from, for example, antibodies and single chain antibodies, where antigen binding activity is generally contributed by both a heavy chain variable domain and a light chain variable domain. It is contemplated that a plurality of single domain polypeptides of the sort disclosed herein could be connected to create a composite molecule with increased avidity. Likewise, a single domain polypeptide may be attached (e.g., as a fusion protein) to any number of other polypeptides, such as fluorescent polypeptides, targeting polypeptides and polypeptides having a distinct therapeutic effect.

Figure 22:
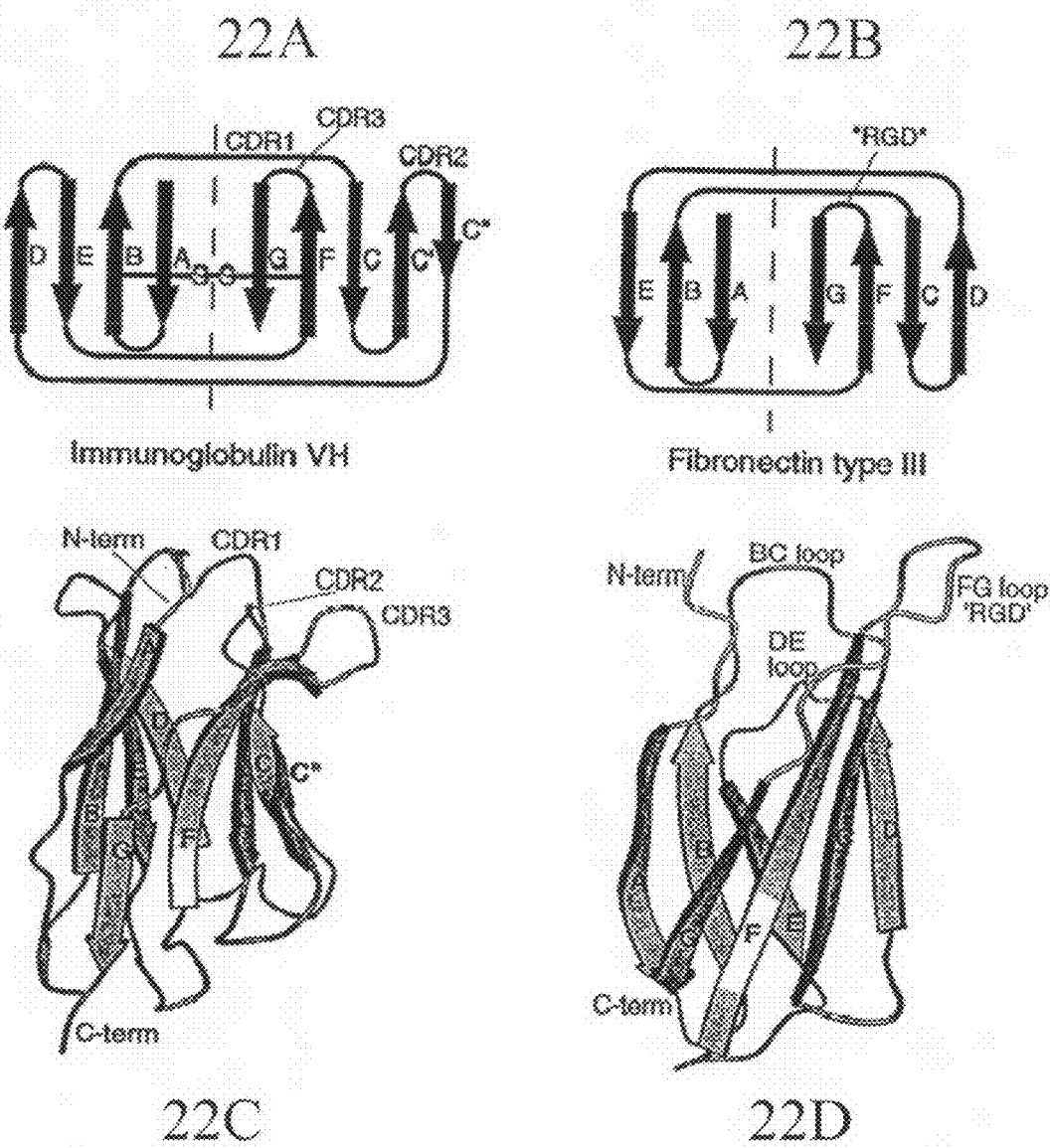
FIG. 22A-D shows the structural organization for a single domain polypeptide having an immunoglobulin fold (a $V_H$ domain of an immunoglobulin, FIGS. 22A and 22C) and a single domain polypeptide having an immunoglobulin-like fold (a $^{10}$Fn3 domain, FIGS. 22B and 22D).

Single domain polypeptides of either the immunoglobulin or immunoglobulin-like scaffold will tend to share certain structural features. For example, the polypeptide may comprise between about 80 and about 150 amino acids, which amino acids are structurally organized into a set of beta or beta-like strands, forming beta sheets, where the beta or beta-like strands are connected by intervening loop portions. Examples of the structural organization for the heavy chain variable domain and the $^{10}$Fn3 domain are shown in FIG. 22. The beta sheets form the stable core of the single domain polypeptides, while creating two "faces" composed of the loops that connect the beta or beta-like strands. As described herein, these loops can be varied to create customized ligand binding sites, and, with proper control, such variations can be generated without disrupting the overall stability of the protein. In antibodies, three of these loops are the well-known Complementarity Determining Regions (or "CDRs").

Scaffolds for formation of a single domain polypeptides should be highly soluble and stable in physiological conditions. Examples of immunoglobulin scaffolds are the single domain $V_H$ or $V_L$ scaffold, as well as a single domain camelid $V_{HH}$ domain (a form of variable heavy domain found in camelids) or other immunoglobulin variable domains found in nature or engineered in the laboratory. In the single domain format disclosed herein, an immunoglobulin polypeptide need not form a dimer with a second polypeptide in order to achieve binding activity. Accordingly, any such polypeptides that naturally contain a cysteine which mediates disulfide cross-linking to a second protein can be altered to eliminate the cysteine. Alternatively, the cysteine may be retained for use in conjugating additional moieties, such as PEG, to the single domain polypeptide.

Other scaffolds may be non-antibody scaffold proteins. By "non-antibody scaffold protein or domain" is meant a non-antibody polypeptide having an immunoglobulin-like fold. By "immunoglobulin-like fold" is meant a protein domain of between about 80-150 amino acid residues that includes two layers of antiparallel beta-sheets, and in which the flat, hydrophobic faces of the two beta-sheets are packed against each other. An example of such a scaffold is the "fibronectin-based scaffold protein", by which is meant a polypeptide based on a fibronectin type III domain (Fn3). Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperoning, and carbohydrate-binding domains for reviews, see Bork & Doolittle, Proc Natl Acad Sci USA. 1992 Oct. 1; 89(19):8990-4; Bork et al., J Mol Biol. 1994 Sep. 30; 242(4): 309-20; Campbell & Spitzfaden, Structure. 1994 May 15; 2(5):333-7; Harpez & Chothia, J Mol Biol. 1994 May 13; 238(4):528-39).

Preferably, the fibronectin-based scaffold protein is a "$^{10}$FN3" scaffold, by which is meant a polypeptide variant based on the tenth module of the human fibronectin type III protein in which one or more of the solvent accessible loops has been randomized or mutated, particularly one or more of the three loops identified as the BC loop (amino acids 23-30), DE loop (amino acids 52-56) and FG loop (amino acids 77-87) (the numbering scheme is based on the sequence on the tenth Type III domain of human fibronectin, with the amino acids Val-Ser-Asp-Val-Pro representing amino acids numbers 1-5). The amino acid sequence of the wild-type tenth module of the human fibronectin type III domain is: VSDVPRDLEVVAATPTSLLISWDAPAVTVRYYRITYGETGGNSPVQEFTVPGSKS TATISGLKPGVDYTITGYAVTGRGDSPASSKPISINYRT (SEQ ID NO:5). Thus, the wild-type BC loop comprises the sequence of DAPAVTVR; the wild-type DE loop comprises the sequence of GSKST; the wild-type FG loop comprises the sequence of GRGDSPASSKP. The sequences flanking the BC, DE, and FG loops are also termed Frameworks 1, 2, 3, and 4, e.g., in Tables 1-3.

A variety of improved mutant $^{10}$Fn3 scaffolds have been identified. A modified Asp7, which is replaced by a non-negatively charged amino acid residue (e.g., Asn, Lys, etc.). Both of these mutations have the effect of promoting greater stability of the mutant $^{10}$Fn3 at neutral pH as compared to the wild-type form. A variety of additional alterations in the $^{10}$Fn3 scaffold that are either beneficial or neutral have been disclosed. See, for example, Batori et al. Protein Eng. 2002 December; 15(12):1015-20; Koide et al., Biochemistry 2001 Aug. 28; 40(34):10326-33.

Additionally, several novel modifications to the $^{10}$Fn3 scaffold are disclosed here. Of particular significance, it was discovered that a deletion of the first 8 amino acids of the wild type human $^{10}$Fn3 led to roughly three-fold improved VEGFR-2 binding. Because the first 8 amino acids tend to fold into a position that is close to the BC, DE and FG loops, it is expected that this mutation will also improve target binding in other $^{10}$Fn3 scaffolds selected for binding to different targets. Accordingly, one may construct a library of nucleic acids encoding $^{10}$Fn3 scaffold that lack the first 8 amino acids and conduct screening in this improved library.

Both the variant and wild-type $^{10}$Fn3 proteins are characterized by the same structure, namely seven beta-strand domain sequences (designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID No:5, the AB loop corresponds to residues 15-16, the BC loop corresponds to residues 22-30, the CD loop corresponds to residues 39-45, the DE loop corresponds to residues 51-55, the EF loop corresponds to residues 60-66, and the FG loop corresponds to residues 76-87. As shown in FIG. 22, the BC loop, DE loop, and FG loop are all located at the same end of the polypeptide. Similarly, immunoglobulin scaffolds tend to have at least seven beta or beta-like strands, and often nine beta or beta-like strands.

A single domain polypeptide disclosed herein may have at least five to seven beta or beta-like strands distributed between at least two beta sheets, and at least one loop portion connecting two beta or beta-like strands, which loop portion participates in binding to VEGFR-2, particularly KDR, with the binding characterized by a dissociation constant that is less than $1 \times 10^{-6}$M, and preferably less than $1 \times 10^{-8}$M. As described herein, polypeptides having a dissociation constant of less than $5 \times 10^{-9}$M are particularly desirable for therapeutic use in vivo to inhibit VEGF signaling. Polypeptides having a dissociation constant of between $1 \times 10^{-6}$M and $5 \times 10^{-9}$M may be desirable for use in detecting or labeling, ex vivo or in vivo, VEGFR-2 proteins.

Optionally, the VEGFR-2 binding protein will bind specifically to VEGFR-2 relative to other related proteins from the same species. By "specifically binds" is meant a polypeptide that recognizes and interacts with a target protein (e.g., VEGFR-2) but that does not substantially recognize and interact with other molecules in a sample, for example, a biological sample. In preferred embodiments a polypeptide of the invention will specifically bind a VEGFR with a $K_D$ at least as tight as 500 nM. Preferably, the polypeptide will specifically bind a VEGFR with a $K_D$ of 1 pM to 500 nM, more preferably 1 pM to 100 nM, more preferably 1 pM to 10 nM, and most preferably 1 pM to 1 nM or lower.

In general, a library of scaffold single domain polypeptides is screened to identify specific polypeptide variants that can bind to a chosen target. These libraries may be, for example, phage display libraries or PROfusion™ libraries.

In an exemplary embodiment, we have exploited a novel in vitro RNA-protein fusion display technology to isolate polypeptides that bind to both human (KDR) and mouse (Flk-1) VEGFR-2 and inhibit VEGF-dependent biological activities. These polypeptides were identified from libraries of fibronectin-based scaffold proteins (Koide et al, JMB 284: 1141 (1998)) and libraries of $V_L$ domains in which the diversity of CDR3 has been increased by swapping with CDR3 domains from a population of $V_H$ molecules. $^{10}$FN3 comprises approximately 94 amino acid residues, as shown in SEQ ID NO:5.

In addition, as described above, amino acid sequences at the N-terminus of $^{10}$Fn3 can also be mutated or deleted. For example, randomization of the BC, DE, and FG loops can occur in the context of a full-length 10Fn3 or in the context of a $^{10}$Fn3 having a deletion or mutation of 1-8 amino acids of the N-terminus. For example, the L at position 8 can be mutated to a Q. After randomization to create a diverse library, fibronectin-based scaffold proteins can be used in a screening assay to select for polypeptides with a high affinity for a protein, in this case the VEGFR. (For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Numbers WO 00/34784; WO 01/64942; WO 02/032925; and Roberts and Szostak, Proc Natl. Acad. Sci. 94:12297-12302, 1997, herein incorporated by reference.)

For the initial selection described herein, three regions of the $^{10}$Fn3 at positions 23-29, 52-55 and 77-86 were randomized and used for in vitro selection against the extracellular domain of human VEGFR-2 (amino acids 1-764 of KDR fused to human IgG1Fc). Using mRNA display (RNA-protein fusion) and in vitro selection, we sampled a $^{10}$Fn3-based library with approximately ten trillion variants. The initial selection identified polypeptides with moderate affinity ($K_D$=10-200 nM) that competed with VEGF for binding to KDR (human VEGFR-2). Subsequently, a single clone ($K_D$=11-13 nM) from the initial selection was subjected to mutagenesis and further selection. This affinity maturation process yielded new VEGFR binding polypeptides with dissociation constants between 60 pM to 2 nM. KDR binders are shown in Table 3. In addition, we also isolated polypeptides that could bind to Flk-1, the mouse KDR homolog, from mutagenized populations of KDR binders that initially had no detectable binding affinity to Flk-1, resulting in the isolation of polypeptides that exhibit dual specificities to both human and mouse VEGFR-2. These polypeptides are shown to bind cells that display KDR or Flk-1 extracellular domains. They also inhibited cell growth in a VEGF-dependent proliferation assay. Polypeptides that bind to KDR and Flk-1 are shown in Table 2, while a selection of preferred KDR binders and KDR/Flk-1 binders are shown in Table 1.

Using the VEGFR-2 binding polypeptides identified in these selections we determined FG loop amino acid consensus sequences required for the binding of the polypeptides to the VEGFR-2. The sequences are listed as SEQ ID NOs:1-4 below.

VEGFR-2 binding polypeptides, such as those of SEQ ID NOs:1-4, may be formulated alone (as isolated peptides), as part of a $^{10}$Fn3 single domain polypeptide, as part of a full-length fibronectin, (with a full-length amino terminus or a deleted amino terminus) or a fragment thereof, in the context of an immunoglobulin (particularly a single domain immunoglobulin), in the context of another protein having an immunoglobulin-like fold, or in the context of another, unrelated protein. The polypeptides can also be formulated as part of a fusion protein with a heterologous protein that does not itself bind to or contribute in binding to a VEGFR. In addition, the polypeptides of the invention can also be fused to nucleic acids. The polypeptides can also be engineered as monomers, dimers, or multimers.

Sequences of the Preferred Consensus VEGFR-2 Binding Peptides:

SEQ ID NO:1—(L/M)GXN(G/D)(H/R)EL(L/M)TP

[X can be any amino acid; (/) represents alternative amino acid for the same position]

SEQ ID NO:2—XERNGRXL(L/M/N)TP

[X can be any amino acid; (/) represents alternative amino acid for the same position]

SEQ ID NO:3—(D/E)GXNXRXXIP

[X can be any amino acid; (/) represents alternative amino acid for the same position]

SEQ ID NO:4—(D/E)G(R/P)N(G/E)R(S/L)(S/F)IP

[X can be any amino acid; (/) represents alternative amino acid for the same position]

Sequences of the Preferred VEGFR-2 Binding $^{10}$Fn3 Polypeptides:

SEQ ID NO:6
EVVAATPTSLLISWRHPHFPTRYYRITYGETGGNSPVQEFTVPLQPPTAT
ISGLKPGVDYTITGYAVTMGLYGHELLTPISINYRT

SEQ ID NO:7
EVVAATPTSLLISWRHPHFPTRYYRITYGETGGNSPVQEFTVPLQPPTAT
ISGLKPGVDYTITGYAVTDGENGQFLLVPISINYRT

SEQ ID NO:8
EVVAATPTSLLISWRHPHFPTRYYRITYGETGGNSPVQEFTVPLQPPTAT
ISGLKPGVDYTITGYAVTMGPNDNELLTPISINYRT

SEQ ID NO:9
EVVAATPTSLLISWRHPHFPTRYYRITYGETGGNSPVQEFTVPLQPPTAT
ISGLKPGVDYTITGYAVTAGWDDHELFIPISINYRT

SEQ ID NO:10
EVVAATPTSLLISWRHPHFPTRYYRITYGETGGNSPVQEFTVPLQPPTAT
ISGLKPGVDYTITGYAVTSGHNDHMLMIPISINYRT

SEQ ID NO:11
EVVAATPTSLLISWRHPHFPTRYYRITYGETGGNSPVQEFTVPLQPPTAT
ISGLKPGVDYTITGYAVTAGYNDQILMTPISINYRT

SEQ ID NO:12
EVVAATPTSLLISWRHPHFPTRYYRITYGETGGNSPVQEFTVPLQPPTAT
ISGLKPGVDYTITGYAVTFGLYGKELLIPISINYRT

SEQ ID NO:13
EVVAATPTSLLISWRHPHFPTRYYRITYGETGGNSPVQEFTVPLQPPTAT
ISGLKPGVDYTITGYAVTTGPNDRLLFVPISINYRT

SEQ ID NO:14
EVVAATPTSLLISWRHPHFPTRYYRITYGETGGNSPVQEFTVPLQPPTAT
ISGLKPGVDYTITGYAVTDVYNDHEIKTPISINYRT

SEQ ID NO:15
EVVAATPTSLLISWRHPHFPTRYYRITYGETGGNSPVQEFTVPLQPPTAT
ISGLKPGVDYTITGYAVTDGKDGRVLLTPISINYRT

SEQ ID NO:16
EVVAATPTSLLISWRHPHFPTRYYRITYGETGGNSPVQEFTVPLQPPTAT
ISGLKPGVDYTITGYAVTEVHHDREIKTPISINYRT

SEQ ID NO:17
EVVAATPTSLLISWRHPHFPTRYYRITYGETGGNSPVQEFTVPLQPPTAT
ISGLKPGVDYTITGYAVTQAPNDRVLYTPISINYRT

SEQ ID NO:18
EVVAATPTSLLISWRHPHFPTRYYRITYGETGGNSPVQEFTVPLQPPTAT
ISGLKPGVDYTITGYAVTREENDHELLIPISINYRT

SEQ ID NO:19
EVVAATPTSLLISWRHPHFPTRYYRITYGETGGNSPVQEFTVPLQPPTAT
ISGLKPGVDYTITGYAVTVTHNGHPLMTPISINYRT

SEQ ID NO:20
EVVAATPTSLLISWRHPHFPTRYYRITYGETGGNSPVQEFTVPLQPPTAT
ISGLKPGVDYTITGYAVTLALKGHELLTPISINYRT

SEQ ID NO:21
VSDVPRDLEVVAATPTSLLISWRHPHFPTRYYRITYGETGGNSPVQEFTV
PLQPPTATISGLKPGVDYTITGYAVTVAQNDHELITPISINYRT

SEQ ID NO:22
VSDVPRDL/QEVVAATPTSLLISWRHPHFPTRYYRITYGETGGNSPVQEF
TVPLQPPAATISGLKPGVDYTITGYAVTMAQSGHELFTPISINYRT

SEQ ID NO:24
EVVAATPTSLLISWRHPHFPTRYYRITYGETGGNSPVQEFTVPLQPPTAT
ISGLKPGVDYTITGYAVTVERNGRVLMTPISINYRT

SEQ ID NO:25
EVVAATPTSLLISWRHPHFPTRYYRITYGETGGNSPVQEFTVPLQPPTAT
ISGLKPGVDYTITGYAVTVERNGRHLMTPISINYRT

SEQ ID NO:33
EVVAATPTSLLISWRHPHFPTRYYRITYGETGGNSPVQEFTVPLQPPTAT
ISGLKPGVDYTITGYAVTLERNGRELMTPISINYRT

SEQ ID NO:45
EVVAATPTSLLISWRHPHFPTRYYRITYGETGGNSPVQEFTVPLQPPTAT
ISGLKPGVDYTITGYAVTEERNGRTLRTPISINYRT

SEQ ID NO:53
EVVAATPTSLLISWRHPHFPTRYYRITYGETGGNSPVQEFTVPLQPPTAT
ISGLKPGVDYTITGYAVTVERNDRVLFTPISINYRT

SEQ ID NO:57
EVVAATPTSLLISWRHPHFPTRYYRITYGETGGNSPVQEFTVPLQPPTAT
ISGLKPGVDYTITGYAVTVERNGRELMTPISINYRT

SEQ ID NO:62
EVVAATPTSLLISWRHPHFPTRYYRITYGETGGNSPVQEFTVPLQPPTAT
ISGLKPGVDYTITGYAVTLERNGRELMVPISINYRT

SEQ ID NO:63
EVVAATPTSLLISWRHPHFPTRYYRITYGETGGNSPVQEFTVPLQPPTAT
ISGLKPGVDYTITGYAVTDGRNDRKLMVPISINYRT

SEQ ID NO:68
EVVAATPTSLLISWRHPHFPTRYYRITYGETGGNSPVQEFTVPLQPPTAT
ISGLKPGVDYTITGYAVTDGQNGRLLNVPISINYRT

SEQ ID NO:91
EVVAATPTSLLISWRHHPHFPTRYYRITYGETGGNSPVQEFTVPLQPPTA
TISGLKPGVDYTITGYAVTVHWNGRELMTPISINYRT

SEQ ID NO:92
EVVAATPTSLLISWRHPHFPTRYYRITYGETGGNSPVQEFTVPLQPPTAT
ISGLKPGVDYTITGYAVTEEWNGRVLMTPISINYRT

SEQ ID NO:93
EVVAATPTSLLISWRHPHFPTRYYRITYGETGGNSPVQEFTVPLQPPTAT
ISGLKPGVDYTITGYAVTVERNGHTLMTPISINYRT

SEQ ID NO:94
EVVAATPTSLLISWRHPHFPTRYYRITYGETGGNSPVQEFTVPLQPPTAT
ISGLKPGVDYTITGYAVTVEENGRQLMTPISINYRT

SEQ ID NO:95
EVVAATPTSLLISWRHPHFPTRYYRITYGETGGNSPVQEFTVPLQPPTAT
ISGLKPGVDYTITGYAVTLERNGQVLFTPISINYRT

SEQ ID NO:96
EVVAATPTSLLISWRHPHFPTRYYRITYGETGGNSPVQEFTVPLQPPTAT
ISGLKPGVDYTITGYAVTVERNGQVLYTPISINYRT

SEQ ID NO:97
EVVAATPTSLLISWRHPHFPTRYYRITYGETGGNSPVQEFTVPLQPPTAT
ISGLKPGVDYTITGYAVTWGYKDHELLIPISINYRT

SEQ ID NO:98
EVVAATPTSLLISWRHPHFPTRYYRITYGETGGNSPVQEFTVPLQPPTAT
ISGLKPGVDYTITGYAVTLGRNDRELLTPISINYRT

SEQ ID NO:99
EVVAATPTSLLISWRHPHFPTRYYRITYGETGGNSPVQEFTVPLQPPTAT
ISGLKPGVDYTITGYAVTDGPNDRLLNIPISINYRT

SEQ ID NO:100
EVVAATPTSLLISWRHPHFPTRYYRITYGETGGNSPVQEFTVPLQPPTAT
ISGLKPGVDYTITGYAVTFARDGHEILTPISINYRT

SEQ ID NO:101
EVVAATPTSLLISWRHPHFPTRYYRITYGETGGNSPVQEFTVPLQPPTAT
ISGLKPGVDYTITGYAVTLEQNGRELMTPISINYRT

SEQ ID NO:102
EVVAATPTSLLISWRHPHFPTRYYRITYGETGGNSPVQEFTVPLQPPTAT
ISGLKPGVDYTITGYAVTVEENGRVLNTPISINYRT

SEQ ID NO:103
EVVAATPTSLLISWRHPHFPTRYYRITYGETGGNSPVQEFTVPLQPPTAT
ISGLKPGVDYTITGYAVTLEPNGRYLMVPISINYRT

SEQ ID NO:104
EVVAATPTSLLISWRHPHFPTRYYRITYGETGGNSPVQEFTVPLQPPTAT
ISGLKPGVDYTITGYAVTEGRNGRELFIPISINYRT

SEQ ID NO:154
VSDVPRDLEVVAATPTSLLISWRHPHFPTRYYRITYGETGGNSPVQEFTV
PLQPPAATISGLKPGVDYTITGYAVTWERNGRELFTPISINYRT

SEQ ID NO:156
VSDVPRDLEVVAATPTSLLISWRHPHFPTRYYRITYGETGGNSPVQEFTV
PLQPPAATISGLKPGVDYTITGYAVTKERNGRELFTPISINYRT

SEQ ID NO:172
VSDVPRDLEVVAATPTSLLISWRHPHFPTHYYRITYGETGGNSPVQEFTV
PLQPPAATISGLKPGVDYTITGYAVTTERTGRELFTPISINYRT

SEQ ID NO:173
VSDVPRDLEVVAATPTSLLISWRHPHFPTHYYRITYGETGGNSPVQEFTV
PLQPPAATISGLKPGVDYTITGYAVTKERSGRELFTPISINYRT

SEQ ID NO:175
VSDVPRDLEVVAATPTSLLISWRHPHFPTHYYRITYGETGGNSPVQEFTV
PLQPPAATISGLKPGVDYTITGYAVTLERDGRELFTPISINYRT

SEQ ID NO:177
VSDVPRDLEVVAATPTSLLISWRHPHFPTRYYRITYGETGGNSPVQEFTV
PLQPPLATISGLKPGVDYTITG/VYAVTKERNGRELFTPISINYRT

SEQ ID NO:180
VSDVPRDLEVVAATPTSLLISWRHPHFPTRYYRITYGETGGNSPVQEFTV
PLQPTTATISGLKPGVDYTITGYAVTWERNGRELFTPISINYRT

SEQ ID NO:181
VSDVPRDLEVVAATPTSLLISWRHPHFPTRYYRITYGETGGNSPVQEFTV
PLQPTVATISGLKPGVDYTITGYAVTLERNDRELFTPISINYRT

SEQ ID NO:186
MGEVVAATPTSLLISWRHPHFPTRYYRITYGETGGNSPVQEFTVPLQPPT
ATISGLKPGVDYTITVYAVTDGRNGRLLSIPISINYRTEIDKPSQ

SEQ ID NO:187
MGEVVAATPTSLLISWRHPHFPTRYYRITYGETGGNSPVQEFTVPLQPPT
ATISGLKPGVDYTITVYAVTDGRNGRLLSIPISINYRTEIDKPCQ

SEQ ID NO:188
MVSDVPRDLEVVAATPTSLLISWRHPHFPTRYYRITYGETGGNSPVQEFT
VPLQPPTATISGLKPGVDYTITVYAVTDGRNGRLLSIPISINYRTEIDKP
SQ

SEQ ID NO:189
MGEVVAATPTSLLISWRHPHFPTRYYRITYGETGGNSPVQEFTVPLQPPT
ATISGLKPGVDYTITVYAVTDGWNGRLLSIPISINYRT

SEQ ID NO:190
MGEVVAATPTSLLISWRHPHFPTRYYRITYGETGGNSPVQEFTVPLQPPT
ATISGLKPGVDYTITVYAVTEGPNERSLFIPISINYRT

SEQ ID NO:191
MVSDVPRDLEVVAATPTSLLISWRHPHFPTRYYRITYGETGGNSPVQEFT
VPLQPPTATISGLKPGVDYTITVYAVTEGPNERSLFIPISINYRT

-continued

```
                                                   SEQ ID NO:192
(A core form of the polypeptide referred to herein
as CT-01):

EVVAATPTSLLISWRHPHFPTRYYRITYGETGGNSPVQEFTVPLQPPTAT

ISGLKPGVDYTITVYAVTDGRNGRLLSIPISTNYRT
```

The CT-01 molecule above has a deletion of the first 8 amino acids and may include additional amino acids at the N- or C-termini. For example, an additional MG sequence may be placed at the N-terminus. The M will usually be cleaved off, leaving a GEV . . . sequence at the N-terminus. The re-addition of the normal 8 amino acids at the N-terminus also produces a KDR binding protein with desirable properties. The N-terminal methionine is generally cleaved off to yield a sequence:

(SEQ ID NO:193)
VSDVPRDLEVVAATPTSLLISWRHPHFPTRYYRITYGETGGNSPVQEFTV
PLQPPTATISGLKPGVDYTITVYAVTDGRNGRLLSIPISINYRT.

A polypeptide disclosed herein may be modified by one or more conservative substitutions, particularly in portions of the protein that are not expected to interact with a target protein. It is expected that as many as 5%, 10%, 20% or even 30% or more of the amino acids in an immunoglobulin or immunoglobulin-like domain may be altered by a conservative substitution without substantially altering the affinity of the protein for target. It may be that such changes will alter the immunogenicity of the polypeptide in vivo, and where the immunogenicity is decreased, such changes will be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

Polypeptides disclosed herein may also be modified in order to improve potency, bioavailability, chemical stability, and/or efficacy. For example, within one embodiment of the invention D-amino acid peptides, or retroenantio peptide sequences may be generated in order to improve the bioactivity and chemical stability of a polypeptide structure (see, e.g., Juvvadi et al., J. Am. Chem. Soc. 118: 8989-8997, 1996; Freidinger et al., Science, 210: 656-658, 1980). Lactam constraints (see Freidinger, supra), and/or azabicycloalkane amino acids as dipeptide surrogates can also be utilized to improve the biological and pharmacological properties of the native peptides (see, e.g., Hanessian et al., Tetrahedron 53:12789-12854, 1997).

Amide bond surrogates, such as thioamides, secondary and tertiary amines, heterocycles among others (see review in Spatola, A. F. in "Chemistry and Biochemistry of Amino Acids, Peptides and Proteins" Wenstein, B. Ed. Marcel Dekker, New York, 1983 Vol. 7, pp 267-357) can also be utilized to prevent enzymatic degradation of the polypeptide backbone thereby resulting in improved activity. Conversion of linear polypeptides to cyclic polypeptide analogs can also be utilized to improve metabolic stability, since cyclic polypeptides are much less sensitive to enzymatic degradation (see generally, Veber, et al. Nature 292:55-58, 1981).

Polypeptides can also be modified utilizing end group capping as esters and amides in order to slow or prevent metabolism and enhance lipophilicity. Dimers of the peptide attached by various linkers may also enhance activity and specificity (see for example: Y. Shimohigashi et al, in Peptide Chemistry 1988, Proceedings of the 26th Symposium on Peptide Chemistry, Tokyo, Oct. 24-26, pgs. 47-50, 1989). For additional examples of polypeptide modifications, such as non-natural amino acids, see U.S. Pat. No. 6,559,126.

For use in vivo, a form suitable for pegylation may be generated. For example, a C-terminal tail comprising a cysteine was added and expressed, as shown below for a CT-01 form lacking the eight N-terminal amino acids (EIDKPCQ is added at the C-terminus). GEVVAATPTSLLISWRHPHFPTRYYRITYGETGGNSPVQEFTVPLQPPTATISGLKPGVDYTITVYAVTDGRNGRLLSIPISINYRTEIDKPCQ (SEQ ID NO:194). The pegylated form of this molecule is used in the in vivo experiments described below. A control form with a serine instead of a cysteine was also used:

(SEQ ID NO:195)
GEVVAATPTSLLISWRHPHFPTRYYRITYGETGGNSPVQEFTVPLQPPTA
TISGLKPGVDYTITVYAVTDGRNGRLLSIPISINYRTEIDKPSQ.

The same C-terminal tails may also be added to CT-01 forms having the N-terminal eight amino acids, such as is shown in SEQ ID NO:193. Additional variants with desirable KDR binding properties were isolated. The following core sequence has a somewhat different FG loop, and may be expressed with, for example, an N-terminal MG sequence, an N-terminal sequence that restores the 8 deleted amino acids, and/or a C-terminal tail to provide a cysteine for pegylation. EVVAATPTSLLISWRHPHFPTRYYRITYGETGGNSPVQEFTVPLQPPTATISGLKPGVDYTITVYAVTEGPNERSLFIPISINYRT (SEQ ID NO:196). Another such variant has the core sequence:

(SEQ ID NO:197)
VSDVPRDLEVVAATPTSLLISWRHPHFPTRYYRITYGETGGNSPVQEFTV
PLQPPTATISGLKPGVDYTITVYAVTEGPNERSLFIPISINYRT.

Additionally, preferred single domain immunoglobulin polypeptides in a $V_L$ framework were isolated by similar methodology and are disclosed in FIG. 21.

Also included in the present invention are nucleic acid sequences encoding any of the polypeptides described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a polypeptide described herein may be modified slightly in sequence and yet still encode its respective gene product.

In addition, the polypeptides of the present invention can be used as lead polypeptides that can be further mutated and screened for polypeptides that bind VEGFR with an even greater affinity. In one example, a polypeptide described herein is used as a lead polypeptide which is further mutated or randomized to produce polypeptides with amino acid mutations distinct from the lead polypeptide. The further randomized polypeptides can then be used to screen for polypeptides that inhibit VEGF biological activity as described herein (e.g., bind to a VEGFR and block binding of VEGF to the same receptor).

3. Nucleic Acids and Production of Polypeptides

Polypeptides of the present invention can be produced using any standard methods known in the art.

In one example, the polypeptides are produced by recombinant DNA methods by inserting a nucleic acid sequence (e.g., a cDNA) encoding the polypeptide into a recombinant expression vector and expressing the DNA sequence under conditions promoting expression. Examples of nucleic acid sequences encoding a CT-01 polypeptide disclosed herein are:

```
                                           SEQ ID NO:184
atgggcgaagttgttgctgcgaccccaccagcctactgatcagctggcg ccacccgcacttcccgactagatattacaggatcacttacggagaaacag gaggaaatagccctgtccaggagttcactgtgcctctgcagcccccaca gctaccatcagcggccttaaacctggagttgattataccatcactgtgta tgctgtcactgacggccggaacgggcgcctcctgagcatcccaatttcca ttaattaccgcacagaaattgacaaaccatgccag
                                           SEQ ID NO:185
Atgggcgaagttgttgctgcgaccccaccagcctactgatcagctggcg ccacccgcacttcccgactagatattacaggatcacttacggagaaacag gaggaaatagccctgtccaggagttcactgtgcctctgcagcccccaca gctaccatcagcggccttaaacctggagttgattataccatcactgtgta tgctgtcactgacggccggaacgggcgcctcctgagcatcccaatttcca ttaattaccgcaca
```

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

VEGFR-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptide of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

4. Post-Translational Modifications of Polypeptides

In certain embodiments, the binding polypeptides of the invention may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See, e.g., Raju et al. Biochemistry. 2001 Jul. 31; 40(30):8868-76. Effects of such non-amino acid elements on the functionality of a polypeptide may be tested for its antagonizing role in VEGFR-2 or VEGF function, e.g., its inhibitory effect on angiogenesis or on tumor growth.

In one specific embodiment of the present invention, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. Examples of the modified polypeptide of the invention include PEGylated M5FL and PEGylated CT-01.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula:

X—O($CH_2CH_2O$)$_{n-1}$$CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

Although PEG is well-known, this is, to our knowledge, the first demonstration that a pegylated $^{10}$Fn3 polypeptide can be pegylated and retain ligand binding activity. In a preferred embodiment, the pegylated $^{10}$Fn3 polypeptide is produced by site-directed pegylation, particularly by conjugation of PEG to a cysteine moiety at the N- or C-terminus. Accordingly, the present disclosure provides a target-binding $^{10}$Fn3 polypeptide with improved pharmacokinetic properties, the polypeptide comprising: a $^{10}$Fn3 domain having from about 80 to about 150 amino acids, wherein at least one of the loops of said $^{10}$Fn3 domain participate in target binding; and a covalently bound PEG moiety, wherein said $^{10}$Fn3 polypeptide binds to the target with a $K_D$ of less than 100 nM and has a clearance rate of less than 30 mL/hr/kg in a mammal. The PEG moiety may be attached to the $^{10}$Fn3 polypeptide by site directed pegylation, such as by attachment to a Cys residue, where the Cys residue may be positioned at the N-terminus of the $^{10}$Fn3 polypeptide or between the N-terminus and the most N-terminal beta or beta-like strand or at the C-terminus of the $^{10}$Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, J. Biol. Chem., 252, 3571 (1977) and J. Biol. Chem., 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to VEGFR-2 binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the invention, a VEGFR-2 binding polypeptide is covalently linked to one poly(ethylene glycol) group of the formula: —CO—$(CH_2)_x$—($OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, an binding polypeptide's ε-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In one embodiment of the invention, PEG molecules may be activated to react with amino groups on a binding polypeptide, such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of a $^{10}$Fn3 polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylated at an ϵ-amino group of a binding polypeptide lysine or the N-terminal amino group of the binding polypeptide.

In another embodiment, PEG molecules may be coupled to sulfhydryl groups on a binding polypeptide (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into an binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414(6866):933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication No. 2002/0044921 and in WO94/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5):1005-1009.

Monopegylation of a binding polypeptide can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70% least 80%, 85%, 90%, 95% or 100% of the biological activity associated with the unmodified protein. In one embodiment, biological activity refers to its ability to bind to VEGFR-2, as assessed by KD, $k_{on}$, or $k_{off}$. In one specific embodiment, the pegylated binding polypeptide protein shows an increase in binding to VEGFR relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

5. Therapeutic Formulations and Modes of Administration

The present invention features methods for treating conditions or preventing pre-conditions which respond to an inhibition of VEGF biological activity. Preferred examples are conditions that are characterized by inappropriate angiogenesis. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present invention may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

6. Exemplary Uses

The VEGFR-2 binding proteins described herein and their related variants are useful in a number of therapeutic and diagnostic applications. These include the inhibition of the biological activity of VEGF by competing for or blocking the binding to a VEGFR-2 as well as the delivery of cytotoxic or imaging moieties to cells, preferably cells expressing VEGFR-2.

The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of VEGF biological activity, the polypeptides of the invention are effective against a number of conditions associated with inappropriate angiogenesis, including but not limited to autoimmune disorders (e.g., rheumatoid arthritis, inflammatory bowel disease or psoriasis); cardiac disorders (e.g., atherosclerosis or blood vessel restenosis); retinopathies (e.g., proliferative retinopathies generally, diabetic retinopathy, age-related macular degeneration or neovascular glaucoma), renal disease (e.g., diabetic nephropathy, malignant nephrosclerosis, thrombotic microangiopathy syndromes; transplant rejection; inflammatory renal disease; glomerulonephritis; mesangioproliferative glomerulonephritis; haemolytic-uraemic syndrome; and hypertensive nephrosclerosis); hemangioblastoma; hemangiomas; thyroid hyperplasias; tissue transplantations; chronic inflammation; Meigs's syndrome; pericardial effusion; pleural effusion; autoimmune diseases; diabetes; endometriosis; chronic asthma; undesirable fibrosis (particularly hepatic fibrosis) and cancer, as well as complications arising from cancer, such as pleural effusion and ascites. Preferably, the VEGFR-binding polypeptides of the invention can be used for the treatment of prevention of hyperproliferative diseases or cancer and the metastatic spread of cancers. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer. Additional treatable conditions can be found in U.S. Pat. No. 6,524,583, herein incorporated by reference. Other references describing uses for VEGFR-2 binding polypeptides include: McLeod D S et al., Invest Ophthalmol Vis Sci. 2002 February; 43(2):474-82; Watanabe et al. Exp Dermatol. 2004 November; 13(11):671-81; Yoshiji H et al., Gut. 2003 September; 52(9):1347-54; Verheul et al., Oncologist. 2000; 5 Suppl 1:45-50; Boldicke et al., Stem Cells. 2001; 19(1):24-36.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, coronary collaterals, ischemic limb angiogenesis, corneal diseases, rubeosis, arthritis, diabetic neovascularization, fractures, vasculogenesis, hematopoiesis.

A VEGFR-2 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject therapeutic agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disrupters such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disrupters.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

The VEGFR-2 binding proteins described herein can also be detectably labeled and used to contact cells expressing VEGFR-2 for imaging applications or diagnostic applications. For diagnostic purposes, the polypeptide of the invention is preferably immobilized on a solid support. Preferred solid supports include columns (for example, affinity columns, such as agarose-based affinity columns), microchips, or beads.

In one example of a diagnostic application, a biological sample, such as serum or a tissue biopsy, from a patient suspected of having a condition characterized by inappropriate angiogenesis is contacted with a detectably labeled polypeptide of the invention to detect levels of VEGFR-2. The levels of VEGFR-2 detected are then compared to levels of VEGFR-2 detected in a normal sample also contacted with the labeled polypeptide. An increase of at least 10%, 20%, 30%, 40%, 50%, 60%, 70%, 80%, or 90% in the levels of the VEGFR-2 may be considered a diagnostic indicator of a condition characterized by inappropriate angiogenesis.

In certain embodiments, the VEGFR-2 binding polypeptides of the invention are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using VEGFR-2 binding polypeptides directed at VEGFR may be used to detect and/or diagnose cancers and vasculature. For example, any of the binding polypeptide against the VEGFR-2 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The VEGFR-2 binding polypeptides of the present invention can also be used to deliver additional therapeutic agents (including but not limited to drug compounds, chemotherapeutic compounds, and radiotherapeutic compounds) to a cell or tissue expressing VEGFR-2. In one example, the VEGFR-2 binding polypeptide is fused to a chemotherapeutic agent for targeted delivery of the chemotherapeutic agent to a tumor cell or tissue expressing VEGFR-2.

The VEGFR-2 binding polypeptides of the present invention are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides of the present invention can be used to detect or measure the expression of VEGFR-2, for example, on endothelial cells (e.g., venous endothelial cells), or on cells transfected with a VEGFR-2 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to VEGFR-2. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a VEGFR-2 protein is combined with the subject binding polypeptides, binding occurs between the binding polypeptides and the VEGFR-2 protein. In one embodiment, a sample containing cells expressing a VEGFR protein (e.g., endothelial cells) is combined with the subject antibodies, and binding occurs between the binding polypeptides and cells bearing a VEGFR-2 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a VEGFR-2 protein in a biological sample can also be prepared. Such kits will include an VEGFR-2 binding polypeptide which binds to a VEGFR-2 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of VEGFR-2, wherein a composition comprising a cell or fraction thereof (e.g., membrane fraction) is contacted with a binding polypeptide which binds to a VEGFR-2 or portion of the receptor under conditions appropriate for binding thereto, and the binding is monitored. Detection of the binding polypeptide, indicative of the formation of a complex between binding polypeptide and VEGFR-2 or a portion thereof, indicates the presence of the receptor. Binding of a polypeptide to the cell can be determined by standard methods, such as those described in the working examples. The method can be used to detect expression of VEGFR-2 on cells from an individual. Optionally, a quantitative expression of VEGFR-2 on the surface of endothelial cells can be evaluated, for instance, by flow cytometry, and the staining intensity can be correlated with disease susceptibility, progression or risk.

The present invention also relates to a method of detecting the susceptibility of a mammal to certain diseases. To illustrate, the method can be used to detect the susceptibility of a mammal to diseases which progress based on the amount of VEGFR-2 present on cells and/or the number of VEGFR-2-positive cells in a mammal. In one embodiment, the invention relates to a method of detecting susceptibility of a mammal to a tumor. In this embodiment, a sample to be tested is contacted with a binding polypeptide which binds to a VEGFR-2 or portion thereof under conditions appropriate for binding thereto, wherein the sample comprises cells which express VEGFR-2 in normal individuals. The binding and/or amount of binding is detected, which indicates the susceptibility of the individual to a tumor, wherein higher levels of receptor correlate with increased susceptibility of the individual to a tumor.

EXAMPLES

The following examples are for the purposes of illustrating the invention, and should not be construed as limiting.

Example 1

Initial Identification of KDR Binding Molecules

A library of approximately $10^{13}$ RNA-protein fusion variants was constructed based on the scaffold of the tenth type 3 domain of human fibronectin with three randomized regions at positions 23-29, 52-55 and 77-86 (amino acid nos. are referenced to SEQ ID NO:5) (three loop library; Xu et al, Chemistry & Biology 9:933-942, 2002). Similar libraries were constructed containing randomized regions only at positions 23-29 and 77-86 (two loop library) or only at positions 77-86 (one loop library). A mixture of these three libraries was used for in vitro selection against the extracellular domain of human VEGFR-2 (KDR, extracellular domain, residues 1-764 fused to human IgG1 Fc). For the purposes of this application, the amino acid positions of the loops will be defined as residues 23-30 (BC Loop), 52-56 (DE Loop) and 77-87 (FG Loop). The target binding population was analyzed by DNA sequencing after six rounds of selection and was found to be diverse, with some replicates present. Proteins encoded by fifteen independent clones were screened for binding to KDR, (FIG. 1A) and the best binders were subsequently analyzed for inhibition of target binding in the presence of VEGF (FIG. 1B). Multiple clones were identified that inhibited KDR-VEGF binding, suggesting that these clones bound KDR at or near the natural ligand (VEGF) binding site. The ability of two of the binding molecules (VR28 and VR12) to directly inhibit VEGF-KDR interaction was evaluated in a BIAcore assay using immobilized VEGF and a mobile phase containing KDR-Fc with or without a selected binding protein. VR28 and, to a lesser extent, VR12, but not a non-competing clone (VR17), inhibited KDR binding to VEGF in a dose dependent manner (FIG. 1C). Finally, in addition to binding to purified recombinant KDR, VR28 also appeared to bind to KDR-expressing recombinant CHO cells, but not to control CHO cells (FIG. 1D).

The sequence of the binding loops of the VR28 clone is shown in the first row of Table 4.

While VR28 was not the most abundant clone in the sequenced binding population (one copy out of 28 sequenced clone), its binding affinity to KDR was the best among the tested clones from this binding population, with a dissociation constant of 11-13 nM determined in a radioactive equilibrium binding assay (FIG. 3 and Table 5) and BIAcore assays (Table 7). There were no changes from wild type $^{10}$Fn3 in the remaining scaffold portion of the molecule (following correction of an incidental scaffold change at position 69 that had no effect on binding). However, VR28 showed little inhibition of VEGF-KDR signaling in a VEGF-dependent cell proliferation assay. Thus, while the selection from the naïve library yielded antibody mimics that interfered with the interaction between VEGF and KDR in biochemical binding studies, affinity improvements were useful for neutralizing function in a biological signal transduction assay.

Example 2

Affinity Maturation of Clone VR28

A mutagenesis strategy focusing on altering sequences only in the binding loops was employed. To initially test which loops were more likely to result in improvement, loop-directed hypermutagenic PCR was carried out to introduce up to 30% mutations independently into each loop of VR28. After three rounds of selection against KDR, multiple clones with improved binding to KDR-Fc were observed. Sequence analysis of the selection pools revealed that the majority of mutations were accumulated in the FG loop while the BC and DE loops remained almost intact. This result indicated that the FG loop was the most suitable target for further modification.

Figure 2:
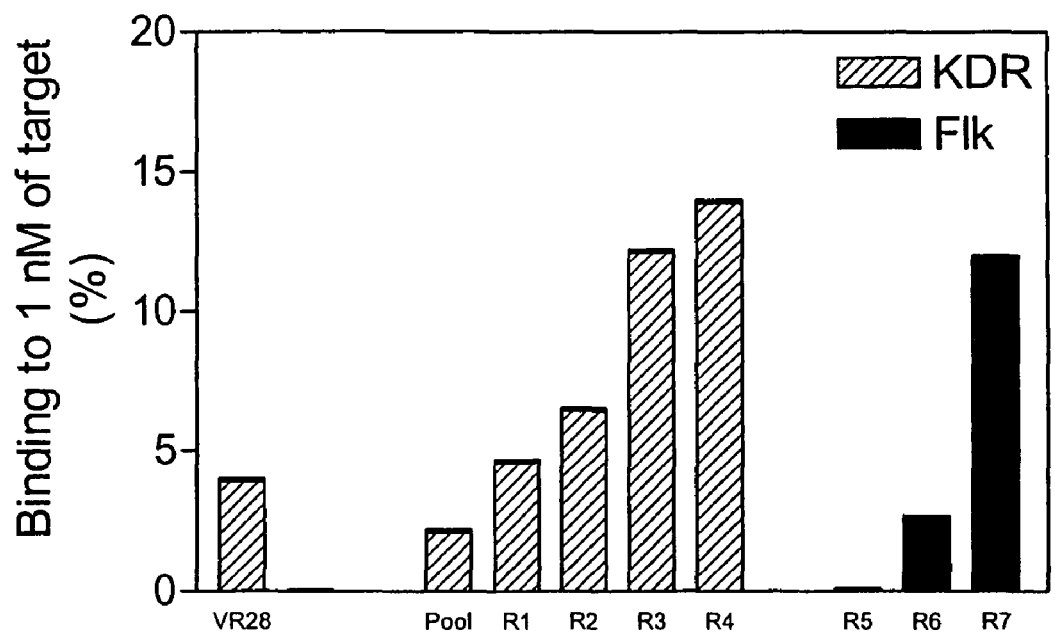
FIG. 2 is a graph showing the selection profile for the affinity maturation of VR28 KDR binder. Shown at left is binding of the VR28 clone to KDR-Fc and Flk1-Fc (very low, unlabeled bar). Shown at center is binding of a crude mutagenized pool and subsequent enrichment rounds to KDR-Fc. Shown at right is binding of further enrichment rounds to Flk-1-Fc. Binding was estimated in radioactive equilibrium binding assay as a percentage of input, using 1 nM KDR-Fc or Flk1-Fc.
Figures 3A, 3B:
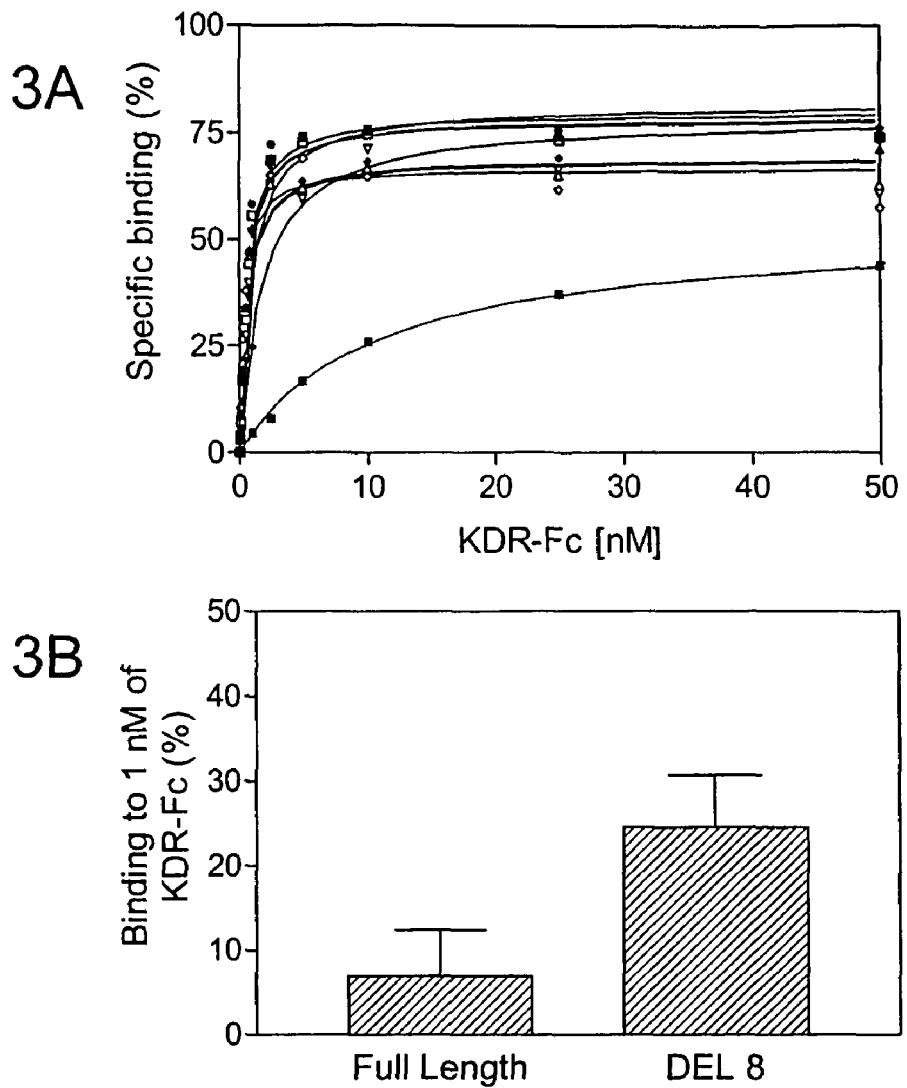
FIGS. 3A and 3B are graphs depicting the characterization of KDR-binding single clones from Round 4 of anti-KDR affinity maturation of VR28 binder.

Consequently, a new library of approximately $10^{12}$ variants was constructed by altering the sequence of VR28 in the FG loop using oligonucleotide mutagenesis. For each of the FG loop positions (residues 77-86 [VAQNDHELIT (SEQ ID NO:198)] as well as the following Proline [residue 87]), a 50:50 mixture of the VR28-encoding DNA and NNS was introduced at each position. DNA sequence analysis of a random sample of approximately 80 clones revealed an average of six amino acid changes per clone as expected. Lower KDR-Fc concentrations were utilized during selection to favor clones with better affinities to the target. The profile of target binding during the four rounds of selection is shown in FIG. 2. After four rounds of selection the binding population was subcloned and analyzed. Table 5 and FIG. 3A summarize affinity measurements of individual binding clones. The measured binding constants to KDR-Fc ranged from <0.4 to <1.8 nM, a 10-30 improvement over VR28 (11 nM).

Sequence analysis, some of which is shown in Table 4 (K clones), revealed that while the binding population was diverse, several consensus motifs could be identified among the clones. Most noticeably, Pro87 and Leu84 were found in nearly all clones (as in VR28), suggesting that these residues may be essential for the structure of the binding site. A positively charged amino acid at position 82 appears to be required since only H82K or H82R changes were seen in the sequenced clones and an aliphatic amino acid was predominant at position 78. D81 was often mutated to a G, resulting in the loss of negative charge at this position and a gain in flexibility. In addition, the overall mutation rate in the selected population was comparable to the pool prior to selection, which suggested that the FG loop is very open to changes.

Several residues in the N-terminus of the $^{10}$Fn3 domain of human fibronectin are located in close proximity to the FG loop, as suggested by structural determinations (Main et al, Cell 71:671-678, 1992). The close proximity of the two regions could potentially have a negative impact on target binding. Two incidental mutations in the N-terminal region, L8P and L8Q, resulted in better binding to KDR in a number of selected clones, presumably due to a change of the location of the N-terminus relative to the FG loop. To further test the impact of the N-terminus, we created binding molecules for 23 different KDR binders in which the N-terminal first eight residues before the β-sheet were deleted. We then compared target binding to the non-deleted counterparts. On average, binding to KDR-Fc was about 3-fold better with the deletion, as shown in FIG. 3B.

Example 3

Selection of Binders with Dual Specificities to Human (KDR) and Mouse (Flk-1) VEGFR-2

Figure 4:
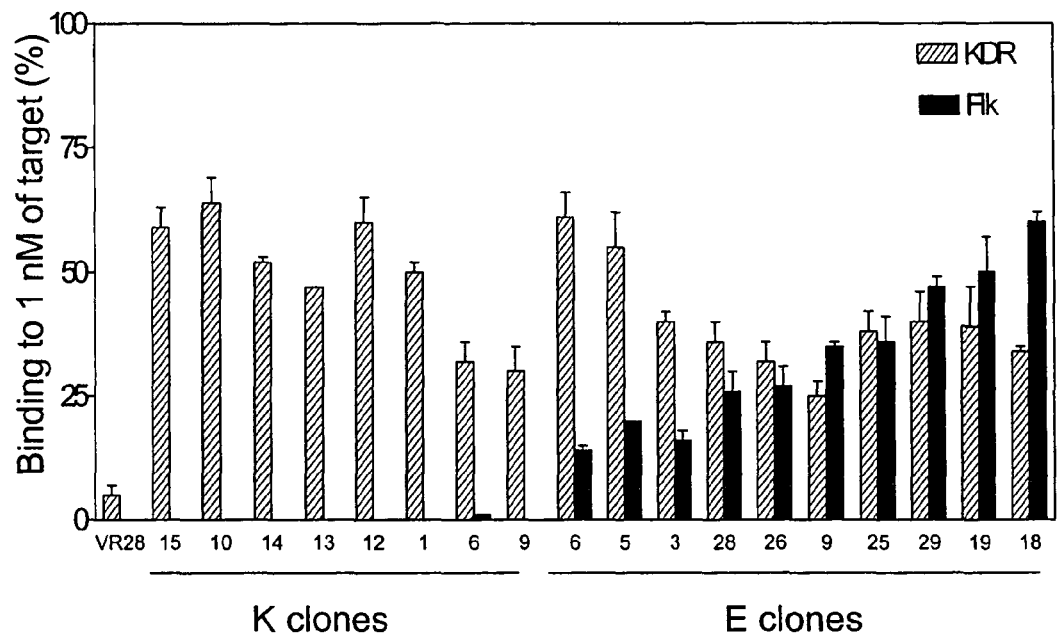
FIG. 4 is a graph showing the binding of the selected clones to KDR and Flk-1. Specific binding of VR28 and selected clones after four rounds of affinity maturation to human KDR (K clones) and seven rounds of affinity maturation to human (KDR) and mouse (flk-1) (E clones). VEGFR-2-Fc chimeras were compared in radioactive equilibrium binding assay. The data represents an average of 3 independent experiments. As shown here, maturation against both mouse and human VEGFR-2 proteins produces binders that bind to both proteins.

VR28 and most of the affinity matured variants (K clones) failed to bind the mouse homolog of KDR, Flk1, as shown in FIG. 4. However, since KDR and Flk1 share a high level of sequence identity (85%, Claffey et al., J. Biol. Chem. 267: 16317-16322 (1992), Shima et al., J. Biol. Chem. 271:3877-3883 (1996)), it is conceivable to isolate antibody mimics that can bind both KDR and Flk1. Such dual binders were desirable because they would allow the same molecule to be tested in functional studies in animal models and subsequently in humans.

Figures 5A, 5B:
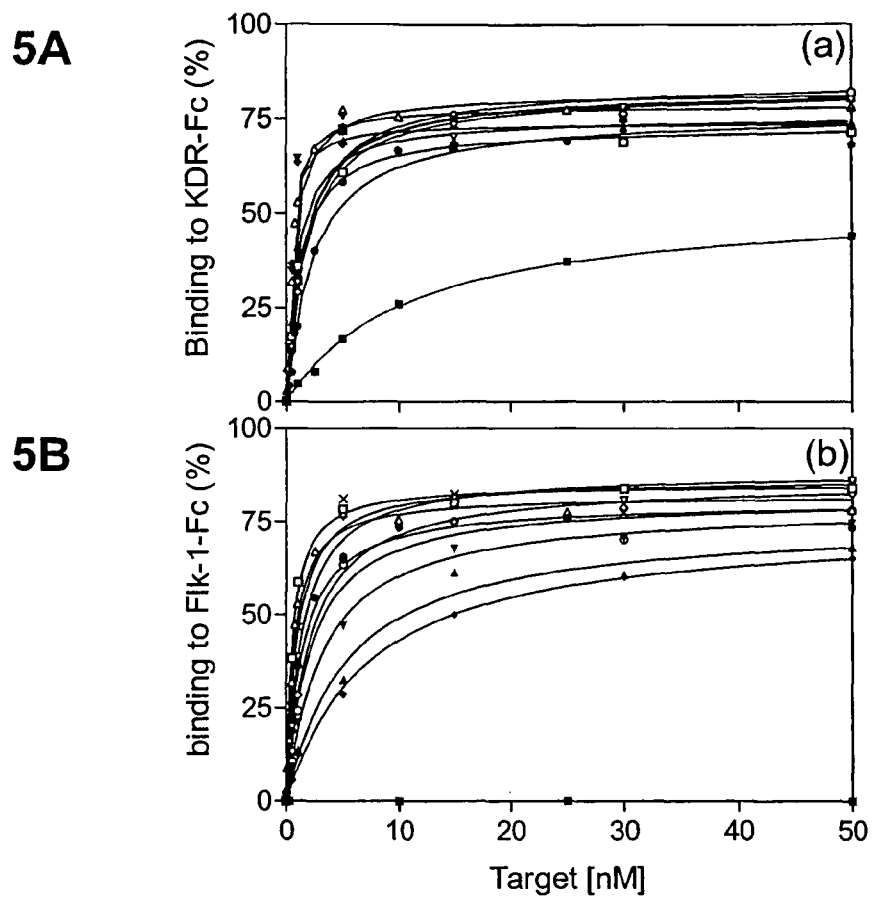
FIGS. 5A and 5B are graphs showing the characterization of VEGFR-2-binding single clones from Round 7 of affinity maturation of VR28 binder. Saturation binding of VR28 (-■-) and specificity matured E3 (-▲-), E5 (-▼-), E6 (-◆-), E9 (-●-), E18 (-□-), E19 (-Δ-), E25 (-∇-), E26 (-◇-), E28 (-○-), E29 (-x-) clones to KDR (FIG. 5A) and Flk1 (FIG. 5B)-Fc chimeras was tested in radioactive equilibrium binding assay.

The population of clones following FG loop mutagenesis and selection against KDR for four rounds was further selected against Flk1 for an additional three rounds. As shown in FIG. 2 an increase in binding to Flk1 was observed from Round 5 to Round 7, indicating enrichment of Flk1 binders. Analysis of binding for multiple individual clones revealed that in contrast to the clones selected against KDR only (K clones), most clones derived from additional selection against Flk1 (E clones) are able to interact with both KDR and Flk1. The binding constants to both targets, as determined using a radioactive equilibrium binding assay (Table 6 and FIG. 5) and BIAcore (Table 7), indicate that individual clones were able to bind both targets with high affinities.

For example, E19 has a Kd of 60 pM to KDR, and 340 pM to Flk-1. These results demonstrate that a simple target switch strategy in the selection process, presumably through selection pressures exerted by both targets, has allowed the isolation of molecules with dual binding specificities to both KDR and Flk-1 from a mutagenized population of VR28, a moderate KDR binder that was not able to bind Flk-1. The selected fibronectin-based binding proteins are highly specific to VEGFR-2 (KDR) as no substantial binding to VEGFR1 was observed at high target concentration.

Figures 6A, 6B:
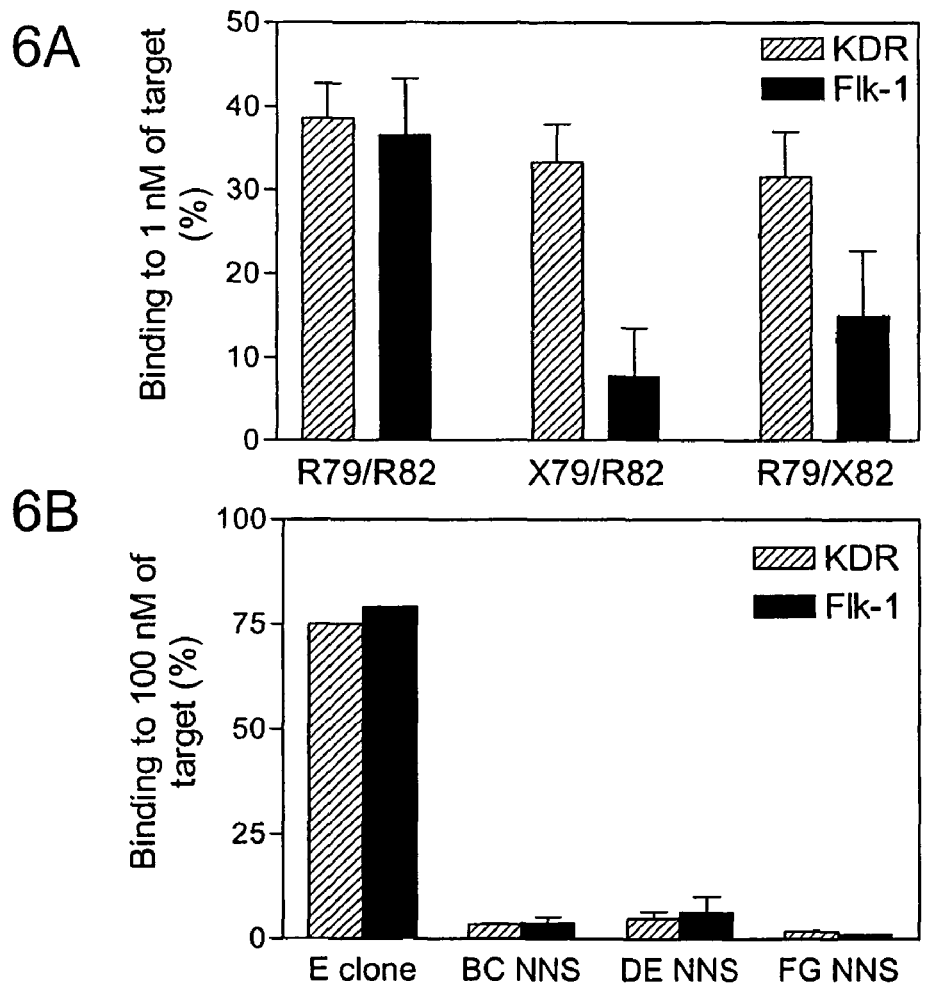
FIGS. 6A and 6B are graphs showing the characterization of VEGFR-2 binding by single clones from Round 7 of affinity maturation of the VR28 binder.

Sequence analysis revealed some motifs similar to those observed in the KDR binder pool (Leu and Pro at residues 84 and 87 respectively; positively charged amino acid at residue 82, predominantly Arg) and some that were not maintained (aliphatic at position 78). In addition, the motif ERNGR (residues 78-82) was present in almost all clones binding to Flk-1 (Table 4); this motif was barely discernable in the KDR binding pool. R79 and R82 appear to be particularly important for high affinity binding to Flk-1, since binding to Flk-1, but not KDR, is greatly reduced when a different residue is present at this position (FIG. 6A). To determine the importance of each loop in binding to KDR and Flk-1, the loops of clones E6 and E26 shown in Table 4, were substituted one loop at a time by NNS randomized sequence. As shown in FIG. 6B, after the substitution, the proteins are no longer able to bind either KDR or Flk-1. These results indicate that each loop is required for binding to the targets, suggesting a cooperative participation of all three loops in interacting with the targets.

An alternative mutagenesis strategy was independently employed to produce clones capable of binding to both targets. The clone 159Q(8)L (Table 4), the product of hypermutagenic PCR affinity maturation of VR28 that binds KDR with high affinity (Kd=2 nM; Table 7) and Flk-1 with poor affinity (Kd=3000 nM), was chosen as a starting point. The first six amino acids of the FG loop were fully randomized (NNS), leaving the following five residues (ELFTP) intact. After six rounds of selection against Flk-1, the binding pool was re-randomized at the DE loop (positions 52-56) and the selection was performed for three additional rounds against Flk-1 and one round against KDR. A number of high affinity binding molecules to both KDR and Flk-1 were thus obtained (Tables 4 and FIG. 4). For example, clone M5FL, while retaining high binding affinity to KDR (Kd=890 pM), can bind Flk-1 at a Kd of 2.1 nM, a 1000-fold improvement over the original clone. Interestingly, the ERNGR motif, found in Flk-1 binding molecules selected from a mutagenized population of VR28, was also present in multiple clones derived from clone 159Q(8)L mutagenesis and selection, despite a full randomization of this region of the FG loop. The isolation of similar binding molecules from two independent libraries suggests that the affinity maturation process is robust for isolating optimal Flk-1 binding motifs located in the FG loop.

Example 4

Cell Surface Binding and Neutralization of VEGF Activity In Vitro

Figures 7A, 7B:
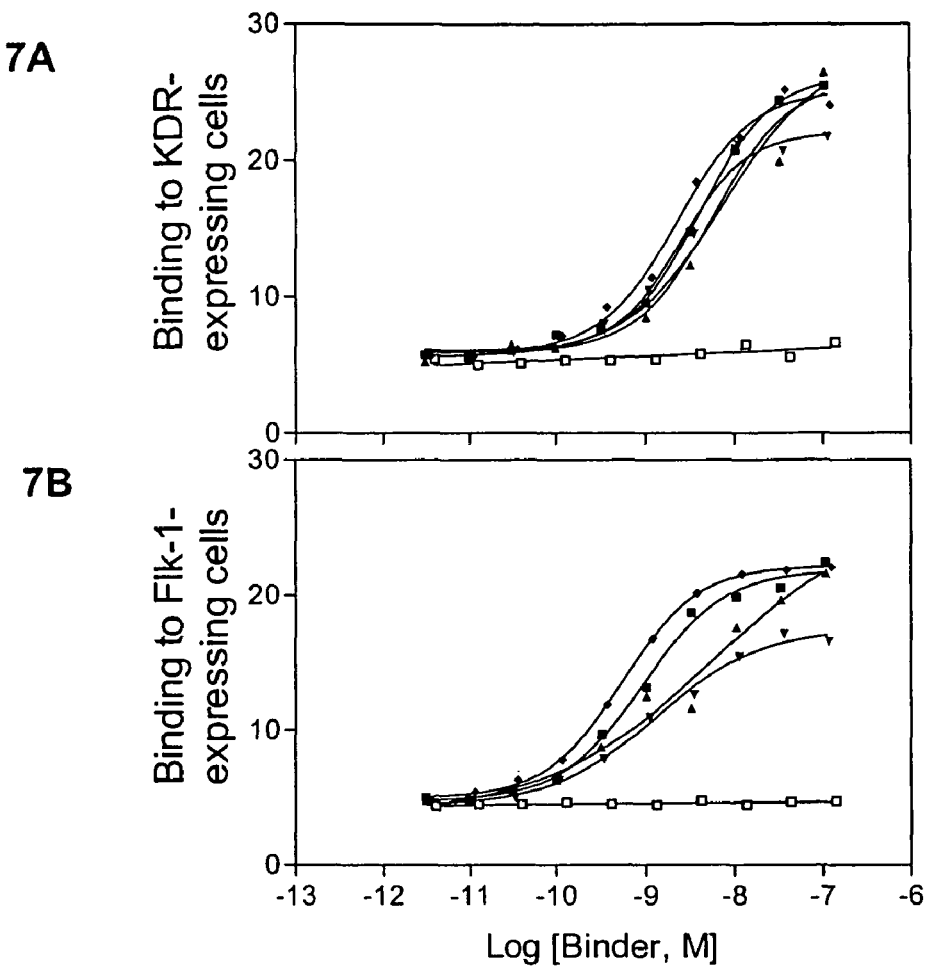
FIGS. 7A and 7B are graphs showing the binding of selected fibronectin-based binding proteins to CHO cells expressing human KDR receptor (FIG. 7A) and EpoR-Flk1 chimera (FIG. 7B). E18 (-■-), E19 (-▲-), E26 (-▼-), E29 (-◆-) and WT (-□-) fibronectin-based scaffold proteins were tested. No binding to control CHO cells was observed (data not shown).

The functionality of KDR and Flk-1 binding molecules in a cell culture model system was evaluated with E. coli produced binding molecules. Using a detection system consisting of anti-His6 tag murine antibody (the E. coli expressed proteins were expressed with a His tag) and an anti-murine fluorescently labeled antibody the binding molecules were shown to bind specifically to mammalian cells expressing KDR or Flk-1 with low nanomolar EC50s, (FIG. 7 and Table 8).

More importantly, using recombinant BA/F3 cells (DSMZ-Deutsche Sammlung von Mikroorganismen und Zellkulturen GmbH) expressing the extracellular KDR or Flk-1 domain linked to the erythropoietin receptor signaling domain, these molecules inhibited VEGF-stimulated cell proliferation in a dose dependent fashion, with IC50 3-12 mM for KDR expressing cells, and 2-5 nM for Flk-1 expressing cells.

Figures 8A, 8B:
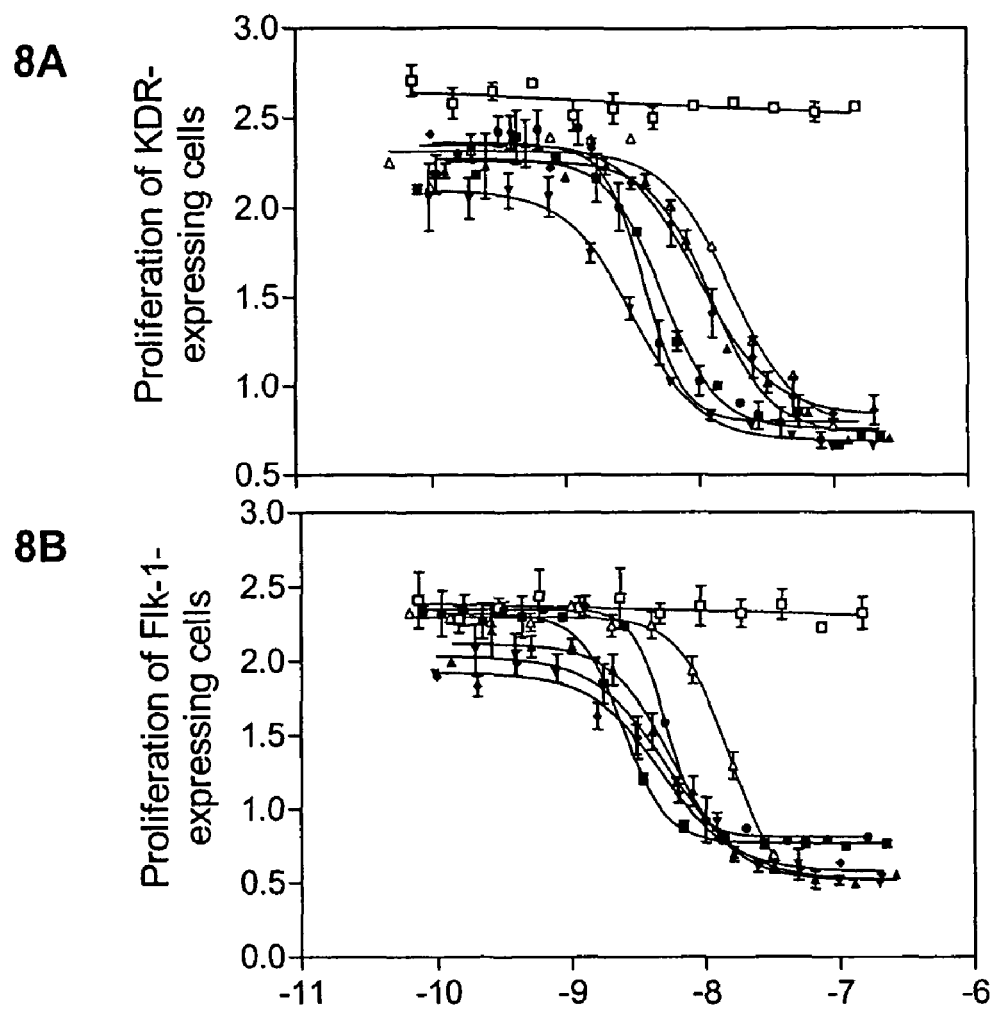
FIGS. 8A and 8B are graphs showing the inhibition of VEGF-induced proliferation of Ba/F3-KDR (FIG. 8A) and Ba/F3-Flk1 (FIG. 8B) cells, expressing KDR and Flk1 in the presence of different amounts of fibronectin-based binding proteins: E18 (-■-), E19 (-▲-), E26 (-▼-), E29 (-◆-), M5 (-●-), WT (-□-) and anti-KDR or anti-flk-1 Ab (-Δ-). The data represents an average of 2 independent experiments.

The potency of inhibition appears to be similar to control anti-KDR and anti-Flk-1 monoclonal antibodies, as shown in FIG. 8 and Table 9.

Figure 9:
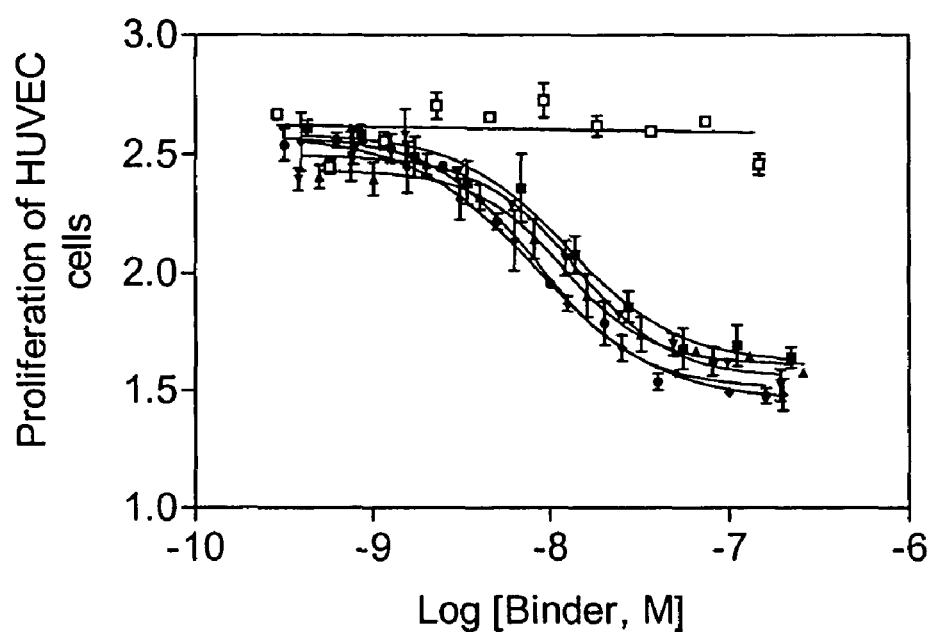
FIG. 9 is a graph showing the results of a HUVEC proliferation assay in the presence of different amounts of fibronectin-based scaffold proteins: E18 (-■-), E19 (-▲-), E26 (-▼-), E29 (-◆-), M5 (-●-), WT (-□-). The data represents an average of 2 independent experiments. As shown, the KDR binding proteins caused a decrease in proliferation by approximately 40%.

A number of clones were further tested for VEGF-inhibition of the growth of HUVEC cells (Human Umbilical Vein Endothelial Cells). HUVEC cells are natural human cells that are closely related to cells in the body that respond to VEGF. As shown in FIG. 9 and Table 10, the fibronectin-based binding proteins were also active in inhibiting VEGF activity in this human-derived cell system while the wild type fibronectin-based scaffold protein was inactive.

Example 5

Thermal Stability and Reversible Refolding of M5FL Protein

The thermal stability of KDR-binder M5FL was established using differential scanning calorimetry (DSC). Under standard PBS buffer conditions (sodium phosphate pH 7.4, 150 mM NaCl), M5FL was found to have a single non-reversible thermal melting transition at 56° C. Subsequently, sodium acetate pH 4.5 was identified as a favorable buffer for M5FL protein solubility. DSC experiments in this buffer (100 mM) demonstrated that M5FL is more stable under these conditions (Tm=67-77° C.) and that the melting transition is reversible (FIG. 10). Reversible thermal transitions have been used to identify favorable conditions that support long-term storage of protein therapeutics (Remmele et al, Biochemistry 38:5241 (1999), so Na-acetate pH 4.5 has been identified as an optimized buffer for storing the M5FL protein.

Example 6

In Vitro Binding and Cell-Based Activity of PEGylated M5FL Protein

The M5FL protein was produced in an *E. coli* expression system with a C-terminal extension to yield the following protein sequence (a significant percentage of protein is produced with the initial methionine removed):

(SEQ ID NO:199)
MGVSDVPRDLEVVAATPTSLLISWRHPHFPTRYYRITYGETGGNSPVQEF

TVPLQPPLATISGLKPGVDYTITVYAVTKERNGRELFTPISINYRTEIDK

PCQHHHHHH

The single sulfhydryl of the cysteine residue at position 102 was used to couple to PEG variants using standard maleimide chemistry to yield two different PEGylated forms of M5FL. Both a linear 20 kD PEG and a branched 40 kD PEG (Shearwater Corporation) were conjugated to M5FL to produce M5FL-PEG20 and M5FL-PEG40, respectively. The PEGylated protein forms were purified from unreacted protein and PEG by cation exchange chromatography. Covalent linkage of the two PEG forms of M5FL was verified by SDS-PAGE (FIG. 11) and mass spectroscopy.

In vitro affinity measurements were made using surface plasmon resonance (SPR) (BIAcore) with both the human and mouse VEGF-receptor target proteins immobilized via amide chemistry on the BIAcore chip. For both target proteins, both the 20 and 40 kD PEGylated M5FL forms were found to have slower on-rates (ka) relative to unmodified M5FL with little effect on off-rates (kd; Table 11).

The functionality of the PEGylated M5FL preparations was tested using the Ba/F3 system described in Example 4.

Figure 12:
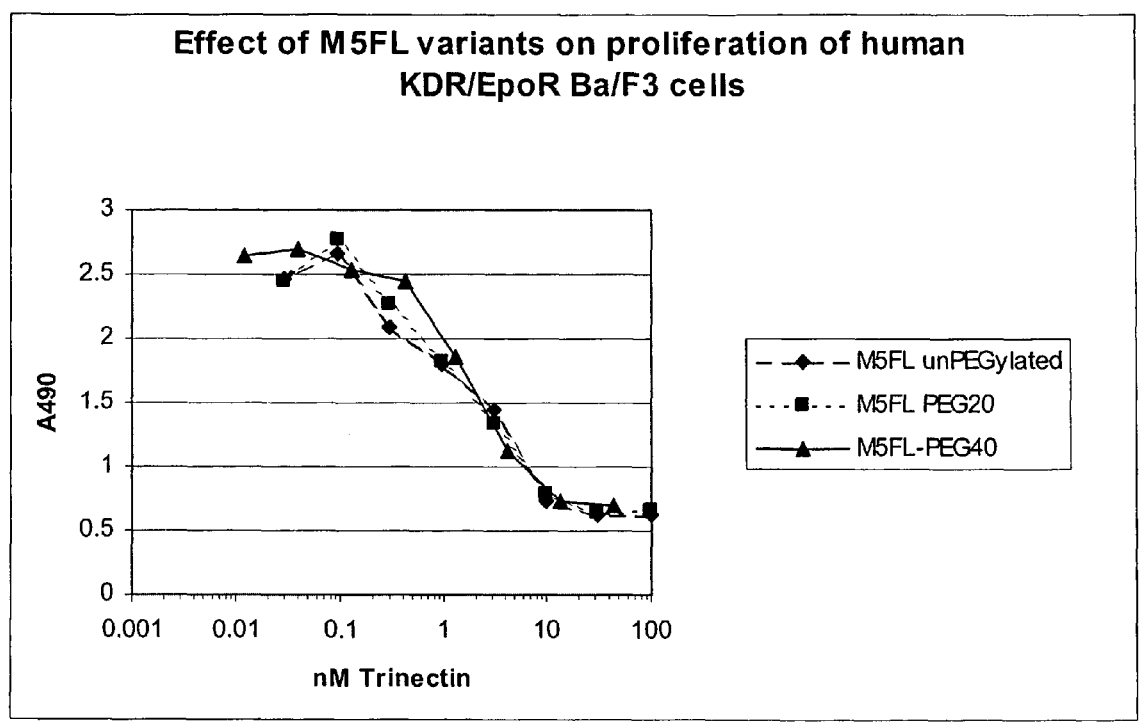
FIG. 12 is a graph showing the inhibition of VEGF-induced proliferation of Ba/F3-KDR cells with differing amounts of M5FL (-◆-), M5FL PEG20 (-■-) and M5FL PEG40 (-▲-), respectively. Pegylation has little or no effect on M5FL activity in this assay.

FIG. 12 shows a plot of A490 (representing the extent of cell proliferation) as a function of concentration of each of the binders. The curves were nearly identical, indicating there was little effect of PEGylation on the biological activity of either of the PEGylated forms.

The $k_{on}$, $k_{off}$ and $K_D$ were analyzed for a subset of KDR-binding polypeptides and compared to the EC50 for the BaF3 cell-based VEGF inhibition assay. Scatter plots showed that the kon was well-correlated with the EC50, while koff was poorly correlated. Greater than 90% of KDR-binding proteins with a kon of 105 s-1 or greater had an EC50 of 10 nM or less. KD is a ratio of kon and koff, and, as expected, exhibits an intermediate degree of correlation with EC50.

Many of the KDR-binding proteins, including CT-01, were assessed for binding to VEGFR-1, VEGFR-2 and VEGFR-3. The proteins showed a high degree of selectivity for VEGFR-2.

Example 6

Preparation of KDR Binding Protein CT-01 Blocks VEGFR-2 Signaling in Human Endothelial Cells Following the methodologies described in the preceding Examples, additional [10]Fn3-based KDR binding proteins were generated. As described for the development of the M5FL protein in Example 5, above, proteins were tested for $K_D$ against human KDR and mouse Flk-1 using the BIAcore binding assay and for IC50 in a Ba/F3 assay. A protein termed CT-01 exhibited desirable properties in each of these assays and was used in further analysis.

The initial clone from which CT-01 was derived had a sequence: GEVVAATPTSLLISWRHPHFPTRYYRI-TYGETGGNSPVQEFTVPLQPPTATISGLK PGVDYTITVYAVT<u>DGWNGRLLSIPI</u>SINYRT (SEQ ID NO:200). The FG loop sequence is underlined.

Affinity maturation as described above produced a core form of CT-01:

(SEQ ID NO:192)
EVVAATPTSLLISWRHPHFPTRYYRITYGETGGNSPVQEFTVPLQPPTAT

ISGLKPGVDYTITVYAVT<u>DGRNGRLLSIPI</u>SINYRT.

The CT-01 molecule above has a deletion of the first 8 amino acids and may include additional amino acids at the N- or C-termini. For example, an additional MG sequence may be placed at the N-terminus. The M will usually be cleaved off, leaving a GEV . . . sequence at the N-terminus. The re-addition of the normal 8 amino acids at the N-terminus also produces a KDR binding protein with desirable properties. The N-terminal methionine is generally cleaved off to yield a sequence:

(SEQ ID NO:193)
VSDVPRDLEVVAATPTSLLISWRHPHFPTRYYRITYGETGGNSPVQEFTV

PLQPPTATISGLKPGVDYTITVYAVTDGRNGRLLSIPISINYRT.

For use in vivo, a form suitable for PEGylation may be generated. For example, a C-terminal tail comprising a cysteine was added and expressed, as shown below for a form lacking the eight N-terminal amino acids. GEV-VAATPTSLLISWRHPHFPTRYYRI-TYGETGGNSPVQEFTVPLQPPTATISGLK PGVDYTITVYAVT<u>DGRNGRLLSIPI</u>SINYRTEIDKPCQ (SEQ ID NO:194). The PEGylated form of this molecule is used in the in vivo experiments described below. A control form with a serine instead of a cysteine was also used:

GEVVAATPTSLLISWRHPHFPTRYYRITYGETGGNSPVQEFTVPLQPPTA (SEQ ID NO:195)

TISGLKPGVDYTITVYAVT<u>DGRNGRLLSIP</u>ISINYRTEIDKPSQ.

The same C-terminal tails may also be added to CT-01 forms having the N-terminal eight amino acids, such as is shown in SEQ ID NO:193.

Additional variants with desirable KDR binding properties were isolated. The following core sequence has a somewhat different FG loop, and may be expressed with, for example, an N-terminal MG sequence, an N-terminal sequence that restores the 8 deleted amino acids, and/or a C-terminal tail to provide a cysteine for PEGylation. EVVAATPTSLLISWRHPHFPTRYYRI-TYGETGGNSPVQEFTVPLQPPTATISGLKP GVDYTITVYAVT<u>EGPNERSLFIP</u>ISINYRT (SEQ ID NO:196). Another such variant has the core sequence:

VSDVPRDLEVVAATPTSLLISWRHPHFPTRYYRITYGETGGNSPVQEFTV (SEQ ID NO:197)

PLQPPTATISGLKPGVDYTITVYAVT<u>EGPNERSLFIP</u>ISINYRT.

A comparison of these variants shows a consensus sequence for the FG loop of: D/EGXNXRXXIP (SEQ ID NO:3). With greater particularity, the consensus sequence may be expressed as (D/E)G(R/P)N(G/E)R(S/L)(S/F)IP (SEQ ID NO:4).

Example 7

CT-01 Blocks VEGFR-2 Signaling in Human Endothelial Cells

As shown in FIG. 13, VEGF-A signaling through VEGFR-2 is mediated by phosphorylation of the intracellular domain of VEGFR-2, followed by activation of pathway involving phospholipase C gamma (PLCγ), Protein Kinase C (PKC), Raf-1, MEK1/2, ERK1/2, leading to endothelial cell proliferation.

To assess whether KDR binders disclosed herein inhibited activation of this signaling pathway, Human Microvascular Endothelial Cells were treated with a VEGFR binding polypeptide (e.g., CT-01) for 30 min and stimulated with VEGF-A for 5 min. Total cell lysates were analyzed by SDS-PAGE and western analysis, using antibodies specific to phospho-VEGFR-2, non-phospho-VEGFR-2, phosphor-ERK1/2 and non-phospho-ERK1/2.

As shown in FIG. 13, 130 pM CT-01 inhibits formation of phosphor-VEGFR-2 and also decreases the formation of the downstream phosphorylated ERK1/2. Phosphorylated ERK1/2 is not entirely eliminated, probably due to the fact that ERK1/2 receives signals from a number of additional signaling pathways.

Example 8

Fibronectin-Based KDR Binding Proteins Disrupt Signaling by VEGF-A and VEGF-D

VEGFR-2 is a receptor for three VEGF species, VEGF-A, VEGF-C and VEGF-D. Experiments were conducted to evaluate the effects of fibronectin-based KDR binding proteins on VEGF-A and VEGF-D mediated signaling through KDR.

A Ba/F3 cell line dependent on Flk-1 mediated signaling was generated. As shown in the left panel of FIG. 14, cell viability could be maintained by treating the cells with VEGF-A or VEGF-D, although significantly higher levels of VEGF-D were required.

As shown in the middle panel of FIG. 14, cells were maintained in the presence of 15 ng/ml of VEGF-A and contacted with the M5FL or CT-01 proteins disclosed herein, or with the DC-101 anti-Flk-1 antibody. Each reagent reversed the VEGF-A-mediated cell viability, indicating that VEGF-A signaling through Flk-1 was blocked.

As shown in the right panel of FIG. 14, cells were maintained in the presence of 300 ng/ml of VEGF-D and contacted with the M5FL or F10 proteins disclosed herein, or with an anti-VEGF-A antibody. M5FL and F10 reversed the VEGF-D-mediated cell viability, indicating that VEGF-D signaling through Flk-1 was blocked. The anti-VEGF-A antibody had no effect, demonstrating the specificity of the assay.

Example 9

Pharmacokinetics

Pharmacokinetic Studies: Native CT-01 or a pegylated form (40 kDa PEG, CT-01PEG40) were iodinated with $^{125}$I. 10-20 mCi of iodinated proteins were injected into adult male rats either i.v. or i.p. and iodinated proteins levels were determined at the indicated times. For tissue distribution studies, rats were sacrificed at 15 min, 2 hr and 6 hr and radioactivity levels determined. See FIGS. 15 and 16. Unmodified CT-01 is a 12 kDa protein that is rapidly cleared from the blood. The area-under-curve value (AUC) value is 14.6 hr*mg/mL with a clearance of 69.9 mL/hr/kg, a maximum serum concentration of 9.1 mg/ml. The initial half-life (α) is 0.3 hours and the second phase half-life (β) is 13.5 hours. By comparison, i.v. PEGylated CT-01 has greatly increased presence in the blood, mostly because of a dramatic decrease in the initial phase of clearance. The AUC is increased greater than 10 fold to 193, the clearance rate is decreased by greater than 10 fold to 5.2, the Cmax is 12.9 mg/mL. The α half-life is increased to 1 hour, and the β is increased to 16.2 hours. These pharmacokinetics in rats are equivalent to a twice-weekly dosing regimen in humans, a rate of dosing that is well within acceptable ranges.

Intraperitoneal (i.p.) administration of PEGylated CT-01 had reservoir-like pharmacokinetics. There was no initial spike in the blood concentration of CT-01. Instead, the amount of CT-01 built up more slowly and decreased slowly. Such pharmacokinetics may be desirable where there is concern about side effects from the initial spike in CT-01 concentration upon intravenous administration. It is likely that other $^{10}$FN3-based agents would exhibit similar behavior in i.p. administration. Accordingly, this may be a generalizable mode for achieving a time-delayed dosing effect with $^{10}$Fn3-based agents.

As shown in FIG. 16, the liver is the primary route for secretion of the PEGylated form of CT-01. No long term accumulation of CT-01 was detected.

Similar results were obtained using a CT-01 conjugated to a 20 kDa PEG moiety.

Example 10

In Vivo Efficacy of CT-01

The Miles assay, as outlined in FIG. 17, is used to evaluate Dose, Schedule and Administration parameters for the tumor efficacy studies. Balb/c female mice were injected i.p. with buffer or CT-01PEG40 at 1, 5 and 20 mg/kg 4 hr prior to VEGF challenge. Intradermal focal administration of VEGF-A into the back skin induces vessel leakage of Evans blue dye (FIGS. 17 and 18).

Mice treated with a KDR binding agent showed a statistically significant decrease in the level of VEGF-mediated vessel leakage. Both 5 mg/kg and 20 mg/kg dosages with CT-01 showed significant results. Therefore, a 5 mg/kg dosage was selected for mouse tumor model studies.

Example 11

CT-01 Inhibits Tumor Growth

B16-F10 Murine Melanoma Tumor Assay:

$2\times10^6$ B16-F10 murine melanoma tumor cells were implanted subcutaneously into C57/BL male mice at Day 1. At day 6 a palpable mass was detected. On day 8 when tumors were of measurable size, daily i.p. injections of either Vehicle control, 5, 15, or 40 mg/kg CT-01PEG40 were started. The lowest dose 5 mg/kg decreased tumor growth. At day 18, mice treated with 15 and 40 mg/kg showed 50% and 66% reduction in tumor growth. See FIG. 19.

U87 Human Glioblastoma Assay:

$5\times10^6$ U87 human glioblastoma tumor cells were implanted subcutaneously into nude male mice. When tumor volume reached approximately 50 mm3 treatment started (day 0). Vehicle control, 3, 10, or 30 mg/kg CT-01PEG40 were injected i.v. every other day (EOD). The anti-Flk-1 antibody DC101 was injected at 40 mg/kg twice a week as published for its optimal dose schedule. The lowest dose 3 mg/kg decreased tumor growth. At day 12, mice treated with 10 and 30 mg/kg showed 50% reduction in tumor growth. See FIG. 20. Effectiveness is comparable to that of the anti-Flk-1 antibody.

The following materials and methods were used for the experiments described in Examples 1-11.

Recombinant Proteins:

Recombinant human $VEGF_{165}$, murine $VEGF_{164}$, human neurotrophin-4 (NT4), human and mouse vascular endothelial growth factor receptor-2 Fc chimeras (KDR-Fc and Flk-1-Fc) were purchased from R&D systems (Minneapolis, Minn.). Biotinylation of the target proteins was carried out in 1×PBS at 4° C. for 2 hours in the presence of EZ-Link™ Sulfo-NHS-LC-LC-Biotin (Pierce, Ill.). Excess of EZ-Link™ Sulfo-NHS-LC-LC-Biotin was removed by dialysis against 1×PBS. The level of biotinylation was determined by mass spectroscopy and target protein concentrations were determined using Coomassie Protein Plus Assay (Pierce, Ill.).

Primers:

The following oligonucleotides were prepared by chemical synthesis for eventual use in library construction and mutagenesis of selected clones.

T7 TMV Fn:
(SEQ ID NO:201)
5' GCG TAA TAC GAC TCA CTA TAG GGA CAA TTA CTA TTT ACA ATT ACA ATG GTT TCT GAT GTT CCG AGG 3'

T7 TMV N-terminus deletion:
(SEQ ID NO:202)
5' GCG TAA TAC GAC TCA CTA TAG GGA CAA TTA CTA TTT ACA ATT ACA ATG GAA GTT GTT GCT GCG ACC CCC ACC AGC CTA 3'

MK165-4 A20:
(SEQ ID NO:203)
5' TTT TTT TTT TTT TTT TTT TTA AAT AGC GGA TGC CTT GTC GTC GTC GTC CTT GTA GTC 3'

N-terminus forward:
(SEQ ID NO:204)
5' ATG GTT TCT GAT GTT CCG AGG GAC CTG GAA GTT GTT GCT GCG ACC CCC ACC AGC CTA CTG ATC AGC TGG 3'

BCDE reverse:
(SEQ ID NO:205)
5' AGG CAC AGT GAA CTC CTG GAC AGG GCT ATT TCC TCC TGT TTC TCC GTA AGT GAT CCT GTA ATA TCT 3'

BCDE forward:
(SEQ ID NO:206)
5' AGA TAT TAC AGG ATC ACT TAC GGA GAA ACA GGA GGA AAT AGC CCT GTC CAG GAG TTC ACT GTG CCT 3'

DEFG reverse:
(SEQ ID NO:207)
5' AGT GAC AGC ATA CAC AGT GAT GGT ATA ATC AAC TCC AGG TTT AAG GCC GCT GAT GGT AGC TGT 3'

DEFG forward:
(SEQ ID NO:208)
5' ACA GCT ACC ATC AGC GGC CTT AAA CCT GGA GTT GAT TAT ACC ATC ACT GTG TAT GCT GTC ACT 3'

C-terminus polyA:
(SEQ ID NO:209)
5' TTT TTT TTT TTT TTT TTT TAA ATA GCG GAT GCC TTG TCG TCG TCG TCC TTG TAG TCT GTT CGG TAA TTA ATG GAA AT 3'

Hu3'FLAGSTOP:
(SEQ ID NO:210)
5' TTT TAA ATA GCG GAT GCC TTG TCG TCG TCG TCC TTG TAG TCT GTT CGG TAA TTA ATG G 3'

VR28FG-50:
(SEQ ID NO:211)
5' GTG TAT GCT GTC ACT 123 145 463 665 165 465 163 425 625 645 447 ATT TCC ATT AAT TAC 3',, where 1 = 62.5% G + 12.5% A + 12.5% T + 12.5% C;

2 = 2.5% G + 12.5% A + 62.5% T + 12.5% C; 3 = 75% G + 25% C; 4 = 12.5% G + 12.5% A + 12.5% T

-continued 62.5% C; 5 = 25% G + 75% C; 6 = 12.5% G + 62.5%
A + 12.5% T + 12.5% C; 7: 25% G + 50% A + 25% C F1U2:
(SEQ ID NO:212)
5' TAA TAC GAC TCA CTA TAG GGA CAA TTA CTA TTT ACA
ATT CTA TCA ATA CAA TGG TGT CTG ATG TG CCG 3'

F2:
(SEQ ID NO:213)
5' CCA GGA GAT CAG CAG GGA GGT CGG GGT GGC AGC CAC
CAC TTC CAG GTC GCG CGG CAC ATC AGA CAC CAT TGT 3'

F3159:
(SEQ ID NO:214)
5' ACC TCC CTG CTG ATC TCC TGG CGC CAT CCG CAT TTT
CCG ACC CGC TAT TAC CGC ATC ACT TAC G 3'

F4:
(SEQ ID NO:215)
5' CAC AGT GAA CTC CTG GAC CGG GCT ATT GCC TCC TGT
TTC GCC GTA AGT GAT GCG GTA ATA GCG 3'

F5159:
(SEQ ID NO:216)
5' CGG TCC AGG AGT TCA CTG TGC CGC TGC AGC CGC CGG
CGG CTA CCA TCA GCG GCC TTA AAC C 3'

F5-X5:
(SEQ ID NO:217)
5' CG GTC CAG GAG TTC ACT GTG CCG NNS NNS NNS NNS
NNS GCT ACC ATC AGC GGC CTT AAA CC 3'

F6:
(SEQ ID NO:218)
5' AGT GAC AGC ATA CAC AGT GAT GGT ATA ATC AAC GCC
AGG TTT AAG GCC GCT GAT GGT AG 3'

F7X6159:
(SEQ ID NO:219)
5' ACC ATC ACT GTG TAT GCT GTC ACT NNS NNS NNS NNS
NNS NNS GAA CTG TTT ACC CCA ATT CCA TCA ACA TAC
CGC ACA GAC TAC AAG 3'

F8:
(SEQ ID NO:220)
5' AAA TAG CGG ATG CGC GTT TGT TCT GAT CTT CCT TAT
TTA TGT GAT GAT GGT GGT GAT GCT TGT CGT CGT CGT
CCT TGT AGT CTG TGC GGT AGT TGA T 3'

C2asaiA20:
(SEQ ID NO:221)
5' TTT TTT TTT TTT TTT TTT TTA AAT AGC GGA TGC GCG
TTT GTT CTG ATC TTC 3'

C2RT:
(SEQ ID NO:222)
5' GCG CGT TTG TTC TGA TCT TCC 3' hf01 BC reverse:
(SEQ ID NO:223)
5' TGCC TCC TGT TTC GCC GTA AGT GAT GCG GTA ATA
GCG SNN SNN SNN SNN SNN SNN SNN CCA GCT GAT CAG
CAG 3' hf01 DE reverse:
(SEQ ID NO:224)
5' GAT GGT AGC TGT SNN SNN SNN SNN AGG CAC AGT GAA
CTC CTG GAC AGG GCT ATT GCC TCC TGT TTC GCC 3' hf01 FG reverse:
(SEQ ID NO:225)
5' GT GCG GTA ATT AAT GGA AAT TGG SNN SNN SNN SNN
SNN SNN SNN SNN SNN SNN AGT GAC AGC ATA CAC 3'

BCDE rev:
(SEQ ID NO:226)
5' CCT CCT GTT TCT CCG TAA GTG 3'

BCDEfor:
(SEQ ID NO:227)
5' CAC TTA CGG AGA AAC AGG AGG 3' hf01 DE-FG forward:
(SEQ ID NO:228)
5' ACA GCT ACC ATC AGC GGC CTT AAA CCT GGC GTT GAT
TAT ACC ATC ACT GTG TAT GCT GTC ACT 3'

Front FG reverse:
(SEQ ID NO:229)
5' AGT GAC AGC ATA CAC AGT 3' hf01 RT Flag PolyA reverse:
(SEQ ID NO:230)
5' TTT TTT TTT TTT TTT TTT TTA AAT AGC GGA TGC CTT
GTC GTC GTC GTC CTT GTA GTC TGT GCG GTA ATT AAT
GGA 3'

5-RI-hKDR-1B:
(SEQ ID NO:231)
5' TAG AGA ATT CAT GGA GAG CAA GGT GCTG 3'

3-EPO/hKDR-2312B:
(SEQ ID NO:232)
5' AGG GAG AGC GTC AGG ATG AGT TCC AAG TTC GTC TTT
TCC 3'

5-RI-mKDR-1:
(SEQ ID NO:233)
5' TAG AGA ATT CAT GGA GAG CAA GGC GCT G 3'

3-EPO/mKDR-2312:
(SEQ ID NO:234)
5' AGG GAG AGC GTC AGG ATG AGT TCC AAG TTG GTC TTT
TCC 3'

5-RI-hTrkB-1:
(SEQ ID NO:235)
5' TAG AGA ATT CAT GAT GTC GTC CTG GAT AAG GT 3'

3-EpoR/hTrkB-1310:
(SEQ ID NO:236)
5' AGG GAG AGC GTC AGG ATG AGA TGT TCC CGA CCG GTT
TTA 3'

5-hKDR/EPO-2274B:

-continued 5-mKDR/EPO-2247:
(SEQ ID NO:237)
5' GGA AAA GAC GAA CTT GGA ACT CAT CCT GAC GCT CTC
CCT 3'

5-mKDR/EPO-2274:
(SEQ ID NO:238)
5' GGA AAA GAC CAA CTT GGA ACT CAT CCT GAC GCT CTC
CCT 3'

3-XHO-EpoR-3066:
(SEQ ID NO:239)
5' TAG ACT CGA GTC AAG AGC AAG CCA CAT AGCT 3'

5'hTrkB/EpoR-1274:
(SEQ ID NO:240)
5' TAA AAC CGG TCG GGA ACA TCT CAT CCT GAC GCT CTC
CCT 3'

Buffers

The following buffers were utilized in the experiments described herein. Buffer A (100 mM Tris HCl, 1M NaCl, 0.05% Tween-20, pH 8.0); Buffer B (1×PBS, 0.02% Triton X100); Buffer C (100 mM Tris HCl, 60 mM EDTA, 1M NaCl, 0.05% Triton X100, pH 8.0); Buffer Ca (100 mM Tris HCl, 1M NaCl, 0.05% Triton X100, pH 8.0); Buffer D (2M NaCl, 0.05% Triton); Buffer E (1×PBS, 0.05% Triton X100, pH 7.4); Buffer F (1×PBS, 0.05% Triton X100, 100 mM imidazole, pH 7.4); Buffer G (50 mM HEPES, 150 mM NaCl, 0.02% Triton X-100, 1 mg/ml bovine serum albumin, 0.1 mg/ml salmon sperm DNA, pH 7.4); Buffer H (50 mM HEPES, 150 mM NaCl, 0.02% Triton X-100, pH 7.4); Buffer I (1×PBS, 0.02% Triton X-100, 1 mg/ml bovine serum albumin, 0.1 mg/ml salmon sperm DNA, pH 7.4); Buffer J (1×PBS, 0.02% Triton X-100, pH 7.4); Buffer K (50 mM NaH$_2$PO$_4$, 0.5 M NaCl, 5% glycerol, 5 mM CHAPS, 25 mM imidazole, 1× Complete™ Protease Inhibitor Cocktail (Roche), pH 8.0); Buffer L (50 mM NaH$_2$PO$_4$, 0.5 M NaCl, 5% glycerol, 25 mM imidazole, pH 8.0); Buffer M (1×PBS, pH 7.4, 25 mM imidazole, pH 7.4); Buffer N (1×PBS, 250 mM imidazole, pH 7.4); Buffer 0 (10 mM HEPES, 150 mM NaCl, 0.005% Tween 20, pH 7.4).

Primary Library Construction:

The construction of the library using the tenth domain of human fibronectin as a scaffold was previously described (Xu et al, 2002, supra). Three loop regions, corresponding to positions 23-29, 52-55, and 77-86, respectively, were randomized using NNS (standard nucleotide mixtures, where N=equimolar mixture of A, G, T, C; S=equimolar mixture of G and C) as the coding scheme. Similar libraries were constructed containing randomized regions only at positions 23-29 and 77-86 (two loop library) or only at positions 77-86 (one loop library). These libraries were mixed in approximately equimolar amounts. This mixed library contained ~1×10$^{13}$ clones and was used in the KDR selection that identified VR28.

Mutagenic Library Construction:

Hypermutagenic PCR. Scaffold mutation T(69)I in VR28 clone was corrected back to wild type sequence by PCR (see below) and no change in binding characteristics of VR28 binder to KDR was observed. Mutations were introduced into the loop regions of VR28 using conditions described previously (Vartanian et al, Nuc. Acid Res. 24:2627-2631, 1996). Three rounds of hypermutagenic PCR were conducted on a VR28 template using primer pairs flanking each loop (N-terminus forward/BCDE reverse, BCDE forward/DEFG reverse, DEFG forward/C-terminus polyA). The resulting fragments were assembled using overlap extension and PCR with flanking primers T7TMV Fn and MK165-4 A20. DNA sequencing of the clones from the final PCR reaction confirmed correct assembly of the library. Up to 30% mutagenesis rate was observed in the loop regions, as compared to 1.5% in the scaffold regions.

Oligo mutagenesis. Oligo mutagenesis of the FG loop of VR28 by PCR utilized the VR28FG-50 primer, DEFG reverse primer and flanking primers. At each nucleotide position encoding the FG loop, primer VR28FG-50 contained 50% of the VR28 nucleotide and 50% of an equimolar mixture of all four nucleotides (N) or of G or C(S). This scheme was designed to result in approximately 67% of the amino acids of the VR28 FG loop being randomly replaced by another amino acid which was confirmed by DNA sequencing.

159 (Q8L) randomized sub-libraries. Oligo mutagenesis of the FG loop of Clone 159 (Q8L) clone, a three-step extension and amplification was performed. For the first extension, pairs of primers (a: F1U2/F2, b: F3159/F4, c: F5159/F6, d: F7X6159/F8) were mixed in equal concentrations (100 pmol each) and amplified for 10 cycles. For the second extension, 1/20 of the first reactions were combined (a/b and c/d) and amplification was continued for another 10 cycles. To bias the amplification in favor of extension rather than re-annealing of fully complementary fragments, a linear amplification of the half-construct products (0.5 pmol each) was performed for an additional 20 cycles using 50 pmol of either F1U2 forward primer for fragment ab, or the C2asaiA20 reverse primer for fragment cd. Finally, the extended half-construct fragments ab and cd were combined and amplified for 20 cycles without any additional components. Primer F7X6159 contained NNS at each of the first 6 coding positions of Clone 159 (Q8L) and was otherwise identical to Clone 159 (Q8L). Correct assembly of the library 159 (Q8L)-FGX6 was confirmed by DNA sequencing of clones from the final PCR reaction. The sub-library contained ~$1\times10^9$ clones.

For randomization of the DE loop of post round 6 (PR6) selection pool of the 159 (Q8L)-FGX6 library, two half-construct fragments were prepared by PCR using primers F1U2/F4 and F5×5/C2asaiA20. The F5×5 primer contained NNS at the four positions of the DE loop as well as at position 56. Then, the extended fragments ab and cd were combined and amplified for 20 cycles without any additional components.

Introduction of Point Mutations, Deletion and Random (NNS) Loop Sequences into Fibronectin-Based Scaffold Proteins:

Scaffold mutation T(69)I of VR28 binder was corrected back to wild type sequence in two-step PCR using VR28 clone as a template. Half-construct fragments, obtained with primers N-terminus forward/DEFG reverse and DEFG forward/C-terminus polyA, were combined and the whole VR28 (169T) clone (designated as VR28 in the text) was constructed using primers T7TMV Fn and MK165-4 A20. Correction of N-terminus mutations in clone 159 (Q8 to L) was performed by PCR with primers N-terminus forward/C-terminus polyA followed by extension with primers T7TMV Fn and MK165-4 A20.

Introduction of deletion Δ 1-8 into the N-terminus of fibronectin-based scaffold proteins was performed by amplification using primers T7 TMV N-terminus deletion and MK165-4 A20.

Construction of the chimeras of E clones containing NNS loop sequences was performed by two-step PCR. Loop regions were amplified using primers T7 TMV N-terminus deletion/BCDE rev (a: BC loop of E clones); N-terminus forward/hf01 BC reverse (b: BC NNS); BCDE for/Front FG reverse (c: DE loop of E clones); BCDE for/hf01 DE reverse (d: DE NNS); hf01 DE-FG forward/hf01 RT-Flag PolyA reverse (e: FG of E clones); hf01 DE-FG forward/hf01 FG reverse (f: FG NNS). Fragments b/c/e, a/d/e, a/c/f were combined and the whole pools were constructed by extension and amplification using primers T7Tmv N-terminus deletion and hf01 RTFlag PolyA reverse.

All constructs were verified and/or analyzed by DNA sequencing. All constructs and mutagenic libraries contained T7 TMV promoter at the 5' flanking region and Flag tag or $His_6$ tag sequences at 3' flanking region for RNA-protein fusion production and purification in vitro.

RNA-Protein Fusion Production

For each round of selection PCR DNA was transcribed using MegaScript transcription kit (Ambion) at 37° C. for 4 hours. Template DNA was removed by DNase I (Ambion) digestion at 37° C. for 20 minutes. RNA was purified by phenol/chloroform extraction followed by gel filtration on a NAP-25 column (Amersham). The puromycin linker PEG 6/10 (5' Pso u agc gga ugc XXX XXX CC Pu 3', where Pso=C6-Psoralen, u,a,g,c=2'OMe-RNA, C=standard amidities, X: Spacer Phosphoramidite 9 (9-O-Dimethoxytrityl-triethylene glycol, 1-[(2-cyanoethyl)-(N,N-diisopropyl)]-phosphoramidite); Pu=Puromycin-CPG) was synthesized as described previously (Kurz et al, Nuc. Acid Res. 28:83, 2000). The linker was annealed to the library RNA in 0.1 M NaCl, 25 mM Tris HCl, pH 7.0, by gradient temperature decrease from 85° C. to 4° C. The linker and RNA were then cross linked by exposing to UV light (365 nm) for 15 minutes. The cross-linked mixture (600 pmol RNA) was included in an in vitro translation reaction using rabbit reticulocyte lysate translation kit (Ambion) in the presence of $^{35}$S-labeled methionine at 30° C. for 60 minutes. To enhance fusion formation, 0.5 M KCl and 0.05 M $MgCl_2$ were added to the reaction and incubated for 30 minutes at 4° C. Fusion molecules were purified using oligo-dT cellulose (Sigma) chromatography as follows. The translation and fusion mix was diluted into buffer A (100 mM Tris HCl, 1M NaCl, 0.05% Tween-20, pH 8.0) and added to oligo dT cellulose. The slurry was rotated at 4° C. for 1 hour and transferred to a spin column. Oligo dT cellulose beads were washed on the column with 10 column volumes of buffer A and eluted with 3 column volumes of $H_2O$. Reverse transcription reaction was conducted with SuperScript II Reverse Transcription kit (Invitrogen) for 1 hour at 42° C. using primer Hu3'FLAGSTOP. To decrease potential non-specific binding through reactive cysteines the thiol groups were reacted with 1 mM of 2-nitro-5-thiocyanatobenzoic acid (NTCB) or N-ethylmaleimide (NEM) alternatively over the course of the selection. The reaction was carried out for 1 hour at room temperature. Fusion molecules were further purified by anti-FLAG affinity chromatography using M2 agarose (Sigma). The M2 beads were added to the reaction and rotated in buffer B (1×PBS, 0.02% Triton X100) for 1 hour at 4° C. Then the beads were applied to a spin column, washed with 5 column volumes of buffer B and fusion molecules were eluted with 3 column volumes of 100 μM Flag peptide DYKDDDDK (Sigma) in buffer G. Fusion yield was calculated based on specific activity measured by scintillation counting of $^{35}$S-methionine in the samples.

For the 159 (Q8L) randomized library, RNA-protein fusion was prepared using a streamlined, semi-automated procedure in a Kingfisher™ (ThermoLabSystems). The steps were similar to the procedure described above except for several steps described below. Purification of the RNA-protein fusion molecules was performed in buffer C (100 mM Tris HCl, 60 mM EDTA, 1M NaCl, 0.05% Triton X100, pH 8.0) on magnetic oligo dT beads (GenoVision). The beads were washed with 10 reaction volumes of buffer Ca (100 mM Tris HCl, 1M NaCl, 0.05% Triton X100, pH 8.0) and fusion proteins were eluted with one volume of $H_2O$. Reverse transcription (RT) was conducted using primer C2RT. Fusion proteins were further purified by His-tag affinity chromatography using Ni-NTA magnetic beads (Qiagen). The RT reaction was incubated with Ni-NTA beads in buffer D (2M NaCl, 0.05% Triton) for 20 minutes at room temperature, the beads were then washed with 10 reaction volumes of buffer E (1×PBS, 0.05% Triton X100, pH 7.4) and fusion molecules were eluted with one volume of buffer F (1×PBS, 0.05% Triton X100, 100 mM imidazole, pH 7.4).

Selection:

Primary selection against KDR. Fusion library (~$10^{13}$ clones in 1 ml) was incubated with 150 μl of Protein A beads (Dynal) which was pre-immobilized with 200 nM of human IgG1 for 1 hour at 30° C. prior to selection to reduce non-specific binding to both Protein A beads and Fc protein (pre-clear). The supernatant was then incubated in buffer G (50 mM HEPES, 150 mM NaCl, 0.02% Triton X-100, 1 mg/ml bovine serum albumin, 0.1 mg/ml salmon sperm DNA, pH 7.4) with KDR-Fc chimera for 1 hour at 30° C. with end-over-end rotation. Final concentrations of KDR-Fc were 250 nM for Round 1, 100 nM for rounds 2-4 and 10 nM for rounds 5 and 6. The target was captured on 300 μl of Protein A beads (Round 1) or 100 μl of Protein A beads (Rounds 2-6) for 30 minutes at 30° C. with end-over-end rotation and beads were washed 5 times with 1 ml of buffer G (50 mM HEPES, 150 mM NaCl, 0.02% Triton X-100, pH 7.4). Bound fusion molecules were eluted with 100 μl of 0.1 M KOH into 50 μl of 1 M Tris HCl, pH 8.0. DNA was amplified from elution by PCR using flanking primers T7TMV Fn and MK165-4 A20.

Affinity and specificity maturation of KDR binder VR28. Clone VR28 was mutagenized by hypermutagenic PCR or oligo-directed mutagenesis as described above and fusion sub-libraries were constructed. Following pre-clear with Protein A beads selection was performed in buffer I (1×PBS, 0.02% Triton X-100, 1 mg/ml bovine serum albumin, 0.1 mg/ml salmon sperm DNA, pH 7.4) for four rounds according to procedure described above. DNA was amplified from elution by PCR using primers T7TMV Fn and MK165-4 A20. Lower target concentrations (0.1 nM KDR for first four rounds of selection) were used for libraries derived from oligo mutagenesis and then 1 nM mouse VEGF-R2 (Flk-1) was introduced for three additional rounds of selection. Primers T7 TMV N-terminus deletion and MK165-4 A20 were used for PCR in the last 3 rounds.

For specificity maturation of KDR binder 159 first 6 positions of the FG loop of clone 159 Q(8)L were randomized by PCR as described above. Binding of the fusion sub-library to biotinylated mouse VEGF-R2 (70 nM) was performed in buffer I at room temperature for 30 minutes. The rest of the selection procedure was continued in Kingfisher™ (ThermoLabSystems). The biotinylated target was captured on 50 μl of streptavidin-coated magnetic beads (Dynal) and the beads were washed with 10 volumes of buffer I and one volume of buffer J (1×PBS, 0.02% Triton X-100, pH 7.4). Bound fusion molecules were eluted with 100 μl of 0.1 M KOH into 50 μl of 1 M Tris HCl, pH 8.0. DNA was amplified from elution by PCR using primers F1U2 and C2asaiA20. After four rounds of selection an off-rate/rebinding selection against 7 nM Flk-1 was applied for another two rounds as follows. After the binding reaction with biotinylated mouse Flk-1 had progressed for 30 minutes, a 100-fold excess of non-biotinylated Flk-1 was added and the reaction continued for another 6 hours to allow time for the weak binders to dissociate. The biotinylated target was captured on 50 μl of streptavidin beads (Dynal) and beads were washed 5 times with 1 ml of buffer J. Bound fusion molecules were eluted by incubation at 75° C. for 5 minutes. Supernatant was subjected to re-binding to 7 nM Flk-1 and standard selection procedure was continued. DNA from the final elution pool was subjected to DE loop randomization (see above) and fusion sub-library was selected against 7 nM mouse VEGF-R2 for three rounds. At the fourth round an off-rate selection was applied with re-binding to 1 nM human VEGF-R2. Final DNA was amplified from elution by PCR using primers F1U2 and C2asaiA20.

Radioactive Equilibrium Binding Assay

To prepare $^{35}$S-labeled binding proteins for analysis, mRNA was prepared as described above for RNA-protein fusion production but the linker ligation step was omitted. The mRNA was expressed using rabbit reticulocyte lysate translation kit (Ambion) in the presence of $^{35}$S-labeled Met at 30° C. for 1 hour. Expressed protein was purified on M2-agarose Flag beads (Sigma) as described above. This procedure produced the encoded protein without the nucleic acid tail. In a direct binding assay, VEGF-R2-Fc fusions in concentrations ranging from 0 to 200 nM were added to a constant concentration of the purified protein (0.2 or 0.5 nM) and incubated at 30° C. for 1 hour in buffer B. The receptor-binder complexes were captured using Protein A magnetic beads for another 10 minutes at room temperature using a Kingfisher™. The beads were washed with six reaction volumes of buffer B. The protein was eluted from the beads with 100 μL of 0.1 M KOH. 50 μL of the reaction mixture and elution were dried onto a LumaPlate-96 (Packard) and the amount of $^{35}$S on the plate was measured using a TopCount NXT instrument (Packard). The amount of fibronectin-based scaffold protein bound to the target was estimated as a percent of radioactivity eluted from Protein A magnetic beads compare to radioactivity in the reaction mixture. Nonspecific binding of fibronectin-based scaffold proteins to the beads was determined by measuring binding in the absence of KDR-Fc and represented less than 1-2% of the input. Specific binding was obtained through subtraction of nonspecific binding from total binding. Data was analyzed using the GraphPad Prizm software (GraphPad Software, Inc, San Diego, Calif.), fitted using a one site, non-linear binding equation.

Expression and Purification of Soluble Fibronectin-Based Scaffold Protein Binders:

For expression in *E. coli* residues 1-101 of each clone followed by the His$_6$ tag were cloned into a pET9d-derived vector and expressed in *E. coli* BL21 (DE3) pLysS cells (Invitrogen). 20 ml of overnight culture was used to inoculate 1 liter of LB medium containing 50 μg/mL kanamycin and 34 μg/mL chloramphenicol. The culture was grown at 37° C. until A$_{600}$ 0.4-0.6. After induction with 1 mM isopropyl-β-thiogalactoside (IPTG, Invitrogen) the culture was grown for another 3 hours at 37° C. and harvested by centrifugation for 30 minutes at 3,000 g at 4° C. The cell pellet was resuspended in 50 mL of lysis buffer K (50 mM NaH$_2$PO$_4$, 0.5 M NaCl, 5% glycerol, 5 mM CHAPS, 25 mM imidazole, 1× Complete™ Protease Inhibitor Cocktail (Roche), pH 8.0) BufferL and sonicated on ice at 80 W for four 15 second pulses separated by ten-second pauses. The soluble fraction was separated by centrifugation for 30 minutes at 30,000 g at 4° C. The supernatant was rotated for 1 hour at 4° C. with 10 mL of TALON™ Superflow™ Metal Affinity Resin (Clontech) pre-equilibrated with wash buffer L (50 mM NaH$_2$PO$_4$, 0.5 M NaCl, 5% glycerol, 25 mM imidazole, pH 8.0). The resin was then washed with 10 column volumes of buffer L and 30 column volumes of buffer M (1×PBS, pH 7.4, 25 mM imidazole, pH 7.4). Protein was eluted with 5 column volumes of buffer N (1×PBS, 250 mM imidazole, pH 7.4) and dialyzed against 1×PBS at 4° C. Any precipitate was removed by filtering at 0.22 μm (Millipore).

BIAcore Analysis of the Soluble Fibronectin-Based Scaffold Proteins:

The binding kinetics of fibronectin-based scaffold proteins binding proteins to the target was measured using BIAcore 2000 biosensor (Pharmacia Biosensor). Human and mouse VEGF-R2-Fc fusions were immobilized onto a CM5 sensor chip and soluble binding proteins were injected at concentrations ranging from 0 to 100 nM in buffer 0 (10 mM HEPES, 150 mM NaCl, 0.005% Tween 20, pH 7.4). Sensorgrams were obtained at each concentration and were evaluated using a program, BIA Evaluation 2.0 (BIAcore), to determine the rate constants $k_a$ ($k_{on}$) and $k_d$ ($k_{off}$). The affinity constant, $K_D$ was calculated from the ratio of rate constants $k_{off}/k_{on}$.

For inhibition experiments, human VEGF$_{165}$ was immobilized on a surface of CM-5 chip and KDR-Fc was injected at a concentration of 20 nM in the presence of different concentrations of soluble binding proteins ranging from 0 to 100 nM. IC$_{50}$ was determined at a concentration when only 50% of KDR-Fc binding to the chip was observed.

Reversible Refolding of a VEGFR Binding Polypeptide:

Differential scanning calorimetry (DSC) analysis was performed on M5FL protein in 100 mM sodium acetate buffer (pH 4.5). An initial DSC run (Scan 1) was performed in a N-DSC II calorimeter (Calorimetry Sciences Corp) by ramping the temperature from 5-95° C. at a rate of 1 degree per minute, followed by a reverse scan (not shown) back to 10 degrees, followed by a second run (Scan 2). Under these conditions, data were best fit using a two transition model (Tm=77° C. and 67° C. using Orgin software (OrginLab Corp)). See FIG. 10.

Figure 11:
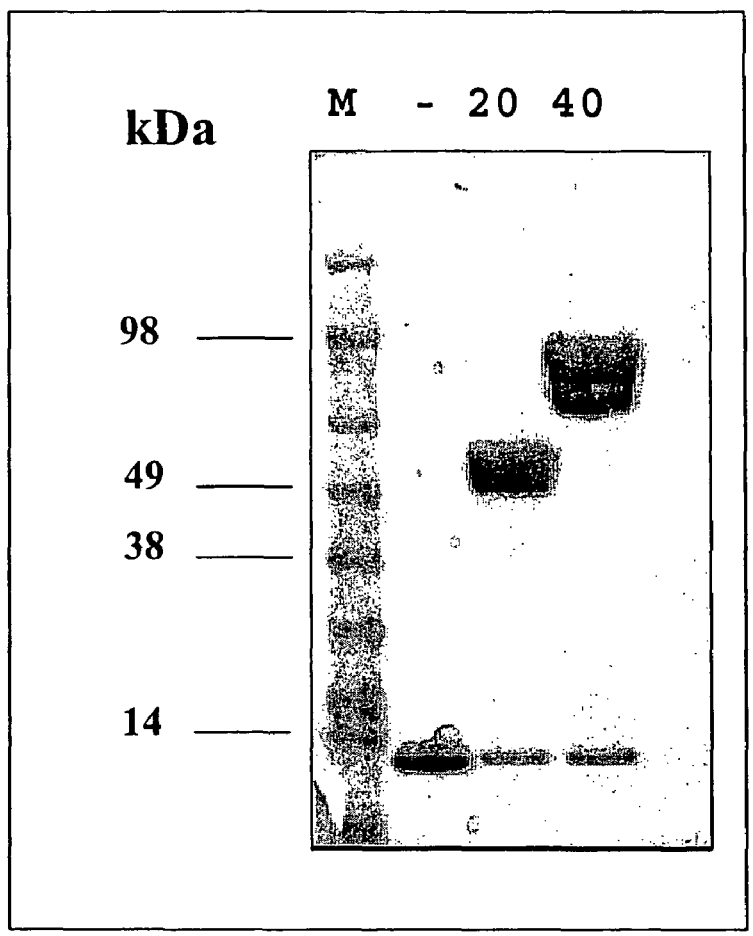
FIG. 11 is an image showing SDS-PAGE analysis of pegylated forms of M5FL. M, molecular weight markers [Sea Blue Plus, Invitrogen]; -, M5FL alone; 20, M5FL with 20 kD PEG; 40, M5FL with 40 kD PEG.

PEGylation of the M5FL Protein:

The C100-form of the M5FL protein, which has the complete sequence of M5FL with the Ser at position 100 mutated to a Cysteine including the additional C-terminal His-tag used to purify the protein. The purified M5FL-C100 protein was modified at the single cysteine residue by conjugating various maleimide-derivatized PEG forms (Shearwater). The resulting reacted proteins were run on a 4-12% polyacrylamide gel (FIG. 11).

Construction of Cell Lines:

Plasmid construction. Plasmids, encoding chimeric receptors composed of the transmembrane and cytoplasmic domains of the human erythropoietin receptor (EpoR) fused to the extracellular domains of KDR, Flk-1, or human TrkB were constructed by a two-step PCR procedure. PCR products encoding the extracellular domains were amplified from plasmids encoding the entire receptor gene: KDR (amino acids 1 to 764) was derived from clone PR1371_H11 (OriGene Technologies, Rockville, Md.) with primers 5-RI-hKDR-1B/3-EPO/hKDR-2312B, flk-1 (amino acids 1 to 762) was derived from clone #4238984 (IMAGE) with primers 5-RI-mKDR-1/3-EPO/mKDR-2312, and human TrkB (from amino acids 1 to 430) from clone #X75958 (Invitrogen Genestorm) with primers 5-RI-hTrkB-1/3-EpoR/hTrkB-1310. PCR products encoding the EpoR transmembrane and cytoplasmic domains (amino acids 251 to 508) were amplified from clone #M60459 (Invitrogen Genestorm) with the common primer 3-XHO-EpoR-3066 and one of three gene-specific primers 5-hKDR/EPO-2274B (KDR), 5-mKDR/EPO-2274 (flk-1), and 5'hTrkB/EpoR-1274 (human TrkB), which added a short sequence complementary to the end of the receptor fragment PCR product. Second, PCR products encoding the two halves of the chimeric genes were mixed and amplified with 3-XHO-EpoR-3066 and the 5' primers (5-RI-hKDR-1B, 5-RI-mKDR-1, and 5-RI-hTrkB-1) specific for each gene used in the previous cycle of amplification. The resulting PCR products were digested with EcoRI and XhoI and cloned into pcDNA3.1 (+) (Invitrogen) to generate the plasmids phKE8 (human KDR/EpoR fusion), pmKE2 (flk-1/EpoR fusion), and phTE (TrkB/EpoR fusion).

Construction of cell lines for flow cytometry. CHO-K1 cells (American Type Culture Collection, Manassas, Va.) were stably transfected using Lipofectamine 2000 (Invitrogen) with either pcDNA 3.1 (Invitrogen) alone, pmKE2 alone, or a mixture of pcDNA 3.1 and a plasmid encoding full-length human KDR (Origene Inc., clone PR1371-H11). Stable transfectants were selected and maintained in the presence of 0.5 mg/ml of Geneticin (Invitrogen). The human KDR-expressing clone designated CHO-KDR and the murine VEGFR-2/EpoR-chimera-expressing population designated CHO-Flk were obtained by fluorescence activated cell sorting of the transfected population following staining with an anti-KDR polyclonal antiserum (R&D Systems). CHO-KDR and CHO-Flk cell lines were grown routinely in Dulbecco's modified Eagle's medium (DMEM; Gibco) supplemented with 10% (v/v) fetal bovine serum (FBS), 0.5 mg/ml Geneticin, 100 U/ml penicillin, 0.25 µg/ml amphotericin B, 100 µg/ml streptomycin and 2 mM L-glutamine.

Construction of Ba/F3 cell lines. Cell lines that would proliferate in response to VEGF binding by VEGFR-2 were constructed by transfection of the murine pre-B cell line Ba/F3 (DSMZ, Braunschweig, Germany) with phKE8 or pmKE2, receptor chimeras consisting of the extracellular domains of human or murine VEGFR-2 fused to the transmembrane and cytoplasmic domains of the human erythropoietin receptor (see above). Ba/F3 cells were maintained in minimal Ba/F3 medium (RPMI-1640 (Gibco) containing 10% FBS, 100 U/ml penicillin, 0.25 µg/ml amphotericin B, 100 µg/ml streptomycin and 2 mM L-glutamine) supplemented with 10% conditioned medium from WEHI-3B cells (DSMZ; grown in Iscove's modified Dulbecco's medium (Gibco)/10% FBS/25 µM β-mercaptoethanol) as a source of essential growth factors. Following electroporation with the plasmids pmKE2 or phKE8, stable transfectants were selected in 0.75 mg/ml Geneticin. Geneticin-resistant populations were transferred to minimal Ba/F3 medium containing 100 ng/ml of human $VEGF_{165}$ (R&D Systems), and the resulting VEGF-dependent populations were designated Ba/F3-Flk and Ba/F3-KDR. Control cell line expressing a chimeric TrkB receptor (Ba/F3-TrkB) that would be responsive to stimulation by NT-4, the natural ligand for TrkB was similarly constructed using the plasmid phTE and human NT-4 (R&D Systems).

Analysis of Cell Surface Binding of Fibronectin-Based Scaffold Proteins:

Binding of fibronectin-based scaffold protein to cell-surface KDR and Flk-1 was analyzed simultaneously on VEGF-R2-expressing and control cells by flow cytometry. CHO-pcDNA3 cells (control) were released from their dishes with trypsin-EDTA, washed in Dulbecco's PBS without calcium and magnesium (D-PBS$^-$; Invitrogen), and stained for 30 minutes at 37° C. with 1.5 µM CMTMR (5-(and -6)-(((4-chloromethyl)benzoyl)amino)-tetramethylrhodamine) (Molecular Probes). The cells were washed in D-PBS$^-$ and incubated for a further 30 minutes at 37° C., and then resuspended in blocking buffer (D-PBS$^-$/10% fetal bovine serum) on ice. CHO-KDR or CHO-Flk cells were treated identically except that CMTMR was omitted. 75,000 of CMTMR-stained CHO-pcDNA3 cells were mixed with an equal number of unstained CHO-KDR or CHO-Flk cells in each well of a V-bottom 96-well plate. All antibodies and fibronectin-based scaffold proteins were diluted in 25 µl/well of blocking buffer, and each treatment was conducted for 1 hour at 4° C. Cell mixtures were stained with $His_6$-tagged fibronectin-based scaffold proteins, washed twice with cold D-PBS$^-$, and then treated with 2.5 µg/ml anti-$His_6$ MAb (R&D Systems), washed, and stained with 4 µg/ml Alexa Fluor 488-conjugated anti-mouse antibody (Molecular Probes). For cells treated with an anti-KDR mouse monoclonal antibody (Accurate Chemical, Westbury, N.Y.) or an anti-flk-1 goat polyclonal antibody (R&D Systems), the anti-$His_6$ step was omitted, and antibody binding was detected with the species-appropriate Alexa Fluor 488 conjugated secondary antibody (Molecular Probes). Following staining, cells were resuspended in 200 µl/well D-PBS$^-$/1% FBS/1 µg/ml 7-aminoactinomycin D (7-AAD; Molecular Probes) and analyzed by flow cytometry on a FACSCalibur (Becton Dickinson, San Jose, Calif.) equipped with a 488 nM laser. Following gating to exclude dead cells (7-AAD positive), VEGFR-2-expressing cells and CHO-pcDNA3 cells were measured independently for Alexa Fluor 488 fluorescence by gating on the CMTMR-negative or -positive populations, respectively. Control experiments showed that staining with CMTMR did not interfere with the detection of Alexa Fluor 488-conjugated antibodies on the surface of the stained cells.

Cell-surface binding was also assessed by fluorescence microscopy using the secondary antibodies described above. For these studies, antibodies were diluted in D-PBS containing calcium and magnesium (D-PBS$^+$)/10% FBS. Cells were grown on 24- or 96-well plates, and following staining were kept in D-PBS$^+$ for observation on an inverted fluorescence microscope.

Ba/F3 Cell Proliferation Assay:

Ba/F3 cells were washed three times in minimal Ba/F3 medium and resuspended in the same medium containing 15.8 ng/ml of proliferation factor (human $VEGF_{165}$, murine $VEGF_{164}$, or hNT-4 for Ba/F3-KDR, Ba/F3-Flk, or Ba/F3-TrkB cells, respectively), and 95 µl containing $5\times10^4$ Ba/F3-KDR cells or $2\times10^4$ Ba/F3-Flk or Ba/F3-TrkB cells were added per well to a 96-well tissue culture plate. 5 µl of serial dilutions of test protein in PBS was added to each well for a final volume of 100 µl Ba/F3 medium/5% PBS/15 ng/ml growth factor. After incubation for 72 hours at 37° C., proliferation was measured by addition of 20 µl of CellTiter 96® Aqueous One Solution Reagent (Promega) to each well, incubation for 4 hours at 37° C., and measurement of the absorbance at 490 nm using a microtiter plate reader (Molecular Dynamics).

HUVEC Cell Proliferation Assay:

HUVEC cells (Clonetics, Walkersville, Md.) from passage 2-6 were grown in EGM-2 medium (Clonetics). 5000 cells/well were resuspended in 200 µl starvation medium (equal volumes of DMEM (Gibco) and F-12K medium (ATCC), supplemented with 0.2% fetal bovine serum and 1× penicillin/streptomycin/fungizone solution (Gibco)), plated in 96-well tissue culture plates and incubated for 48 hours. Fibronectin-based binding proteins were added to the wells and incubated for 1 hour at 37°, and then human $VEGF_{165}$ was added to a final concentration of 16 ng/ml. After 48 hours incubation, cell viability was measured by addition of 30 µl/well of a mixture of 1.9 mg/ml CellTiter96® AQueous MTS reagent (Promega) with 44 µg/ml phenazine methosulfate (Sigma) and measurement of absorbance at 490 nm as described above for Ba/F3 cells.

Example 12

Antibody Light Chain-Based VEGFR Binding Polypeptides

Figure 21B:
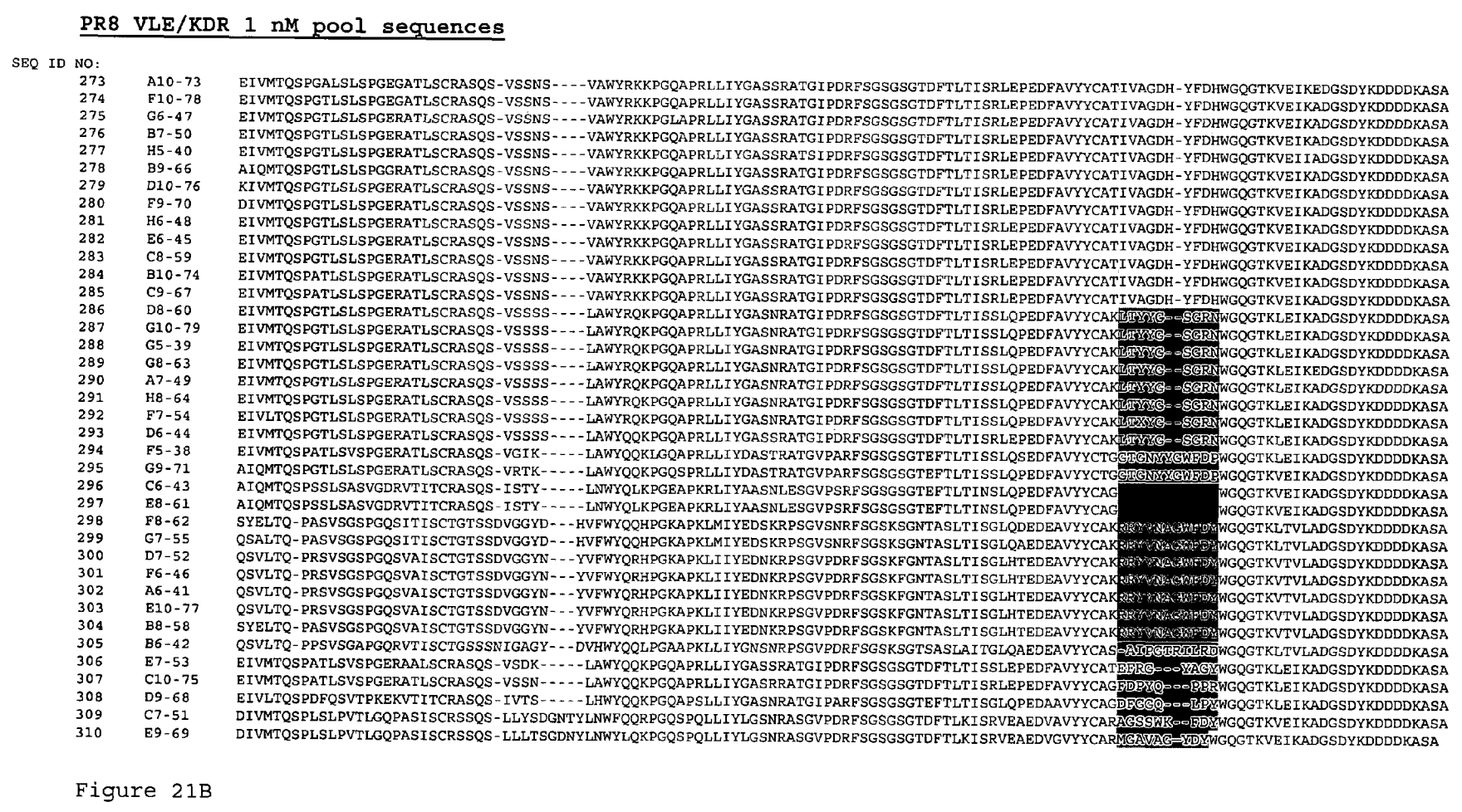

FIGS. 21A and 21B show amino acid sequences of VEGFR binding polypeptides (SEQ ID NOs:241-310) based on an antibody light chain variable region (VL) framework/scaffold.

Light chain variable domain proteins were generated using the PROfusion™ system, as described above for use with $^{10}$Fn3-derived proteins.

All references cited herein are hereby incorporated by reference in their entirety.

TABLE 1

Preferred Specific Peptide Sequences

| SEQ ID NO | Clone Name | N-terminus | BC Loop | DE Loop | FG Loop | | | | | | | | | | Binding to 1 nM KDR, % | Kd KDR, nM | Binding to 1 nM FLK, % | Kd FLK, nM |
|---|---|---|---|---|---|---|---|---|---|---|---|---|---|---|---|---|---|---|
| KDR Binders |
| 6 | K1 | Del 1-8 | RHPHFPTR | LQPPT | M | G | L | Y | G | H | E | L | L | T | P | 48 | 0.55 | | |
| 7 | K2 | Del 1-8 | RHPHFPTR | LQPPT | D | G | E | N | G | Q | F | L | L | V | P | 48 | 1.19 | | |
| 8 | K5 | Del 1-8 | RHPHFPTR | LQPPT | M | G | P | N | D | N | E | L | L | T | P | 47 | 1.54 | | |
| 9 | K3 | Del 1-8 | RHPHFPTR | LQPPT | A | G | W | D | D | H | E | L | F | I | P | 45 | 1.15 | | |
| 10 | K7 | Del 1-8 | RHPHFPTR | LQPPT | S | G | H | N | D | H | M | L | M | I | P | 40 | 2.2 | | |
| 11 | K4 | Del 1-8 | RHPHFPTR | LQPPT | A | G | Y | N | D | Q | I | L | M | T | P | 38 | 1.95 | | |
| 12 | K9 | Del 1-8 | RHPHFPTR | LQPPT | F | G | L | Y | G | K | E | L | L | I | P | 35 | 1.8 | | |
| 13 | K10 | Del 1-8 | RHPHFPTR | LQPPT | T | G | P | N | D | R | L | L | F | V | P | 33 | 0.57 | | |
| 14 | K12 | Del 1-8 | RHPHFPTR | LQPPT | D | V | Y | N | D | H | E | I | K | T | P | 29 | 0.62 | | |
| 15 | K6 | Del 1-8 | RHPHFPTR | LQPPT | D | G | K | D | G | R | V | L | L | T | P | 27 | 0.93 | | |
| 16 | K15 | Del 1-8 | RHPHFPTR | LQPPT | E | V | H | H | D | R | E | I | K | T | P | 25 | 0.35 | | |
| 17 | K11 | Del 1-8 | RHPHFPTR | LQPPT | Q | A | P | N | D | R | V | L | Y | T | P | 24 | 1.16 | | |
| 18 | K14 | Del 1-8 | RHPHFPTR | LQPPT | R | E | E | N | D | H | E | L | L | I | P | 20 | 0.57 | | |
| 19 | K8 | Del 1-8 | RHPHFPTR | LQPPT | V | T | H | N | G | H | P | L | M | T | P | 18 | 3.3 | | |
| 20 | K13 | Del 1-8 | RHPHFPTR | LQPPT | L | A | L | K | G | H | E | L | L | T | P | 17 | 0.58 | | |
| 21 | VR28 | WT | RHPHFPTR | LQPPT | V | A | Q | N | D | H | E | L | I | T | P | 3 | 11 | | |
| 22 | 159 | WT | RHPHFPTR | LQPPA | M | A | Q | S | G | H | E | L | F | T | P | | | | |
| KDR and FLK Binders |
| 24 | E29 | Del 1-8 | RHPHFPTR | LQPPT | V | E | R | N | G | R | V | L | M | T | P | 41 | 44 | 1.51 | 0.91 |
| 25 | E19 | Del 1-8 | RHPHFPTR | LQPPT | V | E | R | N | G | R | H | L | M | T | P | 38 | 40 | 1.3 | 0.66 |
| 33 | E25 | Del 1-8 | RHPHFPTR | LQPPT | L | E | R | N | G | R | E | L | M | T | P | 41 | 28 | 1.58 | 1.3 |
| 45 | E9 | Del 1-8 | RHPHFPTR | LQPPT | E | E | R | N | G | R | T | L | R | T | P | 24 | 34 | 2.37 | 1.4 |
| 50 | E24 | Del 1-8 | RHPHFPTR | LQPPT | V | E | R | N | D | R | V | L | F | T | P | 24 | 29 | | |
| 54 | E26 | Del 1-8 | RHPHFPTR | LQPPT | V | E | R | N | G | R | E | L | M | T | P | 27 | 20 | 1.66 | 2.05 |
| 59 | E28 | Del 1-8 | RHPHFPTR | LQPPT | L | E | R | N | G | R | E | L | M | V | P | 19 | 21 | 1.63 | 2.1 |
| 60 | E3 | Del 1-8 | RHPHFPTR | LQPPT | D | G | R | N | D | R | K | L | M | V | P | 37 | 14 | 0.96 | 5.4 |
| 65 | E5 | Del 1-8 | RHPHFPTR | LQPPT | D | G | Q | N | G | R | L | L | N | V | P | 26 | 10 | 0.4 | 3.2 |
| 91 | E23 | Del 1-8 | RHHPHFPTR | LQPPT | V | H | W | N | G | R | E | L | M | T | P | 36 | 7 | | |
| 92 | E8 | Del 1-8 | RHPHFPTR | LQPPT | E | E | W | N | G | R | V | L | M | T | P | 51 | 10 | | |
| 93 | E27 | Del 1-8 | RHPHFPTR | LQPPT | V | E | R | N | G | H | T | L | M | T | P | 37 | 9 | | |
| 94 | E16 | Del 1-8 | RHPHFPTR | LQPPT | V | E | E | N | G | R | Q | L | M | T | P | 35 | 0 | | |
| 95 | E14 | Del 1-8 | RHPHFPTR | LQPPT | L | E | R | N | G | Q | V | L | F | T | P | 33 | 11 | | |
| 96 | E20 | Del 1-8 | RHPHFPTR | LQPPT | V | E | R | N | G | Q | V | L | Y | T | P | 43 | 11 | | |
| 97 | E21 | Del 1-8 | RHPHFPTR | LQPPT | W | G | Y | K | D | H | E | L | L | I | P | 47 | 1 | | |
| 98 | E22 | Del 1-8 | RHPHFPTR | LQPPT | L | G | R | N | D | R | E | L | L | T | P | 45 | 3 | | |
| 99 | E2 | Del 1-8 | RHPHFPTR | LQPPT | D | G | P | N | D | R | L | L | N | I | P | 53 | 10 | | |
| 100 | E12 | Del 1-8 | RHPHFPTR | LQPPT | F | A | R | D | G | H | E | I | L | T | P | 36 | 1 | | |
| 101 | E13 | Del 1-8 | RHPHFPTR | LQPPT | L | E | Q | N | G | R | E | L | M | T | P | 38 | 1 | | |
| 102 | E17 | Del 1-8 | RHPHFPTR | LQPPT | V | E | E | N | G | R | V | L | N | T | P | 32 | 10 | | |
| 103 | E15 | Del 1-8 | RHPHFPTR | LQPPT | L | E | P | N | G | R | Y | L | M | V | P | 52 | 2 | | |
| 104 | E10 | Del 1-8 | RHPHFPTR | LQPPT | E | G | R | N | G | R | E | L | F | I | P | 53 | 3 | | |
| 154 | M2 | WT | RHPHFPTR | LQPPA | W | E | R | N | G | R | E | L | F | T | P | | | | |
| 156 | M3 | WT | RHPHFPTR | LQPPA | K | E | R | N | G | R | E | L | F | T | P | | | | |
| 172 | M4 | WT | RHPHFPTH | LQPPA | T | E | R | T | G | R | E | L | F | T | P | | | | |
| 173 | M8 | WT | RHPHFPTH | LQPPA | K | E | R | S | G | R | E | L | F | T | P | | | | |
| 175 | M6 | WT | RHPHFPTH | LQPPA | L | E | R | D | G | R | E | L | F | T | P | | | | |
| 180 | M7 | WT | RHPHFPTR | LQPTT | W | E | R | N | G | R | E | L | F | T | P | | | | |
| 181 | M1 | WT | RHPHFPTR | LQPTV | L | E | R | N | D | R | E | L | F | T | P | | | | |
| 177 | M5FL | WT | RHPHFPTR | LQPPL | K | E | R | N | G | R | E | L | F | T | P | | | | |

TABLE 2

KDR & FLK binders

| SEQ ID NO | Clone Name | N-terminus | N-Terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 23 | D12 | Del 1-8 | EVVAATPTSLLISW | RHPHFPTR | YYRITYGETGGNSPVQEFTVP | LQPPT | ATISGLKPGVDYTITGYAVT | VERNGRKLMTP | ISINYRT | 46 | 47 | | |
| 24 | E29 | Del 1-8 | EVVAATPTSLLISW | RHPHFPTR | YYRITYGETGGNSPVQEFTVP | LQPPT | ATISGLKPGVDYTITGYAVT | VERNGRVLMTP | ISINYRT | 41 | 44 | 1.51 | 0.91 |
| 25 | E19 | Del 1-8 | EVVAATPTSLLISW | RHPHFPTR | YYRITYGETGGNSPVQEFTVP | LQPPT | ATISGLKPGVDYTITGYAVT | VERNGRHLMTP | ISINYRT | 38 | 40 | 1.3 | 0.66 |
| 26 | D1 | Del 1-8 | EVVAATPTSLLISW | RHPHFPTR | YYRITYGETGGNSPVQEFTVP | LQPPT | ATISGLKPGVDYTITGYAVT | VERNGRMLMTP | ISINYRT | 38 | 38 | | |
| 27 | C6 | Del 1-8 | EVVAATPTSLLISW | RHPHFPTR | YYRITYGETGGNSPVQEFTVP | LQPPT | ATISGLKPGVDYTITGYAVT | LERNGRVLMTP | ISINYRT | 36 | 49 | | |
| 28 | EGE5 | Del 1-8 | EVVAATPTSLLISW | RHPHFPTR | YYRITYGETGGNSPVQEFTVP | LQPPT | ATISGLKPGVDYTITGYAVT | LERNGRVLNTP | ISINYRT | 32 | 47 | | |
| 29 | EGE2 | Del 1-8 | EVVAATPTSLLISW | RHPHFPTR | YYRITYGETGGNSPVQEFTVP | LQPPT | ATISGLKPGVDYTITGYAVT | VERNGRQLMTP | ISINYRT | 42 | 33 | | |
| 30 | D4 | Del 1-8 | EVVAATPTSLLISW | RHPHFPTR | YYRITYGETGGNSPVQEFTVP | LQPPT | ATISGLKPGVDYTITGYAVT | VERNGRTLFTP | ISINYRT | 27 | 44 | | |
| 31 | E25 | Del 1-8 | EVVAATPTSLLISW | RHPHFPTR | YYRITYGETGGNSPVQEFTVP | LQPPT | ATISGLKPGVDYTITGYAVT | LERNGRELMTP | ISINYRT | 41 | 28 | 1.58 | 1.3 |
| 32 | EGE6 | Del 1-8 | EVVAATPTSLLISW | RHPHFPTR | YYRITYGETGGNSPVQEFTVP | LQPPT | ATISGLKPGVDYTITGYAVT | LERNGRLLNTP | ISINYRT | 33 | 40 | | |
| 33 | C7 | Del 1-8 | EVVAATPTSLLISW | RHPHFPTR | YYRITYGETGGNSPVQEFTVP | LQPPT | ATISGLKPGVDYTITGYAVT | HERNGRVLMTP | ISINYRT | 32 | 40 | | |
| 34 | D9 | Del 1-8 | EVVAATPTSLLISW | RHPHFPTR | YYRITYGETGGNSPVQEFTVP | LQPPT | ATISGLKPGVDYTITGYAVT | EERNGRVLFTP | ISINYRT | 31 | 40 | | |
| 35 | EGE3 | Del 1-8 | EVVAATPTSLLISW | RHPHFPTR | YYRITYGETGGNSPVQEFTVP | LQPPT | ATISGLKPGVDYTITGYAVT | VERNGRQLYTP | ISINYRT | 34 | 38 | | |
| 36 | D3 | Del 1-8 | EVVAATPTSLLISW | RHPHFPTR | YYRITYGETGGNSPVQEFTVP | LQPPT | ATISGLKPGVDYTITGYAVT | VERNGRALMTP | ISINYRT | 36 | 30 | | |
| 37 | D2 | Del 1-8 | EVVAATPTSLLISW | RHPHFPTR | YYRITYGETGGNSPVQEFTVP | LQPPT | ATISGLKPGVDYTITGYAVT | LERNGRNLMTP | ISINYRT | 35 | 30 | | |
| 38 | C8 | Del 1-8 | EVVAATPTSLLISW | RHPHFPTR | YYRITYGETGGNSPVQEFTVP | LQPPT | ATISGLKPGVDYTITGYAVT | VERNGRVLITP | ISINYRT | 30 | 34 | | |
| 39 | EGE4 | Del 1-8 | EVVAATPTSLLISW | RHPHFPTR | YYRITYGETGGNSPVQEFTVP | LQPPT | ATISGLKPGVDYTITGYAVT | VERNGRVLNTP | ISINYRT | 26 | 41 | | |
| 40 | D7 | Del 1-8 | EVVAATPTSLLISW | RHPHFPTR | YYRITYGETGGNSPVQEFTVP | LQPPT | ATISGLKPGVDYTITGYAVT | VERNGKVLMTP | ISINYRT | 39 | 27 | | |
| 41 | D5 | Del 1-8 | EVVAATPTSLLISW | RHPHFPTR | YYRITYGETGGNSPVQEFTVP | LQPPT | ATISGLKPGVDYTITGYAVT | VERNGRTLMMP | ISINYRT | 38 | 23 | | |
| 42 | B3 | Del 1-8 | EVVAATPTSLLISW | RHPHFPTR | YYRITYGETGGNSPVQEFTVP | LQPPT | ATISGLKPGVDYTITGYAVT | MERNGRELMTP | ISINYRT | 33 | 27 | | |
| 43 | E9 | Del 1-8 | EVVAATPTSLLISW | RHPHFPTR | YYRITYGETGGNSPVQEFTVP | LQPPT | ATISGLKPGVDYTITGYAVT | EERNGRTLRTP | ISINYRT | 24 | 34 | 2.37 | 1.4 |

TABLE 2-continued

KDR & FLK binders

| SEQ ID NO | Clone Name | N-Terminus | N-terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 44 | D6 | Del 1-8 | EVVAATPTSLLISW | RHPHFPTR | YYRITYGETGGNSPVQEFTVP | LQPPT | ATISGLKPGVDYTITGYAVT | V E R N G K T L M T P | ISINYRT | 32 | 30 | | |
| 45 | EGE7 | Del 1-8 | EVVAATPTSLLISW | RHPHFPTR | YYRITYGETGGNSPVQEFTVP | LQPPT | ATISGLKPGVDYTITGYAVT | L E R N D R V L L T P | ISINYRT | 31 | 30 | | |
| 46 | EGE1 | Del 1-8 | EVVAATPTSLLISW | RHPHFPTR | YYRITYGETGGNSPVQEFTVP | LQPPT | ATISGLKPGVDYTITGYAVT | L E R N G R K L M T P | ISINYRT | 30 | 29 | | |
| 47 | F9 | Del 1-8 | EVVAATPTSLLISW | RHPHFPTR | YYRITYGETGGNSPVQEFTVP | LQPPT | ATISGLKPGVDYTITGYAVT | V E P N G R V L N T P | ISINYRT | 32 | 23 | | |
| 48 | E24 | Del 1-8 | EVVAATPTSLLISW | RHPHFPTR | YYRITYGETGGNSPVQEFTVP | LQPPT | ATISGLKPGVDYTITGYAVT | V E R N D R V L F T P | ISINYRT | 24 | 29 | | |
| 49 | B11 | Del 1-8 | EVVAATPTSLLISW | RHPHFPTR | YYRITYGETGGNSPVQEFTVP | LQPPT | ATISGLKPGVDYTITGYAVT | V E R N G R E L K T P | ISINYRT | 29 | 21 | | |
| 50 | B12 | Del 1-8 | EVVAATPTSLLISW | RHPHFPTR | YYRITYGETGGNSPVQEFTVP | LQPPT | ATISGLKPGVDYTITGYAVT | V E R N G R E L R T P | ISINYRT | 29 | 21 | | |
| 51 | B5 | Del 1-8 | EVVAATPTSLLISW | RHPHFPTR | YYRITYGETGGNSPVQEFTVP | LQPPT | ATISGLKPGVDYTITGYAVT | Q E R N G R E L M T P | ISINYRT | 27 | 24 | | |
| 52 | E26 | Del 1-8 | EVVAATPTSLLISW | RHPHFPTR | YYRITYGETGGNSPVQEFTVP | LQPPT | ATISGLKPGVDYTITGYAVT | V E R N G R E L M T P | ISINYRT | 27 | 20 | 1.66 | 2.05 |
| 53 | C12 | Del 1-8 | EVVAATPTSLLISW | RHPHFPTR | YYRITYGETGGNSPVQEFTVP | LQPPT | ATISGLKPGVDYTITGYAVT | V E R N G R V L S V P | ISINYRT | 24 | 20 | | |
| 54 | F4 | Del 1-8 | EVVAATPTSLLISW | RHPHFPTR | YYRITYGETGGNSPVQEFTVP | LQPPT | ATISGLKPGVDYTITGYAVT | V E R N G R T L R T P | ISINYRT | 31 | 18 | | |
| 55 | E18 | Del 1-8 | EVVAATPTSLLISW | RHPHFPTR | YYRITYGETGGNSPVQEFTVP | LQPPT | ATISGLKPGVDYTITGYAVT | V E R N G R E L N T P | ISINYRT | 17 | 29 | 1.2 | 0.53 |
| 56 | C11 | Del 1-8 | EVVAATPTSLLISW | RHPHFPTR | YYRITYGETGGNSPVQEFTVP | LQPPT | ATISGLKPGVDYTITGYAVT | V E R N G R V L I V P | ISINYRT | 19 | 21 | | |
| 57 | E28 | Del 1-8 | EVVAATPTSLLISW | RHPHFPTR | YYRITYGETGGNSPVQEFTVP | LQPPT | ATISGLKPGVDYTITGYAVT | V E R N G R E L M V P | ISINYRT | 19 | 21 | 1.63 | 2.1 |
| 58 | E3 | Del 1-8 | EVVAATPTSLLISW | RHPHFPTR | YYRITYGETGGNSPVQEFTVP | LQPPT | ATISGLKPGVDYTITGYAVT | D G R N D R K L M V P | ISINYRT | 37 | 14 | 0.96 | 5.4 |
| 59 | F8 | Del 1-8 | EVVAATPTSLLISW | RHPHFPTR | YYRITYGETGGNSPVQEFTVP | LQPPT | ATISGLKPGVDYTITGYAVT | V E H N G R T S F T P | ISINYRT | 33 | 13 | | |
| 60 | F3 | Del 1-8 | EVVAATPTSLLISW | RHPHFPTR | YYRITYGETGGNSPVQEFTVP | LQPPT | ATISGLKPGVDYTITGYAVT | V E R D G R K L Y T P | ISINYRT | 27 | 15 | | |
| 61 | B10 | Del 1-8 | EVVAATPTSLLISW | RHPHFPTR | YYRITYGETGGNSPVQEFTVP | LQPPT | ATISGLKPGVDYTITGYAVT | L E R N G R E L N T P | ISINYRT | 15 | 23 | | |
| 62 | E6 | Del 1-8 | EVVAATPTSLLISW | RHPHFPTR | YYRITYGETGGNSPVQEFTVP | LQPPT | ATISGLKPGVDYTITGYAVT | D G W N G R L L S I P | ISINYRT | 36 | 7 | 0.35 | 7.1 |
| 63 | E5 | Del 1-8 | EVVAATPTSLLISW | RHPHFPTR | YYRITYGETGGNSPVQEFTVP | LQPPT | ATISGLKPGVDYTITGYAVT | D G Q N G R L L N V P | ISINYRT | 26 | 10 | | |
| 64 | G4 | Del 1-8 | EVVAATPTSLLISW | RHPHFPTR | YYRITYGETGGNSPVQEFTVP | LQPPT | ATISGLKPGVDYTITGYAVT | I E K N G R H L N I P | ISINYRT | 21 | 12 | 0.4 | 3.2 |
| 65 | A3 | Del 1-8 | EVVAATPTSLLISW | RHPHFPTR | YYRITYGETGGNSPVQEFTVP | LQPPT | ATISGLKPGVDYTITGYAVT | D G W N G K M L S V P | ISINYRT | 33 | 7 | | |

TABLE 2-continued

KDR & FLK binders

| SEQ ID NO | Clone Name | N-Terminus | N-terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 66 | A4 | Del 1-8 | EVVAATPTSLLISW | RHPHFPTR | YYRITYGETGGNSPVQEFTVP | LQPPT | ATISGLKPGVDYTITGYAVT | DGVNDRLLFIP | ISINYRT | 46 | 2 | | |
| 67 | A6 | Del 1-8 | EVVAATPTSLLISW | RHPHFPTR | YYRITYGETGGNSPVQEFTVP | LQPPT | ATISGLKPGVDYTITGYAVT | DGPNDRLLNIP | ISINYRT | 18 | 2 | | |
| 68 | A7 | Del 1-8 | EVVAATPTSLLISW | RHPHFPTR | YYRITYGETGGNSPVQEFTVP | LQPPT | ATISGLKPGVDYTITGYAVT | DGPNNRELIVP | ISINYRT | 18 | 2 | | |
| 69 | A8 | Del 1-8 | EVVAATPTSLLISW | RHPHFPTR | YYRITYGETGGNSPVQEFTVP | LQPPT | ATISGLKPGVDYTITGYAVT | DGLNGKYLFVP | ISINYRT | 38 | 4 | | |
| 70 | A9 | Del 1-8 | EVVAATPTSLLISW | RHPHFPTR | YYRITYGETGGNSPVQEFTVP | LQPPT | ATISGLKPGVDYTITGYAVT | EGWNDRELFVP | ISINYRT | 31 | 4 | | |
| 71 | A10 | Del 1-8 | EVVAATPTSLLISW | RHPHFPTR | YYRITYGETGGNSPVQEFTVP | LQPPT | ATISGLKPGVDYTITGYAVT | FGWNGRELLTP | ISINYRT | 34 | 4 | | |
| 72 | EGE11 | Del 1-8 | EVVAATPTSLLISW | RHPHFPTR | YYRITYGETGGNSPVQEFTVP | LQPPT | ATISGLKPGVDYTITGYAVT | FGWNDRELLIP | ISINYRT | 50 | 0 | | |
| 73 | A11 | Del 1-8 | EVVAATPTSLLISW | RHPHFPTR | YYRITYGETGGNSPVQEFTVP | LQPPT | ATISGLKPGVDYTITGYAVT | LEWNNRRVLMTP | ISINYRT | 26 | 6 | | |
| 74 | A12 | Del 1-8 | EVVAATPTSLLISW | RHPHFPTR | YYRITYGETGGNSPVQEFTVP | LQPPT | ATISGLKPGVDYTITGYAVT | VEWNGRVLMTP | ISINYRT | 40 | 10 | | |
| 75 | B4 | Del 1-8 | EVVAATPTSLLISW | RHPHFPTR | YYRITYGETGGNSPVQEFTVP | LQPPT | ATISGLKPGVDYTITGYAVT | NERNGRELMTP | ISINYRT | 19 | 12 | | |
| 76 | B6 | Del 1-8 | EVVAATPTSLLISW | RHPHFPTR | YYRITYGETGGNSPVQEFTVP | LQPPT | ATISGLKPGVDYTITGYAVT | LERNGKELMTP | ISINYRT | 23 | 11 | | |
| 77 | B7, B8 | Del 1-8 | EVVAATPTSLLISW | RHPHFPTR | YYRITYGETGGNSPVQEFTVP | LQPPT | ATISGLKPGVDYTITGYAVT | VERNGRELLTP | ISINYRT | 18 | 10 | | |
| 78 | B11 | Del 1-8 | EVVAATPTSLLISW | RHPHFPTR | YYRITYGETGGNSPVQEFTVP | LQPPT | ATISGLKPGVDYTITGYAVT | QERNGRELKTP | ISINYRT | 29 | 21 | | |
| 79 | C1 | Del 1-8 | EVVAATPTSLLISW | RHPHFPTR | YYRITYGETGGNSPVQEFTVP | LQPPT | ATISGLKPGVDYTITGYAVT | VERNGRELRTP | ISINYRT | 28 | 13 | | |
| 80 | C2 | Del 1-8 | EVVAATPTSLLISW | RHPHFPTR | YYRITYGETGGNSPVQEFTVP | LQPPT | ATISGLKPGVDYTITGYAVT | VERNGRELWP | ISINYRT | 40 | 16 | | |
| 81 | C3 | Del 1-8 | EVVAATPTSLLISW | RHPHFPTR | YYRITYGETGGNSPVQEFTVP | LQPPT | ATISGLKPGVDYTITGYAVT | LERNGRELMIP | ISINYRT | 31 | 17 | | |
| 82 | C9 | Del 1-8 | EVVAATPTSLLISW | RHPHFPTR | YYRITYGETGGNSPVQEFTVP | LQPPT | ATISGLKPGVDYTITGYAVT | VERNGLVLIIP | ISINYRT | 33 | 7 | | |
| 83 | C10 | Del 1-8 | EVVAATPTSLLISW | RHPHFPTR | YYRITYGETGGNSPVQEFTVP | LQPPT | ATISGLKPGVDYTITGYAVT | VERNGRVLIIP | ISINYRT | 24 | 17 | | |
| 84 | D11 | Del 1-8 | EVVAATPTSLLISW | RHPHFPTR | YYRITYGETGGNSPVQEFTVP | LQPPT | ATISGLKPGVDYTITGYAVT | VERNGHKLFTP | ISINYRT | 24 | 3 | | |
| 85 | EGE8 | Del 1-8 | EVVAATPTSLLISW | RHPHFPTR | YYRITYGETGGNSPVQEFTVP | LQPPT | ATISGLKPGVDYTITGYAVT | VERNERVLMTP | ISINYRT | 26 | 20 | | |
| 86 | EGE9 | Del 1-8 | EVVAATPTSLLISW | RHPHFPTR | YYRITYGETGGNSPVQEFTVP | LQPPT | ATISGLKPGVDYTITGYAVT | FGPNDRELLTP | ISINYRT | 32 | 1 | | |

TABLE 2-continued

KDR & FLK binders

| SEQ ID NO | Clone Name | N-Terminus | N-terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 87 | EGE10 | Del 1-8 | EVVAATPTSLLISW | RHPHFPTR | YYRITYGETGGNSPVQEFTVP | LQPPT | ATISGLKPGVDYTITGYAVT | M G P N D R E L L T P | ISINYRT | 37 | 1 | | |
| 88 | EGE11 | Del 1-8 | EVVAATPTSLLISW | RHPHFPTR | YYRITYGETGGNSPVQEFTVP | LQPPT | ATISGLKPGVDYTITGYAVT | M G K N D R E L L T P | ISINYRT | 32 | 1 | | |
| 89 | E23 | Del 1-8 | EVVAATPTSLLISW | RHPHFPTR | YYRITYGETGGNSPVQEFTVP | LQPPT | ATISGLKPGVDYTITGYAVT | V H W N G R E L M T P | ISINYRT | 36 | 7 | | |
| 90 | E8 | Del 1-8 | EVVAATPTSLLISW | RHPHFPTR | YYRITYGETGGNSPVQEFTVP | LQPPT | ATISGLKPGVDYTITGYAVT | E E W N G R V L M T P | ISINYRT | 51 | 10 | | |
| 91 | E27 | Del 1-8 | EVVAATPTSLLISW | RHPHFPTR | YYRITYGETGGNSPVQEFTVP | LQPPT | ATISGLKPGVDYTITGYAVT | V E R N G H T L M T P | ISINYRT | 37 | 9 | | |
| 92 | E16 | Del 1-8 | EVVAATPTSLLISW | RHPHFPTR | YYRITYGETGGNSPVQEFTVP | LQPPT | ATISGLKPGVDYTITGYAVT | V E E N G R Q L M T P | ISINYRT | 35 | 0 | | |
| 93 | E14 | Del 1-8 | EVVAATPTSLLISW | RHPHFPTR | YYRITYGETGGNSPVQEFTVP | LQPPT | ATISGLKPGVDYTITGYAVT | L E R N G Q V L F T P | ISINYRT | 33 | 11 | | |
| 94 | E20 | Del 1-8 | EVVAATPTSLLISW | RHPHFPTR | YYRITYGETGGNSPVQEFTVP | LQPPT | ATISGLKPGVDYTITGYAVT | V E R N G Q V L Y T P | ISINYRT | 43 | 11 | | |
| 95 | E21 | Del 1-8 | EVVAATPTSLLISW | RHPHFPTR | YYRITYGETGGNSPVQEFTVP | LQPPT | ATISGLKPGVDYTITGYAVT | W G Y K D H E L L I P | ISINYRT | 47 | 1 | | |
| 96 | E22 | Del 1-8 | EVVAATPTSLLISW | RHPHFPTR | YYRITYGETGGNSPVQEFTVP | LQPPT | ATISGLKPGVDYTITGYAVT | L G R N D R E L L T P | ISINYRT | 45 | 3 | | |
| 97 | E2 | Del 1-8 | EVVAATPTSLLISW | RHPHFPTR | YYRITYGETGGNSPVQEFTVP | LQPPT | ATISGLKPGVDYTITGYAVT | D G P N D R L L N I P | ISINYRT | 53 | 10 | | |
| 98 | E12 | Del 1-8 | EVVAATPTSLLISW | RHPHFPTR | YYRITYGETGGNSPVQEFTVP | LQPPT | ATISGLKPGVDYTITGYAVT | F A R D G H E I L T P | ISINYRT | 36 | 1 | | |
| 99 | E13 | Del 1-8 | EVVAATPTSLLISW | RHPHFPTR | YYRITYGETGGNSPVQEFTVP | LQPPT | ATISGLKPGVDYTITGYAVT | L E Q N G R E L M T P | ISINYRT | 38 | 1 | | |
| 100 | E17 | Del 1-8 | EVVAATPTSLLISW | RHPHFPTR | YYRITYGETGGNSPVQEFTVP | LQPPT | ATISGLKPGVDYTITGYAVT | V E E N G R V L N T P | ISINYRT | 32 | 10 | | |
| 101 | E15 | Del 1-8 | EVVAATPTSLLISW | RHPHFPTR | YYRITYGETGGNSPVQEFTVP | LQPPT | ATISGLKPGVDYTITGYAVT | L E P N G R V L M V P | ISINYRT | 52 | 2 | | |
| 102 | E10 | Del 1-8 | EVVAATPTSLLISW | RHPHFPTR | YYRITYGETGGNSPVQEFTVP | LQPPT | ATISGLKPGVDYTITGYAVT | E G R N G R E L F I P | ISINYRT | 53 | 3 | | |
| 103 | F1 | Del 1-8 | EVVAATPTSLLISW | RHPHFPTR | YYRITYGETGGNSPVQEFTVP | LQPPT | ATISGLKPGVDYTITGYAVT | S G R N D R E L L V P | ISINYRT | 18 | 2 | | |
| 104 | F5 | Del 1-8 | EVVAATPTSLLISW | RHPHFPTR | YYRITYGETGGNSPVQEFTVP | LQPPT | ATISGLKPGVDYTITGYAVT | V E R D G R E L N I P | ISINYRT | 12 | 8 | | |
| 105 | F6 | Del 1-8 | EVVAATPTSLLISW | RHPHFPTR | YYRITYGETGGNSPVQEFTVP | LQPPT | ATISGLKPGVDYTITGYAVT | V E Q N G R V L M T P | ISINYRT | 37 | 2 | | |
| 106 | F7 | Del 1-8 | EVVAATPTSLLISW | RHPHFPTR | YYRITYGETGGNSPVQEFTVP | LQPPT | ATISGLKPGVDYTITGYAVT | V E H N G R V L N I P | ISINYRT | 30 | 7 | | |
| 107 | F10 | Del 1-8 | EVVAATPTSLLISW | RHPHFPTR | YYRITYGETGGNSPVQEFTVP | LQPPT | ATISGLKPGVDYTITGYAVT | M A P N G R E L L T P | ISINYRT | 29 | 1 | | |

TABLE 2-continued

KDR & FLK binders

| SEQ ID NO | Clone Name | N-terminus | N-Terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 108 | F11 | Del 1-8 | EVVAATPTSLLISW | RHPHFPTR | YYRITYGETGGNSPVQEFTVP | LQPPT | ATISGLKPGVDYTITGYAVT | V E Q N G R V L N T P | ISINYRT | 20 | 8 | | |
| 109 | F12 | Del 1-8 | EVVAATPTSLLISW | RHPHFPTR | YYRITYGETGGNSPVQEFTVP | LQPPT | ATISGLKPGVDYTITGYAVT | D G R N G H E L M T P | ISINYRT | 17 | 1 | | |
| 110 | G1 | Del 1-8 | EVVAATPTSLLISW | RHPHFPTR | YYRITYGETGGNSPVQEFTVP | LQPPT | ATISGLKPGVDYTITGYAVT | E G R N G R E L M V P | ISINYRT | 22 | 2 | | |
| 111 | G2 | Del 1-8 | EVVAATPTSLLISW | RHPHFPTR | YYRITYGETGGNSPVQEFTVP | LQPPT | ATISGLKPGVDYTITGYAVT | L E R N N R E L L T P | ISINYRT | 25 | 9 | | |
| 112 | G3 | Del 1-8 | EVVAATPTSLLISW | RHPHFPTR | YYRITYGETGGNSPVQEFTVP | LQPPT | ATISGLKPGVDYTITGYAVT | M E R S G R E L M T P | ISINYRT | 28 | 10 | | |
| 113 | MWF10 | WT | VSDVPRDLEVVAATPTSLLISW | RHPHFPTR | YYRITYGETGGNSPVQEFTVP | LQPPA | ATISGLKPGVDYTITGYAVT | R A L L S I E L F T P | ISINYRT | | | | |
| 114 | MWA10 | WT | VSDVPRDLEVVAATPTSLLISW | RHPHFPTR | YYRITYGETGGNSPVQEFTVP | LQPPA | ATISGLKPGVDYTITGYAVT | F A R K G T E L F T P | ISINYRT | | | | |
| 115 | MWA2 | WT | VSDVPRDLEVVAATPTSLLISW | RHPHFPTR | YYRITYGETGGNSPVQEFTVP | LQPPA | ATISGLKPGVDYTITGYAVT | L E R C G R E L F T P | ISINYRT | | | | |
| 116 | MWC10 | WT | VSDVPRDLEVVAATPTSLLISW | RHPHFPTR | YYRITYGETGGNSPVQEFTVP | LQPPA | ATISGLKPGVDYTITGYAVT | R E R N G R E L F T P | ISINYRT | | | | |
| 117 | MWB7 | WT | VSDVPRDLEVVAATPTSLLISW | RHPHFPTR | YYRITYGETGGNSPVQEFTVP | LQPPA | ATISGLKPGVDYTITGYAVT | K E R N G R E L F T P | ISINYRT | | | | |
| 118 | MWH8 | WT | VSDVPRDLEVVAATPTSLLISW | RHPHFPTR | YYRITYGETGGNSPVQEFTVP | LQPPA | ATISGLKPGVDYTITGYAVT | C E R N G R E L F T P | ISINYRT | | | | |
| 119 | MWA10 | WT | VSDVPRDLEVVAATPTSLLISW | RHPHFPTR | YYRITYGETGGNSPVQEFTVP | LQPPA | ATISGLKPGVDYTITGYAVT | L E R T G R E L F T P | ISINYRT | | | | |
| 120 | MWB2 | WT | VSDVPRDLEVVAATPTSLLISW | RHPHFPTR | YYRITYGETGGNSPVQEFTVP | LQPPA | ATISGLKPGVDYTITGYAVT | W E R T G K E L F T P | ISINYRT | | | | |
| 121 | MWC3-f1 | WT | VSDVPRDLEVVAATPTSLLISW | RHPHFPTR | YYRITYGETGGNSPVQEFTVP | LQPPA | ATISGLKPGVDYTITGYAVT | I E R T C R E L F T P | ISINYRT | | | | |
| 122 | MWG11 | WT | VSDVPRDLEVVAATPTSLLISW | RHPHFPTR | YYRITYGETGGNSPVQEFTVP | LQPPA | ATISGLKPGVDYTITGYAVT | G G M I V R E L F T P | ISINYRT | | | | |
| 123 | MWG11 | WT | VSDVPRDLEVVAATPTSLLISW | RHPHFPTR | YYRITYGETGGNSPVQEFTVP | LQPPA | ATISGLKPGVDYTITGYAVT | F G R S S R E L F T P | ISINYRT | | | | |
| 124 | MWD3-f1 | WT | VSDVPRDLEVVAATPTSLLISW | RHPHFPTR | YYRITYGETGGNSPVQEFTVP | LQPPA | ATISGLKPGVDYTITGYAVT | R H K S R G E L F T P | ISINYRT | | | | |
| 125 | MWE11 | WT | VSDVPRDLEVVAATPTSLLISW | RHPHFPTR | YYRITYGETGGNSPVQEFTVP | LQPPA | ATISGLKPGVDYTITGYAVT | R H R D K R E L F T P | ISINYRT | | | | |
| 126 | MWD10 | WT | VSDVPRDLEVVAATPTSLLISW | RHPHFPTR | YYRITYGETGGNSPVQEFTVP | LQPPA | ATISGLKPGVDYTITGYAVT | Y H R G R E L F T P | ISINYRT | | | | |
| 127 | MWC1 | WT | VSDVPRDLEVVAATPTSLLISW | RHPHFPTR | YYRITYGETGGNSPVQEFTVP | LQPPA | ATISGLKPGVDYTITGYAVT | R H R G C R E L F T P | ISINYRT | | | | |
| 128 | MWA12 | WT | VSDVPRDLEVVAATPTSLLISW | RHPHFPTR | YYRITYGETGGNSPVQEFTVP | LQPPA | ATISGLKPGVDYTITGYAVT | S H R L R K E L F T P | ISINYRT | | | | |

TABLE 2-continued

KDR & FLK binders

| SEQ ID NO | Clone Name | N-terminus | N-Terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 129 | MWB3-f1 | WT | VSDVPRDLEVVAATPTSLLISW | RHPHFPTR | YYRITYGETGGNSPVQEFTVP | LQPPA | ATISGLKPGVDYTITGYAVT | M H Q R G E L | F T P ISINYRT | | | | |
| 130 | MWA11 | WT | VSDVPRDLEVVAATPTSLLISW | RHPHFPTR | YYRITYGETGGNSPVQEFTVP | LQPPA | ATISGLKPGVDYTITGYAVT | F H R R R G E L | F T P ISINYRT | | | | |
| 131 | MWG12 | WT | VSDVPRDLEVVAATPTSLLISW | RHPHFPTR | YYRITYGETGGNSPVQEFTVP | LQPPA | ATISGLKPGVDYTITGYAVT | F H R R R G E L | F T P ISINYRT | | | | |
| 132 | MWH11 | WT | VSDVPRDLEVVAATPTSLLISW | RHPHFPTR | YYRITYGETGGNSPVQEFTVP | LQPPA | ATISGLKPGVDYTITGYAVT | S H R R N E L | F T P ISINYRT | | | | |
| 133 | MWD12 | WT | VSDVPRDLEVVAATPTSLLISW | RHPHFPTR | YYRITYGETGGNSPVQEFTVP | LQPPA | ATISGLKPGVDYTITGYAVT | L H R R V R E L | F T P ISINYRT | | | | |
| 134 | MWH5 | WT | VSDVPRDLEVVAATPTSLLISW | RHPHFPTR | YYRITYGETGGNSPVQEFTVP | LQPPA | ATISGLKPGVDYTITGYAVT | R H R R R G E L | F T P ISINYRT | | | | |
| 135 | MWA1 | WT | VSDVPRDLEVVAATPTSLLISW | RHPHFPTR | YYRITYGETGGNSPVQEFTVP | LQPPA | ATISGLKPGVDYTITGYAVT | W H R S R K E L | F T P ISINYRT | | | | |
| 136 | MWG4-f1 | WT | VSDVPRDLEVVAATPTSLLISW | RHPHFPTR | YYRITYGETGGNSPVQEFTVP | LQPPA | ATISGLKPGVDYTITGYAVT | R H R S R G E L | F T P ISINYRT | | | | |
| 137 | MWA12 | WT | VSDVPRDLEVVAATPTSLLISW | RHPHFPTR | YYRITYGETGGNSPVQEFTVP | LQPPA | ATISGLKPGVDYTITGYAVT | V H R T G R E L | F T P ISINYRT | | | | |
| 138 | MWG11 | WT | VSDVPRDLEVVAATPTSLLISW | RHPHFPTR | YYRITYGETGGNSPVQEFTVP | LQPPA | ATISGLKPGVDYTITGYAVT | W H R V R G E L | F T P ISINYRT | | | | |
| 139 | MWC12 | WT | VSDVPRDLEVVAATPTSLLISW | RHPHFPTR | YYRITYGETGGNSPVQEFTVP | LQPPA | ATISGLKPGVDYTITGYAVT | W H R V R G E L | F T P ISINYRT | | | | |
| 140 | MWF11 | WT | VSDVPRDLEVVAATPTSLLISW | RHPHFPTR | YYRITYGETGGNSPVQEFTVP | LQPPA | ATISGLKPGVDYTITGYAVT | W H R W R G E L | F T P ISINYRT | | | | |
| 141 | MWE11 | WT | VSDVPRDLEVVAATPTSLLISW | RHPHFPTR | YYRITYGETGGNSPVQEFTVP | LQPPA | ATISGLKPGVDYTITGYAVT | W K R S G G E L | F T P ISINYRT | | | | |
| 142 | MWD10 | WT | VSDVPRDLEVVAATPTSLLISW | RHPHFPTR | YYRITYGETGGNSPVQEFTVP | LQPPA | ATISGLKPGVDYTITGYAVT | R L X N X V E L | F T P ISINYRT | | | | |
| 143 | MWC4-f1 | WT | VSDVPRDLEVVAATPTSLLISW | RHPHFPTR | YYRITYGETGGNSPVQEFTVP | LQPPA | ATISGLKPGVDYTITGYAVT | W R T P H A E L | F T P ISINYRT | | | | |
| 144 | MWF3 | WT | VSDVPRDLEVVAATPTSLLISW | RHPHFPTR | YYRITYGETGGNSPVQEFTVP | LQPPA | ATISGLKPGVDYTITGYAVT | L S P H S V E L | F T P ISINYRT | | | | |
| 145 | MWB2 | WT | VSDVPRDLEVVAATPTSLLISW | RHPHFPTR | YYRITYGETGGNSPVQEFTVP | LQPPA | ATISGLKPGVDYTITGYAVT | V S R Q K A E L | F T P ISINYRT | | | | |
| 146 | MWE10 | WT | VSDVPRDLEVVAATPTSLLISW | RHPHFPTR | YYRITYGETGGNSPVQEFTVP | LQPPA | ATISGLKPGVDYTITGYAVT | S S Y S K L E L | F T P ISINYRT | | | | |
| 147 | MWD9 | WT | VSDVPRDLEVVAATPTSLLISW | RHPHFPTR | YYRITYGETGGNSPVQEFTVP | LQPPA | ATISGLKPGVDYTITGYAVT | L T D R G S E L | F T P ISINYRT | | | | |
| 148 | MWH3-f1 | WT | VSDVPRDLEVVAATPTSLLISW | RHPHFPTR | YYRITYGETGGNSPVQEFTVP | LQPPA | ATISGLKPGVDYTITGYAVT | G T R T R S E L | F T P ISINYRT | | | | |

TABLE 2-continued

KDR & FLK binders

| SEQ ID NO | Clone Name | N-terminus | N-Terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 149 | MwG10 | WT | VSDVPRDLEVVAATPTSLLISW | RHPHFPTR | YYRITYGETGGNSPVQEFTVP | LQPPA | ATISGLKPGVDYTITGYAVT | P V A G C S E | LFTP | ISINYRT | | | | |
| 150 | MwH11 | WT | VSDVPRDLEVVAATPTSLLISW | RHPHFPTR | YYRITYGETGGNSPVQEFTVP | LQPPA | ATISGLKPGVDYTITGYAVT | W W Q T P R E | LFTP | ISINYRT | | | | |
| 151 | MwF11 | WT | VSDVPRDLEVVAATPTSLLISW | RHPHFPTR | YYRITYGETGGNSPVQEFTVP | LQPPA | ATISGLKPGVDYTITGYAVT | W W Q T P R E | LFTP | ISINYRT | | | | |
| 152 | M2 | WT | VSDVPRDLEVVAATPTSLLISW | RHPHFPTR | YYRITYGETGGNSPVQEFTVP | LQPPA | ATISGLKPGVDYTITGYAVT | W E R N G R E | LFTP | ISINYRT | | | | |
| 153 | MwB09-f1 | WT | VSDVPRDLEVVAATPTSLLISW | RHPHFPTR | YYRITYGETGGNSPVQEFTVP | LQPPA | ATISGLKPGVDYTITGYAVT | W E W N G R E | LFTP | ISINYRT | | | | |
| 154 | M3 | WT | VSDVPRDLEVVAATPTSLLISW | RHPHFPTR | YYRITYGETGGNSPVQEFTVP | LQPPA | ATISGLKPGVDYTITGYAVT | K E R N G R E | LFTP | ISINYRT | | | | |
| 155 | MwA3 | WT | VSDVPRDLEVVAATPTSLLISW | LHPHFPTH | YYRITYGETGGNSPVQEFTVP | LQPPA | ATISGLKPGVDYTITGYAVT | G A L N T S E | LFTP | ISINYRT | | | | |
| 156 | MwE10 | WT | VSDVPRDLEVVAATPTSLLISW | RHPHFPTH | YYRITYGETGGNSPVQEFTVP | LQPPA | ATISGLKPGVDYTITGYAVT | F G R E R R E | LFTP | ISINYRT | | | | |
| 157 | MwG33 | WT | VSDVPRDLEVVAATPTSLLISW | LHPHFPTH | YYRITYGETGGNSPVQEFTVP | LQPPA | ATISGLKPGVDYTITGYAVT | S G R V S F E | LFTP | ISINYRT | | | | |
| 158 | MwD5 | WT | VSDVPRDLEVVAATPTSLLISW | RHPHFPTH | YYRITYGETGGNSPVQEFTVP | LQPPA | ATISGLKPGVDYTITGYAVT | F H R R R G E | LFTP | ISINYRT | | | | |
| 159 | MwC3 | WT | VSDVPRDLEVVAATPTSLLISW | LHPHFPTH | YYRITYGETGGNSPVQEFTVP | LQPPA | ATISGLKPGVDYTITGYAVT | L I R M N T E | LFTP | ISINYRT | | | | |
| 160 | MwH3 | WT | VSDVPRDLEVVAATPTSLLISW | LHPHFPTH | YYRITYGETGGNSPVQEFTVP | LQPPA | ATISGLKPGVDYTITGYAVT | C L H L I T E | LFTP | ISINYRT | | | | |
| 161 | MwC2 | WT | VSDVPRDLEVVAATPTSLLISW | LHPHFPTH | YYRITYGETGGNSPVQEFTVP | LQPPA | ATISGLKPGVDYTITGYAVT | V L K L T L E | LFTP | ISINYRT | | | | |
| 162 | MwE2 | WT | VSDVPRDLEVVAATPTSLLISW | LHPHFPTH | YYRITYGETGGNSPVQEFTVP | LQPPA | ATISGLKPGVDYTITGYAVT | V L K L T L E | LFTP | ISINYRT | | | | |
| 163 | MwA2 | WT | VSDVPRDLEVVAATPTSLLISW | FHPHFPTH | YYRITYGETGGNSPVQEFTVP | LQPPA | ATISGLKPGVDYTITGYAVT | V L K L T L E | LFTP | ISINYRT | | | | |
| 164 | MwD3 | WT | VSDVPRDLEVVAATPTSLLISW | LHPHFPTH | YYRITYGETGGNSPVQEFTVP | LQPPA | ATISGLKPGVDYTITGYAVT | A L M A S G E | LFTP | ISINYRT | | | | |
| 165 | MwE3 | WT | VSDVPRDLEVVAATPTSLLISW | LHPHFPTH | YYRITYGETGGNSPVQEFTVP | LQPPA | ATISGLKPGVDYTITGYAVT | S M K N R L E | LFTP | ISINYRT | | | | |
| 166 | MwB3 | WT | VSDVPRDLEVVAATPTSLLISW | FHPHFPTH | YYRITYGETGGNSPVQEFTVP | LQPPA | ATISGLKPGVDYTITGYAVT | L R C L I P E | LFTP | ISINYRT | | | | |
| 167 | MwD2 | WT | VSDVPRDLEVVAATPTSLLISW | LHPHFPTH | YYRITYGETGGNSPVQEFTVP | LQPPA | ATISGLKPGVDYTITGYAVT | V S R Q K A E | LFTP | ISINYRT | | | | |
| 168 | MwC11 | WT | VSDVPRDLEVVAATPTSLLISW | RHPHFPTH | YYRITYGETGGNSPVQEFTVP | LQPPA | ATISGLKPGVDYTITGYAVT | W S R T G R E | LFTP | ISINYRT | | | | |

TABLE 2-continued

KDR & FLK binders

| SEQ ID NO | Clone Name | N-Terminus | N-terminus Framework 1 | BC Loop | Framework 2 | DE Loop | Framework 3 | FG Loop | Framework 4 | Binding to 1 nM KDR, % | Binding to 1 nM Flk-1, % | Kd KDR, nM | Kd Flk, nM |
|---|---|---|---|---|---|---|---|---|---|---|---|---|---|
| 169 | MWH2 | WT | VSDVPRDLEVVAATPTSLLISW | RHPHFPTH | YYRITYGETGGNSPVQEFTVP | LQPPA | ATISGLKPGVDYTITGYAVT | V W R T G R E L F T P | ISINYRT | | | | |
| 170 | M4 | WT | VSDVPRDLEVVAATPTSLLISW | RHPHFPTH | YYRITYGETGGNSPVQEFTVP | LQPPA | ATISGLKPGVDYTITGYAVT | T E R T G R E L F T P | ISINYRT | | | | |
| 171 | M8 | WT | VSDVPRDLEVVAATPTSLLISW | RHPHFPTH | YYRITYGETGGNSPVQEFTVP | LQPPA | ATISGLKPGVDYTITGYAVT | K E R S G R E L F T P | ISINYRT | | | | |
| 172 | MWF10-f1 | WT | VSDVPRDLEVVAATPTSLLISW | RHPHFPTH | YYRITYGETGGNSPVQEFTVP | LQPPA | ATISGLKPGVDYTITGYAVT | L E R N D R E L F T P | ISINYRT | | | | |
| 173 | M6 | WT | VSDVPRDLEVVAATPTSLLISW | RHPHFPTR | YYRITYGETGGNSPVQEFTVP | LQPPA | ATISGLKPGVDYTITGYAVT | L E R D G R E L F T P | ISINYRT | | | | |
| 174 | MWB6 | WT | VSDVPRDLEVVAATPTSLLISW | RHPHFPTR | YYRITYGETGGNSPVQEFTVP | LQPPT | ATISGLKPGVDYTITGYAVT | Q G R H K R E L F T P | ISINYRT | | | | |
| 175 | M5FL | WT | VSDVPRDLEVVAATPTSLLISW | RHPHFPTR | YYRITYGETGGNSPVQEFTVP | LQPPL | ATISGLKPGVDYTITGYAVT | K E R N G R E L F T P | ISINYRT | | | | |
| 176 | MWG10-f1 | WT | VSDVPRDLEVVAATPTSLLISW | RHPHFPTR | YYRITYGETGGNSPVQEFTVP | LQPPI | ATISGLKPGVDYTITGYAVT | M A Q N D H E L I T P | ISINYRT | | | | |
| 177 | WD08-f1; N4 | WT | VSDVPRDLEVVAATPTSLLISW | RPPHFPTR | YYRITYGETGGNSPVQEFTVP | LQPPI | ATISGLKPGVDYTITGYAVT | M A Q N D H E L I T P | ISINYRT | | | | |
| 178 | M7 | WT | VSDVPRDLEVVAATPTSLLISW | RHPHFPTR | YYRITYGETGGNSPVQEFTVP | LQPTT | ATISGLKPGVDYTITGYAVT | W E R N G R E L F T P | ISINYRT | | | | |
| 179 | M1 | WT | VSDVPRDLEVVAATPTSLLISW | RHPHFPTR | YYRITYGETGGNSPVQEFTVP | LQPTV | ATISGLKPGVDYTITGYAVT | L E R N D R E L F T P | ISINYRT | | | | |
| 180 | MWA07-f1 | WT | VSDVPRDLEVVAATPTSLLISW | RHPHFPTR | YYRITYGETGGNSPVQEFTVP | LQPTV | ATISGLKPGVDYTITGYAVT | L E R S G R E L F T P | ISINYRT | | | | |
| 181 | MWH11-f1 | WT | VSDVPRDLEVVAATPTSLLISW | RHPHFPTR | YYRITYGETGGNSPVQEFTVP | PQPPA | ATISGLKPGVDYTITGYAVT | K E R S G R E L F T P | ISINYRT | | | | |
| 182 | WF09-f1; F4 | WT | VSDVPRDLEVVAATPTSLLISW | RHPHFPTR | YYRITYGETGGNSPVQEFTVP | PQPPA | ATISGLKPGVDYTITGYAVT | L E R N D R E L F T P | ISINYRT | | | | |
| 183 | MWG12-f1 | WT | VSDVPRDLEVVAATPTSLLISW | CHPHFPTR | YYRITYGETGGNSPVQEFTVP | LQPPI | ATISGLKPGVDYTITGYAVT | M A Q N D H E L I T P | ISINYRT | | | | |

TABLE 3

KDR binders

| SEQ ID NO | Clone Name | N-terminus | BC Loop | DE Loop | FG Loop | | | | | | | | | Binding to 1 nM KDR, % | Kd KDR, nM |
|---|---|---|---|---|---|---|---|---|---|---|---|---|---|---|---|
| 6 | K1 | Del 1-8 | RHPHFPTR | LQPPT | M | G | L | Y | G | H | E | L | L | T | P | 48 | 0.55 |
| 7 | K2 | Del 1-8 | RHPHFPTR | LQPPT | D | G | E | N | G | Q | F | L | L | V | P | 48 | 1.19 |
| 8 | K5 | Del 1-8 | RHPHFPTR | LQPPT | M | G | P | N | D | N | E | L | L | T | P | 47 | 1.54 |
| 9 | K3 | Del 1-8 | RHPHFPTR | LQPPT | A | G | W | D | D | H | E | L | F | I | P | 45 | 1.15 |
| 311 | 3'E9 PR4 | Del 1-8 | RHPHFPTR | LQPPT | V | E | Q | D | G | H | V | L | Y | I | P | 44 | |
| 312 | 2'Del E6 PR4 | Del 1-8 | RHPHFPTR | LQPPT | M | G | K | N | G | H | E | L | L | T | P | 43 | |
| 313 | 3'D3 PR4 | Del 1-8 | RHPHFPTR | LQPPT | P | G | P | G | D | R | E | L | I | T | P | 42 | |
| 314 | 2'Del F8 PR4 | Del 1-8 | RHPHFPTR | LQPPT | A | G | P | G | A | H | E | L | L | T | P | 42 | |
| 315 | 4'B3 PR4 | Del 1-8 | RHPHFPTR | LQPPT | M | A | Q | N | N | R | E | L | L | T | P | 42 | |
| 316 | 3'E3 PR4 | Del 1-8 | RHPHFPTR | LQPPT | M | A | Q | Y | G | R | E | L | L | T | P | 41 | |
| 10 | K7 | Del 1-8 | RHPHFPTR | LQPPT | S | G | H | N | D | H | M | L | M | I | P | 40 | 2.2 |
| 317 | 3'H11 PR4 | Del 1-8 | RHPHFPTR | LQPPT | L | A | H | N | G | N | E | L | L | T | P | 39 | |
| 318 | 3'B4 PR4 | Del 1-8 | RHPHFPTR | LQPPT | V | A | W | N | G | H | E | L | M | T | P | 38 | |
| 11 | K4 | Del 1-8 | RHPHFPTR | LQPPT | A | G | Y | N | D | Q | I | L | M | T | P | 38 | 1.95 |
| 319 | 2'Del F7 PR4 | Del 1-8 | RHPHFPTR | LQPPT | L | G | L | R | D | R | E | L | F | V | P | 38 | |
| 320 | 2'Del D3 PR4 | Del 1-8 | RHPHFPTR | LQPPT | S | G | L | N | D | R | V | L | F | I | P | 38 | |
| 321 | 3'C6 PR4 | Del 1-8 | RHPHFPTR | LQPPT | M | G | P | N | D | R | E | L | L | T | P | 37 | |
| 322 | 3'F3 PR4 | Del 1-8 | RHPHFPTR | LQPPT | L | G | H | N | D | R | E | L | L | T | P | 37 | |
| 323 | 3'H3 PR4 | Del 1-8 | RHPHFPTR | LQPPT | L | G | L | N | D | R | E | L | M | T | P | 36 | |
| 324 | 1'Del G10 PR4 | Del 1-8 | RHPHFPTR | LQPPT | M | A | Q | N | G | H | K | L | M | T | P | 36 | |
| 12 | K9 | Del 1-8 | RHPHFPTR | LQPPT | F | G | L | Y | G | K | E | L | L | I | P | 35 | 1.8 |
| 325 | 2'DelE4 PR4 | Del 1-8 | RHPHFPTR | LQPPT | V | H | W | N | G | H | E | L | M | T | P | 34 | |
| 326 | 2'Del C6 PR4 | Del 1-8 | RHPHFPTR | LQPPT | M | G | F | M | A | H | E | L | M | V | P | 34 | |
| 327 | 2'Del C11 PR4 | Del 1-8 | RHPHFPTR | LQPPT | A | G | L | N | E | H | E | L | L | I | P | 34 | |
| 328 | 2'Del D10 PR4 | Del 1-8 | RHPHFPTR | LQPPT | L | A | D | N | A | R | E | L | L | T | P | 34 | |
| 329 | 2'Del H5 PR4 | Del 1-8 | RHPHFPTR | LQPPT | L | G | K | D | V | R | E | L | L | T | P | 34 | |
| 330 | 3'A7 PR4 | Del 1-8 | RHPHFPTR | LQPPT | L | S | D | S | G | H | A | L | F | T | P | 34 | |
| 331 | 2'Del E3 PR4 | Del 1-8 | RHPHFPTR | LQPPT | L | G | P | Y | G | H | E | L | L | T | P | 33 | |
| 13 | K10 | Del 1-8 | RHPHFPTR | LQPPT | T | G | P | N | D | R | L | L | F | V | P | 33 | 0.57 |
| 332 | 2'Del B5 PR4 | Del 1-8 | RHPHFPTR | LQPPT | A | G | R | H | D | H | E | L | I | I | P | 33 | |
| 333 | 3'C12 PR4 | Del 1-8 | RHPHFPTR | LQPPT | I | G | P | N | N | H | E | L | L | T | P | 33 | |
| 334 | 2'Del G9 PR4 | Del 1-8 | RHPHFPTR | LQPPT | V | E | Q | N | G | R | E | L | I | I | P | 33 | |
| 335 | 2'Del C1 PR4 | Del 1-8 | RHPHFPTR | LQPPT | A | G | L | D | E | H | E | L | L | I | P | 32 | |
| 336 | 3'E1 PR4 | Del 1-8 | RHPHFPTR | LQPPT | V | A | P | N | G | H | E | L | F | T | P | 32 | |
| 337 | 3'C3 PR4 | Del 1-8 | RHPHFPTR | LQPPT | M | A | Q | N | G | H | A | L | F | T | P | 32 | |
| 338 | 2'DelB7 PR4 | Del 1-8 | RHPHFPTR | LQPPT | V | G | Y | N | N | R | E | L | L | T | P | 32 | |
| 339 | 3'F1 PR4 | Del 1-8 | RHPHFPTR | LQPPT | V | A | Q | D | G | H | F | L | Y | T | P | 31 | |
| 340 | 2'Del B4 PR4 | Del 1-8 | RHPHFPTR | LQPPT | S | G | H | N | G | H | E | V | M | T | P | 31 | |
| 341 | 3'G3 PR4 | Del 1-8 | RHPHFPTR | LQPPT | F | D | Q | S | D | H | E | L | L | T | P | 31 | |
| 342 | 2'DelH4 PR4 | Del 1-8 | RHPHFPTR | LQPPT | V | G | P | N | E | R | M | L | M | T | P | 30 | |
| 343 | 3'D9 PR4 | Del 1-8 | RHPHFPTR | LQPPT | G | Y | Y | N | D | R | E | L | L | T | P | 30 | |
| 344 | 3'G10 PR4 | Del 1-8 | RHPHFPTR | LQPPT | L | T | H | N | D | H | E | L | L | T | P | 30 | |
| 345 | 3'B2 PR4 | Del 1-8 | RHPHFPTR | LQPPT | V | G | R | N | D | R | E | L | L | T | P | 29 | |
| 346 | 2'DelC3 PR4 | Del 1-8 | RHPHFPTR | LQPPT | W | A | Q | N | G | R | E | L | L | T | P | 29 | |
| 347 | 3'F2 PR4 | Del 1-8 | RHPHFPTR | LQPPT | L | G | K | N | D | H | E | L | L | T | P | 29 | |
| 348 | 4'C9 PR4 | Del 1-8 | RHPHFPTR | LQPPT | L | G | P | N | D | H | E | L | M | T | P | 29 | |
| 349 | 2'Del B2 PR4 | Del 1-8 | RHPHFPTR | LQPPT | T | G | W | N | G | N | E | L | F | T | P | 29 | |
| 14 | K12 | Del 1-8 | RHPHFPTR | LQPPT | D | V | Y | N | D | H | E | I | K | T | P | 29 | 0.62 |
| 350 | 4'H7 PR4 | Del 1-8 | RHPHFPTR | LQPPT | L | A | H | N | D | H | E | L | L | T | P | 29 | |
| 351 | 2'Del D1 PR4 | Del 1-8 | RHPHFPTR | LQPPT | L | E | Q | N | D | R | V | L | L | T | P | 28 | |
| 352 | 2'Del H6 PR4 | Del 1-8 | RHPHFPTR | LQPPT | T | G | H | H | D | H | E | L | I | I | P | 28 | |
| 353 | 3'B12 PR4 | Del 1-8 | RHPHFPTR | LQPPT | V | A | H | E | N | R | E | L | L | T | P | 28 | |
| 354 | 4'C5 PR4 | Del 1-8 | RHPHFPTR | LQPPT | L | G | L | N | D | H | E | L | I | T | P | 27 | |
| 15 | K6 | Del 1-8 | RHPHFPTR | LQPPT | D | G | K | D | G | R | V | L | L | T | P | 27 | 0.93 |
| 355 | 3'D8 PR4 | Del 1-8 | RHPHFPTR | LQPPT | A | G | P | N | D | H | Q | L | F | T | P | 27 | |
| 356 | 3'C5 PR4 | Del 1-8 | RHPHFPTR | LQPPT | D | A | M | Y | G | R | E | L | M | T | P | 27 | |
| 357 | 3'A8 PR4 | Del 1-8 | RHPHFPTR | LQPPT | V | A | W | D | D | H | E | L | L | T | P | 27 | |
| 358 | 2'Del F11 PR4 | Del 1-8 | RHPHFPTR | LQPPT | M | G | Q | N | D | K | E | L | I | T | P | 27 | |
| 359 | 4'D8 PR4 | Del 1-8 | RHPHFPTR | LQPPT | L | A | Q | N | G | H | E | L | Y | T | P | 26 | |
| 360 | 2'Del C5 PR4 | Del 1-8 | RHPHFPTR | LQPPT | P | G | H | N | D | H | E | L | M | V | P | 26 | |
| 16 | K15 | Del 1-8 | RHPHFPTR | LQPPT | E | V | H | H | D | R | E | I | K | T | P | 25 | 0.35 |
| 361 | 3'B1 PR4 | Del 1-8 | RHPHFPTR | LQPPT | E | A | R | N | G | R | E | L | L | T | P | 25 | |
| 362 | 3'A9 PR4 | Del 1-8 | RHPHFPTR | LQPPT | L | A | H | N | D | R | E | L | L | T | P | 25 | |
| 363 | 4'B11 PR4 | Del 1-8 | RHPHFPTR | LQPPT | M | A | H | N | D | H | E | L | L | T | P | 25 | |
| 17 | K11 | Del 1-8 | RHPHFPTR | LQPPT | Q | A | P | N | D | R | V | L | Y | T | P | 24 | 1.16 |
| 364 | 3D12 PR3 | Del 1-8 | RHPHFPTR | LQPPT | L | G | Q | N | D | R | Q | L | L | V | P | 24 | |
| 365 | 2'Del H12 PR4 | Del 1-8 | RHPHFPTR | LQPPT | A | G | G | N | G | H | E | L | L | T | P | 24 | |
| 366 | 3'H9 PR4 | Del 1-8 | RHPHFPTR | LQPPT | H | P | Y | D | Q | V | L | L | T | P | | | 24 | |
| 367 | 3'F6 PR4 | Del 1-8 | RHPHFPTR | LQPPT | I | E | Q | S | G | L | Q | L | M | T | P | 24 | |
| 368 | 1'DelE6 PR4 | Del 1-8 | RHPHFPTR | LQPPT | L | A | Q | N | D | R | E | L | L | T | P | 24 | |
| 369 | 3'E5 PR4 | Del 1-8 | RHPHFPTR | LQPPT | V | A | W | D | G | R | E | L | F | T | P | 23 | |
| 370 | 3A3 PR3 | Del 1-8 | RHPHFPTR | LQPPT | L | A | Y | N | G | R | E | I | I | T | P | 23 | |
| 371 | 3A2 PR3 | Del 1-8 | RHPHFPTR | LQPPT | W | S | Q | N | N | R | E | L | F | T | P | 23 | |

TABLE 3-continued

KDR binders

| SEQ ID NO | Clone Name | N-terminus | BC Loop | DE Loop | FG Loop | | | | | | | | | | Binding to 1 nM KDR, % | Kd KDR, nM |
|---|---|---|---|---|---|---|---|---|---|---|---|---|---|---|---|---|
| 372 | 3'B11 PR4 | Del 1-8 | RHPHFPTR | LQPPT | E | T | W | N | D | H | E | I | R | T | P | 23 | |
| 373 | 1'DelA2 PR4 | Del 1-8 | RHPHFPTR | LQPPT | V | A | Q | N | G | H | Q | L | F | T | P | 23 | |
| 374 | 2'D6-PR4 | WT | RHPHFPTR | LQPPT | V | T | H | N | G | H | P | L | M | T | P | 22 | |
| 375 | 3'H1 PR4 | Del 1-8 | RHPHFPTR | LQPPT | F | A | Q | N | D | H | Q | L | F | T | P | 22 | |
| 376 | 2'Del G11 PR4 | Del 1-8 | RHPHFPTR | LQPPT | G | G | Q | M | N | R | V | L | M | T | P | 22 | |
| 377 | 2'Del F5 PR4 | Del 1-8 | RHPHFPTR | LQPPT | L | V | H | N | D | R | E | L | L | T | P | 22 | |
| 378 | 1'DelE7 PR4 | Del 1-8 | RHPHFPTR | LQPPT | V | A | Q | N | G | H | E | L | F | T | P | 22 | |
| 379 | 2'E4-PR4 | WT | RHPHFPTR | LQPPT | V | H | W | N | G | H | E | L | M | T | P | 22 | |
| 380 | 2'Del F6 PR4 | Del 1-8 | RHPHFPTR | LQPPT | L | G | W | N | D | H | E | L | Y | I | P | 22 | |
| 381 | 3'E10 PR4 | Del 1-8 | RHPHFPTR | LQPPT | A | G | H | K | D | Q | E | L | L | T | P | 21 | |
| 382 | 4'A9 PR4 | Del 1-8 | RHPHFPTR | LQPPT | L | A | Q | N | N | H | E | L | L | T | P | 21 | |
| 383 | 4'G12 PR4 | Del 1-8 | RHPHFPTR | LQPPT | V | A | W | N | D | H | E | I | Y | T | P | 21 | |
| 384 | 3'B10 PR4 | Del 1-8 | RHPHFPTR | LQPPT | L | A | Q | T | G | R | E | L | L | T | P | 21 | |
| 385 | 2'DelH9 PR4 | Del 1-8 | RHPHFPTR | LQPPT | V | G | W | S | G | H | E | L | F | V | P | 20 | |
| 386 | 3'H8 PR4 | Del 1-8 | RHPHFPTR | LQPPT | V | G | H | N | D | R | E | L | I | T | P | 20 | |
| 387 | 2'DelA5 PR4 | Del 1-8 | RHPHFPTR | LQPPT | W | N | Q | N | G | Q | E | L | F | T | P | 20 | |
| 388 | 3B5 PR3 | Del 1-8 | RHPHFPTR | LQPPT | F | G | Q | N | G | H | A | L | L | T | P | 20 | |
| 389 | 3C7 PR3 | Del 1-8 | RHPHFPTR | LQPPT | R | G | L | N | D | G | E | L | L | T | P | 20 | |
| 390 | 3G2 PR3 | Del 1-8 | RHPHFPTR | LQPPT | F | G | P | S | D | H | V | L | L | T | P | 20 | |
| 18 | K14 | Del 1-8 | RHPHFPTR | LQPPT | R | E | E | N | D | H | E | L | L | I | P | 20 | 0.57 |
| 391 | 4'B12 PR4 | Del 1-8 | RHPHFPTR | LQPPT | L | A | Q | N | N | H | E | L | L | T | P | 20 | |
| 392 | 4'B8 PR4 | Del 1-8 | RHPHFPTR | LQPPT | V | A | Q | N | D | H | K | L | F | I | P | 20 | |
| 393 | 2'Del F1 PR4 | Del 1-8 | RHPHFPTR | LQPPT | R | D | Q | Y | E | H | E | L | L | T | P | 20 | |
| 394 | 3'G1 PR4 | Del 1-8 | RHPHFPTR | LQPPT | L | A | L | N | G | H | E | L | F | T | P | 19 | |
| 395 | 3'D2 PR4 | Del 1-8 | RHPHFPTR | LQPPT | V | E | S | N | G | H | A | L | F | V | P | 19 | |
| 396 | 2'DelG5 PR4 | Del 1-8 | RHPHFPTR | LQPPT | V | G | Q | N | N | H | E | L | L | T | P | 19 | |
| 397 | 2'DelC7 PR4 | Del 1-8 | RHPHFPTR | LQPPT | W | D | Q | N | G | H | V | L | L | T | P | 19 | |
| 398 | 2'Del E5 PR4 | Del 1-8 | RHPHFPTR | LQPPT | E | G | L | N | D | H | E | L | I | I | P | 19 | |
| 399 | 3'C8 PR4 | Del 1-8 | RHPHFPTR | LQPPT | E | G | L | N | D | H | E | L | M | I | P | 19 | |
| 400 | 3'G7 PR4 | Del 1-8 | RHPHFPTR | LQPPT | E | G | Q | N | D | Q | L | L | F | I | P | 19 | |
| 401 | 3'A6 PR4 | Del 1-8 | RHPHFPTR | LQPPT | L | A | Q | N | G | H | E | L | L | T | P | 19 | |
| 402 | 4'G4 PR4 | Del 1-8 | RHPHFPTR | LQPPT | V | A | Q | N | D | R | E | L | L | T | P | 19 | |
| 403 | 4'H5 PR4 | Del 1-8 | RHPHFPTR | LQPPT | L | A | Q | N | G | H | E | L | F | T | P | 18 | |
| 404 | 1'DelH12 PR4 | Del 1-8 | RHPHFPTR | LQPPT | V | A | Q | N | E | R | E | L | F | T | P | 18 | |
| 19 | K8 | Del 1-8 | RHPHFPTR | LQPPT | V | T | H | N | G | H | P | L | M | T | P | 18 | 3.3 |
| 405 | 2'Del D5 PR4 | Del 1-8 | RHPHFPTR | LQPPT | V | A | W | N | D | H | M | M | M | T | P | 18 | |
| 406 | 3'F9 PR4 | Del 1-8 | RHPHFPTR | LQPPT | L | G | P | N | D | R | E | L | M | T | P | 18 | |
| 407 | 2'H4-PR4 | WT | RHPHFPTR | LQPPT | V | G | P | N | E | R | M | L | M | T | P | 17 | |
| 408 | 4'H12 PR4 | Del 1-8 | RHPHFPTR | LQPPT | V | A | Q | N | D | H | E | L | L | T | P | 17 | |
| 409 | 1'DelD2 PR4 | Del 1-8 | RHPHFPTR | LQPPT | V | A | K | N | D | H | E | L | L | T | P | 17 | |
| 410 | 4'E7 PR4 | Del 1-8 | RHPHFPTR | LQPPT | W | A | Q | N | D | H | E | L | L | T | P | 17 | |
| 411 | 1'DelH10 PR4 | Del 1-8 | RHPHFPTR | LQPPT | F | A | Q | N | D | H | E | L | L | T | P | 17 | |
| 20 | K13 | Del 1-8 | RHPHFPTR | LQPPT | L | A | L | K | G | H | E | L | L | T | P | 17 | 0.58 |
| 412 | 3C3 PR3 | Del 1-8 | RHPHFPTR | LQPPT | M | E | Q | N | G | H | E | L | F | T | P | 17 | |
| 413 | 2'Del B3 PR4 | Del 1-8 | RHPHFPTR | LQPPT | D | A | P | N | G | R | E | L | M | V | P | 17 | |
| 414 | 2'Del A2 PR4 | Del 1-8 | RHPHFPTR | LQPPT | G | G | R | N | G | H | T | L | L | T | P | 17 | |
| 415 | 3'F12 PR4 | Del 1-8 | RHPHFPTR | LQPPT | L | S | Q | T | D | H | E | L | L | T | P | 17 | |
| 416 | 3B4 PR3 | Del 1-8 | RHPHFPTR | LQPPT | V | G | Q | N | E | H | E | L | L | T | P | 17 | |
| 417 | 3F8 PR3 | Del 1-8 | RHPHFPTR | LQPPT | V | A | Q | N | G | H | E | L | K | T | P | 17 | |
| 418 | 1'DelH5 PR4 | Del 1-8 | RHPHFPTR | LQPPT | V | A | Q | N | D | R | E | L | F | T | P | 17 | |
| 419 | 1'DelD5 PR4 | Del 1-8 | RHPHFPTR | LQPPT | V | G | Q | N | H | H | E | L | F | T | P | 17 | |
| 420 | 3'E11 PR4 | Del 1-8 | RHPHFPTR | LQPPT | V | G | P | H | D | R | E | L | L | T | P | 17 | |
| 421 | 2'C6-PR4 | WT | RHPHFPTR | LQPPT | M | G | F | M | A | H | E | L | M | V | P | 16 | |
| 422 | 4C9 PR3 | Del 1-8 | RHPHFPTR | LQPPT | L | A | Q | N | D | H | E | L | L | T | P | 16 | |
| 423 | 3C9 PR3 | Del 1-8 | RHPHFPTR | LQPPT | L | V | R | N | D | H | E | L | L | T | P | 16 | |
| 424 | 3F10 PR3 | Del 1-8 | RHPHFPTR | LQPPT | L | A | Q | D | D | H | E | L | L | T | P | 16 | |
| 425 | 2'Del A11 PR4 | Del 1-8 | RHPHFPTR | LQPPT | E | D | I | R | V | L | W | L | N | T | T | 16 | |
| 426 | 1'DelD1 PR4 | Del 1-8 | RHPHFPTR | LQPPT | V | T | Q | N | D | H | E | L | L | T | P | 16 | |
| 427 | 1'DelE2 PR4 | Del 1-8 | RHPHFPTR | LQPPT | V | G | Q | N | D | H | E | L | L | T | P | 16 | |
| 428 | 1'DelF3 PR4 | Del 1-8 | RHPHFPTR | LQPPT | M | A | Q | N | D | H | K | L | F | T | P | 16 | |
| 429 | 4'A5 PR4 | Del 1-8 | RHPHFPTR | LQPPT | L | A | Q | N | D | H | E | L | L | T | P | 16 | |
| 430 | 1'DelB8 PR4 | Del 1-8 | RHPHFPTR | LQPPT | M | A | Q | N | D | H | K | L | F | T | P | 16 | |
| 431 | 4'B7 PR4 | Del 1-8 | RHPHFPTR | LQPPT | V | A | Q | N | N | H | E | L | L | T | P | 16 | |
| 432 | 4F4 PR3 | Del 1-8 | RHPHFPTR | LQPPT | L | A | Q | N | D | R | E | L | I | T | P | 15 | |
| 433 | 4B11 PR3 | Del 1-8 | RHPHFPTR | LQPPT | V | G | Q | N | N | H | E | L | I | T | P | 15 | |
| 434 | 3'G2 PR4 | Del 1-8 | RHPHFPTR | LQPPT | L | A | Q | N | G | H | E | L | I | T | P | 15 | |
| 435 | 2'Del C8 PR4 | Del 1-8 | RHPHFPTR | LQPPT | T | A | H | N | G | H | E | L | L | T | P | 15 | |
| 436 | 3'B8 PR4 | Del 1-8 | RHPHFPTR | LQPPT | L | G | Y | H | D | H | A | L | F | T | P | 14 | |
| 437 | 3'H10 PR4 | Del 1-8 | RHPHFPTR | LQPPT | W | A | W | N | D | H | E | L | M | T | P | 14 | |
| 438 | 1'DelA1 PR4 | Del 1-8 | RHPHFPTR | LQPPT | V | A | Q | N | D | H | E | L | L | T | P | 14 | |
| 439 | 4'D6 PR4 | Del 1-8 | RHPHFPTR | LQPPT | M | A | Q | N | D | H | E | L | M | T | P | 14 | |
| 440 | 4F9 PR3 | Del 1-8 | RHPHFPTR | LQPPT | M | A | Q | N | D | H | E | L | L | T | P | 14 | |
| 441 | 4H5 PR3 | Del 1-8 | RHPHFPTR | LQPPT | V | A | Q | N | G | H | E | L | I | T | P | 14 | |

TABLE 3-continued

KDR binders

| SEQ ID NO | Clone Name | N-terminus | BC Loop | DE Loop | FG Loop | | | | | | | | | | Binding to 1 nM KDR, % | Kd KDR, nM |
|---|---|---|---|---|---|---|---|---|---|---|---|---|---|---|---|---|
| 442 | 2D12 PR3 | WT | RHPHFPTR | LQPPT | E | G | W | I | D | H | E | I | M | I | P | 14 | |
| 443 | 3'F7 PR4 | Del 1-8 | RHPHFPTR | LQPPT | E | G | Q | N | G | S | E | L | I | V | P | 14 | |
| 444 | 4C11 PR3 | Del 1-8 | RHPHFPTR | LQPPT | M | A | Q | N | D | R | E | L | I | T | P | 14 | |
| 445 | 4B6 PR3 | Del 1-8 | RHPHFPTR | LQPPT | V | G | Q | N | D | H | E | L | F | T | P | 14 | |
| 446 | 1'DelE12 PR4 | Del 1-8 | RHPHFPTR | LQPPT | V | A | Q | S | D | H | E | L | F | T | P | 13 | |
| 447 | 1'DelC2 PR4 | Del 1-8 | RHPHFPTR | LQPPT | V | D | R | N | D | H | E | L | F | T | P | 13 | |
| 448 | 1'DelA9 PR4 | Del 1-8 | RHPHFPTR | LQPPT | L | A | Q | N | D | H | E | L | M | T | P | 13 | |
| 449 | 1'DelA4 PR4 | Del 1-8 | RHPHFPTR | LQPPT | V | A | Q | N | D | H | E | L | F | T | P | 13 | |
| 450 | 3G5 PR3 | Del 1-8 | RHPHFPTR | LQPPT | L | G | E | N | D | R | K | L | I | T | P | 13 | |
| 451 | 4A12 PR3 | Del 1-8 | RHPHFPTR | LQPPT | V | A | Q | N | D | H | E | L | L | T | P | 13 | |
| 452 | 2'Del E12 PR4 | Del 1-8 | RHPHFPTR | LQPPT | E | G | P | N | G | H | E | L | I | T | P | 13 | |
| 453 | 3G1 PR3 | Del 1-8 | RHPHFPTR | LQPPT | M | A | Q | N | V | R | E | L | L | T | P | 13 | |
| 454 | 4F12 PR3 | Del 1-8 | RHPHFPTR | LQPPT | V | T | Q | N | G | H | E | L | I | T | P | 13 | |
| 455 | 4B7 PR3 | Del 1-8 | RHPHFPTR | LQPPT | V | T | Q | N | D | H | E | L | F | T | P | 13 | |
| 456 | 4'G8 PR4 | Del 1-8 | RHPHFPTR | LQPPT | V | A | Q | N | G | H | E | L | L | T | P | 13 | |
| 457 | 3'E8 PR4 | Del 1-8 | RHPHFPTR | LQPPT | V | A | Q | N | D | R | Q | L | F | T | P | 12 | |
| 458 | 3'E4 PR4 | Del 1-8 | RHPHFPTR | LQPPT | V | G | P | N | D | R | E | L | I | V | P | 12 | |
| 459 | 1'DelC6 PR4 | Del 1-8 | RHPHFPTR | LQPPT | V | A | Q | N | E | H | E | L | L | T | P | 12 | |
| 460 | 1'DelD3 PR4 | Del 1-8 | RHPHFPTR | LQPPT | L | A | Q | N | N | H | E | L | I | T | P | 12 | |
| 461 | 3A8 PR3 | Del 1-8 | RHPHFPTR | LQPPT | E | A | H | H | G | H | E | L | M | I | P | 12 | |
| 462 | 3C5 PR3 | Del 1-8 | RHPHFPTR | LQPPT | G | D | H | N | D | R | E | L | M | T | P | 12 | |
| 463 | 2'G11-PR4 | WT | RHPHFPTR | LQPPT | G | G | Q | M | N | R | V | L | M | T | P | 12 | |
| 464 | 3'D4 PR4 | Del 1-8 | RHPHFPTR | LQPPT | L | A | H | N | D | R | E | L | I | T | P | 12 | |
| 465 | 3E6 PR3 | Del 1-8 | RHPHFPTR | LQPPT | V | P | Q | N | G | H | E | L | I | T | M | 12 | |
| 466 | 1'DelA11 PR4 | Del 1-8 | RHPHFPTR | LQPPT | L | A | Q | N | D | H | E | L | F | T | P | 12 | |
| 467 | 4'D12 PR4 | Del 1-8 | RHPHFPTR | LQPPT | V | D | Q | N | D | H | E | L | F | T | P | 12 | |
| 468 | 2'D5-PR4 | WT | RHPHFPTR | LQPPT | V | A | W | N | D | H | M | L | M | T | P | 11 | |
| 469 | 2'A1-PR4 | WT | RHPHFPTR | LQPPT | S | G | H | N | D | H | M | L | M | I | P | 11 | |
| 470 | 1'DelG11 PR4 | Del 1-8 | RHPHFPTR | LQPPT | L | A | Q | N | G | H | V | L | I | T | P | 11 | |
| 471 | 2'DelB10 PR4 | Del 1-8 | RHPHFPTR | LQPPT | V | T | H | N | D | H | E | L | L | T | P | 11 | |
| 472 | 2'DelB11 PR4 | Del 1-8 | RHPHFPTR | LQPPT | V | G | Q | N | D | H | E | L | M | T | P | 11 | |
| 473 | 1'DelC5 PR4 | Del 1-8 | RHPHFPTR | LQPPT | L | A | Q | N | D | H | E | I | M | T | P | 11 | |
| 474 | 4'B6 PR4 | Del 1-8 | RHPHFPTR | LQPPT | L | A | Q | N | D | H | E | L | I | T | P | 11 | |
| 475 | 3H9 PR3 | Del 1-8 | RHPHFPTR | LQPPT | V | S | Q | Q | N | H | E | L | L | T | P | 11 | |
| 476 | 4E10 PR3 | Del 1-8 | RHPHFPTR | LQPPT | V | A | Q | N | D | H | E | L | M | T | P | 11 | |
| 477 | 3F5 PR3 | Del 1-8 | RHPHFPTR | LQPPT | V | A | Y | N | E | H | E | L | Y | T | P | 11 | |
| 478 | 4A9 PR3 | Del 1-8 | RHPHFPTR | LQPPT | V | A | Q | H | D | H | E | L | L | T | P | 11 | |
| 479 | 1'DelH7 PR4 | Del 1-8 | RHPHFPTR | LQPPT | V | G | Q | N | D | Q | E | L | L | T | P | 11 | |
| 480 | 1'DelB10 PR4 | Del 1-8 | RHPHFPTR | LQPPT | V | A | R | N | D | H | E | L | M | T | P | 11 | |
| 481 | 2'DelB9 PR4 | Del 1-8 | RHPHFPTR | LQPPT | V | G | P | T | D | H | E | L | L | T | P | 11 | |
| 482 | 3F11 PR3 | Del 1-8 | RHPHFPTR | LQPPT | V | G | L | T | D | H | V | L | L | T | P | 10 | |
| 483 | 4C4 PR3 | Del 1-8 | RHPHFPTR | LQPPT | V | A | Q | D | D | H | E | L | F | T | P | 10 | |
| 484 | 4B5 PR3 | Del 1-8 | RHPHFPTR | LQPPT | L | A | Q | N | D | H | E | L | F | T | P | 10 | |
| 485 | 3D4 PR3 | Del 1-8 | RHPHFPTR | LQPPT | V | G | W | N | D | H | E | L | I | T | P | 10 | |
| 486 | 4A4 PR3 | Del 1-8 | RHPHFPTR | LQPPT | V | A | Q | N | D | H | E | L | F | T | P | 10 | |
| 487 | 3D11 PR3 | Del 1-8 | RHPHFPTR | LQPPT | L | G | Q | E | N | Q | E | L | I | T | P | 10 | |
| 488 | 2H10 PR3 | WT | RHPHFPTR | LQPPT | L | A | P | S | A | R | E | L | M | T | P | 10 | |
| 489 | 3G10 PR3 | Del 1-8 | RHPHFPTR | LQPPT | V | V | H | N | G | H | E | L | I | L | P | 10 | |
| 490 | 3F4 PR3 | Del 1-8 | RHPHFPTR | LQPPT | M | G | Y | E | D | H | E | L | I | T | P | 10 | |
| 491 | 2H12 PR3 | WT | RHPHFPTR | LQPPT | E | G | Y | Q | N | H | E | L | S | V | P | 10 | |
| 492 | 4C2 PR3 | Del 1-8 | RHPHFPTR | LQPPT | V | D | Q | N | D | H | E | L | F | T | P | 10 | |
| 493 | 1'DelG9 PR4 | Del 1-8 | RHPHFPTR | LQPPT | V | A | Q | S | D | H | E | L | M | T | P | 10 | |
| 494 | 1'DelH9 PR4 | Del 1-8 | RHPHFPTR | LQPPT | V | G | Q | N | D | H | E | L | I | T | P | 10 | |
| 495 | 1'DelB3 PR4 | Del 1-8 | RHPHFPTR | LQPPT | V | A | Q | N | D | H | E | L | M | T | P | 10 | |
| 496 | 1'DelH1 PR4 | Del 1-8 | RHPHFPTR | LQPPT | V | A | Q | N | G | H | E | L | I | T | P | 9 | |
| 497 | 3'A3 PR4 | Del 1-8 | RHPHFPTR | LQPPT | R | A | Q | N | D | H | E | L | I | T | P | 9 | |
| 498 | 1'DelC4 PR4 | Del 1-8 | RHPHFPTR | LQPPT | V | A | Q | S | N | H | E | L | M | T | P | 9 | |
| 499 | 1'DelE11 PR4 | Del 1-8 | RHPHFPTR | LQPPT | V | A | Q | N | D | R | E | L | I | T | P | 9 | |
| 500 | 3F1 PR3 | Del 1-8 | RHPHFPTR | LQPPT | L | T | H | N | E | Q | Y | L | F | T | P | 9 | |
| 501 | 2G9 PR3 | WT | RHPHFPTR | LQPPT | E | I | Y | N | D | H | E | L | M | T | P | 9 | |
| 502 | 3'D11 PR4 | Del 1-8 | RHPHFPTR | LQPPT | M | A | Q | N | D | H | E | L | I | T | P | 9 | |
| 503 | 2'DelH2 PR4 | Del 1-8 | RHPHFPTR | LQPPT | V | S | Q | Y | G | H | E | L | I | T | P | 8 | |
| 504 | 1'DelC10 PR4 | Del 1-8 | RHPHFPTR | LQPPT | V | A | K | N | D | H | E | L | I | T | P | 8 | |
| 505 | 4D2 PR3 | Del 1-8 | RHPHFPTR | LQPPT | V | A | Q | N | N | H | E | L | I | T | P | 8 | |
| 506 | 4A9 PR3 | Del 1-8 | RHPHFPTR | LQPPT | V | A | Q | H | D | H | E | L | L | T | P | 8 | |
| 507 | 2F3 PR3 | WT | RHPHFPTR | LQPPT | L | S | H | Y | G | K | E | L | R | T | P | 8 | |
| 508 | 4A2 PR3 | Del 1-8 | RHPHFPTR | LQPPT | V | A | Q | N | A | H | E | L | M | T | P | 8 | |
| 509 | 4G4 PR3 | Del 1-8 | RHPHFPTR | LQPPT | L | G | Q | N | D | H | E | L | L | T | P | 8 | |
| 510 | 1'DelB7 PR4 | Del 1-8 | RHPHFPTR | LQPPT | V | A | Q | N | D | H | E | L | K | T | P | 8 | |
| 511 | 3'D12 PR4 | Del 1-8 | RHPHFPTR | LQPPT | G | E | Q | N | D | Y | E | L | L | V | P | 7 | |
| 512 | 2'Del F12 PR4 | Del 1-8 | RHPHFPTR | LQPPT | L | T | Q | H | D | H | E | L | L | T | P | 7 | |
| 513 | 4E2 PR3 | Del 1-8 | RHPHFPTR | LQPPT | M | A | Q | N | D | H | E | L | I | T | P | 7 | |
| 514 | 2C9 PR3 | WT | RHPHFPTR | LQPPT | E | A | P | N | G | R | E | L | R | T | P | 7 | |

TABLE 3-continued

KDR binders

| SEQ ID NO | Clone Name | N-terminus | BC Loop | DE Loop | FG Loop | | | | | | | | | | | Binding to 1 nM KDR, % | Kd KDR, nM |
|---|---|---|---|---|---|---|---|---|---|---|---|---|---|---|---|---|---|
| 515 | 2'B9-PR4 | WT | RHPHFPTR | LQPPT | V | G | P | T | D | H | E | L | L | T | P | 7 | |
| 516 | 1'DelH6 PR4 | Del 1-8 | RHPHFPTR | LQPPT | V | G | Q | Y | D | H | E | L | I | T | P | 6 | |
| 517 | 4A3 PR3 | Del 1-8 | RHPHFPTR | LQPPT | V | A | Q | D | E | H | E | L | I | T | P | 6 | |
| 518 | 2C12 PR3 | WT | RHPHFPTR | LQPPT | D | A | Q | N | V | Q | A | P | I | A | Q | 6 | |
| 519 | 2G12 PR3 | WT | RHPHFPTR | LQPPT | S | G | Q | N | D | H | A | L | L | I | P | 6 | |
| 520 | 2'A11-PR4 | WT | RHPHFPTR | LQPPT | E | D | I | R | V | L | W | L | N | T | T | 6 | |
| 521 | 2'C7-PR4 | WT | RHPHFPTR | LQPPT | W | D | Q | N | G | H | V | L | L | T | P | 5 | |
| 522 | 2'F7-PR4 | WT | RHPHFPTR | LQPPT | L | G | L | R | D | R | E | L | F | V | P | 5 | |
| 523 | 2C6 PR3 | WT | RHPHFPTR | LQPPT | V | E | P | N | G | H | K | L | A | I | P | 5 | |
| 524 | 3'E6 PR4 | Del 1-8 | RHPHFPTR | LQPPT | F | G | Q | N | G | K | E | F | R | I | P | 5 | |
| 525 | 2'B4-PR4 | WT | RHPHFPTR | LQPPT | S | G | H | N | G | H | E | V | M | T | P | 4 | |
| 526 | 2'F6-PR4 | WT | RHPHFPTR | LQPPT | L | G | W | N | D | H | E | L | Y | I | P | 4 | |
| 527 | 2'H5-PR4 | WT | RHPHFPTR | LQPPT | L | G | K | D | V | R | E | L | L | T | P | 3 | |
| 528 | 2F10 PR3 | WT | RHPHFPTR | LQPPT | L | A | L | F | D | H | E | L | L | T | P | 3 | |
| 21 | VR28 | WT | RHPHFPTR | LQPPT | V | A | Q | N | D | H | E | L | I | T | P | 3 | 11 |
| 22 | 159 | WT | RHPHFPTR | LQPPA | M | A | Q | S | G | H | E | L | F | T | P | | |

TABLE 4

Sequences of characterized VEGF-R2 binding clones

| Clone | BC loop (23-30) | DE loop (52-56) | FG loop (77-87) |
|---|---|---|---|
| VR28 | RHPHFPTR | LQPPT | VAQNDHELITP |
| K1 | RHPHRPTR | LQPPT | ▨▨▨HEL▨TP |
| K6 | RHPHRPTR | LQPPT | ▨▨▨▨L▨TP |
| K9 | RHPHFPTR | LQPPT | ▨▨▨EL▨P |
| K10 | RHPHFPTR | LQPPT | ▨ND▨L▨VP |
| K12 | RHPHFPTR | LQPPT | ▨NDHE▨TP |
| K13 | RHPHFPTR | LQPPT | ▨A▨▨HEL▨TP |
| K14 | RHPHFPTR | LQPPT | ▨NDHEL▨IP |
| K15 | RHPHFPTR | LQPPT | ▨D▨E▨TP |
| 159 (Q8L) | RHPHFPTR | LQPPA | ▨AQ▨GHE▨FTP |
| E3 | RHPHFPTR | LQPPT | ▨N▨▨I▨P |
| E5 | RHPHRPTR | LQPPT | ▨QN▨L▨P |
| E6 | RHPHRPTR | LQPPT | ▨N▨L▨P |
| E9 | RHPHFPTR | LQPPT | ▨▨▨L▨TP |
| E18 | RHPHFPTR | LQPPT | V▨N▨EL▨TP |
| E19 | RHPHFPTR | LQPPT | R▨N▨L▨TP |
| E25 | RHPHFPTR | LQPPT | ▨▨EL▨TP |
| E26 | RHPHFPTR | LQPPT | V▨N▨EL▨TP |
| E28 | RHPHFPTR | LQPPT | ▨N▨EL▨VP |
| E29 | RHPHFPTR | LQPPT | V▨N▨P▨TR |
| M1 | RHPHFPTR | LQP▨ | ▨NL▨EL▨TP |
| M2 | RHPHRPTR | LQPP▨ | ▨N▨▨HI▨TP |
| M3 (D60) | RHPHRPT▨ | LQPP▨ | ▨N▨▨EL▨TP |
| M4 | RHPHFPTR▨ | LQPP▨ | ▨▨▨HF▨TP |
| M5 FL | RHPHFPTR | LQPP▨ | ▨N▨▨RF▨TP |
| M6 | RHPHFPT▨ | LQPP▨ | ▨▨▨RR▨TP |
| M7 | RHPHFPT▨ | LQP▨ | ▨▨RR▨TP |
| M8 | RHPHFPT▨ | LQPP▨ | ▨▨▨TR▨RP |
| WT | VSDVPRDLEVVAATPTSLLISW DAPAVTVR YYRITYGETGGNSPVQEPTVP GSKST ATISGLKPGVDYTITVYAVT GRGDSPASSKP ISINYRT | | |

TABLE 5

Affinities of the trinectin binders to KDR-Fc determined in radioactive equilibrium binding assay

| Clone | KDR (Kd, nM) |
|---|---|
| VR28 | 11.0 ± 0.5 |
| K1 | <0.6 ± 0.1 |
| K6 | <0.9 ± 0.1 |
| K9 | <1.8 ± 0.4 |
| K10 | <0.6 ± 0.1 |
| K12 | <0.6 ± 0.1 |
| K13 | <0.6 ± 0.1 |
| K14 | <0.6 ± 0.1 |
| K15 | <0.4 ± 0.1 |

TABLE 6

Affinities of the trinectin binders to KDR and Flk-1 determined in radioactive equilibrium binding assay

| Clone | KDR (Kd, nM) | Flk-1 (Kd, nM) |
|---|---|---|
| VR28 | 11.0 ± 0.5 | nd* |
| E3 | <1.0 ± 0.2 | 5.4 ± 1.5 |
| E5 | <0.4 ± 0.1 | 3.2 ± 0.3 |
| E6 | <0.4 ± 0.1 | 7.1 ± 1.1 |
| E9 | 2.4 ± 0.3 | <1.4 ± 0.1 |
| E18 | <1.2 ± 0.2 | <0.5 ± 0.1 |
| E19 | <1.3 ± 0.2 | <0.7 ± 0.1 |
| E25 | <1.6 ± 0.4 | <1.3 ± 0.2 |
| E26 | <1.7 ± 0.4 | 2.0 ± 0.3 |
| E28 | <1.6 ± 0.4 | 2.1 ± 0.6 |
| E29 | <1.5 ± 0.4 | <0.9 ± 0.2 |

*nd - binding is not detected at 100 nM of target

TABLE 7

Determination of ka, kd and Kd by BIAcore assay

| Clone | Target | ka (1/M*s) × $10^{-4}$ | kd (1/s) × $10^{+5}$ | Kd (nM) |
|---|---|---|---|---|
| E6 | KDR | 89 | 6.7 | 0.08 |
|  | Flk-1 | 67 | 136.0 | 2.02 |
| E18 | KDR | 26 | 12.1 | 0.46 |
|  | Flk-1 | 60 | 19.5 | 0.33 |
| E19 | KDR | 30 | 1.7 | 0.06 |
|  | Flk-1 | 66 | 22.3 | 0.34 |
| E25 | KDR | 25 | 5.2 | 0.21 |
|  | Flk-1 | 50 | 37.8 | 0.76 |
| E26 | KDR | 11 | 5.8 | 0.51 |
|  | Flk-1 | 22 | 47.7 | 2.14 |
| E29 | KDR | 36 | 7.0 | 0.19 |
|  | Flk-1 | 79 | 28.8 | 0.37 |
| M5FL | KDR | 10 | 9.2 | 0.89 |
|  | Flk-1 | 28 | 58.2 | 2.10 |
| VR28 | KDR | 3 | 34 | 13 |
| 159(Q8L) | KDR | 5 | 10 | 2 |

TABLE 8

Binding to KDR (CHO KDR) and Flk-1 (CHO Flk-1) expressing cells

| Clone | CHO KDR (EC50, nM) | CHO Flk-1 (EC50, nM) |
|---|---|---|
| E18 | 4.2 ± 1.0 | 0.9 ± 0.4 |
| E19 | 7.6 ± 1.7 | 5.3 ± 2.5 |
| E26 | 2.6 ± 1.2 | 1.3 ± 0.7 |
| E29 | 2.3 ± 1.0 | 0.6 ± 0.1 |
| WT | no | no |

TABLE 9

Inhibition of VEGF-induced proliferation of KDR (Ba/F3-KDR) and Flk-1 (Ba/F3-Flk) expressing cells

| Clone | Ba/F3-KDR (IC50, nM) | Ba/F3-Flk (IC50, nM) |
|---|---|---|
| E18 | 5.4 ± 1.2 | 2.4 ± 0.2 |
| E19 | 12.3 ± 2.6 | 5.8 ± 1.0 |
| E26 | 3.2 ± 0.5 | 5.3 ± 1.7 |
| E29 | 10.0 ± 2.1 | 4.7 ± 1.2 |
| M5FL | 3.9 ± 1.1 | 5.1 ± 0.2 |
| WT | no | no |
| Anti-KDR Ab | 17.3 ± 7.7 | ND |
| Anti-Flk-1 Ab | ND | 15.0 ± 3.2 |

TABLE 10

Inhibition of VEGF-induced proliferation of HUVEC cells

| Clone | (IC50, nM) |
|---|---|
| E18 | 12.8 ± 4.6 |
| E19 | 11.8 ± 2.7 |
| E26 | 14.0 ± 5.9 |
| E29 | 8.4 ± 0.8 |
| M5FL | 8.5 ± 2.8 |
| WT | no |

TABLE 11

| | hKDR | | | Flk-1 | | |
|---|---|---|---|---|---|---|
| | $k_a$ (1/Ms) × $10^{-4}$ | $k_d$ (1/s) × $10^5$ | $K_D$ (nM) | $k_a$ (1/Ms) × $10^{-4}$ | $k_d$ (1/s) × $10^5$ | $K_D$ (nM) |
| M5FL C100 | 7.4 | 6.7 | 0.9 | 14.6 | 30 | 2.1 |
| M5FL 20K PEG | 0.9 | 5.4 | 5.9 | 2.4 | 55 | 22.8 |
| M5FL 40K PEG | 0.5 | 5.9 | 1.3 | 1.0 | 54 | 57.1 |

We claim:

1. A polypeptide comprising a fibronectin type III tenth ($^{10}$Fn3) domain of 80 to 150 amino acids, wherein the $^{10}$Fn3 domain binds to a target molecule with a $K_D$ of less than 100 nM and comprises an amino acid sequence at least 60% identical to SEQ ID NO:5; wherein the $^{10}$Fn3 domain further comprises a C-terminal tail having the sequence of EIDKPCQ (residues 97-103 of SEQ ID NO: 199), and wherein the cysteine residue of the C-terminal tail is conjugated to a moiety selected from the group consisting of: a polyoxyalkylene moiety, a radioactive moiety, a chemotherapeutic agent, and a label.

2. The polypeptide of claim 1, wherein the polypeptide binds to the target molecule with a $K_D$ of less than 10 nM.

3. The polypeptide of claim 1, wherein the moiety is a polyoxyalkylene moiety.

4. The polypeptide of claim 3, wherein the polyoxyalkylene moiety is a polyethylene glycol (PEG) moiety.

5. The polypeptide of claim 4, wherein the PEG moiety has a mass of 40 kDa.

6. The polypeptide of claim 1, wherein the moiety is a radioactive moiety.

7. The polypeptide of claim 1, wherein the moiety is a chemotherapeutic agent.

8. The polypeptide of claim 1, wherein the moiety is a label.

9. A pharmaceutical preparation comprising a polypeptide of claim 1 and a pharmaceutically acceptable carrier.

10. The pharmaceutical preparation of claim 9, wherein the moiety is a polyoxyalkylene moiety.

11. The pharmaceutical preparation of claim 10, wherein the polyoxyalkylene moiety is a polyethylene glycol (PEG) moiety.

12. The pharmaceutical preparation of claim 11, wherein the PEG moiety has a mass of 40 kDa.

13. The pharmaceutical preparation of claim 9, wherein the moiety is a radioactive moiety.

14. The pharmaceutical preparation of claim 9, wherein the moiety is a chemotherapeutic agent.

15. The pharmaceutical preparation of claim 9, wherein the moiety is a label.

* * * * *

UNITED STATES PATENT AND TRADEMARK OFFICE
CERTIFICATE OF CORRECTION

| | | |
|---|---|---|
| PATENT NO. | : 7,847,062 B2 | Page 1 of 1 |
| APPLICATION NO. | : 11/482641 | |
| DATED | : December 7, 2010 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 94 days.

Signed and Sealed this
Twenty-sixth Day of July, 2011

David J. Kappos
*Director of the United States Patent and Trademark Office*